(12) United States Patent
Donovan et al.

(10) Patent No.: US 9,858,389 B2
(45) Date of Patent: Jan. 2, 2018

(54) METHOD AND SYSTEM FOR DETERMINING THE RISK OF OCCURRENCE OF PROSTATE CANCER

(75) Inventors: Michael Donovan, Cambridge, MA (US); Faisal Khan, Fishkill, NY (US); Gerardo Fernandez, Yorktown Heights, NY (US); Ali Tabesh, Montvale, NJ (US); Ricardo Mesa-Tejada, Pleasantville, NY (US); Carlos Cordon-Cardo, New York, NY (US); Jose Costa, Guilford, CT (US); Stephen Fogarasi, Pawling, NY (US); Yevgen Vengrenyuk, Mamaroneck, NY (US)

(73) Assignee: Fundação D. Anna de Sommer Champalimaud e Dr. Carlos Montez Champalimaud, Lisbon (PT)

( * ) Notice: Subject to any disclaimer, the term of this patent is extended or adjusted under 35 U.S.C. 154(b) by 810 days.

(21) Appl. No.: 12/462,041

(22) Filed: Jul. 27, 2009

(65) Prior Publication Data

US 2010/0177950 A1    Jul. 15, 2010

Related U.S. Application Data

(60) Provisional application No. 61/135,926, filed on Jul. 25, 2008, provisional application No. 61/135,925, filed on Jul. 25, 2008, provisional application No. 61/190,537, filed on Aug. 28, 2008, provisional application No. 61/204,606, filed on Jan. 7, 2009, provisional application No. 61/217,832, filed on Jun. 4, 2009.

(51) Int. Cl.
*G06G 7/48*    (2006.01)
*G06F 19/00*    (2011.01)

(52) U.S. Cl.
CPC ........ *G06F 19/3437* (2013.01); *G06F 19/345* (2013.01); *G06F 19/3443* (2013.01)

(58) Field of Classification Search
None
See application file for complete search history.

(56) References Cited

U.S. PATENT DOCUMENTS

| | | | |
|---|---|---|---|
| 6,995,020 B2 | 2/2006 | Capodieci et al. | |
| 7,321,881 B2 | 1/2008 | Saidi et al. | |
| 7,425,700 B2 | 9/2008 | Stults et al. | |
| 7,461,048 B2 | 12/2008 | Teverovskiy et al. | |
| 7,467,119 B2 | 12/2008 | Saidi et al. | |
| 7,483,554 B2 | 1/2009 | Kotsianti et al. | |
| 7,505,948 B2 * | 3/2009 | Saidi | G06F 17/18 706/14 |
| 2005/0262031 A1* | 11/2005 | Saidi | G06F 19/345 706/21 |
| 2006/0064248 A1 | 3/2006 | Saidi et al. | |
| 2007/0019854 A1 | 1/2007 | Gholap et al. | |
| 2007/0099219 A1 | 5/2007 | Teverovskiy et al. | |
| 2007/0112716 A1 | 5/2007 | Sapir et al. | |
| 2007/0154958 A1* | 7/2007 | Hamann et al. | 435/7.2 |
| 2010/0088264 A1 | 4/2010 | Teverovskiy et al. | |

FOREIGN PATENT DOCUMENTS

WO    WO 2008/124138 A1    10/2008

OTHER PUBLICATIONS

Weyn et al. (Cytometry, 1999, 35:23-29).*
Kayser et al. (Pathol Res Pract. May 1986;181(2):153-8; Abstract).*
Partin et al. (JAMA, 1997; 277:1445-1451) i.*
Buhmedia et al. (Diagnostic Pathology, 2006, 1:4, p. 1-15).*
European Search Report in corresponding European Application No. 09 789 022.2-1952, dated Apr. 19, 2017.
Scott Doyle et al: "Automated Grading of Prostate Cancer Using Architectural and Textural Image Features", Biomedical Imaging: From Nano to Macro, 2007. ISBI 2007.4th IEEE Inte Rnational Symposium on, IEEE, PI, Apr. 1, 2007 (Apr. 1, 2007), pp. 1284-1287.

* cited by examiner

*Primary Examiner* — Pablo S Whaley
(74) *Attorney, Agent, or Firm* — Leason Ellis LLP

(57) ABSTRACT

Clinical information, molecular information and/or computer-generated morphometric information is used in a predictive model for predicting the occurrence of a medical condition. In an embodiment, a model predicts risk of prostate cancer progression in a patient, where the model is based on features including one or more (e.g., all) of preoperative PSA, dominant Gleason Grade, Gleason Score, at least one of a measurement of expression of AR in epithelial and stromal nuclei and a measurement of expression of Ki67-positive epithelial nuclei, a morphometric measurement of average edge length in the minimum spanning tree (MST) of epithelial nuclei, and a morphometric measurement of area of non-lumen associated epithelial cells relative to total tumor area. In some embodiments, the morphometric information is based on image analysis of tissue subject to multiplex immunofluorescence and may include characteristic(s) of a minimum spanning tree (MST) and/or a fractal dimension observed in the images.

9 Claims, 18 Drawing Sheets

|  | Feature | $\chi^2$ p-value | CI |
|---|---|---|---|
| FD | Gland Boundaries (w/ Stroma) | < 0.0001 | 0.348 |
|  | Gland Boundaries (All) | < 0.0001 | 0.343 |
| MST | Mean Edge Length (All) | 0.0043 | 0.416 |
|  | Mean Edge Length (Intra-Gland) | 0.0044 | 0.418 |
|  | Mean Edge Length (Inter-Gland) | 0.3130 | 0.459 |
|  | Std Dev of Edge Lengths (All) | 0.1220 | 0.446 |
|  | Std Dev of Edge Lengths (Intra-Gland) | 0.0295 | 0.424 |
|  | Std Dev of Edge Lengths (Inter-Gland) | 0.2564 | 0.470 |
|  | Degree Distribution for Degree 1 ($d_1$) | 0.0032 | 0.403 |
|  | Degree Distribution for Degree 2 ($d_2$) | 0.0018 | 0.606 |
|  | Degree Distribution for Degree 3 ($d_3$) | 0.0001 | 0.364 |
| Combined | FD (Gland-Stroma) + Gleason Grade | < 0.0001 | 0.321 |
|  | Mean Edge Length (All) + Gleason Grade | < 0.0001 | 0.330 |
|  | $d_3$ + Gleason grade | < 0.0001 | 0.321 |

FIG. 9

Features Selected for Prediction of Disease Progression

| Feature | Univariate P Value | Weight in Model |
|---|---|---|
| Clinical | | |
| Preoperative PSA | <0.00001 | -24.479 |
| Dominant Biopsy Gleason Grade | <0.0001 | 23.140 |
| Biopsy Gleason Score | <0.00001 | -17.512 |
| | | |
| Molecular (Combined) | | |
| Combined AR Dynamic Range at Low bGG, Total Ki67 at High bGG | <0.00001 | -16.005 |
| | | |
| Morphometric (Combined) | | |
| Combined Mean Distance Between Epithelial Tumor Cells (MST) at Low bGG, Actual Grade at High bGG | <0.00001 | -13.521 |
| | | |
| Morphometric | | |
| Area of Isolated (Non-Lumen Associated) Tumor Epithelial Cells Relative to Total Tumor Area | <0.00001 | -6.852 |

FIG. 11

METHOD AND SYSTEM FOR DETERMINING THE RISK OF OCCURRENCE OF PROSTATE CANCER

CROSS-REFERENCE TO RELATED APPLICATIONS

This claims priority to U.S. Provisional Application Nos. 61/135,926, filed Jul. 25, 2008, 61/135,925, filed Jul. 25, 2008, 61/190,537, filed Aug. 28, 2008, 61/204,606, filed Jan. 7, 2009, and 61/217,832, filed Jun. 4, 2009, all of which are hereby incorporated by reference herein in their entireties.

FIELD OF THE INVENTION

Embodiments of the present invention relate to methods and systems for predicting the occurrence of a medical condition such as, for example, the presence, recurrence, or progression of disease (e.g., cancer), responsiveness or unresponsiveness to a treatment for the medical condition, or other outcome with respect to the medical condition. For example, in some embodiments of the present invention, systems and methods are provided that use clinical information, molecular information, and/or computer-generated morphometric information in a predictive model that predicts the risk of disease progression in a patient. The morphometric information used in a predictive model according to some embodiments of the present invention may be generated based on image analysis of tissue (e.g., tissue subject to multiplex immunofluorescence (IF)) and may include morphometric information pertaining to a minimum spanning tree (MST) and/or a fractal dimension (FD) observed in the tissue or images of such tissue.

BACKGROUND OF THE INVENTION

Physicians are required to make many medical decisions ranging from, for example, whether and when a patient is likely to experience a medical condition to how a patient should be treated once the patient has been diagnosed with the condition. Determining an appropriate course of treatment for a patient may increase the patient's chances for, for example, survival, recovery, and/or improved quality of life. Predicting the occurrence of an event also allows individuals to plan for the event. For example, predicting whether a patient is likely to experience occurrence (e.g., presence, recurrence, or progression) of a disease may allow a physician to recommend an appropriate course of treatment for that patient.

When a patient is diagnosed with a medical condition, deciding on the most appropriate therapy is often confusing for the patient and the physician, especially when no single option has been identified as superior for overall survival and quality of life. Traditionally, physicians rely heavily on their expertise and training to treat, diagnose and predict the occurrence of medical conditions. For example, pathologists use the Gleason scoring system to evaluate the level of advancement and aggression of prostate cancer, in which cancer is graded based on the appearance of prostate tissue under a microscope as perceived by a physician. Higher Gleason scores are given to samples of prostate tissue that are more undifferentiated. Although Gleason grading is widely considered by pathologists to be reliable, it is a subjective scoring system. Particularly, different pathologists viewing the same tissue samples may make conflicting interpretations.

Current preoperative predictive tools have limited utility for the majority of contemporary patients diagnosed with organ-confined and/or intermediate risk disease. For example, prostate cancer remains the most commonly diagnosed non-skin cancer in American men and causes approximately 29,000 deaths each year [1]. Treatment options include radical prostatectomy, radiotherapy, and watchful waiting; there is, however, no consensus on the best therapy for maximizing disease control and survival without overtreating, especially for men with intermediate-risk prostate cancer (prostate-specific antigen 10-20 ng/mL, clinical stage T2b-c, and Gleason score 7). The only completed, randomized clinical study has demonstrated lower rates of overall death in men with T1 or T2 disease treated with radical prostatectomy; however, the results must be weighed against quality-of-life issues and co-morbidities [2, 3]. It is fairly well accepted that aggressive prostate-specific antigen (PSA) screening efforts have hindered the general utility of more traditional prognostic models due to several factors including an increased (over-diagnosis) of indolent tumors, lead time (clinical presentation), grade inflation and a longer life expectancy [4-7]. As a result, the reported likelihood of dying from prostate cancer 15 years after diagnosis by means of prostate-specific antigen (PSA) screening is lower than the predicted likelihood of dying from a cancer diagnosed clinically a decade or more ago further confounding the treatment decision process [8].

Several groups have developed methods to predict prostate cancer outcomes based on information accumulated at the time of diagnosis. The recently updated Partin tables [9] predict risk of having a particular pathologic stage (extracapsular extension, seminal vesicle invasion, and lymph node invasion), while the 10-year preoperative nomogram [10] provides a probability of being free of biochemical recurrence within 10 years after radical prostatectomy. These approaches have been challenged due to their lack of diverse biomarkers (other than PSA), and the inability to accurately stratify patients with clinical features of intermediate risk. Since these tools rely on subjective clinical parameters, in particular the Gleason grade which is prone to disagreement and potential error, having more objective measures would be advantageous for treatment planning. Furthermore, biochemical or PSA recurrence alone generally is not a reliable predictor of clinically significant disease [11]. Thus, it is believed by the present inventors that additional variables or endpoints are required for optimal patient counseling.

In view of the foregoing, it would be desirable to provide systems and methods for treating, diagnosing and predicting the occurrence of medical conditions, responses, and other medical phenomena with improved predictive power. For example, it would be desirable to provide systems and methods for predicting disease (e.g., cancer) progression at, for example, the time of diagnosis prior to treatment for the disease.

SUMMARY OF THE INVENTION

Embodiments of the present invention provide automated systems and methods for predicting the occurrence of medical conditions. As used herein, predicting an occurrence of a medical condition may include, for example, predicting whether and/or when a patient will experience an occurrence (e.g., presence, recurrence or progression) of disease such as cancer, predicting whether a patient is likely to respond to one or more therapies (e.g., a new pharmaceutical drug), or predicting any other suitable outcome with respect to the medical condition. Predictions by embodiments of the present invention may be used by physicians or other individuals, for example, to select an appropriate course of treatment for a patient, diagnose a medical condition in the patient, and/or predict the risk of disease progression in the patient.

In some embodiments of the present invention, systems, apparatuses, methods, and computer readable media are provided that use clinical information, molecular information and/or computer-generated morphometric information in a predictive model for predicting the occurrence of a medical condition. For example, a predictive model according to some embodiments of the present invention may be provided which is based on one or more of the features listed in Tables 1-5 and 9 and FIGS. 9 and 11 and/or other features.

For example, in an embodiment, a predictive model is provided predicts a risk of prostate cancer progression in a patient, where the model is based on one or more (e.g., all) of the features listed in FIG. 11 and optionally other features. For example, the predictive model may be based on features including one or more (e.g., all) of preoperative PSA, dominant Gleason Grade, Gleason Score, at least one of a measurement of expression of AR in epithelial and/or stromal nuclei (e.g., tumor epithelial and/or stromal nuclei) and a measurement of expression of Ki67-positive epithelial nuclei (e.g., tumor epithelial nuclei), a morphometric measurement of average edge length in the minimum spanning tree (MST) of epithelial nuclei, and a morphometric measurement of area of non-lumen associated epithelial cells relative to total tumor area. In some embodiments, the dominant Gleason Grade comprises a dominant biopsy Gleason Grade. In some embodiments, the Gleason Score comprises a biopsy Gleason Score.

In some embodiments of the present invention, two or more features (e.g., clinical, molecular, and/or morphometric features) may be combined in order to construct a combined feature for evaluation within a predictive model. For example, in the embodiment of a predictive model predictive of prostate cancer progression described above, the measurement of the expression of androgen receptor (AR) in nuclei (e.g., epithelial and/or stromal nuclei) may form a combined feature with the measurement of the expression of Ki67-positive epithelial nuclei. When a dominant Gleason Grade for the patient is less than or equal to 3, the predictive model may evaluate for the combined feature the measurement of the expression of androgen receptor (AR) in epithelial and stromal nuclei. Conversely, when the dominant Gleason Grade for the patient is 4 or 5, the predictive model may evaluate for the combined feature the measurement of the expression of Ki67-positive epithelial nuclei.

Additional examples of combined features according to some embodiments of the present invention are described below in connection with, for example, FIG. 9. For example, in the embodiment of a predictive model predictive of prostate cancer progression described above, the morphometric measurement of average edge length in the minimum spanning tree (MST) of epithelial nuclei may form a combined feature with dominant Gleason Grade. When the dominant Gleason Grade for the patient is less than or equal to 3, the predictive model may evaluate for the combined feature the measurement of average edge length in the minimum spanning tree (MST) of epithelial nuclei. Conversely, when the dominant Gleason Grade for the patient is 4 or 5, the predictive model may evaluate the dominant Gleason Grade for the combined feature.

In some embodiments of the present invention, a model is provided which is predictive of an outcome with respect to a medical condition (e.g., presence, recurrence, or progression of the medical condition), where the model is based on one or more computer-generated morphometric features generated from one or more images of tissue subject to multiplex immunofluorescence (IF). For example, due to highly specific identification of molecular components and consequent accurate delineation of tissue compartments attendant to multiplex IF (e.g., as compared to the stains used in light microscopy), multiplex IF microscopy may provide the advantage of more reliable and accurate image segmentation. The model may be configured to receive a patient dataset for the patient, and evaluate the patient dataset according to the model to produce a value indicative of the patient's risk of occurrence of the outcome. In some embodiments, the predictive model may also be based on one or more other morphometric features, one or more clinical features, and/or one or more molecular features.

For example, in some embodiments of the present invention, the predictive model may be based on one or more computer-generated morphometric feature(s) including one or more measurements of the minimum spanning tree (MST) (e.g., the MST of epithelial nuclei) identified in the one or more images of tissue subject to multiplex immunofluorescence (IF). For example, the one or more measurements of the minimum spanning tree (MST) may include the average edge length in the MST of epithelial nuclei. Other measurements of the MST according to some embodiments of the present invention are described below in connection with, for example, FIG. 9.

In some embodiments of the present invention, the predictive model may be based on one or more computer-generated morphometric feature(s) including one or more measurements of the fractal dimension (FD) (e.g., the FD of one or more glands) measured in the one or more images of tissue subject to multiplex immunofluorescence (IF). For example, the one or more measurements of the fractal dimension (FD) may include one or more measurements of the fractal dimension of gland boundaries between glands and stroma. In another example, the one or more measurements of the fractal dimension (FD) may include one or more measurements of the fractal dimension of gland boundaries between glands and stroma and between glands and lumen.

In an aspect of embodiments of the present invention, systems and methods are provided for segmenting and classifying objects in images of tissue subject to multiplex immunofluorescence (IF). For example, such segmentation and classification may include initial segmentation into primitives, classification of primitives into nuclei, cytoplasm, and background, and refinement of the classified primitives to obtain the final segmentation, in the manner described below in connection with FIG. 6.

In some embodiments, an apparatus is provided for identifying objects of interest in images of tissue, where the apparatus includes an image analysis tool configured to segment a tissue image into pathological objects comprising glands. Starting with lumens in the tissue image identified as seeds, the image analysis tool is configured to perform controlled region growing on the image including initiating growth around the lumen seeds in the tissue image thus encompassing epithelial cells identified in the image through the growth. The image analysis tool continues growth of each gland around each lumen seed so long as the area of each successive growth ring is larger than the area of the preceding growth ring. The image analysis tool discontinues the growth of the gland when the area of a growth ring is less than the area of the preceding growth ring for the gland.

In some embodiments, an apparatus is provided for measuring the expression of one or more biomarkers in images of tissue subject to immunofluorescence (IF), where the apparatus includes an image analysis tool configured to measure within an IF image of tissue the intensity of a biomarker (e.g., AR) as expressed within a particular type of pathological object (e.g., epithelial nuclei). Specifically, a plurality of percentiles of the intensity of the biomarker as expressed within the particular type of pathological object are determined. The image analysis tool identifies one of the plurality of percentiles as the percentile corresponding to a positive level of the biomarker in the pathological object. For example, the image analysis tool may identify the percentile correspond to a positive level of the biomarker based at least in part on an intensity in a percentile of another pathological object (e.g., stroma nuclei). In some embodiments, the image analysis tool is further configured to measure one or more features from the image of tissue, wherein the one or more features includes a difference of intensities of the percentile values (e.g., percentiles 90 and 10 of AR in epithelial nuclei). For example, the one or more features may include a difference of intensities of the percentile values normalized by an image threshold or another difference in intensities of percentile values (e.g., percentiles 90 and 10 in stroma nuclei).

In some embodiments, an apparatus is provided for identifying objects of interest in images of tissue, where the apparatus includes an image analysis tool configured to detect the presence of CD34 in an image of tissue subject to immunofluorescence (IF). Based on the detection, the image analysis tool is further configured to detect and segment blood vessels which are in proximity to the CD34.

In another aspect of embodiments of the present invention, systems and methods are provided in which data for a patient is measured at each of a plurality of points in time and evaluated by a predictive model of the present invention. A diagnosis or treatment of the patient may be based on a comparison of the results from each evaluation. Such a comparison may be summarized in, for example, a report output by a computer for use by a physician or other individual. For example, systems and methods may be provided for screening for an inhibitor compound of a medical condition. A first dataset for a patient may be evaluated by a predictive model, where the model is based on clinical data, molecular data, and computer-generated morphometric data. A test compound may be administered to the patient. Following administering of the test compound, a second dataset may be obtained from the patient and evaluated by the predictive model. The results of the evaluation of the first dataset may be compared to the results of the evaluation from the second dataset. A change in the results for the second dataset with respect to the first dataset may indicate that the test compound is an inhibitor compound.

In still another aspect of embodiments of the present invention, a test kit is provided for treating, diagnosing and/or predicting the occurrence of a medical condition. Such a test kit may be situated in a hospital, other medical facility, or any other suitable location. The test kit may receive data for a patient (e.g., including clinical data, molecular data, and/or computer-generated morphometric data), compare the patient's data to a predictive model (e.g., programmed in memory of the test kit) and output the results of the comparison. In some embodiments, the molecular data and/or the computer-generated morphometric data may be at least partially generated by the test kit. For example, the molecular data may be generated by an analytical approach subsequent to receipt of a tissue sample for a patient. The morphometric data may be generated by segmenting an electronic image of the tissue sample into one or more objects, classifying the one or more objects into one or more object classes (e.g., epithelial nuclei, epithelial cytoplasm, stroma, lumen, red blood cells, etc.), and determining the morphometric data by taking one or more measurements for the one or more object classes. In some embodiments, the test kit may include an input for receiving, for example, updates to the predictive model. In some embodiments, the test kit may include an output for, for example, transmitting data, such as data useful for patient billing and/or tracking of usage, to another device or location.

BRIEF DESCRIPTION OF THE DRAWINGS

For a better understanding of embodiments of the present invention, reference is made to the following detailed description, taken in conjunction with the accompanying drawings, in which like reference characters refer to like parts throughout, and in which:

FIG. 9 is a listing of minimum spanning tree (MST) features, fractal dimension (FD) features, combined features, and their respective two-sided p-values and values of the concordance index, which were identified in images of tissue subject to multiplex immunofluorescence (IF) and which may be used in predictive models according to some embodiments of the present invention;

FIG. 11 is a listing of clinical, molecular, and computer-generated morphometric features used by a model to predict disease progression in a patient according to an embodiment of the present invention;

DETAILED DESCRIPTION OF THE INVENTION

Figure 1A:
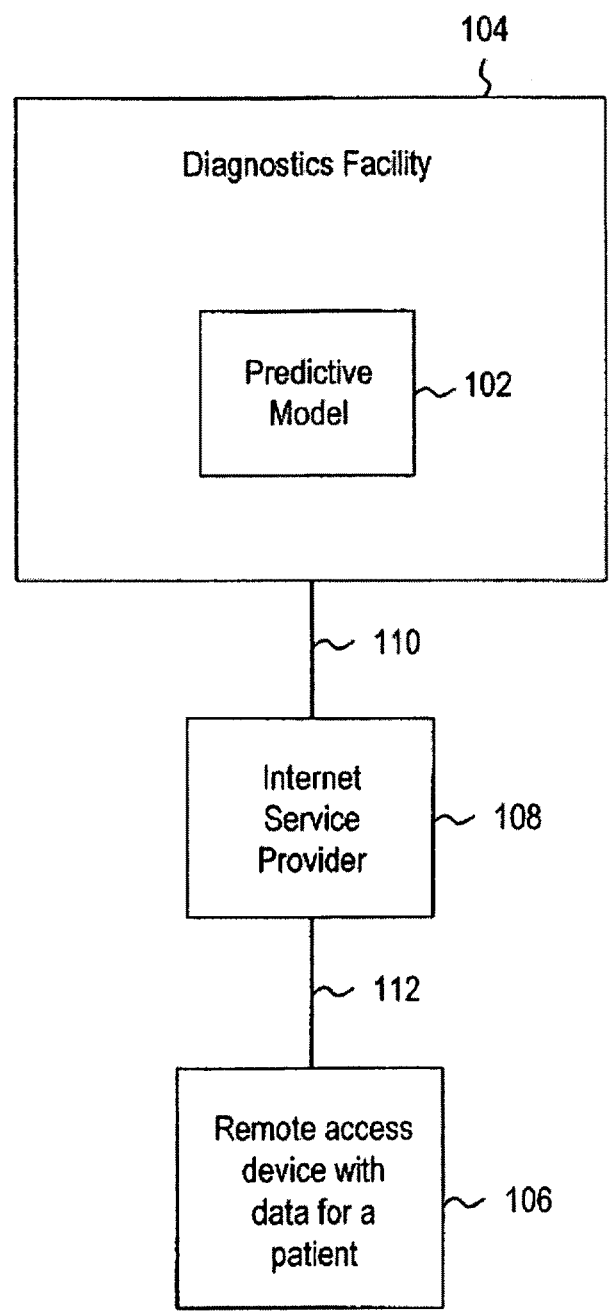
FIGS. 1A and 1B are block diagrams of systems that use a predictive model to treat, diagnose or predict the occurrence of a medical condition according to some embodiments of the present invention.

Embodiments of the present invention relate to methods and systems that use computer-generated morphometric information, clinical information, and/or molecular information in a predictive model for predicting the occurrence of a medical condition. For example, in some embodiments of the present invention, clinical, molecular and computer-generated morphometric information are used to predict the likelihood or risk of progression of a disease such as, for example, prostate cancer. In other embodiments, the teachings provided herein are used to predict the occurrence (e.g., presence, recurrence, or progression) of other medical conditions such as, for example, other types of disease (e.g., epithelial and mixed-neoplasms including breast, colon, lung, bladder, liver, pancreas, renal cell, and soft tissue) and the responsiveness or unresponsiveness of a patient to one or more therapies (e.g., pharmaceutical drugs). These predictions may be used by physicians or other individuals, for example, to select an appropriate course of treatment for a patient, diagnose a medical condition in the patient, and/or predict the risk or likelihood of disease progression in the patient.

In an aspect of the present invention, an analytical tool such as, for example, a module configured to perform support vector regression for censored data (SVRc), a support vector machine (SVM), and/or a neural network may be provided that determines correlations between clinical features, molecular features, computer-generated morphometric features, combinations of such features, and/or other features and a medical condition. The correlated features may form a model that can be used to predict an outcome with respect to the condition (e.g., presence, recurrence, or progression). For example, an analytical tool may be used to generate a predictive model based on data for a cohort of patients whose outcomes with respect to a medical condition (e.g., time to recurrence or progression of cancer) are at least partially known. The model may then be used to evaluate data for a new patient in order to predict the risk of occurrence of the medical condition in the new patient. In some embodiments, only a subset of clinical, molecular, morphometric, and/or other data (e.g., clinical and morphometric data only) may be used by the analytical tool to generate the predictive model. Illustrative systems and methods for treating, diagnosing, and predicting the occurrence of medical conditions are described in commonly-owned U.S. Pat. No. 7,461,048, issued Dec. 2, 2008, U.S. Pat. No. 7,467,119, issued Dec. 16, 2008, and PCT Application No. PCT/US2008/004523, filed Apr. 7, 2008, which are hereby incorporated by reference herein in their entireties.

The clinical, molecular, and/or morphometric data used by embodiments of the present invention may include any clinical, molecular, and/or morphometric data that is relevant to the diagnosis, treatment and/or prediction of a medical condition. For example, features analyzed for correlations with progression of prostate cancer in order to generate a model predictive of prostate cancer progression are described below in connection with Tables 1-5 and 9 and FIG. 9. It will be understood that at least some of these features (e.g., epithelial and mixed-neoplasms) may provide a basis for developing predictive models for other medical conditions (e.g., breast, colon, lung, bladder, liver, pancreas, renal cell, and soft tissue). For example, one or more of the features in Tables 1-5 and 9 and FIG. 9 may be assessed for patients having some other medical condition and then input to an analytical tool that determines whether the features correlate with the medical condition. Generally, features that increase the ability of the model to predict the occurrence of the medical condition (e.g., as determined through suitable univariate and/or multivariate analyses) may be included in the final model, whereas features that do not increase (e.g., or decrease) the predictive power of the model may be removed from consideration. By way of example only, illustrative systems and methods for selecting features for use in a predictive model are described below and in commonly-owned U.S. Publication No. 2007/0112716, published May 17, 2007 and entitled "Methods and Systems for Feature Selection in Machine Learning Based on Feature Contribution and Model Fitness," which is hereby incorporated by reference herein in its entirety.

Using the features in Tables 1-5 and 9 and FIG. 9 as a basis for developing a predictive model may focus the resources of physicians, other individuals, and/or automated processing equipment (e.g., a tissue image analysis system) on obtaining patient data that is more likely to be correlated with outcome and therefore useful in the final predictive model. Moreover, the features determined to be correlated with progression of prostate cancer are shown in Table 9 and FIG. 11. It will be understood that these features may be included directly in final models predictive of progression of prostate cancer and/or used for developing predictive models for other medical conditions.

The morphometric data used in predictive models according to some embodiments of the present invention may include computer-generated data indicating various structural, textural, and/or spectral properties of, for example, tissue specimens. For example, the morphometric data may include data for morphometric features of stroma, cytoplasm, epithelial nuclei, stroma nuclei, lumen, red blood cells, tissue artifacts, tissue background, glands, other objects identified in a tissue specimen or a digitized image of such tissue, or a combination thereof.

In an aspect of the present invention, a tissue image analysis system is provided for measuring morphometric features from tissue specimen(s) (e.g., needle biopsies and/or whole tissue cores) or digitized image(s) thereof. The system may utilize, in part, the commercially-available Definiens Cellenger software. For example, in some embodiments, the image analysis system may receive image(s) of tissue stained with hematoxylin and eosin (H&E) as input, and may output one or more measurements of morphometric features for pathological objects (e.g., epithelial nuclei, cytoplasm, etc.) and/or structural, textural, and/or spectral properties observed in the image(s). For example, such an image analysis system may include a light microscope that captures images of H&E-stained tissue at 20× magnification. Illustrative systems and methods for measuring morphometric features from images of H&E-stained tissue according to some embodiments of the present invention are described below in connection with, for example, FIG. 3 and the illustrative study in which aspects of the present invention were applied to prediction of prostate cancer progression. Computer-generated morphometric features (e.g., morphometric features measurable from digitized images of H&E-stained tissue) which may be used in a predictive model for predicting an outcome with respect to a medical condition according to some embodiments of the present invention are summarized in Table 1.

In some embodiments of the present invention, the image analysis system may receive image(s) of tissue subject to multiplex immunofluorescence (IF) as input, and may output one or more measurements of morphometric features for pathological objects (e.g., epithelial nuclei, cytoplasm, etc.) and/or structural, textural, and/or spectral properties observed in the image(s). For example, such an image analysis system may include a multispectral camera attached to a microscope that captures images of tissue under an excitation light source. Computer-generated morphometric features (e.g., morphometric features measurable from digitized images of tissue subject to multiplex IF) which may be used in a predictive model for predicting an outcome with respect to a medical condition according to some embodiments of the present invention are listed in Table 2. Illustrative examples of such morphometric features include characteristics of a minimum spanning tree (MST) (e.g., MST connecting epithelial nuclei) and/or a fractal dimension (FD) (e.g., FD of gland boundaries) measured in images acquired through multiplex IF microscopy. Illustrative systems and methods for measuring morphometric features from images of tissue subject to multiplex IF according to some embodiments of the present invention are described below in connection with, for example, FIGS. 4B-9 and the illustrative study in which aspects of the present invention were applied to the prediction of prostate cancer progression.

Clinical features which may be used in predictive models according to some embodiments of the present invention may include or be based on data for one or more patients such as age, race, weight, height, medical history, genotype and disease state, where disease state refers to clinical and pathologic staging characteristics and any other clinical features gathered specifically for the disease process under consideration. Generally, clinical data is gathered by a physician during the course of examining a patient and/or the tissue or cells of the patient. The clinical data may also include clinical data that may be more specific to a particular medical context. For example, in the context of prostate cancer, the clinical data may include data indicating blood concentration of prostate specific antigen (PSA), the result of a digital rectal exam, Gleason score, and/or other clinical data that may be more specific to prostate cancer. Clinical features which may be used in a predictive model for predicting an outcome with respect to a medical condition according to some embodiments of the present invention are listed in Table 3.

Molecular features which may be used in predictive models according to some embodiments of the present invention may include or be based on data indicating the presence, absence, relative increase or decrease or relative location of biological molecules including nucleic acids, polypeptides, saccharides, steroids and other small molecules or combinations of the above, for example, glycoroteins and protein-RNA complexes. The locations at which these molecules are measured may include glands, tumors, stroma, and/or other locations, and may depend on the particular medical context.

Generally, molecular data is gathered using molecular biological and biochemical techniques including Southern, Western, and Northern blots, polymerase chain reaction (PCR), immunohistochemistry, and/or immunofluorescence (IF) (e.g., multiplex IF). Molecular features which may be used in a predictive model for predicting an outcome with respect to a medical condition according to some embodiments of the present invention are listed in Table 4. Additional details regarding multiplex immunofluorescence according to some embodiments of the present invention are described in commonly-owned U.S. Patent Application Publication No. 2007/0154958, published Jul. 5, 2007 and entitled "Multiplex In Situ Immunohistochemical Analysis," which is hereby incorporated by reference herein in its entirety. Further, in situ hybridization may be used to show both the relative abundance and location of molecular biological features. Illustrative methods and systems for in situ hybridization of tissue are described in, for example, commonly-owned U.S. Pat. No. 6,995,020, issued Feb. 7, 2006 and entitled "Methods and compositions for the preparation and use of fixed-treated cell-lines and tissue in fluorescence in situ hybridization," which is hereby incorporated by reference herein in its entirety.

Generally, when any clinical, molecular, and/or morphometric features from any of Tables 1-5 and 9 and/or FIGS. 9 and 11 are applied to medical contexts other than the prostate, features from these Tables and/or Figures that are more specific to the prostate may not be considered. Optionally, features more specific to the medical context in question may be substituted for the prostate-specific features. For example, other histologic disease-specific features/manifestations may include regions of necrosis (e.g., ductal carcinoma in situ for the breast), size, shape and regional pattern/ distribution of epithelial cells (e.g., breast, lung), degree of differentiation (e.g., squamous differentiation with non-small cell lung cancer (NSCLC, mucin production as seen with various adenocarcinomas seen in both breast and colon)), morphological/microscopic distribution of the cells (e.g., lining ducts in breast cancer, lining bronchioles in NSCLC), and degree and type of inflammation (e.g., having different characteristics for breast and NSCLC in comparison to prostate).

Figure 1B:
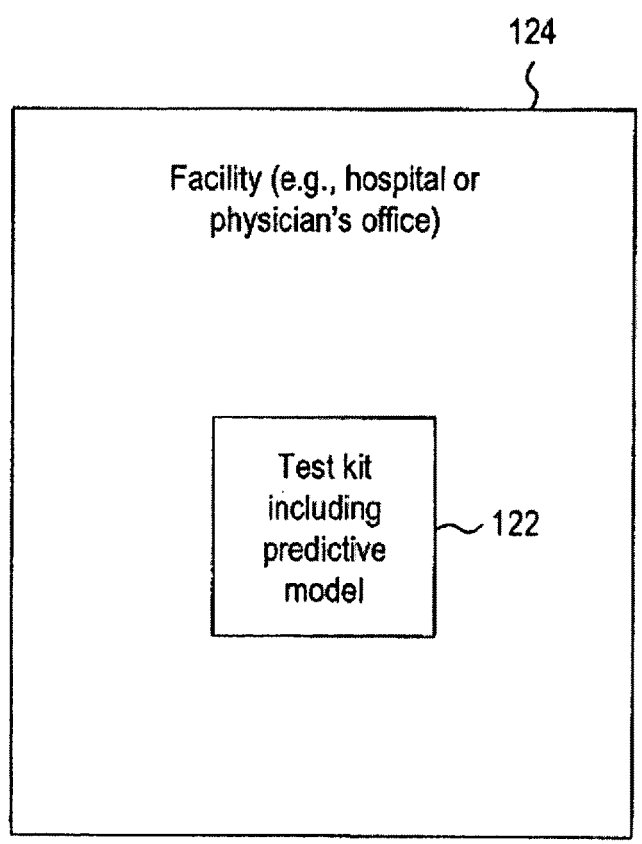

FIGS. 1A and 1B show illustrative systems that use a predictive model to predict the occurrence (e.g., presence, recurrence, or progression) of a medical condition in a patient. The arrangement in FIG. 1A may be used when, for example, a medical diagnostics lab provides support for a medical decision to a physician or other individual associated with a remote access device. The arrangement in FIG. 1B may be used when, for example, a test kit including the predictive model is provided for use in a facility such as a hospital, other medical facility, or other suitable location.

Referring to FIG. 1A, predictive model 102 is located in diagnostics facility 104. Predictive model 102 may include any suitable hardware, software, or combination thereof for receiving data for a patient, evaluating the data in order to predict the occurrence (e.g., presence, recurrence, or progression) of a medical condition for the patient, and outputting the results of the evaluation. In another embodiment, model 102 may be used to predict the responsiveness of a patient to particular one or more therapies. Diagnostics facility 104 may receive data for a patient from remote access device 106 via Internet service provider (ISP) 108 and communications networks 110 and 112, and may input the data to predictive model 102 for evaluation. Other arrangements for receiving and evaluating data for a patient from a remote location are of course possible (e.g., via another connection such as a telephone line or through the physical mail). The remotely located physician or individual may acquire the data for the patient in any suitable manner and may use remote access device 106 to transmit the data to diagnostics facility 104. In some embodiments, the data for the patient may be at least partially generated by diagnostics facility 104 or another facility. For example, diagnostics facility 104 may receive a digitized image of H&E-stained tissue from remote access device 106 or other device and may generate morphometric data for the patient based on the image. In another example, actual tissue samples may be received and processed by diagnostics facility 104 in order to generate morphometric data, molecular data, and/or other data. In other examples, a third party may receive a tissue sample or image for a new patient, generate morphometric data, molecular data and/or other data based on the image or tissue, and provide the morphometric data, molecular data and/or other data to diagnostics facility 104. Illustrative embodiments of suitable image processing tools for generating morphometric data and/or molecular data from tissue images and/or tissue samples according to some embodiments of the present invention are described below in connection with FIGS. 3-8.

Figure 2:
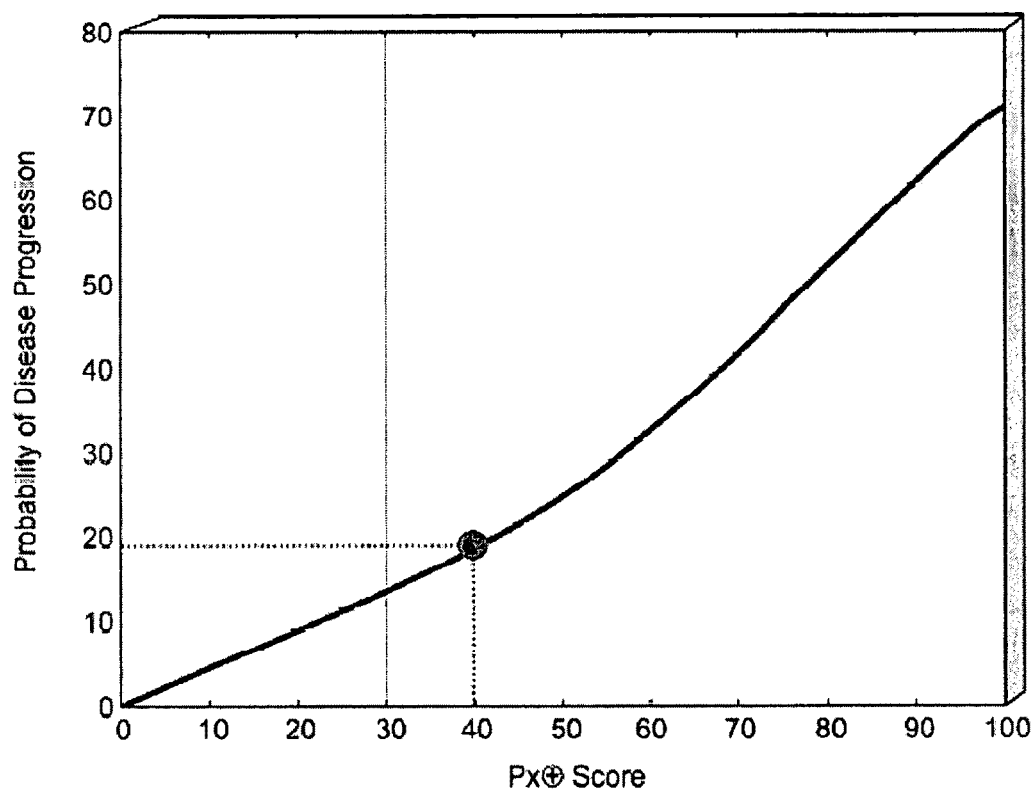
FIG. 2 is a graph illustrating the probability that a patient will experience an outcome with respect to a medical condition (e.g., disease progression) as indicated by the value or score output by a predictive model according to some embodiments of the present invention.

Diagnostics facility 104 may provide the results of the evaluation to a physician or individual associated with remote access device 106 through, for example, a transmission to remote access device 106 via ISP 108 and communications networks 110 and 112 or in another manner such as the physical mail or a telephone call. The results may include a value or "score" (e.g., an indication of the likelihood that the patient will experience one or more outcomes related to the medical condition such as the presence of the medical condition, predicted time to recurrence of the medical condition, or risk or likelihood of progression of the medical condition in the patient), information indicating one or more features analyzed by predictive model 102 as being correlated with the medical condition, image(s) output by the image processing tool, information indicating the sensitivity and/or specificity of the predictive model, explanatory remarks, other suitable information, or a combination thereof. For example, FIG. 2 shows at least a portion of a report for a fictional patient that may be output by, or otherwise generated based on the output of, the predictive model. As shown, the report may indicate that based on the data for the patient input to the predictive model, the predictive model output a value of 40 corresponding to a 19% probability of disease progression (as indicated by castrate PSA rise, metastasis and/or prostate cancer mortality) within eight years after radical prostatectomy, which may place the patient in a high-risk category. (Conversely, as indicated by the vertical line in the embodiment shown in FIG. 2, a values of less than 30.19 output by the predictive model may place the patient in a low-risk category.) Such a report may be used by a physician or other individual, for example, to assist in determining appropriate treatment option(s) for the patient. The report may also be useful in that it may help the physician or individual to explain the patient's risk to the patient.

Remote access device 106 may be any remote device capable of transmitting and/or receiving data from diagnostics facility 104 such as, for example, a personal computer, a wireless device such as a laptop computer, a cell phone or a personal digital assistant (PDA), or any other suitable remote access device. Multiple remote access devices 106 may be included in the system of FIG. 1A (e.g., to allow a plurality of physicians or other individuals at a corresponding plurality of remote locations to communicate data with diagnostics facility 104), although only one remote access device 106 has been included in FIG. 1A to avoid over-complicating the drawing. Diagnostics facility 104 may include a server capable of receiving and processing communications to and/or from remote access device 106. Such a server may include a distinct component of computing hardware and/or storage, but may also be a software application or a combination of hardware and software. The server may be implemented using one or more computers.

Each of communications links 110 and 112 may be any suitable wired or wireless communications path or combination of paths such as, for example, a local area network, wide area network, telephone network, cable television network, intranet, or Internet. Some suitable wireless communications networks may be a global system for mobile communications (GSM) network, a time-division multiple access (TDMA) network, a code-division multiple access (CDMA) network, a Bluetooth network, or any other suitable wireless network.

FIG. 1B shows a system in which test kit 122 including a predictive model in accordance with an embodiment of the present invention is provided for use in facility 124, which may be a hospital, a physician's office, or other suitable location. Test kit 122 may include any suitable hardware, software, or combination thereof (e.g., a personal computer) that is adapted to receive data for a patient (e.g., at least one of clinical, morphometric and molecular data), evaluate the patient's data with a predictive model (e.g., programmed in memory of the test kit), and output the results of the evaluation. For example, test kit 122 may include a computer readable medium encoded with computer executable instructions for performing the functions of the predictive model. The predictive model may be a predetermined model previously generated (e.g., by another system or application such as the system in FIG. 1C). In some embodiments, test kit 122 may optionally include an image processing tool capable of generating data corresponding to morphometric and/or molecular features from, for example, a tissue sample or image. Illustrative embodiments of suitable image processing tools according to some embodiments of the present invention are described below in connection with FIGS. 3-8. In other embodiments, test kit 122 may receive pre-packaged data for the morphometric features as input from, for example, an input device (e.g., keyboard) or another device or location. Test kit 122 may optionally include an input for receiving, for example, updates to the predictive model. The test kit may also optionally include an output for transmitting data, such as data useful for patient billing and/or tracking of usage, to a main facility or other suitable device or location. The billing data may include, for example, medical insurance information for a patient evaluated by the test kit (e.g., name, insurance provider, and account number). Such information may be useful when, for example, a provider of the test kit charges for the kit on a per-use basis and/or when the provider needs patients' insurance information to submit claims to insurance providers.

Figure 1C:
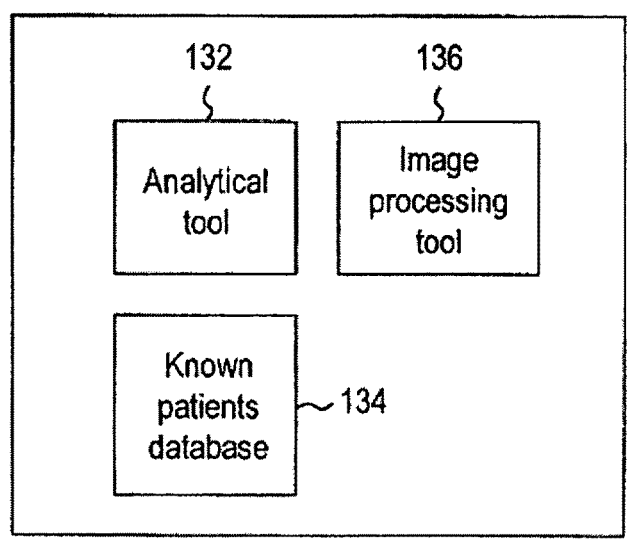
FIG. 1C is a block diagram of a system for generating a predictive model according to some embodiments of the present invention.

FIG. 1C shows an illustrative system for generating a predictive model. The system includes analytical tool 132 (e.g., including a module configured to perform support vector regression for censored data (SVRc), a support vector machine (SVM), and/or a neural network) and database 134 of patients whose outcomes are at least partially known. Analytical tool 132 may include any suitable hardware, software, or combination thereof for determining correlations between the data from database 134 and a medical condition. The system in FIG. 1C may also include image processing tool 136 capable of generating, for example, morphometric data based on H&E-stained tissue or digitized image(s) thereof, morphometric data and/or molecular data based on tissue acquired using multiplex immunofluorescence (IF) microscopy or digitized image(s) of such tissue, or a combination thereof. Tool 136 may generate morphometric data and/or molecular data for, for example, the known patients whose data is included in database 134. Illustrative embodiments of suitable image processing tools according to some embodiments of the present invention are described below in connection with FIGS. 3-8.

Database 134 may include any suitable patient data such as data for clinical features, morphometric features, molecular features, or a combination thereof. Database 134 may also include data indicating the outcomes of patients such as whether and when the patients have experienced a disease or its recurrence or progression. For example, database 134 may include uncensored data for patients (i.e., data for patients whose outcomes are completely known) such as data for patients who have experienced a medical condition or its recurrence or progression. Database 134 may alternatively or additionally include censored data for patients (i.e., data for patients whose outcomes are not completely known) such as data for patients who have not shown signs of a disease or its recurrence or progression in one or more follow-up visits to a physician. The use of censored data by analytical tool 132 may increase the amount of data available to generate the predictive model and, therefore, may advantageously improve the reliability and predictive power of the model. Examples of machine learning approaches, namely support vector regression for censored data (SVRc) and a particular implementation of a neural network (NNci) that can make use of both censored and uncensored data are described below.

In one embodiment, analytical tool 132 may perform support vector regression on censored data (SVRc) in the manner set forth in commonly-owned U.S. Pat. No. 7,505,948, issued Mar. 17, 2009, which is hereby incorporated by reference herein in its entirety. SVRc uses a loss/penalty function which is modified relative to support vector machines (SVM) in order to allow for the utilization of censored data. For example, data including clinical, molecular, and/or morphometric features of known patients from database 134 may be input to the SVRc to determine parameters for a predictive model. The parameters may indicate the relative importance of input features, and may be adjusted in order to maximize the ability of the SVRc to predict the outcomes of the known patients.

The use of SVRc by analytical tool 132 may include obtaining from database 134 multi-dimensional, non-linear vectors of information indicative of status of patients, where at least one of the vectors lacks an indication of a time of occurrence of an event or outcome with respect to a corresponding patient. Analytical tool 132 may then perform regression using the vectors to produce a kernel-based model that provides an output value related to a prediction of time to the event based upon at least some of the information contained in the vectors of information. Analytical tool 132 may use a loss function for each vector containing censored data that is different from a loss function used by tool 132 for vectors comprising uncensored data. A censored data sample may be handled differently because it may provide only "one-sided information." For example, in the case of survival time prediction, a censored data sample typically only indicates that the event has not happened within a given time, and there is no indication of when it will happen after the given time, if at all.

The loss function used by analytical tool 132 for censored data may be as follows:

$$\text{Loss}(f(x), y, s = 1) = \begin{cases} C_s^*(e - \varepsilon_s^*) & e > \varepsilon_s^* \\ 0 & -\varepsilon_s \le e \le \varepsilon_s^* \\ C_s(\varepsilon_s - e) & e < -\varepsilon_s \end{cases}$$

where $e = f(x) - y$; and
$f(x) = W^T \Phi(x) + b$
is a linear regression function on a feature space F. Here, W is a vector in F, and $\Phi(x)$ maps the input x to a vector in F.

In contrast, the loss function used by tool 132 for uncensored data may be:

$$\text{Loss}(f(x), y, s = 0) = \begin{cases} C_n^*(e - \varepsilon_n^*) & e > \varepsilon_n^* \\ 0 & -\varepsilon_n \le e \le \varepsilon_n^* \\ C_n(\varepsilon_n - e) & e < -\varepsilon_n \end{cases}$$

Where $e = f(x) - y$, and s is equal is the censorship status of the corresponding sample x, and y is the target value corresponding to the actual time to the detected event (e.g. recurrence) for non-censored data and the last known time of observation for censored data.

and $\varepsilon_n^* \le \varepsilon_n$ and $C_n^* \ge C_n$.

In the above description, the W and b are obtained by solving an optimization problem, the general form of which is:

$$\min_{W,b} \frac{1}{2} W^T W$$

$$\text{s.t.} \quad y_i - (W^T \phi(x_i) + b) \le \varepsilon$$

$$(W^T \phi(x_i) + b) - y_i \le \varepsilon$$

This equation, however, assumes the convex optimization problem is always feasible, which may not be the case. Furthermore, it is desired to allow for small errors in the regression estimation. It is for these reasons that a loss function is used for SVRc. The loss allows some leeway for the regression estimation. Ideally, the model built will exactly compute all results accurately, which is infeasible. The loss function allows for a range of error from the ideal, with this range being controlled by slack variables $\xi$ and $\xi^*$, and a penalty C. Errors that deviate from the ideal, but are within the range defined by $\xi$ and $\xi^*$, are counted, but their contribution is mitigated by C. The more erroneous the instance, the greater the penalty. The less erroneous (closer to the ideal) the instance is, the less the penalty. This concept of increasing penalty with error results in a slope, and C controls this slope. While various loss functions may be used, for an epsilon-insensitive loss function, the general equation transforms into:

$$\min_{W,b} \quad P = \frac{1}{2} W^T W + C \sum_{i=1}^{l} (\xi_i + \xi_i^*)$$

$$\text{s.t.} \quad y_i - (W^T \Phi(x_i) + b) \leq \varepsilon + \xi_i$$

$$(W^T \Phi(x_i) + b) - y_i \leq \varepsilon + \xi_i^*$$

$$\xi_i, \xi_i^* \geq 0, \quad i = 1 \ldots l$$

For an epsilon-insensitive loss function in accordance with the invention (with different loss functions applied to censored and uncensored data), this equation becomes:

$$\min_{W,b} \quad P_c = \frac{1}{2} W^T W + \sum_{i=1}^{l} (C_i \xi_i + C_i^* \xi_i^*)$$

$$\text{s.t.} \quad y_i - (W^T \Phi(x_i) + b) \leq \varepsilon_i + \xi_i$$

$$(W^T \Phi(x_i) + b) - y_i \leq \varepsilon_i^* + \xi_i^*$$

$$\xi_i^{(*)} \geq 0, \quad i = 1 \ldots l$$

$$\text{where} \quad C_i^{(*)} = s_i C_s^{(*)} + (1 - s_i) C_n^{(*)}$$

$$\varepsilon_i^{(*)} = s_i \varepsilon_s^{(*)} + (1 - s_i) \varepsilon_n^{(*)}$$

The optimization criterion penalizes data points whose y-values differ from $f(x)$ by more than $\in$. The slack variables, $\xi$ and $\xi^*$, correspond to the size of this excess deviation for positive and negative deviations respectively. This penalty mechanism has two components, one for uncensored data (i.e., not right-censored) and one for censored data. Here, both components are represented in the form of loss functions that are referred to as $\in$-insensitive loss functions.

In another embodiment, analytical tool 132 may include a neural network. In such an embodiment, tool 132 preferably includes a neural network that is capable of utilizing censored data. Additionally, the neural network preferably uses an objective function substantially in accordance with an approximation (e.g., derivative) of the concordance index (CI) to train an associated model (NNci). Though the CI has long been used as a performance indicator for survival analysis [12], the use of the CI to train a neural network was proposed in commonly-owned U.S. Pat. No. 7,321,881, issued Jan. 22, 2008, which is hereby incorporated by reference herein in its entirety. The difficulty of using the $C_1$ as a training objective function in the past is that the CI is non-differentiable and cannot be optimized by gradient-based methods. As described in above-incorporated U.S. Pat. No. 7,321,881, this obstacle may be overcome by using an approximation of the CI as the objective function.

For example, when analytical tool 132 includes a neural network that is used to predict prostate cancer progression, the neural network may process input data for a cohort of patients whose outcomes with respect to prostate cancer progression are at least partially known in order to produce an output. The particular features selected for input to the neural network may be selected through the use of the above-described SVRc (e.g., implemented with analytical tool 132) or any other suitable feature selection process. An error module of tool 132 may determine an error between the output and a desired output corresponding to the input data (e.g., the difference between a predicted outcome and the known outcome for a patient). Analytical tool 132 may then use an objective function substantially in accordance with an approximation of the CI to rate the performance of the neural network. Analytical tool 132 may adapt the weighted connections (e.g., relative importance of features) of the neural network based upon the results of the objective function.

The concordance index may be expressed in the form:

$$CI = \frac{\sum_{(i,j) \in \Omega} I(\hat{t}_i, \hat{t}_j)}{|\Omega|}$$

where $$I(\hat{t}_i, \hat{t}_j) = \begin{cases} 1: \hat{t}_i > \hat{t}_j \\ 0: \text{otherwise} \end{cases},$$

and may be based on pair-wise comparisons between the prognostic estimates $\hat{t}_i$ and $\hat{t}_j$ for patients i and j, respectively. In this example, $\Omega$ consists of all the pairs of patients $\{i,j\}$ who meet the following conditions:

both patients i and j experienced recurrence, and the recurrence time $t_i$ of patient i is shorter than patient j's recurrence time $t_j$; or only patient i experienced recurrence and $t_i$ is shorter than patient j's follow-up visit time $t_j$.

The numerator of the CI represents the number of times that the patient predicted to recur earlier by the neural network actually does recur earlier. The denominator is the total number of pairs of patients who meet the predetermined conditions.

Generally, when the CI is increased, preferably maximized, the model is more accurate. Thus, by preferably substantially maximizing the CI, or an approximation of the CI, the performance of a model is improved. In accordance with some embodiments of the present invention, an approximation of the CI is provided as follows:

$$C = \frac{\sum_{(i,j) \in \Omega} R(\hat{t}_i, \hat{t}_j)}{|\Omega|}$$

where $$R(\hat{t}_i, \hat{t}_j) = \begin{cases} (-(\hat{t}_i - \hat{t}_j - \gamma))^n : \hat{t}_i - \hat{t}_j < \gamma \\ 0: \text{otherwise} \end{cases},$$

and where $0<\gamma\leq1$ and $n>1$. $R(\hat{t}_i,\hat{t}_j)$ can be regarded as an approximation to $I(-\hat{t}_i,-\hat{t}_j)$.

Another approximation of the CI provided in accordance with some embodiments of the present invention which has been shown empirically to achieve improved results is the following:

$$C_\omega = \frac{\sum_{(i,j)\in\Omega} -(\hat{t}_i - \hat{t}_j)\cdot R(\hat{t}_i,\hat{t}_j)}{D},$$

where $$D = \sum_{(i,j)\in\Omega} -(\hat{t}_i - \hat{t}_j)$$

is a normalization factor. Here each $R(\hat{t}_i,\hat{t}_j)$ is weighted by the difference between $\hat{t}_i$ and $\hat{t}_j$. The process of minimizing the $C_\omega$ (or C) seeks to move each pair of samples in $\Omega$ to satisfy $\hat{t}_i - \hat{t}_j > \gamma$ and thus to make $I(\hat{t}_i,\hat{t}_j)=1$.

When the difference between the outputs of a pair in $\Omega$ is larger than the margin $\gamma$, this pair of samples will stop contributing to the objective function. This mechanism effectively overcomes over-fitting of the data during training of the model and makes the optimization preferably focus on only moving more pairs of samples in $\Omega$ to satisfy $\hat{t}_i - \hat{t}_j > \gamma$. The influence of the training samples is adaptively adjusted according to the pair-wise comparisons during training. Note that the positive margin $\gamma$ in R is preferable for improved generalization performance. In other words, the parameters of the neural network are adjusted during training by calculating the CI after all the patient data has been entered. The neural network then adjusts the parameters with the goal of minimizing the objective function and thus maximizing the CI. As used above, over-fitting generally refers to the complexity of the neural network. Specifically, if the network is too complex, the network will react to "noisy" data. Overfitting is risky in that it can easily lead to predictions that are far beyond the range of the training data.

Morphometric Data Obtained from H&E-Stained Tissue

As described above, an image processing tool (e.g., image processing tool 136) in accordance with some embodiments of the present invention may be provided that generates digitized images of tissue specimens (e.g., H&E-stained tissue specimens) and/or measures morphometric features from the tissue images or specimens. For example, in some embodiments, the image processing tool may include a light microscope that captures tissue images at 20× magnification using a SPOT Insight QE Color Digital Camera (KAI2000) and produces images with 1600×1200 pixels. The images may be stored as images with 24 bits per pixel in Tiff format. Such equipment is only illustrative and any other suitable image capturing equipment may be used without departing from the scope of the present invention.

In some embodiments, the image processing tool may include any suitable hardware, software, or combination thereof for segmenting and classifying objects in the captured images, and then measuring morphometric features of the objects. For example, such segmentation of tissue images may be utilized in order to classify pathological objects in the images (e.g., classifying objects as cytoplasm, lumen, nuclei, epithelial nuclei, stroma, background, artifacts, red blood cells, glands, other object(s) or any combination thereof). In one embodiment, the image processing tool may include the commercially-available Definiens Cellenger Developer Studio (e.g., v. 4.0) adapted to perform the segmenting and classifying of, for example, some or all of the various pathological objects described above and to measure various morphometric features of these objects. Additional details regarding the Definiens Cellenger product are described in [13].

For example, in some embodiments of the present invention, the image processing tool may classify objects as background if the objects correspond to portions of the digital image that are not occupied by tissue. Objects classified as cytoplasm may be the cytoplasm of a cell, which may be an amorphous area (e.g., pink area that surrounds an epithelial nucleus in an image of, for example, H&E stained tissue). Objects classified as epithelial nuclei may be the nuclei present within epithelial cells/luminal and basal cells of the glandular unit, which may appear as round objects surrounded by cytoplasm. Objects classified as lumen may be the central glandular space where secretions are deposited by epithelial cells, which may appear as enclosed white areas surrounded by epithelial cells. Occasionally, the lumen can be filled by prostatic fluid (which typically appears pink in H&E stained tissue) or other "debris" (e.g., macrophages, dead cells, etc.). Together the lumen and the epithelial cytoplasm and nuclei may be classified as a gland unit. Objects classified as stroma may be the connective tissue with different densities that maintains the architecture of the prostatic tissue. Such stroma tissue may be present between the gland units, and may appear as red to pink in H&E stained tissue. Objects classified as stroma nuclei may be elongated cells with no or minimal amounts of cytoplasm (fibroblasts). This category may also include endothelial cells and inflammatory cells, and epithelial nuclei may also be found scattered within the stroma if cancer is present. Objects classified as red blood cells may be small red round objects usually located within the vessels (arteries or veins), but can also be found dispersed throughout tissue.

In some embodiments, the image processing tool may measure various morphometric features of from basic relevant objects such as epithelial nuclei, epithelial cytoplasm, stroma, and lumen (including mathematical descriptors such as standard deviations, medians, and means of objects), spectral-based characteristics (e.g., red, green, blue (RGB) channel characteristics such as mean values, standard deviations, etc.), texture, wavelet transform, fractal code and/or dimension features, other features representative of structure, position, size, perimeter, shape (e.g., asymmetry, compactness, elliptic fit, etc.), spatial and intensity relationships to neighboring objects (e.g., contrast), and/or data extracted from one or more complex objects generated using said basic relevant objects as building blocks with rules defining acceptable neighbor relations (e.g., 'gland unit' features). In some embodiments, the image processing tool may measure these features for every instance of every identified pathological object in the image, or a subset of such instances. The image processing tool may output these features for, for example, evaluation by predictive model 102 (FIG. 1A), test kit 122 (FIG. 1B), or analytical tool 132 (FIG. 1C). Optionally, the image processing tool may also output an overall statistical summary for the image summarizing each of the measured features.

Figure 3:
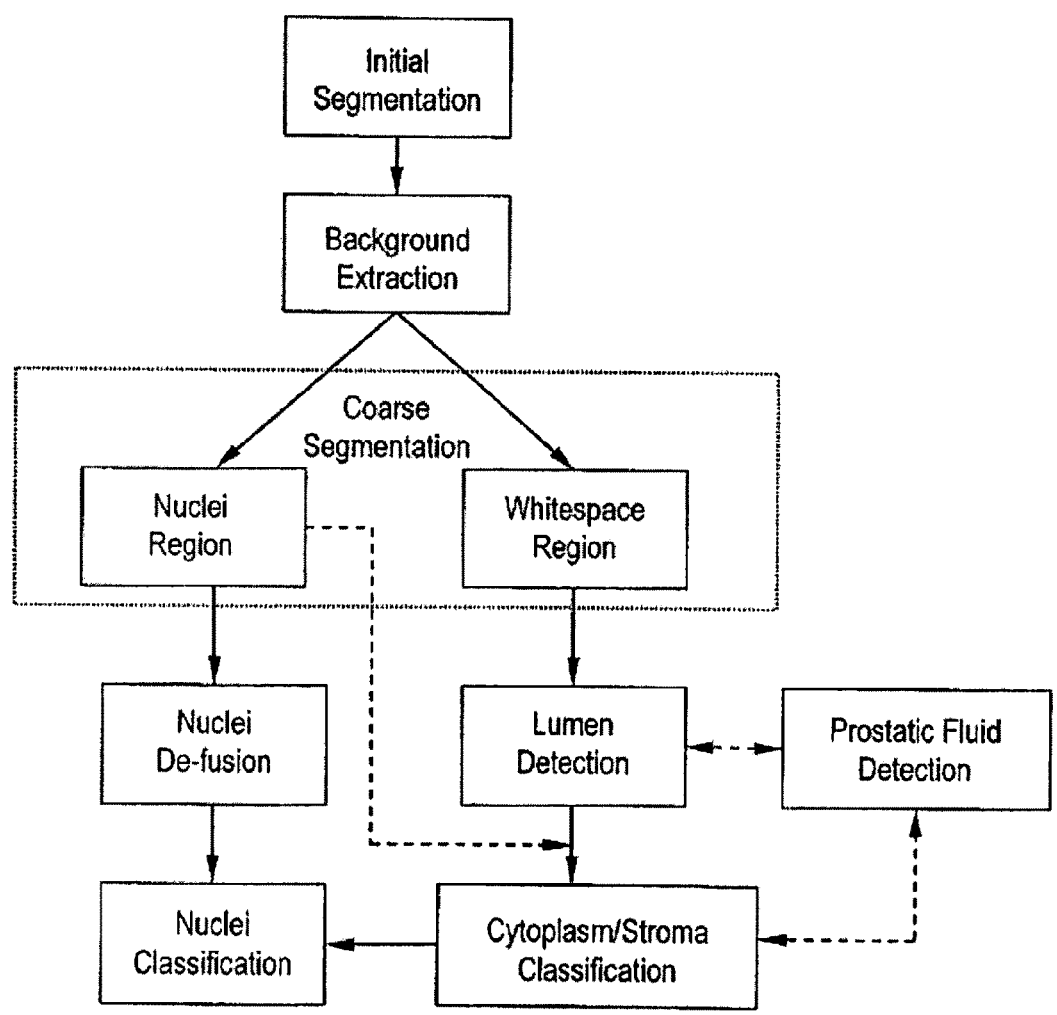
FIG. 3 is a flowchart of illustrative stages involved in image segmentation and object classification in, for example, digitized images of H&E-stained tissue according to some embodiments of the present invention.

FIG. 3 is a flowchart of illustrative stages involved in image segmentation and object classification (e.g., in digitized images of H&E-stained tissue) according to some embodiments of the present invention.

Initial Segmentation. In a first stage, the image processing tool may segment an image (e.g., an H&E-stained needle biopsy tissue specimen, an H&E stained tissue microarray (TMA) image or an H&E of a whole tissue section) into small groups of contiguous pixels known as objects. These objects may be obtained by a region-growing method which finds contiguous regions based on color similarity and shape regularity. The size of the objects can be varied by adjusting a few parameters [14]. In this system, an object rather than a pixel is typically the smallest unit of processing. Thus, some or all of the morphometric feature calculations and operations may be performed with respect to objects. For example, when a threshold is applied to the image, the feature values of the object are subject to the threshold. As a result, all the pixels within an object are assigned to the same class. In one embodiment, the size of objects may be controlled to be 10-20 pixels at the finest level. Based on this level, subsequent higher and coarser levels are built by forming larger objects from the smaller ones in the lower level.

Background Extraction. Subsequent to initial segmentation, the image processing tool may segment the image tissue core from the background (transparent region of the slide) using intensity threshold and convex hull. The intensity threshold is an intensity value that separates image pixels in two classes: "tissue core" and "background." Any pixel with an intensity value greater than or equal to the threshold is classified as a "tissue core" pixel, otherwise the pixel is classified as a "background" pixel. The convex hull of a geometric object is the smallest convex set (polygon) containing that object. A set S is convex if, whenever two points P and Q are inside S, then the whole line segment PQ is also in S.

Coarse Segmentation. In a next stage, the image processing tool may re-segment the foreground (e.g., TMA core) into rough regions corresponding to nuclei and white spaces. For example, the main characterizing feature of nuclei in H&E stained images is that they are stained blue compared to the rest of the pathological objects. Therefore, the difference in the red and blue channels (R−B) intensity values may be used as a distinguishing feature. Particularly, for every image object obtained in the initial segmentation step, the difference between average red and blue pixel intensity values may be determined. The length/width ratio may also be used to determine whether an object should be classified as nuclei area. For example, objects which fall below a (R−B) feature threshold and below a length/width threshold may be classified as nuclei area. Similarly, a green channel threshold can be used to classify objects in the tissue core as white spaces. Tissue stroma is dominated by the color red. The intensity difference d, "red ratio" $r=R/(R+G+B)$ and the red channel standard deviation $\sigma_R$ of image objects may be used to classify stroma objects.

White Space Classification. In the stage of coarse segmentation, the white space regions may correspond to both lumen (pathological object) and artifacts (broken tissue areas) in the image. The smaller white space objects (area less than 100 pixels) are usually artifacts. Thus, the image processing tool may apply an area filter to classify them as artifacts.

Nuclei De-fusion and Classification. In the stage of coarse segmentation, the nuclei area is often obtained as contiguous fused regions that encompass several real nuclei. Moreover, the nuclei region might also include surrounding misclassified cytoplasm. Thus, these fused nuclei areas may need to be de-fused in order to obtain individual nuclei.

The image processing tool may use two different approaches to de-fuse the nuclei. The first approach may be based on a region growing method that fuses the image objects constituting nuclei area under shape constraints (roundness). This approach has been determined to work well when the fusion is not severe.

In the case of severe fusion, the image processing tool may use a different approach based on supervised learning. This approach involves manual labeling of the nuclei areas by an expert (pathologist). The features of image objects belonging to the labeled nuclei may be used to design statistical classifiers.

In some embodiments, the input image may include different kinds of nuclei: epithelial nuclei, fibroblasts, basal nuclei, endothelial nuclei, apoptotic nuclei and red blood cells. Since the number of epithelial nuclei is typically regarded as an important feature in grading the extent of the tumor, it may be important to distinguish the epithelial nuclei from the others. The image processing tool may accomplish this by classifying the detected nuclei into two classes: epithelial nuclei and "the rest" based on shape (eccentricity) and size (area) features.

In one embodiment, in order to reduce the number of feature space dimensions, feature selection may be performed on the training set using two different classifiers: the Bayesian classifier and the k nearest neighbor classifier [12]. The leave-one-out method [13] may be used for cross-validation, and the sequential forward search method may be used to choose the best features. Finally, two Bayesian classifiers may be designed with number of features equal to 1 and 5, respectively. The class-conditional distributions may be assumed to be Gaussian with diagonal covariance matrices.

The image segmentation and object classification procedure described above in connection with FIG. 3 is only illustrative and any other suitable method or approach may be used to measure morphometric features of interest in tissue specimens or images in accordance with the present invention. For example, in some embodiments, a digital masking tool (e.g., Adobe Photoshop 7.0) may be used to mask portion(s) of the tissue image such that only infiltrating tumor is included in the segmentation, classification, and/or subsequent morphometric analysis. Alternatively or additionally, in some embodiments, lumens in the tissue images are manually identified and digitally masked (outlined) by a pathologist in an effort to minimize the effect of luminal content (e.g., crystals, mucin, and secretory concretions) on lumen object segmentation. Additionally, these outlined lumens can serve as an anchor for automated segmentation of other cellular and tissue components, for example, in the manner described below.

In some embodiments of the present invention, the segmentation and classification procedure identifies gland unit objects in a tissue image, where each gland unit object includes lumen, epithelial nuclei, and epithelial cytoplasm. The gland unit objects are identified by uniform and symmetric growth around lumens as seeds. Growth proceeds around these objects through spectrally uniform segmented epithelial cells until stroma cells, retraction artifacts, tissue boundaries, or other gland unit objects are encountered. These define the borders of the glands, where the accuracy of the border is determined by the accuracy of differentiating the cytoplasm from the remaining tissue. In this example, without addition of stop conditions, uncontrolled growth of connected glands may occur. Thus, in some embodiments, firstly the small lumens (e.g., very much smaller than the area of an average nucleus) are ignored as gland seeds. Secondly, the controlled region-growing method continues as long as the area of each successive growth ring is larger than the preceding ring. Segments of non-epithelial tissue are excluded from these ring area measurements and therefore effectively dampen and halt growth of asymmetric glands. The epithelial cells (including epithelial nuclei plus cytoplasm) thus not captured by the gland are classified as outside of, or poorly associated with, the gland unit. In this manner, epithelial cells (including epithelial nuclei plus cytoplasm) outside of the gland units are also identified.

In some embodiments, an image processing tool may be provided that classifies and clusters objects in tissue, which utilizes biologically defined constraints and high certainty seeds for object classification. In some embodiments, such a tool may rely less on color-based features than prior classification approaches. For example, a more structured approach starts with high certainty lumen seeds (e.g., based on expert outlined lumens) and using them as anchors, and distinctly colored object segmented objects. The distinction of lumens from other transparent objects, such as tissue tears, retraction artifacts, blood vessels and staining defects, provides solid anchors and object neighbor information to the color-based classification seeds. The probability distributions of the new seed object features, along with nearest neighbor and other clustering techniques, are used to further classify the remaining objects. Biological information regarding of the cell organelles (e.g., their dimensions, shape and location with respect to other organelles) constrains the growth of the classified objects. Due to tissue-to-tissue irregularities and feature outliers, multiple passes of the above approach may be used to label all the segments. The results are fed back to the process as new seeds, and the process is iteratively repeated until all objects are classified. In some embodiments, since at 20× magnification the nuclei and sub-nuclei objects may be too coarsely resolved to accurately measure morphologic features, measurements of nuclei shape, size and nuclei sub-structures (chromatin texture, and nucleoli) may be measured at 40× magnification (see e.g., Table 1). To reduce the effect of segmentation errors, the 40× measurements may differentiate the feature properties of well defined nuclei (based on strongly defined boundaries of elliptic and circular shape) from other poorly differentiated nuclei.

Figure 4A:
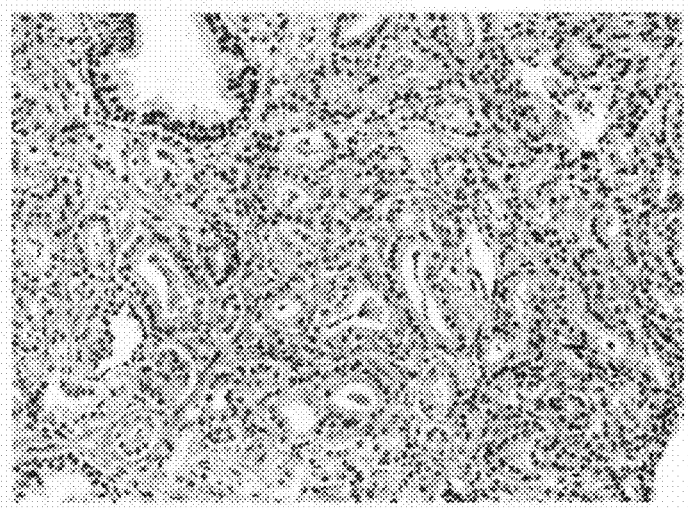
FIG. 4A is an image of prostate tissue obtained via a needle biopsy and subject to staining with hematoxylin and eosin (H&E) according to some embodiments of the present invention.
Figure 4B:
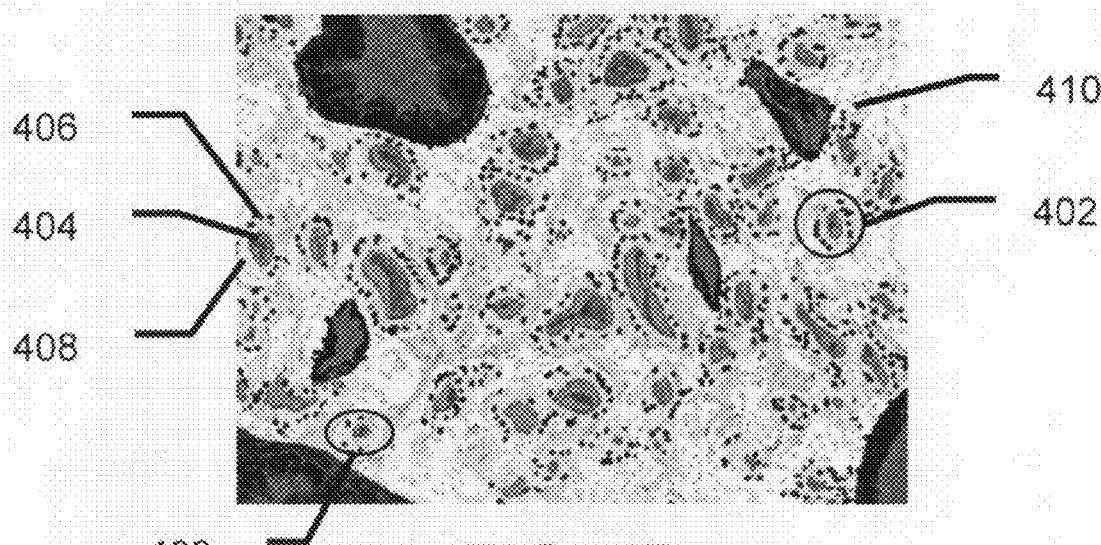
FIG. 4B is a segmented and classified version of the image in FIG. 4A according to some embodiments of the present invention, in which gland unit objects are formed from seed lumen, epithelial nuclei, and epithelial cytoplasm, and in which isolated/non-gland-associated tumor epithelial cells are also identified in the image.

FIG. 4A is an image of typical H&E-stained prostate tissue obtained via a needle biopsy. FIG. 4B is a segmented and classified version of the image in FIG. 4A according to some embodiments of the present invention, showing gland units 402 formed from seed lumen 404, epithelial nuclei 406, and epithelial cytoplasm 408. Also segmented and classified in the processed image are isolated/non-gland-associated tumor epithelial cells 410, which include epithelial nuclei and epithelial cytoplasm. Although in the original image the seed lumen 404, epithelial nuclei 406, and epithelial cytoplasm 408 of the gland units are red, dark blue, and light blue, respectively, and the epithelial nuclei and epithelial cytoplasm of the isolated/non-gland-associated tumor epithelial cells are green and clear, respectively, the image is provided in gray-scale in FIG. 4B for ease of reproducibility. Black/gray areas represent benign elements and tissue artifacts which have been digitally removed by the pathologist reviewing the case.

Illustrative computer-generated morphometric features measurable from, for example, digitized images of H&E-stained tissue, are listed in Table 5. As described in greater detail below, all of the features listed in Table 5 were found to be correlated with prostate cancer progression in univariate analysis. Each feature denoted "IF/H&E" is a combined feature formed by mathematically combining one or more features measured from image(s) of H&E-stained tissue with one or more features measured from image(s) of tissue subject to multiplex immunofluorescence (IF).

TABLE 5

H&E Morphometric Features

| Feature Name | Feature Domain | Description |
| --- | --- | --- |
| HE02_Lum_Are_Median | H&E | Median area of lumens |
| orig_approximation_4 | H&E | Variance of pixel values in the approximation sub-band after applying 4 stages of undecimated wavelet transform to a mask of glands |
| orig_diag_detail_6 | H&E | Variance of pixel values in the diagonal detail sub-band after applying 6 stages of undecimated wavelet transform to a mask of glands |
| HEx2_nta_Lum_Are_Tot | H&E | Relative area of lumens to total total tumor area outlined or otherwise identified |
| HEx2_EpiNucAre2LumMeanAre | H&E | Ratio of the total epithelial nuclear area to the average size of lumens |
| HEx2_nrm_ENWinGU_Are_Tot | H&E | Relative area of epithelial nuclei that are inside (within) gland units |
| HEx2_nrm_ENOutGU_Are_Tot | H&E | Relative area of epithelial nuclei that are outside of gland units |
| HEx2_nrm_CytWinGU_Are_Tot | H&E | Relative area of epithelial cytoplasm inside (within) gland units |
| HEx2_nrm_CytOutGU_Are_Tot | H&E | Relative area of epithelial cytoplasm outside of gland units |
| HEx2_RelArea_EpiNuc_Out2WinGU | H&E | Ratio of the area of epithelial nuclei outside of gland units to the area of epithelial nuclei inside gland units |
| HEx2_RelArea_Cyt_Out2WinGU | H&E | Ratio of the area of epithelial cytoplasm outside of gland units to the area of epithelial cytoplasm within (inside) gland units |
| HEx2_RelArea_ENCyt_Out2WinGU | H&E | Ratio of the area of epithelial cells (nuclei + cytoplasm) outside of gland units to the area of epithelial cells (nuclei + cytoplasm) inside of gland units |

TABLE 5-continued

H&E Morphometric Features

| Feature Name | Feature Domain | Description |
| --- | --- | --- |
| HEx2_ntaENCYtOutGU2Tumor | H&E | Area of epithelial cells (nuclei plus cytoplasm) not associated with lumens normalized to the total tumor area |
| HEx2_nrmLUM_ENOutGU_Are_Tot | H&E | Relative area of epithelial nuclei outside of gland units to the total area of lumens |
| HEx2_nrmLUM_CytWinGU_Are_Tot | H&E | Relative area of epithelial cytoplasm within gland units to the total lumen area |
| HEx2_nrmLUM_CytOutGU_Are_Tot | H&E | Relative area of epithelial cytoplasm outside of gland units to the total lumen area |
| HEx2_nrmLUM_EpiNucCytOutGU | H&E | Relative area of epithelial cells (nuclei + cytoplasm) to the total area of lumens |
| HEx2_nrm_ENCytWinGULum_Are_Tot | H&E | Ratio of the area of epithelial cells (nuclei + cytoplasm) within gland units and the total area of lumens to the tumor area |
| HEx2_RelArea_ENCytLum_Out2WinGU | H&E | Relative area of epithelial cells (nuclei + cytoplasm) outside of gland units to the glandular area, calculated as the sum of epithelial cell (nuclei + cytoplasm) area within gland units and the total area of lumens |
| HEx2_RelArea_EpiNucCyt_Lum | H&E | Ratio of the area of epithelial cells (nuclei + cytoplasm) to the area of lumens |
| HEx2_ntaLumContentArea | H&E | Relative area of luminal content, i.e., non-whitespace constrained within the luminal mask |
| HEx2_nrmEpiNucBand5minus3 | H&E | Measures the areas of epithelial nuclei distributed away from gland units. Calculated by measuring the areas of epithelial nuclei with centers that are in a band a certain distance away from lumen borders. The band includes all epithelial nuclei that are at least three units away from the lumen border but within 5 units of the lumen border; a unit is a fixed number set to be approximately the diameter of one epithelial nucleus. |
| min_orig_L_detail5 | H&E | Minimum of the variances of pixel values in the horizontal and vertical detail sub-bands after applying 5 stages of undecimated wavelet transform to a mask of lumens |
| RelAreaKi67post_2Lumen | IF/H&E | Ratio of the relative area of Ki67 positive epithelial nuclei in IF images to the relative area of lumens in H&E images |
| RelAreapAKTpos_2Lumen | IF/H&E | Ratio of the relative area of pAKT positive epithelial nuclei in IF images to the relative area of lumens in H&E images |
| RelAreaIFM2EpiNuc_2Lumen | IF/H&E | Ratio of the relative area of epithelial nuclei in IF images to the relative area of lumens in H&E images |
| RelAreARpAMACRp2Lumen | IF/H&E | Ratio of the relative area of AR positive and AMACR positive epithelial nuclei in IF images to the relative area of lumens in H&E images |

It will be understood that the computer-generated morphometric features listed in Table 5 are only illustrative and that any suitable computer-generated morphometric features may be utilized without departing from the scope of the present invention. For example, additional computer-generated morphometric features (e.g., morphometric features measurable from digitized images of H&E-stained tissue) which may be used in a predictive model for predicting an outcome with respect to a medical condition are listed in Table 1. It is believed that additional experimentation in the field of prostate cancer, its recurrence, progression, or other outcome with respect to prostate cancer, may provide additional insight regarding the types of features which may be more likely to correlate with outcome. The inventors expect that continued experimentation and/or the use of other suitable hardware, software, or combination thereof will yield various other sets of computer-generated features (e.g., a subset of the features in Tables 1 and 5) that may correlate with these and other medical conditions.

Additional details regarding image segmentation and measuring morphometric features of the classified pathological objects according to some embodiments of the present invention are described in above-incorporated U.S. Pat. No. 7,461,048, issued Dec. 2, 2008, U.S. Pat. No. 7,467,119, issued Dec. 16, 2008, and PCT Application No. PCT/US2008/004523, filed Apr. 7, 2008, as well as commonly-owned U.S. Publication No. 2006/0064248, published Mar. 23, 2006 and entitled "Systems and Methods for Automated Grading and Diagnosis of Tissue Images," and U.S. Pat. No. 7,483,554, issued Jan. 27, 2009 and entitled "Pathological Tissue Mapping," which are hereby incorporated by reference herein in their entireties.

Morphometric Data And/or Molecular Data Obtained from Multiplex IF

In some embodiments of the present invention, an image processing tool (e.g., image processing tool 136) is provided that generates digitized images of tissue specimens subject to immunofluorescence (IF) (e.g., multiplex IF) and/or measures morphometric and/or molecular features from the tissue images or specimens. In multiplex IF microscopy [15], multiple proteins in a tissue specimen are simultaneously labeled with different fluorescent dyes conjugated to antibodies specific for each particular protein. Each dye has a distinct emission spectrum and binds to its target protein within a tissue compartment such as nuclei or cytoplasm. Thus, the labeled tissue is imaged under an excitation light source using a multispectral camera attached to a microscope. The resulting multispectral image is then subjected to spectral unmixing to separate the overlapping spectra of the fluorescent labels. The unmixed multiplex IF images have multiple components, where each component represents the expression level of a protein in the tissue.

In some embodiments of the present invention, images of tissue subject to multiplex IF are acquired with a CRI Nuance spectral imaging system (CRI, Inc., 420-720 nm model) mounted on a Nikon 90i microscope equipped with a mercury light source (Nikon) and an Opti Quip 1600 LTS system. In some embodiments, DAPI nuclear counterstain is recorded at 480 nm wavelength using a bandpass DAPI filter (Chroma). Alexa 488 may be captured between 520 and 560 nm in 10 nm intervals using an FITC filter (Chroma). Alexa 555, 568 and 594 may be recorded between 570 and 670 nm in 10 nm intervals using a custom-made longpass filter (Chroma), while Alexa 647 may be recorded between 640 and 720 nm in 10 nm intervals using a second custom-made longpass filter (Chroma). Spectra of the pure dyes were recorded prior to the experiment by diluting each Alexa dye separately in SlowFade Antifade (Molecular Probes). In some embodiments, images are unmixed using the Nuance software Version 1.4.2, where the resulting images are saved as quantitative grayscale tiff images and submitted for analysis.

Figure 5A:
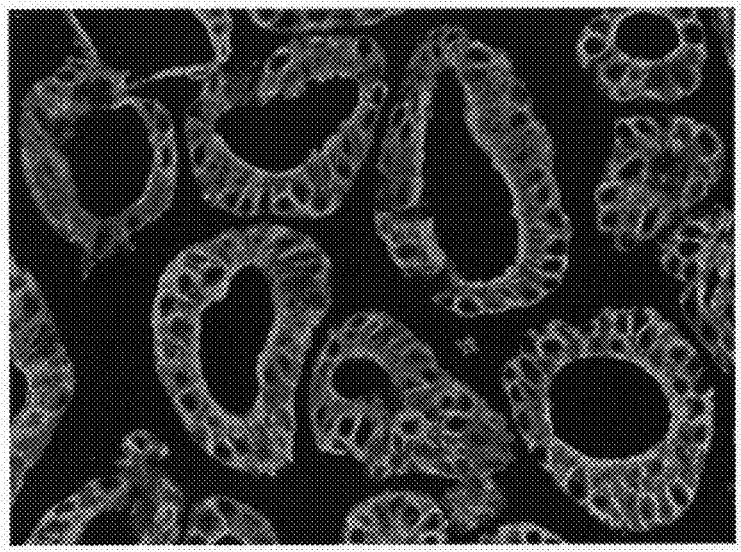
FIG. 5A is an image of tissue subject to multiplex immunofluorescence (IF) in accordance with some embodiments of the present invention.

For example, FIG. 5A shows a multiplex IF image of a tissue specimen labeled with the counterstain 4'-6-diamidino-2-phenylindole (DAPI) and the biomarker cytokeratin 18 (CK18), which bind to target proteins in nuclei and cytoplasm, respectively. Although the original image was a pseudo-color image generally exhibiting blue and green corresponding to DAPI and CK18, respectively, the image is provided in gray-scale in FIG. 5A for ease of reproducibility.

In some embodiments of the present invention, as an alternative to or in addition to the molecular features which are measured in digitized images of tissue subject to multiplex IF, one or more morphometric features may be measured in the IF images. IF morphometric features represent data extracted from basic relevant histologic objects and/or from graphical representations of binary images generated from, for example, a specific segmented view of an object class (e.g., a segmented epithelial nuclei view may be used to generate minimum spanning tree (MST) features as described below). Because of its highly specific identification of molecular components and consequent accurate delineation of tissue compartments—as compared to the stains used in light microscopy—multiplex IF microscopy offers the advantage of more reliable and accurate image segmentation. In some embodiments of the present invention, multiplex IF microscopy may replace light microscopy altogether. In other words, in some embodiments (e.g., depending on the medical condition under consideration), all morphometric and molecular features may be measured through IF image analysis thus eliminating the need for, for example, H&E staining (e.g., some or all of the features listed in tables 1 and 2 could be measured through IF image analysis).

In an immunofluorescence (IF) image, objects are defined by identifying an area of fluorescent staining above a threshold and then, where appropriate, applying shape parameters and neighborhood restrictions to refine specific object classes. In some embodiments, the relevant morphometric IF object classes include epithelial objects (objects positive for cytokeratin 18 (CK18)) and complementary epithelial nuclei (DAPI objects in spatial association with CK18). Specifically, for IF images, the process of deconstructing the image into its component parts is the result of expert thresholding (namely, assignment of the 'positive' signal vs. background) coupled with an iterative process employing machine learning techniques. The ratio of biomarker signal to background noise is determined through a process of intensity thresholding. For the purposes of accurate biomarker assignment and subsequent feature generation, supervised learning is used to model the intensity threshold for signal discrimination as a function of image background statistics. This process is utilized for the initial determination of accurate DAPI identification of nuclei and then subsequent accurate segmentation and classification of DAPI objects as discrete nuclei. A similar process is applied to capture and identify a maximal number of CK18+ epithelial cells, which is critical for associating and defining a marker with a specific cellular compartment. These approaches are then applied to the specific markers of interest, resulting in feature generation which reflects both intensity-based and area-based attributes of the relevant protein under study. Additional details regarding this approach, including sub-cellular compartment co-localization strategies, are described in above-incorporated PCT Application No. PCT/US2008/004523, filed Apr. 7, 2008.

Figure 5B:
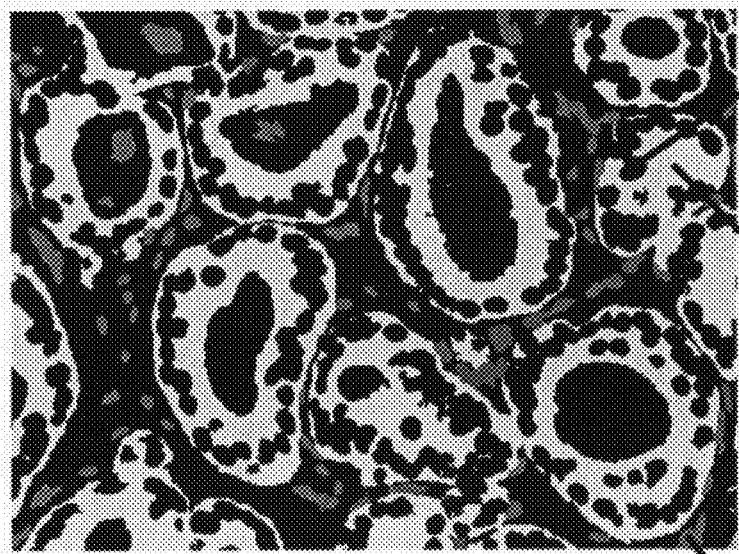
FIG. 5B shows a segmented and classified version of the image in FIG. 4A, in which the objects epithelial nuclei, cytoplasm, and stroma nuclei have been identified according to some embodiments of the present invention.
Figure 6:
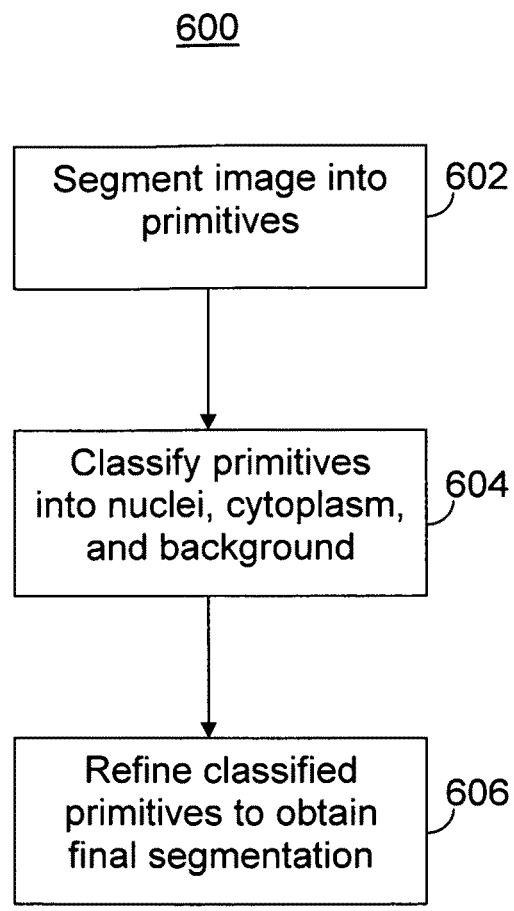
FIG. 6 is a flowchart of illustrative stages involved in image segmentation and object classification in images of tissue subject to multiplex immunofluorescence (IF) according to some embodiments of the present invention.

Multiplex IF Image Segmentation. In some embodiments of the present invention, the image processing tool performs multiplex IF image segmentation as follows. To enable feature extraction, epithelial nuclei (EN) and cytoplasm are segmented from IF images using the Definiens image analysis platform [16, 17]. FIG. 6 is a flowchart 600 of illustrative stages involved in segmenting and classifying multiplex IF images according to some embodiments of the present invention. The segmentation method performed by the image processing tool may consist of three stages of initial segmentation into primitives 602; classification of primitives into nuclei, cytoplasm, and background 604; and refinement of classified primitives to obtain the final segmentation 606. In some embodiments, the segmentation and feature extraction operations may be applied to regions of interest (ROI's) in the image. In some embodiments, these ROI's may be identified by a pathologist and may be free of non-tumor tissue and artifacts. In other embodiments, these regions may be identified automatically. FIG. 5B shows the image in FIG. 5A segmented into epithelial nuclei (EN) 502, cytoplasm 504, and stroma nuclei 506. Although in the original, segmented and classified image the segmented EN 502 are shown in blue, the segmented cytoplasm 504 are shown in green, and the segmented stroma nuclei 506 are shown in purple, the image is provided in gray-scale in FIG. 5B for ease of reproducibility.

Referring to FIG. 6, in a first stage of segmentation 602 image pixels are grouped into small primitive objects. This grouping is based on the similarity of intensity values and shape characteristics of the resulting objects. To obtain the initial primitives, the quad-tree procedure is first applied to the image. The resulting primitives are then grouped further using a multiresolution segmentation procedure [16]. The quad-tree procedure uses color similarity to group pixels, and the multiresolution method uses color similarity and shape regularity to form primitives. A scale parameter controls the average size of the primitives in both methods.

At stage 604, the primitives in the CK18 image are classified into cytoplasm and background prototype objects, where background consists of autofluorescence and non-specific binding of the fluorescent dye to the tissue. This is accomplished via intensity thresholding, wherein the average intensities of primitives are compared to thresholds computed from the intensity statistics of all primitives in the CK18 image. If the average intensity of a primitive is below a threshold $T_{low}$, it is classified as a background prototype object. If the average intensity of the primitive is above a threshold $T_{high}$, it is classified as a cytoplasm prototype object. Thresholds $T_{low}$ and $T_{high}$ are derived from a threshold T as $T_{low}=\alpha_{low}T$ and $T_{high}=\alpha_{high}T$. Threshold T is modeled as a linear function $T=A^TX+b$, where $A=[a_1, \ldots, a_n]^T$ and $X=[x_1, \ldots, x_n]^T$ are model parameters and intensity statistics of all image primitives, respectively, and b is a constant. Parameters {A, b} are obtained by fitting the model to a set of reference thresholds selected by two pathologists on a training image set. To avoid model overfitting, feature selection is performed on x and thus very few elements of $A^T$ are non-zero. Parameters $\alpha_{low}$ and $\alpha_{high}$ control the classification accuracy for the resulting class prototypes. In an illustrative example, conservative values $\alpha_{low}=0.33$ and $\alpha_{high}=1.5$ were used to obtain reliable class prototypes.

The class prototypes obtained using thresholding drive the classification of the rest of the primitives using the nearest neighbor (NN) classification rule. The NN rule classifies each primitive as being a cytoplasm or background object if the closest prototype object to it is a cytoplasm or background object, respectively. The metric for the NN rule is the Euclidean distance and objects are represented using the vector $[m\ s]^T$, where m and s denote the average and standard deviation of the intensity of the object.

At stage 606, the class labels of the cytoplasm and background objects are further refined using neighborhood analysis. Background objects smaller than, for example, 12 pixels in area whose border length with cytoplasm relative to their total border length is 0.6 or more are reclassified as cytoplasm.

Referring back to stage 604, in the first stage of EN segmentation nuclei prototype objects are identified via intensity thresholding. The intensity threshold model is constructed using a similar procedure to that described for classifying cytoplasm prototype objects. Next, background objects whose relative border length to nuclei is 0.66 or more are reclassified as nuclei prototype objects. Moreover, isolated background objects smaller than, for example, 50 pixels in area are reassigned as nuclei prototype objects.

To build individual nuclei, nuclei prototype objects are subjected to two stages of region growing, a multiresolution segmentation stage, and a final cleanup stage. Generally, region growing consists of using brighter prototype objects as seeds and merging the darker neighboring objects with the seeds to form individual nuclei. In the following example, the super-object for a given object is obtained by merging the object with all of its connected neighbors. In the first stage of region growing, prototype objects whose average brightness relative to the brightness of their super-object is 0.66 or more are identified as seeds. These objects are classified as nuclei if they meet certain shape criteria (e.g., width and length≤25 pixels, elliptic fit≥0.6, 35 pixels<area≤350 pixels), where elliptic fit [16] measures the similarity of the object to a perfect ellipse. Each identified nucleus is then grown by merging the darker neighboring objects with it. The above process is repeated on the remaining prototype objects using objects with a relative brightness of 0.9 or more as seeds. Following the above region growing stages, multi-resolution segmentation is applied to the remaining prototype objects to build more nuclei. In the cleanup stage, the remaining prototype objects are merged with the individual nuclei identified in previous stages if possible, or otherwise classified as background. Finally, nuclei whose area has an overlap of, for example, 50% or more with cytoplasm are classified as EN. Otherwise, they are classified as stroma nuclei.

In some embodiments of the present invention, morphometric features for evaluation or use within a predictive model are provided which are derived from (i) the minimum spanning tree (MST) connecting the epithelial nuclei (EN) in multiplex IF image(s) and/or (ii) the fractal dimension (FD) of gland boundaries in multiplex IF image(s). Such features have been determined by the present inventors to be effective for the quantification of tissue architecture and morphology. Fluorescent labels utilized in multiplex IF microscopy enable more reliable and accurate segmentation of tissue compartments over conventional stains used in light microscopy, thus allowing for more robust feature extraction. By way of example only, using univariate analysis and multivariate modeling, the efficacy and robustness of the MST and FD features were demonstrated in the large-scale, multi-institution study described below.

In some embodiments, two or more features (e.g., clinical, molecular, and/or morphometric features) may be combined in order to construct a combined feature for evaluation within a predictive model. For example, a morphometric feature such as, for example, a minimum spanning tree (MST) feature and/or a fractal dimension (FD) feature, may be combined with a clinical feature to form a combined feature. In one embodiment, a combined feature constructed using the mean edge length of the MST (a morphometric feature) and the patient's Gleason grade (a clinical feature) was selected in a multivariate model for the prediction of disease progression. Other suitable combinations of features are of course possible and are fully contemplated as being within the scope of embodiments of the present invention.

Additional examples of combined features are described below in connection with, for example, FIG. 9.

Minimum Spanning Tree (MST) Features. In some embodiments of the present invention, one or more morphometric features used in a predictive model may include or be based on characteristic(s) of a minimum spanning tree (MST) observed in digitized image(s) of tissue subject to multiplex immunofluorescence (IF). As described above, generally IF microscopy offers the advantage of more reliable and accurate image segmentation when compared to traditional light microscopy. For example, features characterizing tissue architecture may be extracted from the MST connecting the centroids of all epithelial nuclei (EN) in a tissue specimen. In some embodiments, after segmentation of an IF image into CK18-positive DAPI objects, this segmented image may be used to create a graph for the derivation of all MST features. The MST of a graph is defined as the tree connecting all vertices (here, EN centroids) such that the sum of the lengths of the lines (edges) connecting the vertices is minimized. Several methods exist for constructing the MST of a graph. In some embodiments of the present invention, Prim's method may be used [35]. In other embodiments of the present invention, other methods of constructing the MST may be utilized.

Figure 7:
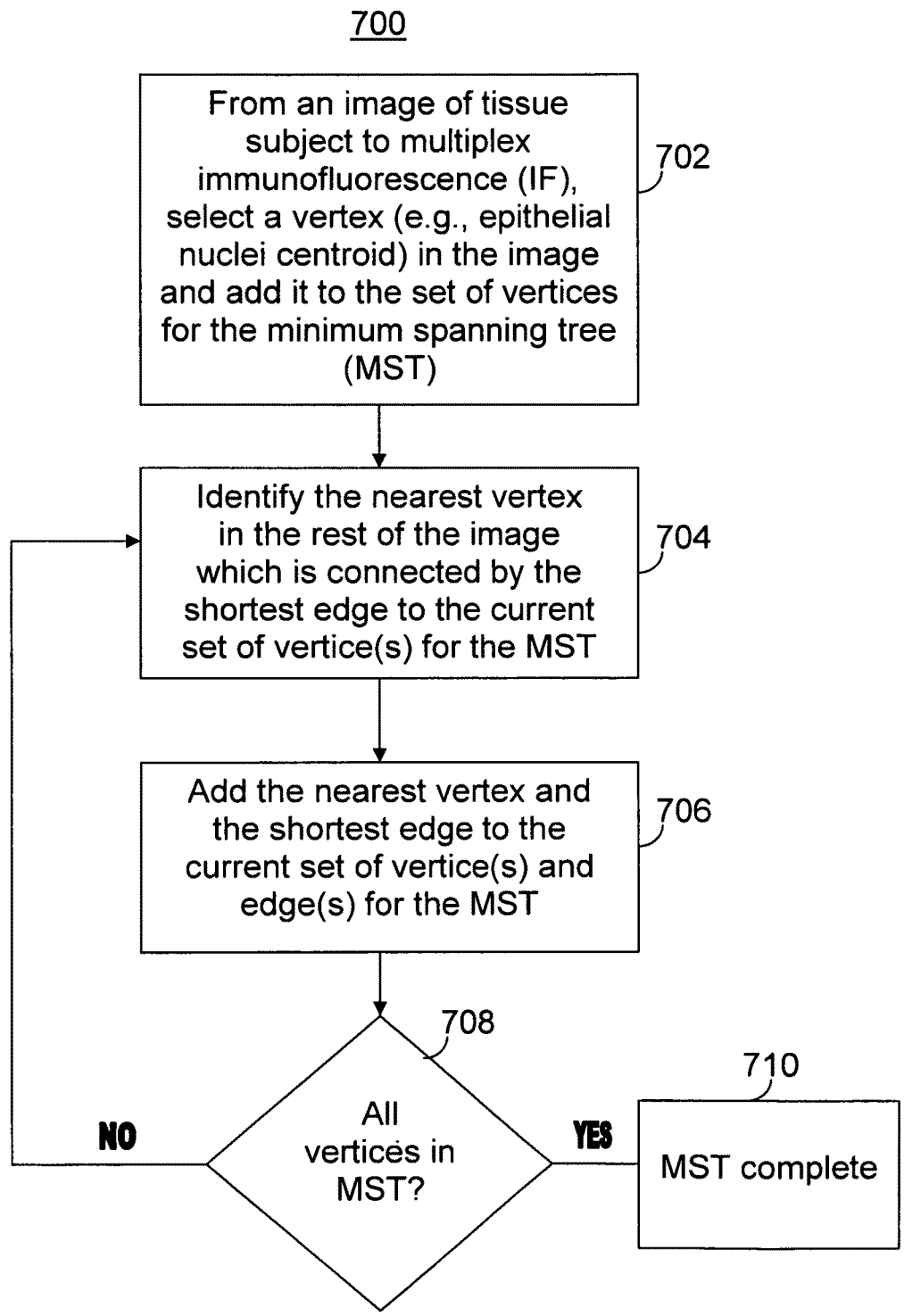
FIG. 7 is a flowchart of illustrative stages involved in constructing the minimum spanning tree (MST) of objects within an image of tissue subject to multiplex immunofluorescence (IF) according to some embodiments of the present invention.

FIG. 7 is a flowchart 700 of illustrative stages involved in constructing a minimum spanning tree (MST) of objects within a digitized image of tissue subject to multiplex immunofluorescence (IF) in accordance with some embodiments of the present invention. Let G={V, E} denote a graph with vertices V and edges E, and let $G_{MST}=\{V_{MST}, E_{MST}\}$ denote the MST of G. Such a procedure may be performed by an image processing tool (e.g., image processing tool 136) or any other suitable hardware, software, or combination thereof. The method starts at stage 702 by adding an arbitrary vertex v in V to $V_{MST}$, that is, $V_{MST}=\{v\}$. Then, at stage 704, the method determines the nearest vertex in the rest of the graph to the current $G_{MST}$. That is, the shortest edge e connecting the vertices u and v is found such that $u \in V_{MST}$ and $v \notin V_{MST}$. In some embodiments, the length of each edge is the Euclidean distance between the pair of vertices (e.g., EN centroids) that it connects. Then, at stage 706, $G_{MST}$ is updated by adding v to $V_{MST}$ and adding e to $E_{MST}$. The process of adding vertices is continued at stage 608 until all of them are included in $V_{MST}$. As indicated at stage 710, the MST is complete once all of the vertices in the graph have been included.

Figure 8A:
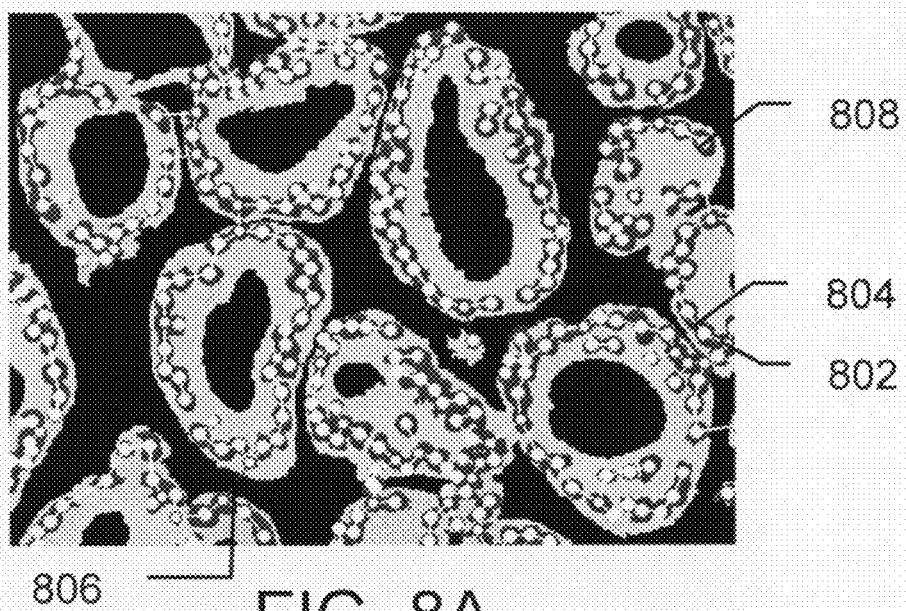
FIG. 8A is an image of tissue subject to multiplex immunofluorescence (IF) in which the minimum spanning tree (MST) of epithelial nuclei (EN) is identified in accordance with some embodiments of the present invention.

FIG. 8A shows an instance of the MST of epithelial nuclei (EN) identified in an image of tissue subject to multiplex immunofluorescence (IF) according to some embodiments of the present invention. As shown, the MST includes vertices (here, EN centroids) 802. The MST also includes intra-gland MST edges 804 and inter-gland edges 806. Although in the original, segmented and classified image the EN centroids 802 and intra-gland MST edges 804 are marked in yellow, the inter-gland edges 806 are marked in red, and the segmented EN and cytoplasm are marked in dark and light gray, respectively (with degree 1 and 3 EN outlined in green and red, respectively, as described below), the image is provided in gray-scale in FIG. 8A for ease of reproducibility. Other compartments in the image are masked out for clarity.

A number of characteristics of the MST of EN have been considered in the literature for cancer diagnosis and prognosis [19-23]; however, a fundamental limitation of the studies was that image analysis was performed on light microscopy images of tissue specimens stained using conventional stains such as hematoxylin and eosin (H&E). In an illustrative example according to some embodiments of the present invention, five MST characteristics from images of tissue subject to multiplex immunofluorescence (IF) were selected for potential use as features within a predictive model. Alternatively or additionally, in other embodiments of the present invention, other MST characteristics can be selected for evaluation or use within a model predictive of a medical condition. The five MST features selected were the mean and standard deviation of edge lengths, and the degree distribution for vertices with degrees 1, 2 and 3 (see FIG. 9). The degree of a vertex refers to the number of edges incident on the vertex. For example, the degree of vertex (EN centroid) 802 in FIG. 8A is 3. Vertex 808 in FIG. 8A has a degree of 1. Here, the degree distribution of an MST, d, is defined as $d_i = n_i/n_t$, where $n_i$ denotes the number of vertices with degree i, and n is the total number of vertices. In this example, the degree distribution up to degree 3 was considered as vertices with higher degrees were rare and thus estimates of their proportions were unreliable. In other embodiments of the present invention, degrees of 4 and higher can be selected as features for evaluation or use within a predictive model.

In the illustrative embodiment shown in FIG. 8A, the MST edges connect epithelial nuclei (EN) within glands (e.g., edge 704) as well as across glands (e.g., edge 706). The present inventors have determined that these intra- and inter-gland edges quantify different tissue characteristics. While the lengths of the intra-gland edges characterize the degree to which the EN are invading the stroma surrounding the gland, inter-gland edges measure the separation between glands, which, for a given Gleason grade, is in part due to the biochemical response of the stroma to cancer resulting in the formation of scar tissue. To decouple these two characteristics, the edges of the MST were classified as being intra- or inter-glandular, and the mean and standard deviation of the edge lengths were separately obtained for each of the two classes of edges. In this illustrative study, the degree distribution for vertices connecting inter-gland edges was uninformative and thus was not considered, although it could be considered in other embodiments. To classify MST edges, connected component analysis was performed on gland regions, where gland regions consisted of the union of EN and cytoplasm regions. Edges connecting EN belonging to the same connected component were classified as intra-glandular. The remaining edges were classified as being inter-glandular. The inter-glandular mean edge length was able to distinguish good and poor outcome patients. In addition, it was correlated with the outcome in the same direction as the MST mean edge length obtained from all EN.

In some embodiments, the MST approach as described above is a graph-based method that operates on a binary mask. For example, such an approach can be applied to binary masks from lumens identified (e.g., in H&E-stained images) or DAPI/CK18 objects in tissue images subject to immunofluorescence (IF). In other embodiments of the present invention, any other suitable graph-based approach(es) and/or mask(s) could be used in connection with measuring features of interest in tissue or image(s) thereof.

Figure 8B:
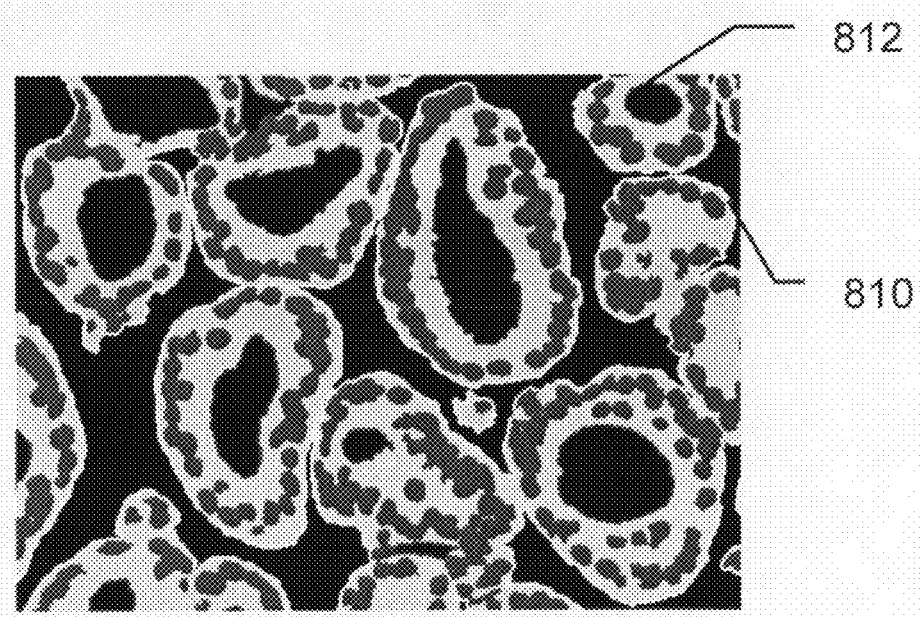
FIG. 8B is an image of tissue subject to multiplex immunofluorescence (IF) in which the boundaries of glands with stroma and the boundaries of glands with lumen are identified according to some embodiments of the present invention.

Fractal Dimension of Gland Boundaries. The present inventors have determined that the fractal dimension (FD) of the boundaries between the glands and the surrounding stroma provides a quantitative measure of the irregularity of the shape of the boundary. In general, the FD is a measure of the space-filling capacity of an object. The FD of a straight line is one, whereas the FD of a more irregular planar curve is between 1 and 2. Gland boundaries with lumen and stroma are defined as pixels that have at least one non-gland and one gland pixel among their 4-connected neighbors (FIG. 8B). As lumens and stroma can appear similar in multiplex IF images, morphological operations were used to distinguish them. Lumens were defined as pixels belonging to holes in the gland regions, namely, pixels that cannot be reached by flood-filling the non-gland region starting from pixels on the edge of the image. Two FD features were considered in an illustrative study: the FD of gland-stroma boundaries, and the FD of gland boundaries with both stroma and lumens (see FIG. 9). FIG. 8B shows boundaries of the glands with stroma 810 and boundaries of the glands with lumen 812 as identified in an image of tissue subject to multiplex immunofluorescence (IF) according to some embodiments of the present invention. Although in the image processed by the image processing tool the boundaries of the glands with stroma 810 and the boundaries of the glands with lumen 812 were shown in yellow and red, respectively, the image is provided in gray-scale in FIG. 8B for ease of reproducibility. The FD was estimated using the box-counting algorithm described below.

In box counting, grids of varying size are placed on the curve of interest and for each grid the grid cells occupied by the curve are counted. For each grid size, the grid is shifted to find the covering of the curve with the smallest number of occupied cells. Let the pair $(s, N_i)$, $i=1, \ldots, p$, denote the grid size and the corresponding cell count, respectively, where p is the number of pairs. The relationship between $\log(N)$ and $\log(s)$ is modeled as a linear function $\log(N)=a \log(s)+b$ via least squares, where a and b denote the slope and intercept of the line. The FD $f$ is then obtained as $f=-a$.

A practical consideration in the estimation of FD is the choice of the range of s. In the present study, due to the finite resolution of digital images, a small s tends to underestimate the FD. On the other hand, because of the finite extent of images, large s values result in few occupied grid cells, causing the FD estimate to have a large variance. Determination of the optimal s is also confounded by the fact that in some instances tumor boundaries may not exhibit fractal behavior at all or do so over a finite range of scales.

The range of s was selected based on the constraints imposed by the finite resolution and size of the images, as well as the predictive power of the resulting feature. Initially, the minimum and maximum box size was set to 2 and 64, respectively, where the choice of maximum size was made empirically to ensure that N was at least 50 for most images. Next, the box sizes were set to $s \in \{2, 3, 4, 6, 8, 12, 16, 24, 32, 48, 64\}$, roughly following a power law. Then, for each pair of consecutive box sizes (i.e., (2, 3), (3, 4), . . . , (48, 64)), the FD was estimated. The predictive power of the FD estimates was then assessed via univariate analysis as described below. The optimal range of s was selected as the range over which the predictive power of the FD remained statistically significant. The final FD feature was obtained based on this range of s.

Analysis of MST and FD Features in IF Images. Biopsy specimens of tissue were labeled with the DAPI counterstain and multiple biomarkers, including the CK18 biomarker, and were imaged using a CRI Nuance multispectral imaging system yielding 12-bit 1280×1024-pixel images. Multiple (typically three) regions of interest (ROI's) were imaged for each patient. Biomarker images obtained from spectral unmixing were segmented and the MST and FD features were extracted from the segmented images. Finally, feature values extracted from the patient's multiple ROI's were aggregated into a single value per feature by taking their median.

The predictive value of the proposed MST and FD features was first established via univariate analysis. This was accomplished by training a univariate Cox proportional hazards model [24] on each feature and testing the significance of the coefficient of the trained model using the Wald $\chi^2$ test. FIG. 8 shows the two-sided p-values and CI's of the minimum spanning tree (MST) and fractal dimension (FD) features on the training set, where the concordance index (CI) values range from 0 to 1. A CI of 0.5 indicates no relationship between the feature and outcome, whereas CI values below and above 0.5 correspond to negative and positive relationships with outcome, respectively. As the table indicates, except for $d_2$, a larger feature value corresponds to a shorter time to clinical failure (CF). Moreover, the present inventors have determined that both FD features and the MST degree distribution for degree 3 ($d_3$) were highly effective for predicting CF in terms of both $\chi^2$ test p-value and CI. It is noted that the two FD features had similar performance. It is believed that the same carcinogenesis process underlying the uninhibited proliferation of epithelial cells drives the irregularity of gland boundaries with both stroma and lumen, resulting in similar feature performance.

The intra-gland and overall mean edge length of the MST also had comparable predictive power. This is believed to be because both features are dominated by intra-gland edges whose number is far larger than that of inter-gland edges. On the other hand, the correlation between the inter-gland mean edge length and CF was not significant in this example. To evaluate whether the inter-gland feature would be useful when considered within a group of patients with similar Gleason grades, particularly Grade 3, the correlation within the grade 3 patient group was evaluated. This correlation was insignificant as well in this example. It is suspected that the relatively small number of inter-gland distances that drive the feature is insufficient for obtaining a stable feature. Thus, larger ROI's or a larger number of ROI's may be needed.

The present inventors have determined that MST degree distribution has an intuitive interpretation in terms of tumor architecture. As shown in FIG. 8A, degree 1 vertices typically occur when an epithelial nuclei (EN) is fairly isolated from other EN. This usually is the case for EN invading the surrounding stroma. Degree 2 vertices, on the other hand, typically correspond to EN regularly arranged within the gland. Finally, degree 3 (and higher degree) vertices usually belong to clusters of EN resulting from uninhibited proliferation. Thus, $d_1$ and $d_3$ are both expected to be negatively correlated with the time to clinical failure (CF), whereas the opposite is expected of $d_2$.

Combined Features. The present inventors noted that the fractal dimension (FD) features were the most effective for patients with Gleason grades 3 and lower (CI=0.395). This was the motivation for creating a combined feature. For Gleason grades 4 or higher, the combined feature was set to the Gleason grade. Otherwise, it was set to the FD feature linearly scaled to the range 0 to 3. The mean edge length of the MST and the degree distribution for degree 3 were also most effective for Gleason grades 3 and lower (CI=0.415 and 0.434, respectively). Thus, a combined feature was constructed for each of these two features by setting the combined feature to the Gleason grade for grades 4 and higher, and setting it to the MST feature scaled linearly to the range 0 to 3 for grades 3 and lower. The univariate CI's for these combined features are also shown in FIG. 9. In other embodiments in accordance with the present invention, any other suitable combined features may be utilized such as, for example, any combination of features listed in Tables 1-5 and 9 and FIG. 9 which is correlated with an outcome of interest (e.g., correlated with the outcome in univariate analysis).

Figure 10:
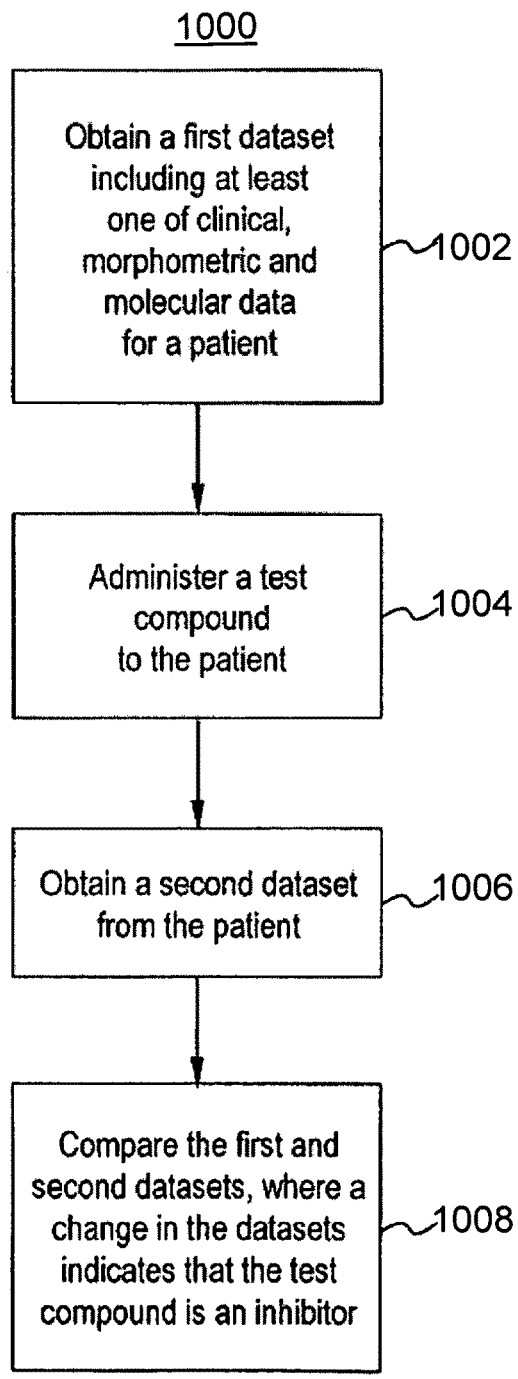
FIG. 10 is a flowchart of illustrative stages involved in screening for an inhibitor compound in accordance with an embodiment of the present invention.

In an aspect of the present invention, systems and methods are provided for screening for an inhibitor compound of a medical condition (e.g., disease). FIG. 10 is a flowchart of illustrative stages involved in screening for an inhibitor compound in accordance with an embodiment of the present invention. At stage 1002, a first dataset for a patient may be obtained that includes one or more of clinical data, morphometric data and molecular data (e.g., morphometric data and/or clinical data corresponding to one or more of the features listed in FIG. 9). A test compound may be administered to the patient at stage 1004. Following stage 1004, a second dataset may be obtained from the patient at stage 1006. The second dataset may or may not include the same data types (i.e., features) included in the first dataset. At stage 1008, the second dataset may be compared to the first dataset, where a change in the second dataset following administration of the test compound indicates that the test compound is an inhibitor compound. Stage 1008 of comparing the datasets may include, for example, comparing an output generated by a predictive model according to an embodiment of the present invention responsive to an input of the first dataset with an output generated by the predictive model responsive to an input of the second dataset, where the predictive model is predictive of the medical condition under consideration. For example, the inhibitor compound may be a given drug and the present invention may determine whether the drug is effective as a medical treatment for the medical condition.

Example: Prediction of Prostate Cancer Progression

In accordance with an illustrative embodiment of the present invention, a predictive model was developed for use on diagnostic biopsy cores of prostate tissue, where the model predicts the likelihood of advanced prostate cancer progression even after a curative-intent radical prostatectomy. This predictive model was developed from data on a multi-institutional patient cohort followed for a median of 8 years. Features evaluated in connection with generating the model included morphometric features extracted from the diagnostic prostate needle biopsy, molecular features corresponding to an expanded in-situ biomarker profile, and several clinical features. The predictive model may be utilized, for example, at the time of diagnosis of prostate cancer and before treatment, to provide an objective assessment of the patient's risk of prostate cancer progression. It is believed that the model resulting from this study, which accurately predicts outcome, will assist in identifying patients who, for example, may benefit from risk-adjusted therapies.

A prospectively designed method was applied retrospectively to a cohort of patients with clinically localized or locally advanced prostate cancer. The study subjects consisted of 1027 men treated with radical prostatectomy between 1989 and 2003 at 5 university hospitals. The model predictive of clinical progression (distant metastasis, androgen-independent recurrence, and/or prostate cancer mortality) was derived from features selected through supervised multivariate learning. Performance of the predictive model was measured by the concordance index.

A risk stratification model was developed using a training set of 686 patients with 87 clinical failure events. Generally, the predictive model includes androgen receptor and Ki67 levels, preoperative PSA, biopsy Gleason score, predominant Gleason grade, and 2 quantitative histomorphometric characteristics of the prostate tissue specimen. The model had a concordance index of 0.74, sensitivity of 78%, specificity of 69%, and hazard ratio 5.12 for predicting clinical progression within 8 years after prostatectomy. Validation on an independent cohort of 341 patients with 44 clinical failure events yielded a concordance index of 0.73, sensitivity 76%, specificity 64%, and hazard ratio 3.47. This was significantly higher than the accuracy (concordance index of 0.69) of the commonly used pre-operative nomogram.

As demonstrated by the present study, the incorporation of morphometry and space-related biomarker data is superior to clinical variables alone (including clinical stage, biopsy Gleason score and PSA) for, for example, predicting disease progression within 8 years after prostatectomy. Biopsy assessment of androgen receptor signaling and proliferative activity is important for accurate patient stratification. Significantly, this study also demonstrated the predictive power of a characteristic of the minimum spanning tree (MST) as obtained from digitized images of tissue subject to multiplex immunofluorescence (IF).

Patients and Samples. Information was compiled on 1487 patients treated with radical prostatectomy between 1989 and 2003 for localized or locally advanced prostate cancer for whom tissue samples were available. Patients were excluded who were treated for prostate cancer before prostatectomy. The cohort (67%-33%) was randomized and split between training and validation sets with similar proportions of clinical failure events and balanced demographically.

Clinical failure (CF) was pre-specified as any of three events: 1) unequivocal radiographic or pathologic evidence of metastasis, castrate or non-castrate (including skeletal disease or soft tissue disease in lymph nodes or solid organs); 2) rising PSA in a castrate state; or 3) death attributed to prostate cancer. The time to clinical failure was defined as the time from radical prostatectomy to the first of these events. If a patient did not experience clinical failure as of his last visit, or his outcome at the time of his most recent visit was unknown, then the patient's outcome was considered censored.

Dominant biopsy Gleason grade (bGG) and Gleason score were obtained from re-evaluation of the primary diagnostic biopsy sections obtained from paraffin block(s) selected by the pathologist. Clinical stage was assessed by retrospective review of clinical records.

Only patients with complete clinicopathologic, morphometric, and molecular data, as well as non-missing outcome information, were further studied; evaluable patients totaled 686 in the training set and 341 in the validation set (See Table 6 below). The characteristics of these 1027 patients were similar to those of the 1487 in the original cohort. 340 (33%) of 1027 patients had PSA recurrence and 338 (33%) had received secondary therapy. 12 of 1027 (1%) died of disease and 157 (15%) died of other causes. Patients were excluded due to poor quality of the biopsy specimen and/or incomplete clinical data. Table 7 below provides a complete review of patient accounting.

TABLE 6

Characteristics of patients in the training and validation cohorts.

| Characteristic | Training n = 686 | Validation n = 341 |
|---|---|---|
| Mean age, years | 63.6 | 64 |
| Pre-operative PSA | | |
| ≤10 ng/ml | 460 (67.1%) | 231 (67.7%) |
| >10 ng/ml | 226 (32.9%) | 110 (32.3%) |
| Dominant Gleason grade | | |
| 2 | 25 (3.6%) | 8 (2.3%) |
| 3 | 524 (76.4%) | 246 (72.1%) |
| 4 | 130 (19.0%) | 85 (24.9%) |
| 5 | 7 (1.0%) | 2 (0.6%) |
| Gleason Score | | |
| 4 | 5 (0.7%) | 4 (1.2%) |
| 5 | 31 (4.5%) | 7 (2.1%) |
| 6 | 294 (42.9%) | 159 (46.6%) |
| 7 | 287 (41.8%) | 137 (40.2%) |
| 8 | 46 (6.7%) | 25 (7.3%) |
| 9 | 17 (2.5%) | 8 (2.3%) |
| 10 | 6 (0.9%) | 1 (0.3%) |
| Clinical Stage | | |
| T1a | 6 (0.9%) | 3 (0.9%) |
| T1c | 263 (38.3%) | 116 (34.0%) |
| T2 | 374 (54.5%) | 198 (58.1%) |
| T3 | 27 (3.9%) | 15 (4.4%) |
| Missing | 16 (2.3%) | 9 (2.6%) |
| Clinical failure events | 87 (12.7%) | 44 (12.9%) |
| Castrate rise in PSA | 77 (11.2%) | 40 (11.7%) |
| Bone scan positive | 9 (1.3%) | 4 (1.2%) |
| Death of prostate cancer | 1 (0.1%) | 0 |

TABLE 7

Patients in full and final cohorts, and clinical failure events in the final cohort.

| | Institution | | | | | |
|---|---|---|---|---|---|---|
| Patients | 1 | 2 | 3 | 4 | 5 | Total |
| Full Cohort | 74 | 501 | 600 | 233 | 79 | 1487 |
| Final Cohort | 50 | 267 | 565 | 131 | 14 | 1027 |
| % Included | 67.6 | 53.3 | 94.2 | 56.2 | 17.7 | 69.1 |
| Training Set | | | | | | |
| Number of Patients | 50 | 182 | 359 | 87 | 8 | 686 |
| Number of CF Events | 9 | 26 | 41 | 11 | 0 | 87 |
| % Events | 18.0 | 14.3 | 11.4 | 12.6 | 0 | 12.7 |
| Validation Set | | | | | | |
| Number of Patients | 0 | 85 | 206 | 44 | 6 | 341 |
| Number of CF Events | 0 | 10 | 27 | 6 | 1 | 44 |
| % CF Events | 0 | 11.8 | 13.1 | 13.6 | 16.7 | 12.9 |

Up to 7 unstained slides and/or paraffin blocks were obtained for each patient. Slides and sections obtained from blocks were stained with hematoxylin and eosin (H&E). Sections with maximum tumor content and representative of the patient's Gleason score, including areas of the patient's highest Gleason grade, were selected for further analysis.

Image Analysis of H&E-Stained Tissue. Up to three digitized H&E images were acquired from whole-section biopsy specimens and independently assessed for overall tumor content, Gleason grade, and quality (staining properties, morphological detail, and artifacts) by three pathologists. Using a digital masking tool (here, Adobe Photoshop 7.0), only infiltrating tumor was included for morphometric analysis. The outline of the lumen of individual tumor-glands was used to accurately reflect overall gland architecture. An image analysis tool was used to generate morphometric features, specifically including quantitative histologic features based on cellular properties of the prostate cancer (e.g., relationship of epithelial nuclear area to gland lumen area.) For a given patient, the final value for each morphometric feature was the median value across a patient's entire tumor available for study.

In the morphometric analysis of H&E-stained tissue, although the "gland unit" object approximates a true gland unit, it is perhaps a misnomer. The intended relationship captured in this object is that between lumens and closely associated epithelial nuclei. Defining such object and therefore a nuclear subclass (here, those closely associated with lumens) allows one, by subtraction, to study nuclei not closely associated with or distant from lumens. It is the variety of possible relationships between the described objects, nuclear subclasses (by extension epithelial cytoplasm subclasses), and total tumor area that comprise features associated (directly or indirectly) with the gland unit. Gland unit objects according to some embodiments of the present invention are created by uniform and symmetric growth around lumens as seeds in the manner described above, which identifies not only gland units but also epithelial cells not captured by the gland, namely, epithelial cells outside of or poorly associated with the gland unit.

The specific H&E feature selected in the multivariate model described in this example (FIG. 11) represents the relative area of the epithelial cells which are poorly associated with the gland units. Specifically, this feature is defined as the area of epithelial cells (nuclei plus cytoplasm) not associated with lumens normalized to the total tumor area. Pathophysiologically this feature as well as most of its variants capture a progression in prostate tumor grade. Most intuitive is the simple progression from a low-grade Gleason pattern 3, in which the majority of epithelial nuclei are closely associated with lumens, to a high-grade Gleason pattern 5, in which most epithelial nuclei are not associated with lumens. Slightly more subtle is the progression of a simple Gleason pattern 3 to a pattern 4. In pattern 4, increased numbers of glands will have very small or no lumens, with epithelial cancer cells either as 'lumen-less' nests or asymmetrically surrounding small lumens, both leading to an increased feature value.

A distinct feature targeting similar tumor characteristics as the gland unit features is the 'epithelial nuclear band 5 minus 3' feature. This feature measures epithelial nuclear area within static concentric rings (bands) around lumens. Subtracting the content of the innermost rings from the outermost rings gives area of nuclei distant from lumens. As expected, the direction of univariate correlation changes for epithelial nuclear area closely associated with lumens (band 1) vs. area more distant from lumens (band 5 minus 3). What differentiates 'band 5 minus 3' from the 'gland unit' feature previously described is that 'band 5 minus 3' includes only epithelial nuclear area associated with a lumen whereas the gland unit includes nuclear area quite distant from or completely unassociated with lumens. These two features therefore overlap, particularly in Gleason pattern 4.

Quantitative Multiplex Immunofluorescence. Multiple antigens were quantified in single tissue sections by immunofluorescence. Two multiplex assays were performed on prostate needle biopsies with Alexa-fluorochrome-labeled antibodies for the following antigens: a) Multiplex 1: androgen receptor (AR), racemase (AMACR), cytokeratin 18 (CK18), TP73L (p63), and high molecular weight keratin; b) Multiplex 2: Ki67, phosphorylated AKT, CD34, CK18 and AMACR (Table 8). Both multiplexes contained 4'-6-diamidino-2-phenylindole (DAPI) to stain nuclei. Based on the distinctive spectral profiles of the fluorochromes, antigen-specific gray-scale images were acquired. An image analysis tool was used to localize the individual antigens. Utilizing antigen distribution and pixel-based intensity maps, the image analysis tool identified cell types and cellular compartments (e.g. luminal epithelial cells, epithelial/stromal nuclei) and quantified AR, Ki67, phosphorylated AKT, CD34, and AMACR in prostate tumor, benign glands, and stroma. Machine learning statistical modeling was employed to determine optimal thresholds for fluorescence intensity and assign classification schemes for positive and negative profiles. For a given patient, the final value for each immunofluorescence feature was the median value across a patient's entire tumor available for study.

Prior to incorporation into immunofluorescent multiplexes, all antibodies were titrated using both immunohistochemical and immunofluorescent standard operating procedures.

De-paraffinization and re-hydration of tissue samples were performed per standard operating procedures. Antigen retrieval was performed by boiling the slides in a microwave oven for 7.5 minutes in 1× Reveal Solution (BioCare Medical). The slides were allowed to cool for 20 minutes at room temperature and then were rinsed under running $dH_2O$. All subsequent steps were performed on a Nemesis 7200 Automated Slide Stainer (BioCare Medical).

The tissue samples underwent the following pre-hybridization treatment steps. To help permeate the cellular structures of the tissue, the samples were incubated in PBT (PBS+0.2% Triton-X 100) at room temperature for thirty minutes, followed by a three minute rinse in TBS. To help reduce tissue auto-fluorescence, the samples were incubated in acid alcohol (1% HCl in 70% ethanol) at room temperature for twenty minutes, followed by a three minute rinse in TBS. Blocking of non-specific binding sites was performed by incubating the slides in IF Blocking Reagent (0.5 mg/ml BSA in PBS) at room temperature for twenty minutes. No washes were performed between the blocking step and the subsequent hybridization step.

Two sets of 5 antibodies each (Table 8) were combined with DAPI into multiplex 'quintplex' assays. The "Multiplex-1" analysis includes a cocktail of anti-racemase (AMACR; clone 13H4, Zeta Corporation) at a 1:50 dilution with high molecular weight cytokeratin (HMW CK; clone 3413E12, Dako) at a 1:50 dilution and p63 (clone BC4A4, BioCare Medical) at a 1:10 dilution made in 1% Blocking Reagent. 400 μl of this antibody mixture was applied to the tissue sample, and the antibodies were allowed to bind at room temperature for one hour. Incubation was followed by one rinse of three minutes in TBS.

For the labeling step, a cocktail of Zenon Alexa Fluor 488 anti-Rabbit IgG Fab fragment, Zenon Alexa Fluor 555 anti-mouse IgG1 Fab fragment, and Zenon Alexa Fluor 594 anti-mouse IgG2a Fab fragment was made in 1% Blocking Reagent at twice the concentrations recommended by the manufacturer (1:50 dilution for each Fab fragment). Approximately 400 μl of this labeling cocktail was applied to the tissue samples, and the tissue samples were incubated at room temperature for 30 minutes. The labeling reaction was followed by one rinse of three minutes in TBS.

The tissue samples were then treated to a second round of antibody binding and labeling. A cocktail of anti-CK-18 (synthetic peptide, CalBiochem) at a 1:1250 dilution and anti-Androgen Receptor (AR, clone AR441, Fisher (LabVision)) at a 1:10 dilution was made in 1% Blocking Reagent. Approximately 400 μl of this antibody cocktail was applied to the tissue sample, and the antibodies were allowed to bind at room temperature for one hour. Hybridization was followed by one rinse of three minutes in TBS.

For the second labeling step, a cocktail of Zenon Alexa Fluor 647 anti-Rabbit IgG Fab fragment and Zenon Alexa Fluor 568 anti-mouse IgG1 Fab fragment was made in 1% Blocking Reagent at twice the concentrations recommended by the manufacturer (1:50 dilution for each Fab fragment). Approximately 400 μl of this labeling cocktail was applied to the tissue samples, and the tissue samples were incubated and rinsed as described for the first labeling step.

The "Multiplex-2" analysis includes a cocktail of anti-racemase (AMACR; clone 13H4, Zeta Corporation) at a 1:50 dilution and Ki67 (clone Ki67, Ventana) at a 1:2 dilution made in 1% Blocking Reagent. 400 μl of this antibody mixture was applied to the tissue sample, and the antibodies were allowed to bind at room temperature for one hour. Incubation was followed by one rinse of three minutes in TBS.

For the labeling step, a cocktail of Zenon Alexa Fluor 488 anti-Rabbit IgG Fab fragment and Zenon Alexa Fluor 555 anti-mouse IgG1 Fab fragment was made in 1% Blocking Reagent at twice the concentrations recommended by the manufacturer (1:50 dilution for each Fab fragment). Approximately 400 μl of this labeling cocktail was applied to the tissue samples, and the tissue samples were incubated at room temperature for 30 minutes. The labeling reaction was followed by one rinse of three minutes in TBS.

The tissue samples were then treated to a second round of antibody binding and labeling. A cocktail of anti-CK-18 (synthetic peptide, CalBiochem) at a 1:1250 dilution and anti-CD34 (clone QBEnd-10, Dako) at a 1:100 dilution was made in 1% Blocking Reagent. Approximately 400 μl of this antibody cocktail was applied to the tissue sample, and the antibodies were allowed to bind at room temperature for one hour. Hybridization was followed by one rinse of three minutes in TBS.

For the second labeling step, a cocktail of Zenon Alexa Fluor 647 anti-Rabbit IgG Fab fragment and Zenon Alexa Fluor 568 anti-mouse IgG1 Fab fragment was made in 1% Blocking Reagent at twice the concentration recommended by the manufacturer (1:50 dilution for the anti-Rabbit IgG Fab fragment) or at the manufacturer's recommended concentration (1:100 dilution for the anti-Mouse IgG1 fragment). Approximately 400 μl of this labeling cocktail was applied to the tissue samples, and the tissue samples were incubated and rinsed as described for the first labeling step.

The tissue samples were then treated to a third round of antibody binding and labeling. Phospho-AKT (clone 736E11, Cell Signaling) was diluted at 1:100 in 1% Blocking Reagent. Approximately 400 μl of this antibody dilution was applied to the tissue sample, and the antibody was allowed to bind at room temperature for one hour. Hybridization was followed by one rinse of three minutes in TBS.

For the third labeling step, Zenon Alexa Fluor 594 anti-Rabbit IgG Fab fragment was made in 1% Blocking Reagent at the manufacturer's recommended concentration (1:100 dilution for the anti-Rabbit IgG fragment). Approximately 400 pa of this labeling cocktail was applied to the tissue samples, and the tissue samples were incubated and rinsed as described for the first labeling step.

A fixation step was performed on all tissue samples by incubating the samples in 10% formalin at room temperature for 10 minutes, followed by one rinse of three minutes in TBS. Samples were then incubated in 0.15 μg/ml DAPI dilactate (Invitrogen) at room temperature for 10 minutes, followed by one rinse of three minutes in TBS.

Approximately 30.0 µl of SlowFade Gold antifade reagent mounting solution (Invitrogen) was applied to the samples, which were then cover slipped. Samples were stored at −20° C. until analysis could be performed.

Images were acquired with the CRI Nuance spectral imaging system (CRI, Inc., 420-720 nm model) described above. Spectra of the pure dyes were recorded prior to the experiment by diluting each Alexa dye separately in Slow-Fade Antifade (Molecular Probes). The diluted dye was then spread out on a glass slide, covered with a coverslip and scanned with the same range and interval as the respective dye in the tissue experiment. Representative regions of background fluorescence were allocated in order to complete the spectral libraries for the spectral unmixing process.

TABLE 8

Antibodies used for quintplex-immunofluorescent multiplexes.

| Multiplex | Antibody | Vendor | Catalog # | Clone | Isotype | Dilution |
|---|---|---|---|---|---|---|
| Multiplex-1 | CK-18 | CalBiochem | AP1021 | Synthetic peptide | RIgG | 1:1250 |
| | AMACR | Zeta Corp. | Z2001 | 13H4 | RIgG | 1:50 |
| | HMW CK | Dako | M0630 | 34βE12 | MIgG1 | 1:50 |
| | p63 | Biocare Medical | CM163 | BC4A4 | MIgG2a | 1:10 |
| | AR | Fisher (LV) | MS-443-P | AR441 | MIgG1 | 1:10 |
| Multiplex-2 | CK-18 | CalBiochem | AP1021 | Synthetic peptide | RIgG | 1:1250 |
| | AMACR | Zeta Corp. | Z2001 | 13H4 | RIgG | 1:50 |
| | Ki67 | Ventana | 790-2910 | K2 | MIgG1 | 1:2 |
| | CD34 | Dako | M7165 | QBEnd-10 | MIgG1 | 1:100 |
| | Phospho-AKT | Cell Signaling | 3787 | 736E11 | RIgG | 1:100 |

From the IF images, the concentration and distribution of biomarkers in tissue can be evaluated by measuring brightness of the elements of the images. Evaluation of IF images allows for objective, automatic evaluation of biomarkers for, for example, prognosis and diagnostics purposes. One of the challenges encountered with IF images is that measured intensity can be associated not only with the particular biomarker for which the antibody is intended, but with nonspecific binding, which often can be stronger that specific binding. For example, nuclei biomarkers are located in epithelial nuclei. In this example, binding of antibody of the nuclear biomarker in stroma would be nonspecific binding. Nonspecific binding of nuclear biomarker can be observed non only outside, but inside nuclei as well, which can cause the measured intensity of biomarker within nuclei to be contaminated by noise.

The measurement of the biomarker within, for example, epithelial nuclei can be presented as sum of two components: noise and signal. "Noise" is the part of the measured intensity attributable to nonspecific binding. "Signal" is the part of intensity in, for example, epithelial nuclei attributable to specific binding and related with the medical condition under consideration. All intensity observed outside of, for example, the epithelial nuclei can be considered "noise" as well. For example, based on observations regarding the AR biomarker, the following hypotheses are made: 1. the noise in the epithelial nuclei is proportional to the noise outside of epithelial nuclei; 2. the same factors affect nonspecific binding in epithelial and stroma nuclei; 3. it is assumed that, for each image, there is a threshold value of intensity of biomarker in the epithelial nuclei such that most of epithelial nuclei with intensity above the threshold contain some excess of the biomarker (even though, nuclei with measured intensity may have some biomarker as well, its level is hard to evaluate, because the measurement is affected by random noise); 4. the excess of the biomarker in epithelial nuclei is related with the progression of the disease, while the noise is not. These hypotheses were supported by analyses on data.

Two types of thresholds were considered: 1. low threshold: nuclei with intensity above this threshold have various levels of concentration of biomarker. To evaluate abundance of biomarker with the low threshold, it is better to use features which take into account variability of the intensity across nuclei. For example, average intensity may be used for this purpose; and 2. high threshold: nuclei with the intensity above this threshold have similar intensity, close to the highest observed. Proportion of nuclei with intensity above the high threshold may be used for estimate abundance of AR in epithelial nuclei. Based hypothesis 2 above, it is proposed to find these thresholds using the values of noise in stroma nuclei.

On each image, a series of percentiles of intensity of biomarker in stroma nuclei were calculated. Usually, the second percentile, all percentiles from fifth to ninety fifth are calculated with the step 5 and the 99th percentile. The goal is to select the same stroma nuclei percentile on all images, as a low threshold (high threshold) for separation of epithelial nuclei with excess of biomarker. To achieve this goal, for each percentile of the intensity in stroma nuclei, all epithelial nuclei are determined having the intensity above the threshold. For these nuclei, their average intensity and relative area are evaluated. Correlation of these characteristics with, for example, the disease progression on our training data is also evaluated. The percentile of stroma nuclei whish produce the most strongly correlated average intensity is selected as low threshold, the percentile which produces the most strongly correlated relative are feature is selected as high threshold.

In various embodiments of the present invention, different approaches may be used to measure features of interest from the IF images and/or to prepare the images for such measurements. For example, in some embodiments, artifacts in tissue images may be outlined by a pathologist or automatically to exclude them from segmentation (e.g., for Mplex-1 described above). In some embodiments, tumor area to segment may be outlined by a pathologist or automatically (e.g., for Mplex-2 described above). In some embodiments, no artifacts or tumor mask may be used (e.g., segmentation may be performed on the entire image). In some embodiments, initial segmentation may be done with a quad-tree approach (e.g., for Mplex-1 and/or Mplex-2 described above) which may result in faster initial segmentation. In other embodiments, a multi-resolution approach to initial segmentation may be used.

In some embodiments, an image-derived CK-18 threshold may be used to classify cytoplasm (e.g., Mplex-1). In other embodiments, an image-derived CK-18 threshold may be used to seed nearest neighbor classification (e.g., Mplex-2), which may make cytoplasm detection more robust across a variety of images.

In some embodiments, an image-derived DAPI threshold, ration of DAPI signal to super-object, multiple passes of multi-resolution segmentation and growing of nuclei may be used to segment nuclei (e.g., Mplex-1 and/or Mplex-2), which may result in, for example, improved nuclei segmentation. In other embodiments, only an image-derived DAPI threshold and multiple passes of multi-resolution segmentation may be used to segment nuclei.

In some embodiments, HMWCK and P63 may be used to find basal cells and exclude them measuring AR in epithelial measurements, which may improve measurement accuracy. In some embodiments, gland units and non-gland units associated epithelial nuclei may be detected (e.g., Mplex-1 and/or Mplex-2). In some embodiments, AMACR association may be evaluated on gland units (e.g., Mplex-1 and/or Mplex-2) or small CK-18 objects.

In some embodiments, epithelial nuclei AR positive classification may be based on a stromal nuclei AR percentiles derived AR threshold (e.g., Mplex-1). In other embodiments, epithelial nuclei AR positive classification may be based on presence of small and bright AR positive sub-objects found using an image-derived threshold. In some embodiments, epithelial nuclei Ki67 positive classification may be performed based on an image Ki67 percentiles derived threshold.

In some embodiments, multiple percentiles of AR signal in epithelial and stromal nuclei are determined for analysis (e.g., Mplex-1 and Mplex-2). In some embodiments, individual nuclei measurements may include area, position and AR mean of each nuclei (e.g., Mplex-1). In some embodiments, individual nuclei measurements may include area, position and Ki67 mean of each nuclei (e.g., Mplex-2) for use in, for example, determining the MST in the image(s).

In some embodiments, epithelial nuclei are binned by AR intensity and nuclei density (e.g., Mplex-1). In some embodiments, blood vessels are detected using CD34 (e.g., Mplex-2). In some embodiments, multiple biomarkers per nuclei may be detected, for example, nuclei expressing Ki67 and pAKT simultaneously (e.g., Mplex-2).

Statistical Analysis. In this example, the predictive model was constructed using support vector regression for censored data (SVRc), which is an approach that takes advantage of the ability of support vector regression to handle high dimensional data but is adapted for use with censored data. This approach can increase a model's predictive accuracy over that of the Cox model.

In conjunction with SVRc, a Bootstrap Feature Selection was employed which was developed specifically for SVRc. In the SVRc with Bootstrap Feature Selection method, an initial filtering step removes features which do not univariately correlate with the outcome of interest. Next, N different splits are made of the training data; in each split approximately two-thirds of the total training instances are randomly assigned to a training subset and approximately one-third of the total training instances are randomly assigned to a testing subset. In this study, N=25 splits were generated.

The method begins with a "greedy-forward" feature selection process starting with all the features which passed the initial filter. Models are built by increasing the number of features, such that the first model is built on a single feature. For each feature, N models are built using this feature on the training subsets across all the splits, then tested on the N respective testing subsets. The overall performance for each feature is averaged across the N runs. The feature with the best overall performance is selected. In the next step, each feature is added to the selected feature and again N models are built and tested across the splits. The feature whose addition resulted in the best overall performance is selected. The method continues in this fashion until there are no more features which will improve the performance.

Subsequently, a "greedy-backward" feature selection approach is employed. Each feature is removed, and N models without that feature across the splits are built and tested. The feature whose removal results in the best overall performance is removed, and the procedure is repeated until the model's performance ceases to improve due to the removal of features. This step simplifies model complexity and removes features which may have initially been significant, but their information contribution is encapsulated within a feature added subsequently.

Finally, the complete SVRc model is trained using all the selected features on the complete training cohort. The weight of each feature within the final model is a measure of the relative contribution of that feature's information in predicting a patient's outcome. A positive weight implies a positive correlation with outcome (increasing values of the feature are associated with longer survival time) whereas a negative weight implies a negative correlation with outcome (increasing values of the feature are associated with shortened time to event).

Four metrics were employed to assess a model's performance: the concordance index (c-index), sensitivity, and specificity, and hazard ratio. The c-index estimates the probability that, of a pair of randomly chosen comparable patients, the patient with the higher predicted time to clinical failure (CF) from the model will experience CF within a shorter time than the other patient. The concordance index is based on pairwise comparisons between two randomly selected patients who meet either of the following criteria: 1) both patients experienced the event and the event time of one patient is shorter than that of the other patient, or 2) only one patient experienced the event and his event time is shorter than the other patient's follow-up time. The concordance index for a multivariable model ranges from 0.5 (model performs the same as a coin toss) to 1.0 (model has perfect ability to discriminate).

In order to estimate sensitivity and specificity, typically evaluated for binary output, a clinically meaningful timeframe (CF within 8 years) was selected to separate early from late events. Patients whose outcome was censored before 8 years were excluded from this estimation. The model's output was inversely scaled to a score between 0 and 100 (longer CF-free times having a lower score and shorter survival times having a higher score). Thereafter every value of the model's score was taken one after another as a potential cut point of the prediction. For each of these potential cut points, the sensitivity and specificity of the classification were evaluated. Sensitivity was defined as the percentage of patients who experienced CF within 8 years that were correctly predicted; specificity was defined as the percentage of patients who did not experience CF within 8 years that were correctly predicted. Every cut point was evaluated by the product of its sensitivity and specificity. The cut point with the highest value of the product was selected as the predictive cut point, and its sensitivity and specificity were considered to be the sensitivity and specificity of the model. In this model, a cut-point of 30.195 was selected, indicating that, if patients with a scaled score above 30.195 are considered as experiencing CF within 8 years post radical-prostatectomy, and patients with a scaled score below 30.195 are considered as being CF-free for 8 years, the model will have a sensitivity and specificity of 78% and 69% in training and 76% and 64% in validation.

The hazard ratio was also calculated to compare stratification for patients at low risk/high risk for CF within 8 years using the same cut-point employed for sensitivity/specificity. The hazard ratio in training was 5.12 and in validation was 3.47.

The c-index was also used to measure univariate correlation with CF for each predictive feature. The interpretation of the c-index for univariate correlation is similar to that for the aforementioned model c-indexes. For univariate correlation, a c-index of 0.5 indicates random correlation. Values between 0.5 and 0 indicate negative correlation with outcome; the closer to 0 the better the predictive power. Values between 0.5 and 1 indicate positive correlation with outcome; the closer to 1 the better the predictive power. A heuristic rule used was that features with a concordance index above 0.6 (for positively correlating features) or below 0.4 (for negatively correlating features) are significant. Values of 0.4 and 0.6 approximate a p-value of 0.05.

A probability for each SVRc model score was generated by analyzing the probability of CF within 8 years in each percentile of the SVRc model scores in the training data. A probability function was then computed to generate a probability of CF within 8 years for each model score.

Results

Patient characteristics in the training set. In the training set of 686 patients, 87 (12.7%) had clinical failure after prostatectomy: 9 with a positive bone scan, 77 with a castrate rise in PSA, and 1 with death from prostate cancer. These 686 patients were followed for a median of 96 months after prostatectomy. Patient characteristics are detailed in Table 6 above. In univariate analyses, preoperative PSA, biopsy Gleason score, and dominant biopsy Gleason grade (bGG) were the only clinical variables associated with clinical failure (concordance index≤0.4 or ≥0.6; Table 9). In Table 9, the features listed in bold were ultimately selected in the final predictive model. The H&E and IF/H&E features are described above in connection with Table 5. The MST/IF features are described above in connection with FIG. 9. In addition, feature "CombIFEpiNucMeanEdgeLengthInter" is a combined feature representing the mean edge length of epithelial nuclei for inter-gland edges for Gleason grades 3 and lower, and the Gleason grade itself for Gleason grades 4 and 5. The MST/IF feature "CombIFEpiNucMeanEdgeLengthIntra" is a combined feature representing the mean edge length of epithelial nuclei for intra-gland edges for Gleason grades 3 and lower, and the Gleason grade itself for Gleason grades 4 and 5. The IF feature "IFx1_RelAreEpi_ARpAMACRp2EN" is a normalized area and intensity feature representing proportion of epithelial nuclei that express positive levels of both AR and AMACR. The feature "CombinedIF_ARepinucnormint" is a combined feature representing the normalized level of AR intensity in epithelial nuclei for Gleason grades 3 and lower, and the Gleason grade itself for Gleason grades 4 and 5. The feature "CombinedIFx1_RelAreNGA2Cyt_4lowG1" is a combined feature representing the relative area of non-gland associated content to cytoplasm for Gleason grades 3 and lower, and the Gleason grade itself for grades 4 and 5. The feature "CombLowGleARpAMACRplum_HighGLKi67" is a combined feature which is different depending on the relative area of lumens in a patient's tissue or image thereof (e.g., image of H&E-stained tissue). An optimal cutpoint is derived for the relative area of lumens. For patients with a value less than or equal to the cutpoint, the IF feature representing the relative area of AR positive and AMACR positive epithelial nuclei is used. For patients with a value greater than the cutpoint, the IF feature representing the proportion of Ki67 positive epithelial nuclei is used.

TABLE 9

Features used as input for model development. Inclusion was based on concordance index for predicting clinical failure in the training cohort in univariate analysis.

| Feature | Feature Domain | Concordance Index |
|---|---|---|
| Preoperative PSA | clinical | 0.373 |
| Dominant biopsy Gleason grade | clinical | 0.371 |
| Biopsy Gleason score | clinical | 0.336 |
| IFx1_RelAreEpi_ARpAMACRp2EN | IF | 0.375 |
| proportion_edge_2_epinuc | MST/IF | 0.606 |
| proportion_edge_3_epinuc | MST/IF | 0.364 |
| HE02_Lum_Are_Median | H&E | 0.654 |
| orig_approximation_4 | H&E | 0.637 |
| orig_diag_detail_6 | H&E | 0.654 |
| HEx2_nta_Lum_Are_Tot | H&E | 0.635 |
| HEx2_EpiNucAre2LumMeanAre | H&E | 0.388 |
| HEx2_nrm_ENWinGU_Are_Tot | H&E | 0.645 |
| HEx2_nrm_ENOutGU_Are_Tot | H&E | 0.355 |
| HEx2_nrm_CytWinGU_Are_Tot | H&E | 0.638 |
| HEx2_nrm_CytOutGU_Are_Tot | H&E | 0.362 |
| HEx2_RelArea_EpiNuc_Out2WinGU | H&E | 0.353 |
| HEx2_RelArea_Cyt_Out2WinGU | H&E | 0.360 |
| HEx2_RelArea_ENCyt_Out2WinGU | H&E | 0.348 |
| HEx2_ntaENCYtOutGU2Tumor | H&E | 0.347 |
| HEx2_nrmLUM_ENOutGU_Are_Tot | H&E | 0.353 |
| HEx2_nrmLUM_CytWinGU_Are_Tot | H&E | 0.341 |
| HEx2_nrmLUM_CytOutGU_Are_Tot | H&E | 0.340 |
| HEx2_nrmLUM_EpiNucCytOutGU | H&E | 0.343 |
| HEx2_nrm_ENCytWinGULum_Are_Tot | H&E | 0.610 |
| HEx2_RelArea_ENCytLum_Out2WinGU | H&E | 0.345 |
| HEx2_RelArea_EpiNucCyt_Lum | H&E | 0.341 |
| HEx2_ntaLumContentArea | H&E | 0.643 |
| HEx2_nrmEpiNucBand5minus3 | H&E | 0.378 |
| min_orig_L_detail5 | H&E | 0.646 |
| CombinedIFEpiNucMeanEdgeLength | MST/IF | 0.330 |
| CombinedIF_ARepinucnormint | IF | 0.324 |
| CombLowGleAR_HighGLKi67 | IF | 0.306 |
| CombinedIFx1_RelAreNGA2Cyt_4lowGl | IF | 0.331 |
| RelAreaKi67post_2Lumen | IF/H&E | 0.315 |
| RelAreapAKTpos_2Lumen | IF/H&E | 0.344 |
| RelAreaIFM2EpiNuc_2Lumen | IF/H&E | 0.383 |
| RelAreARpAMACRp2Lumen | IF/H&E | 0.342 |
| CombLowGleARpAMACRplum_HighGLKi67 | IF | 0.313 |
| CombIFEpiNucMeanEdgeLengthInter | MST/IF | 0.349 |
| CombIFEpiNucMeanEdgeLengthIntra | MST/IF | 0.328 |

Histologic image analysis. From areas of tumor in digitized images of each patient's H&E-stained biopsy cores, a series of morphometric features were generated, reflecting overall tissue architecture, including distribution of tumor cells and their relationship to glandular structures. Twenty-seven histologic features displayed significant association with clinical failure in univariate analyses (concordance index≤0.4 or ≥0.6; see Table 9).

Quantitative immunofluorescence. AMACR as a marker can be used to identify and characterize individual tumor cells [25]. In the current study, AR, Ki67, and phosphorylated AKT were quantified in AMACR-positive and AMACR-negative epithelial tumor cells, and then multiple features related to levels of AR, Ki67, phosphorylated AKT, and AMACR were generated. An endothelial marker, CD34, was also used to assess overall vascularity within the prostate cancer stroma and constructed features of total vessel area and features that related vessel distribution to glandular and epithelial objects. Finally, DAPI and CK18 immunofluorescence were used to quantify tumor morphometry by minimum spanning tree (MST) functions. Generally, the MST characteristics represent proximity between tumor cells and their distribution with respect to glands and each other. For MST characteristics, AR, and Ki67, a series of compound features were constructed that incorporate a clinical trigger, dominant bGG, for determination of marker assessment (e.g. if bGG≤3 use AR feature; bGG>3 use Ki67 feature). One goal was to identify subtle changes in the morphology and biology between dominant bGG 3 and 4 tumors that may affect outcome.

In training, 10% of non-censored patients (36 of 303) with a bGG≤3 had clinical progression within 8 years of prostatectomy. Of this group, 19 of 36 cases (52%) had high levels of AR suggesting that AR expression importantly discriminates significant from indolent disease, especially in low-grade cancers. By comparison, 31 out of 55 non-censored patients (36%) with bGG>3 had clinical progression within 8 years of prostatectomy. In this group, increasing levels of Ki67 were determined to be additive with bGG regarding shortened time to clinical progression.

Model Development. A SVRc model to predict clinical failure was developed from the data on the 686 training-set patients. The modeling began with the 40 variables that displayed association with clinical failure in univariate analyses (Table 9). Supervised multivariate learning resulted in an optimized model containing 6 features (shown in bold in Table 9), which are listed in FIG. 11 in the order of their importance in the final predictive model.

The clinical features selected by the model were preoperative PSA, biopsy Gleason score, and dominant bGG. Generally, the two imaging features, single infiltrating cells and cellular topology, reflect cellular and tissue architecture at the transition between a dominant Gleason pattern 3 and 4. The first, based on H&E in this example, quantifies the proportion of tumor epithelial cells that are not directly associated with an intact gland structure. The second is an MST combined feature, which relies on the dominant bGG as a trigger (≤3 use MST function; >3 use actual Gleason grade (dominant bGG)) and quantifies proximity between tumor cells as affected by degree of differentiation and stromal content. When bGG is evaluated the combined feature it has a negative weight, whereas the standalone bGG feature evaluated in the model has a positive weight.

Figure 12:
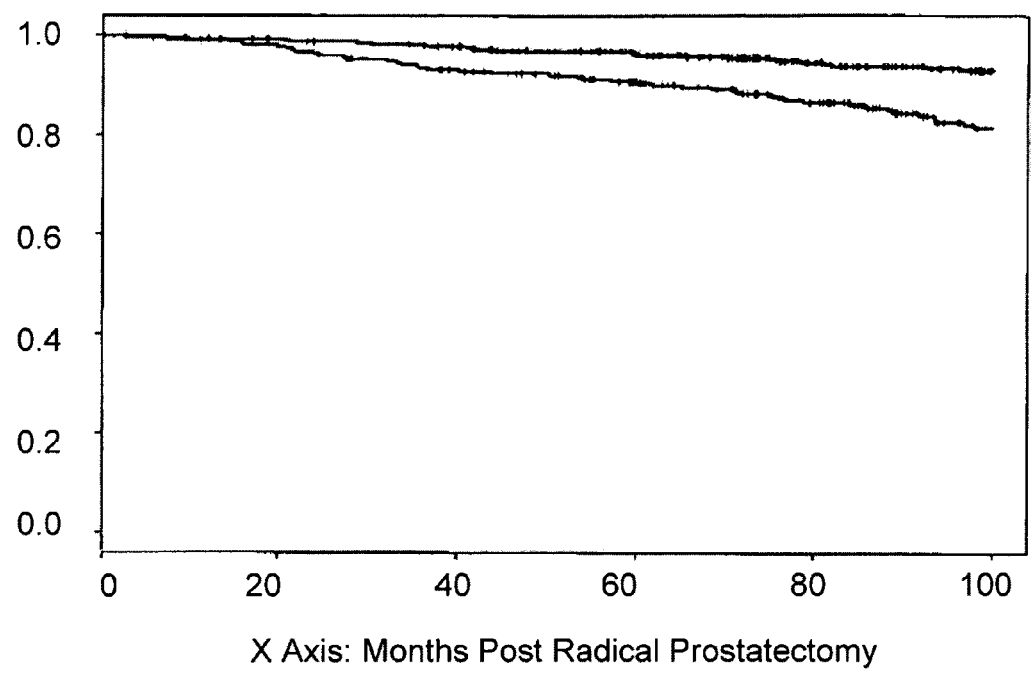
FIG. 12 are Kaplan-Meier curves illustrating the ability of a feature used in the predictive model of FIG. 11 to accurately stratify patients into low and high risk groups, namely the morphometric feature of area of isolated (non-lumen associated) tumor epithelial cells relative to total tumor area.
Figure 13:
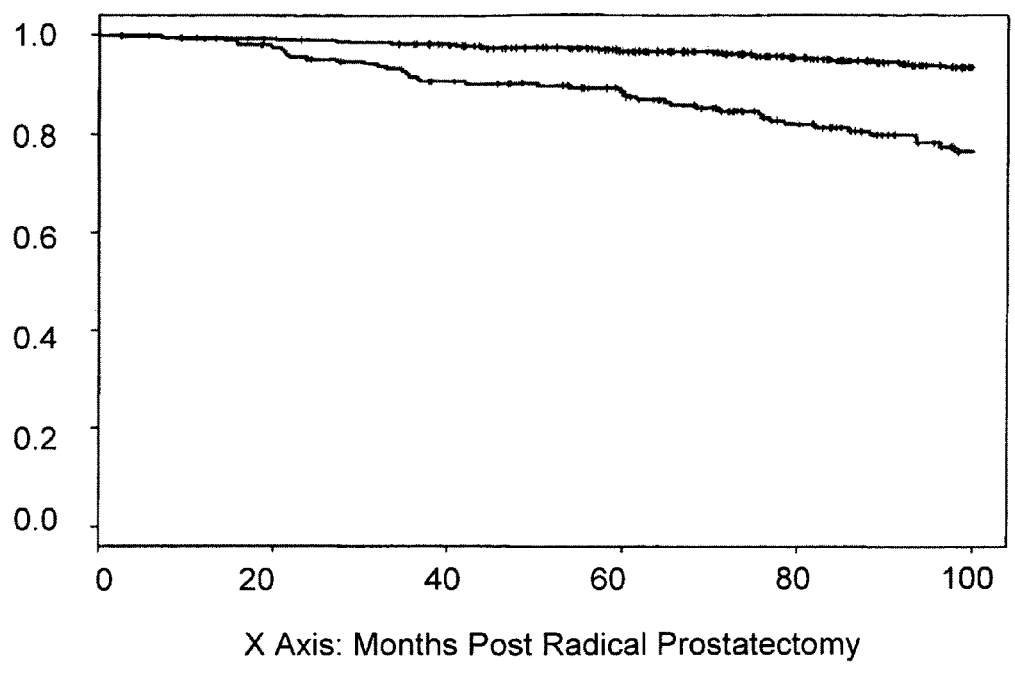
FIG. 13 is a graph of a Kaplan-Meier curve illustrating the ability of another feature used in the predictive model of FIG. 11 to accurately stratify patients into low and high risk groups, namely the morphometric feature of mean edge length in the minimum spanning tree (MST) of all edges connecting epithelial nuclei centroids (for dominant biopsy Gleason grade (bGG)≤3) in combination with the clinical feature of Gleason grade (for bGG=4 or 5)

FIGS. 12 and 13 are Kaplan-Meier curves for the two imaging features which illustrate their ability to accurately stratify patients. FIG. 12 shows the Kaplan-Meier curves for the morphometric feature of area of isolated (non-lumen associated) tumor epithelial cells relative to total tumor area (cut-point 0.31, p<0.00001), as measured in an images of needle biopsy tissue specimens after H&E staining. FIG. 13 shows the Kaplan-Meier curves for the morphometric feature of mean edge length in the minimum spanning tree (MST) of all edges connecting epithelial nuclei centroids, in combination with the clinical feature of Gleason grade (cut-point 3.93, p<0.00001), as measured in an images of needle biopsy tissue specimens subject to multiplex immunofluorescence (IF). In both instances, the optimal cut-point values were calculated using the log rank test.

From the biomarker-based features, the SVRc bootstrap method selected only the combined immunofluorescence (IF) feature of dynamic range of AR and total Ki67 content. Shorter time to clinical failure was predicted by increasing proportion of tumor cells with high AR expression in specimens with clinical bGG≤3, and high Ki67 levels in specimens with bGG 4-5. For AR, the feature calculates the ratio between the $90^{th}$ and $10^{th}$ intensity percentiles of AR in epithelial and stromal nuclei, respectively. It was demonstrated that intensity values of stromal nuclei within the entire tumor compartment were not associated with outcome and represent a good measure of background, namely non-specific fluorescence in the images. This allows for the identification of a true positive signal as well as the distribution of that signal in the epithelial compartment. The AR value is scaled between 0 and 3. Greater values were associated with a shorter time to progression in patients with dominant biopsy Gleason grade of ≤3. For Ki67, the relative area of epithelial nuclei was measured that contains a positive Ki67 signal relative to the total number of epithelial nuclei in the tumor-only area of the needle biopsy. The Ki67 'positive' assignment was based on machine learning models which incorporate mean intensity values for Ki67 in epithelial nuclei followed by thresholding using the stromal nuclei as a baseline for the background fluorescent signal. This Ki67 feature is scaled between 3 and 5. Increasing values in patients with dominant biopsy Gleason grade 4 and 5 were associated with a shortened time to disease progression. In this embodiment, the infiltrative tumor area as denoted for both AR and Ki67 was previously identified and outlined by the pathologist during initial image processing. In other embodiments, such tumor area may be identified automatically.

Figure 14:
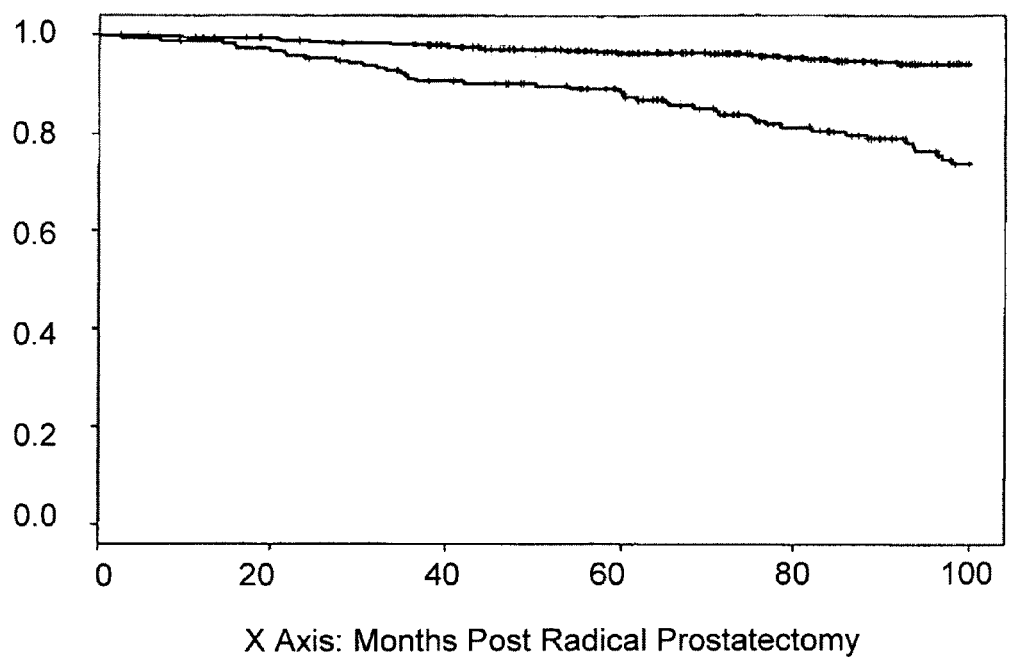
FIG. 14 is a graph of a Kaplan-Meier curve illustrating the ability of yet another feature used in the predictive model of FIG. 11 to accurately stratify patients into low and high risk groups, namely the molecular feature of AR dynamic range (for bGG≤3) in combination with the molecular feature of total Ki67 (for bGG=4 or 5)

FIG. 14 shows the Kaplan-Meier curves for patients stratified according to this combined AR-Ki67 molecular feature, where the combined feature cut-point was 0.943 calculated using the log rank test (p<0.00001). Typical immunofluorescence results (e.g., viewed at magnification ×200) for AR show AR in epithelial nuclei with increasing intensity from blue (least), red (moderate) to yellow (high), gold corresponding to AMACR+, green corresponding to AMACR−, and purple corresponding to stromal nuclei. Typical immunofluorescence results (e.g., viewed at magnification ×200) for Ki67 show Ki67 (yellow) in tumor epithelial nuclei (blue) and purple corresponding to stromal nuclei.

Figure 15:
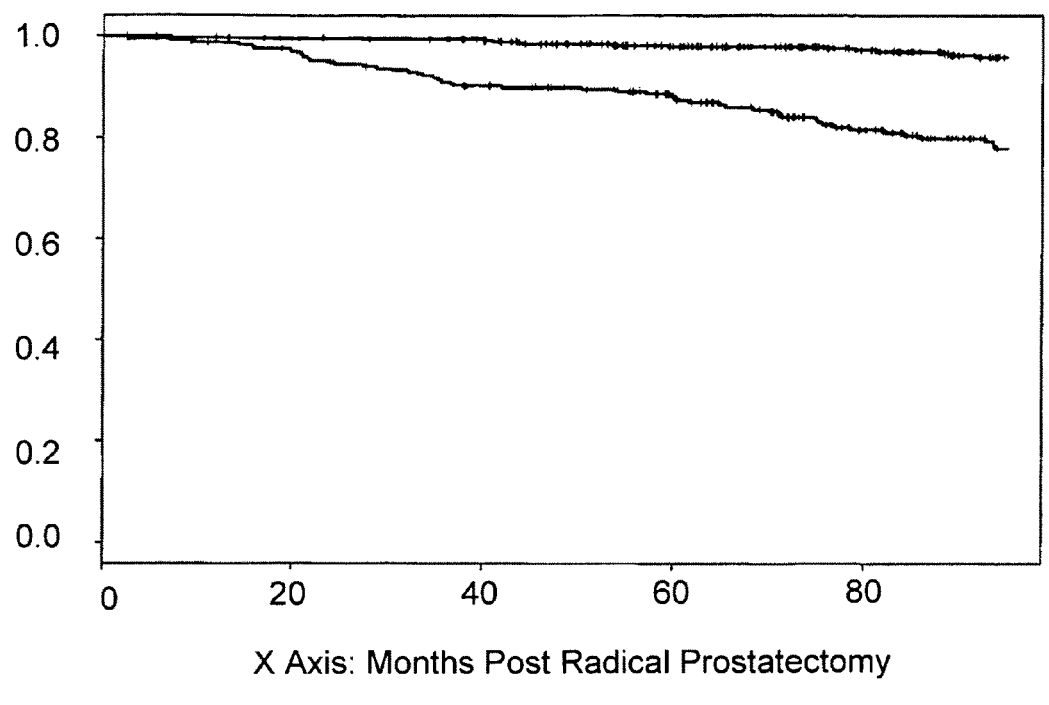
FIG. 15 is a graph of a Kaplan-Meier curve illustrating the ability of the value or score output by the predictive model of FIG. 11 to stratify patients in the training set according to risk.

The training model had a concordance index of 0.74. When patients were stratified by model score below vs. above 30.19 (corresponding to a 13.82% model-predicted probability of clinical failure), the hazard ratio was 5.12, sensitivity 78%, and specificity 69% for correctly predicting clinical failure within 8 years. FIG. 15 shows the Kaplan-Meier curves for patients in the training set stratified by the value or score output by the predictive model, which illustrates the ability of the model to separate patients from the training set according to risk (hazard ratio 5.12). Low risk was predicted for model scores≤30.19, whereas high risk was predicted for model scores>30.19. The probability of remaining free of clinical progression is provided by the y-axis and follow-up time (in months) is given by the x-axis. The p-value (<0.0001) was estimated using the log-rank test.

Figure 16:
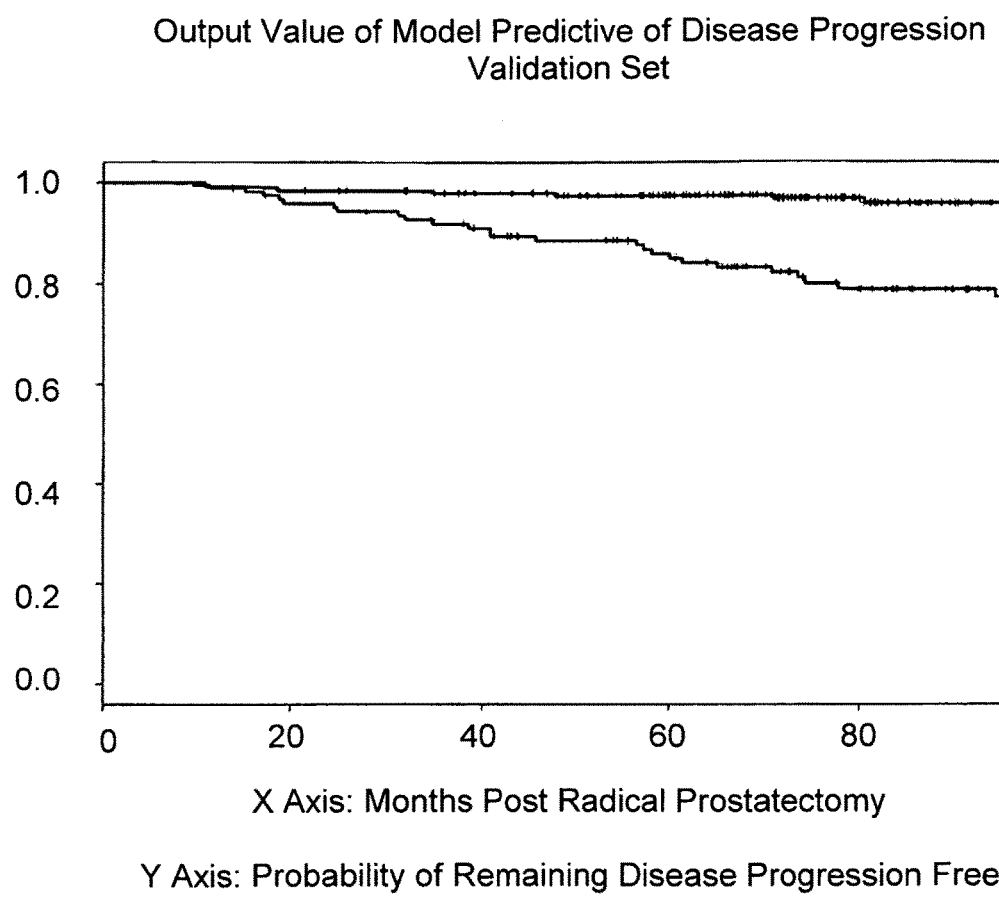
FIG. 16 is a graph of a Kaplan-Meier curve illustrating the ability of the value or score output by the predictive model of FIG. 11 to stratify patients in the validation set according to risk.

Validation. The model was validated using data from 341 patients with a median follow-up of 72 months. Forty-four patients (12.9%) had clinical failure, 4 with a positive bone scan, and 40 with a castrate rise in PSA. The model's performance resulted in a concordance index of 0.73, hazard ratio 3.47, sensitivity 76%, and specificity 64% for predicting clinical failure. Separate Kaplan-Meier curves were generated for patients whose model scores were above or below 30.19 (FIG. 16; hazard ratio 3.47). These two patient groups differed significantly in time to clinical failure (log-rank test P<0.0001).

Discussion

One of the major challenges in the management of patients diagnosed with localized prostate cancer is determining whether a given patient is at high risk for dying of his disease. To address this issue, a predictive tool according to some embodiments of the present invention is provided that can be used at the time of diagnosis: a pretreatment model using clinical variables and features of prostate needle biopsy specimens to predict the objective end-point of clinical failure after prostatectomy. The model performed in validation with a concordance index of 0.73, hazard ratio 3.47 (p<0.0001), sensitivity 76%, and specificity 64%. By comparison, the 10-year biochemical preoperative recurrence nomogram [9] when applied to the same cohort yielded a concordance index of 0.69, and hazard ratio of 2.34 (p=0.01), demonstrating the improved accuracy with a more clinically relevant end-point, obtained with the systems approach. Furthermore, the model, as compared with the 10-year postoperative PSA recurrence nomogram [26], was able to identify twice the number of high-risk patients classified by traditional clinical criteria as intermediate risk group. It is believed that a systems pathology model employing multiple robust tumor characteristics will yield a more objective risk assessment of contemporary patients, particularly in a community practice, where selected pathologic variables are prone to subjectivity.

A strength of the approach was the use of a large cohort from 5 centers in the United States and Europe, which should confer broad applicability. In addition, the features selected in the final model performed uniformly across all cohorts, thus constituting a robust patient profile that should be useful for assessing probable disease course at a time crucial for treatment decisions.

The clinical variables selected in the model were pretreatment PSA, biopsy Gleason score, and dominant bGG. Both PSA and biopsy Gleason score were found to be important predictors for overall survival in an untreated, conservatively managed population-based cohort from the U.K.[27, 28]. In that study, clinical stage also predicted survival, albeit more weakly. In the example presented above, clinical stage was not found to be a significant parameter in univariate analysis, and therefore it was not included in the multivariate model.

Higher bGG was associated with worse outcome in univariate analysis; however, it was associated with better outcome in the multivariate model. This phenomenon illustrates the "reversal paradox" known in statistics; the variable is acting as a control for other factors during modeling [29-32]. It is believed that the reversal in the disease progression model described herein resulted primarily from the impact of the two combined features, which contain the dominant bGG as a trigger (i.e., if bGG≤3 use MST or AR values). Interestingly, several studies have questioned the utility of dominant bGG, especially for 3+4 and 4+3 patterns, given that the associated probabilities of biochemical recurrence overlap substantially, and that bGG is often down-graded upon analysis of the radical prostatectomy specimen [33-35].

A key component for the current study described above is the morphometric and image analysis strategies to assess tissue architecture and cellular distribution. The MST feature in the model (FIG. 11) reflects the spatial distribution of tumor epithelial nuclei in a stromal matrix. It was optimized for bGG≤3 patterns to identify subtle morphologic changes that may relate to properties of de-differentiation. The H&E feature evaluates tumor organization where intact gland structures and cell-to-cell boundaries begin to deteriorate, as identified in progression of Gleason grade 3 to 4 tumors. In the final model, increasing levels for both features were associated with a shortened time to clinical progression, suggesting a more aggressive phenotype capable of invasion within the prostate. By comparison, in this example, morphometric features that were significant in a previous, post-prostatectomy model for clinical failure (e.g., lumen size, tumor cell composition) [36] were not selected by the biopsy model.

A central role has been demonstrated for both AR and Ki67 in prostate cancer growth and progression [25, 36, 37-42]. The current model reveals the importance of AR and Ki67 specifically in specimens of low and high Gleason grade, respectively. It is believed that this differential assessment of AR and Ki67 constitutes a biologic tumor grade that is important for understanding behavior, and that utilizing the dominant bGG as a classifier for feature annotation allows for discrimination of disease progression risk among intermediate-grade cancers. It is further believed that the aberrant activation of AR, possibly combined with an early chromosomal translocation (e.g., TMPRSS2:ERG) may affect downstream signaling pathways, thereby contributing to the evolution of castrate metastatic disease [43].

Prior evidence in both biopsy and prostatectomy specimens has linked Ki67 labeling index with bGG and outcome. However, as with AR, clinical adoption has been challenged due primarily to lack of reproducibility, lack of standardized laboratory practices, and the need for determination of an accurate and generalizable cut-point. The approach of incorporating quantitative immunofluorescence standards and machine learning to normalization and choice of threshold(s) may well have circumvented these limitations.

Finally, although associated with outcome, phosphorylated AKT was not selected in the multivariate model. In addition, the features derived from the CD34 vessel content did not reach univariate statistical significance, although trends were noted. Several studies have demonstrated involvement of phosphorylated AKT in proliferation and survival pathways in prostate cancer, and have linked increased phosphorylated AKT with Ki-67, activated AR, and a hormone-refractory phenotype [44-47]. The role of CD34 is more controversial, primarily due to differing methods for identifying and counting vessels in various sample types [48-50]. In other embodiments, phosphorylated AKT and CD34 could be included as having prognostic and predictive significance in prostate cancer progression and/or with respect to other medical conditions.

To address the robustness of our current model results, the model (generated based on SVRc and systems integration of clinicopathologic data with quantitative H&E image and immunofluorescence analyses) was compared with the traditional clinicopathologic factors, independently and in the Kattan nomograms. There are no available tools for predicting clinical disease progression at the time of diagnosis, thus for comparison the Kattan pre-operative nomograms were used, which predict PSA recurrence at 5- and 10-year intervals. Table 10 illustrates the performance of each method for predicting CF in the validation cohort. Hazard ratios were calculated by identifying the optimal cut-point in the training set and applying it to the validation set, as described above. Additionally, a sensitivity and specificity analysis of the nomograms versus the systems method according to an embodiment of the present invention in low- and intermediate-risk groups (as defined by AUA criteria) indicates that the systems method is twice as effective at identifying patients who are at high risk for CF within 8 years but appear to be low to intermediate risk based on clinical profiles.

TABLE 10

Univariate and Multivariate Results for Predicting CF within 8 years in the validation cohort.

| Predictor | C-Index | Hazard Ratio | Hazard Ratio p-value |
|---|---|---|---|
| Age at biopsy | 0.47 | 0.81 | 0.521 |
| Pre-Operative PSA | 0.67 | 1.93 | 0.030 |
| Clinical Stage | 0.53 | 1.19 | 0.769 |
| Dominant Gleason Grade | 0.60 | 2.29 | 0.007 |
| Gleason Score | 0.68 | 2.92 | 0.002 |
| Kattan 5-year PSA Recurrence Nomogram | 0.69 | 2.34 | 0.0053 |
| Kattan 10-year PSA Recurrence Nomogram | 0.69 | 2.62 | 0.0098 |
| SVRc-based Systems Pathology Model | 0.73 | 3.47 | <0.0001 |

In conclusion, a highly accurate, robust tool for predicting disease progression at the time of initial diagnosis was provided as a result of this study. It is believed that the biologic and morphologic attributes within the model represent a phenotype that will supplement current practice in determining appropriate treatment options and patient follow-up.

Additional Embodiments

Thus it is seen that methods and systems are provided for treating, diagnosing and predicting the occurrence of a medical condition such as, for example, prostate cancer progression. Although particular embodiments have been disclosed herein in detail, this has been done by way of example for purposes of illustration only, and is not intended to be limiting with respect to the scope of the appended claims, which follow. In particular, it is contemplated by the present inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The present inventors reserve the right to pursue such inventions in later claims.

Insofar as embodiments of the invention described above are implementable, at least in part, using a computer system, it will be appreciated that a computer program for implementing at least part of the described methods and/or the described systems is envisaged as an aspect of the present invention. The computer system may be any suitable apparatus, system or device. For example, the computer system may be a programmable data processing apparatus, a general purpose computer, a Digital Signal Processor or a microprocessor. The computer program may be embodied as source code and undergo compilation for implementation on a computer, or may be embodied as object code, for example.

It is also conceivable that some or all of the functionality ascribed to the computer program or computer system aforementioned may be implemented in hardware, for example by means of one or more application specific integrated circuits.

Suitably, the computer program can be stored on a carrier medium in computer usable form, which is also envisaged as an aspect of the present invention. For example, the carrier medium may be solid-state memory, optical or magneto-optical memory such as a readable and/or writable disk for example a compact disk (CD) or a digital versatile disk (DVD), or magnetic memory such as disc or tape, and the computer system can utilize the program to configure it for operation. The computer program may also be supplied from a remote source embodied in a carrier medium such as an electronic signal, including a radio frequency carrier wave or an optical carrier wave.

All of the following disclosures are hereby incorporated by reference herein in their entireties: PCT Application No. PCT/US08/004523, filed Apr. 7, 2008, which claims priority from U.S. Provisional Patent Application Nos. 60/922,163, filed Apr. 5, 2007, 60/922,149, filed Apr. 5, 2007, 60/923,447, filed Apr. 13, 2007, and 61/010,598, filed Jan. 9, 2008; U.S. patent application Ser. No. 11/200,758, filed Aug. 9, 2005; U.S. patent application Ser. No. 11/581,043, filed Oct. 13, 2006; U.S. patent application Ser. No. 11/404,272, filed Apr. 14, 2006; U.S. patent application Ser. No. 11/581,052, filed Oct. 13, 2006, which claims priority from U.S. Provisional Patent Application No. 60/726,809, filed Oct. 13, 2005; and U.S. patent application Ser. No. 11/080,360, filed Mar. 14, 2005, which is: a continuation-in-part of U.S. patent application Ser. No. 11/067,066, filed Feb. 25, 2005 (now U.S. Pat. No. 7,321,881, issued Jan. 22, 2008), which claims priority from U.S. Provisional Patent Application Nos. 60/548,322, filed Feb. 27, 2004, and 60/577,051, filed Jun. 4, 2004; a continuation-in-part of U.S. patent application Ser. No. 10/991,897, filed Nov. 17, 2004, which claims priority from U.S. Provisional Patent Application No. 60/520,815, filed Nov. 17, 2003; a continuation-in-part of U.S. patent application Ser. No. 10/624,233, filed Jul. 21, 2003 (now U.S. Pat. No. 6,995,020, issued Feb. 7, 2006); a continuation-in-part of U.S. patent application Ser. No. 10/991,240, filed Nov. 17, 2004, which claims priority from U.S. Provisional Patent Application No. 60/520,939 filed Nov. 18, 2003; and claims priority from U.S. Provisional Patent Application Nos. 60/552,497, filed Mar. 12, 2004, 60/577,051, filed Jun. 4, 2004, 60/600,764, filed Aug. 11, 2004, 60/620,514, filed Oct. 20, 2004, 60/645,158, filed Jan. 18, 2005, and 60/651,779, filed Feb. 9, 2005.

All of the following references are hereby incorporated by reference herein in their entireties.

1. Jemal A, Siegel R, Ward E, et al. Cancer statistics, 2008. *CA Cancer J Clin.* 2008; 58(2):71-96.
2. Holmberg L, Bill-Axelson A, Helgesen F, et al. A randomized trial comparing radical prostatectomy with watchful waiting in early prostate cancer. *N Engl J Med.* 2002; 347(11):781-789.
3. Bill-Axelson A, Holmberg L, Ruutu M, et al. Radical prostatectomy versus watchful waiting in early prostate cancer. *N Engl J Med.* 2005; 352(19):1977-1984.
4. Klotz L. Active surveillance versus radical treatment for favorable-risk localized prostate cancer. *Curr Treat Options Oncol.* 2006; 7(5):355-362.
5. Dall'Era M A, Cooperberg M R, Chan J M, et al. Active surveillance for early-stage prostate cancer: review of the current literature. *Cancer.* 2008; 112(8):1650-1659.
6. Albertsen P C, Hanley J A, Fine J. 20-year outcomes following conservative management of clinically localized prostate cancer. *Jama.* 2005; 293(17):2095-2101.

7. Telesca D, Etzioni R, Gulati R. Estimating lead time and overdiagnosis associated with PSA screening from prostate cancer incidence trends. Biometrics. 2008; 64(1):10-19.
8. Barry M J, Kaufman D S, Wu C-L. Case 15-2008: A 55 year-old-man with an elevated prostate-specific antigen level and early-stage prostate cancer. *NEJM* 2008; 358: 2161-2168.
9. Makarov D V, Trock B J, Humphreys E B, et al. Updated nomogram to predict pathologic stage of prostate cancer given prostate-specific antigen level, clinical stage, and biopsy Gleason score (Partin tables) based on cases from 2000 to 2005. *Urology.* 2007; 69(6):1095-1101.
10. Stephenson A J, Scardino P T, Eastham J A, et al. Preoperative nomogram predicting the 10-year probability of prostate cancer recurrence after radical prostatectomy. *J Natl Cancer Inst.* 2006; 98(10):715-717.
11. Freedland S J, Humphreys E B, Mangold L A, et al. Risk of prostate cancer-specific mortality following biochemical recurrence after radical prostatectomy. *Jama.* 2005; 294(4):433-439.
12. F. E. Harrell et al., "Evaluating the yield of medical tests," JAMA, 247(18):2543-2546, 1982.
13. Definiens Cellenger Architecture: A Technical Review, April 2004.
14. Baatz M. and Schäpe A., "Multiresolution Segmentation—An Optimization Approach for High Quality Multiscale Image Segmentation," In Angewandte Geographische Informationsverarbeitung XII, Strobl, J., Blaschke, T., Griesebner, G. (eds.), Wichmann-Verlag, Heidelberg, 12-23, 2000.
15. C. Vonesch, F. Aguet, J. L. Vonesch, and M. Unser, "The colored revolution of bioimaging," *IEEE Signal Proc. Mag.,* vol. 23, no. 3, pp. 20-31, May 2006.
16. Definiens A G, *Definiens Developer 6 Reference Book.* Definiens A G, Munich, Germany, 2006.
17. M. Teverovskiy, Y. Vengrenyuk, A. Tabesh, M. Sapir, S. Fogarasi, H. Pang, F. M. Khan, S. Hamann, P. Capodieci, M. Clayton, R. Kim, G. Fernandez, R. Mesa-Tejada, and M. J. Donovan, "Automated localization and quantification of protein multiplexes via multispectral fluorescence imaging," in *Proc. IEEE Int. Symp. Biomed. Imag.,* Paris, France, May 2008, pp. 300-303.
18. T. H. Cormen, C. E. Leiserson, R. L. Rivest, and C. Stein, Introduction to Algorithms, 2nd ed. MIT Press, Cambridge, Mass., 2001.
19. J. Sudbø, R. Marcelpoil, A. Reith, "New algorithms based on the Voronoi diagram applied in a pilot study on normal mucosa and carcinomas," *Anal. Cell. Pathol.,* vol. 21, pp. 71-86, 2000.
20. P. J. van Diest, J. C. Fleege, and J. P. Baak, "Syntactic structure analysis in invasive breast cancer: Analysis of reproducibility, biologic background, and prognostic value," Human Pathol., vol. 23, pp. 876-83, 1992.
21. M. Brinkhuis, J. P. Baak, G. A. Meijer, P. J. van Diest, O. Mogensen, P. Bichel, and J. P. Neijt, "Value of quantitative pathological variables as prognostic factors in advanced ovarian carcinoma,"0.1 *Clin. Pathol.,* vol. 49, 142-148, 1996.
22. K Coleman, P. J. van Diest, J. P. Baak, and J. Mullaney, "Syntactic structure analysis in uveal melanomas," *Br. J. Opthalmol.,* vol. 78, pp. 871-874, 1994.
23. B. Weyn, G. van de Wouwer, S. Kumar-Singh, A. van Daele, P. Scheunders, E. van Marck, and W. Jacob, "Computer-assisted differential diagnosis of malignant mesothelioma based on syntactic structure analysis," *Cytometry,* vol. 35, pp. 23-29, 1999.
24. D. R. Cox, "Regression models and life tables (with discussion)," *J. Roy. Stat. Soc. B, vol.* 34, pp. 187-220, 1972.
25. Donovan M J, Hamann S, Clayton M, et al. A systems pathology approach for the prediction of prostate cancer progression after radical prostatectomy. *J Clin Oncol.* 2008 [in press].
26. Stephenson A J, Scardino P T, Eastham J A, et al. Postoperative nomogram predicting the 10-year probability of prostate cancer recurrence after radical prostatectomy. *J Clin Oncol.* 2005; 23(28):7005-7012.
27. Cuzick J, Fisher G, Kattan M W, et al. Long-term outcome among men with conservatively treated localised prostate cancer. *Br J Cancer.* 2006; 95(9):1186-1194.
28. Kattan M W, Cuzick J, Fisher G, et al. Nomogram incorporating PSA level to predict cancer-specific survival for men with clinically localized prostate cancer managed without curative intent. *Cancer.* 2008; 112(1): 69-74.
29. Tu Y K, Gunnell D, Gilthorpe M S. Simpson's Paradox, Lord's Paradox, and Suppression Effects are the same phenomenon—the reversal paradox. *Emerg Themes Epidemiol.* 2008; 5:2.
30. Bertrand P V, Holder R L. A quirk in multiple regression: the whole regression can be greater than the sum of its parts. *Statistician.* 1988; 37(4/5):371-374.
31. Julious S A, Mullee M A. Confounding and Simpson's paradox. *Bmj.* 1994; 309(6967):1480-1481.
32. Smaletz O, Scher H I, Small E J, et al. Nomogram for overall survival of patients with progressive metastatic prostate cancer after castration. *J Clin Oncol.* 2002; 20(19):3972-3982.
33. Gonzalgo M L, Bastian P J, Mangold L A, et al. Relationship between primary Gleason pattern on needle biopsy and clinicopathologic outcomes among men with Gleason score 7 adenocarcinoma of the prostate. *Urology.* 2006; 67(1):115-119.
34. Grober E D, Tsihlias J, Jewett M A, et al. Correlation of the primary Gleason pattern on prostate needle biopsy with clinico-pathological factors in Gleason 7 tumors. *Can J Urol.* 2004; 11(1):2157-2162.
35. Muntener M, Epstein J I, Hernandez D J, et al. Prognostic significance of Gleason score discrepancies between needle biopsy and radical prostatectomy. *Eur Urol.* 2008; 53(4):767-775; discussion 775-766.
36. Cordon-Cardo C, Kotsianti A, Verbel D A, et al. Improved prediction of prostate cancer recurrence through systems pathology. *J Clin Invest.* 2007; 117(7): 1876-1883.
37. Inoue T, Segawa T, Shiraishi T, et al. Androgen receptor, Ki67, and p53 expression in radical prostatectomy specimens predict treatment failure in Japanese population. *Urology.* 2005; 66(2):332-337.
38. Bettencourt M C, Bauer J J, Sesterhenn I A, Mostofi F K, McLeod D G, Moul J W. Ki-67 expression is a prognostic marker of prostate cancer recurrence after radical prostatectomy. *J. Urol.* 1996; 156(3):1064-1068.
39. Bubendorf L, Tapia C, Gasser T C, et al. *Ki*67 labeling index in core needle biopsies independently predicts tumor-specific survival in prostate cancer. Hum Pathol. 1998; 29(9):949-954.
40. Mucci N R, Rubin M A, Strawderman M S, Montie J E, Smith D C, Pienta K J. Expression of nuclear antigen Ki-67 in prostate cancer needle biopsy and radical prostatectomy specimens. *J Natl Cancer Inst.* 2000; 92(23): 1941-1942.

41. Pollack A, DeSilvio M, Khor L Y, et al. Ki-67 staining is a strong predictor of distant metastasis and mortality for men with prostate cancer treated with radiotherapy plus androgen deprivation: Radiation Therapy Oncology Group Trial 92-02. *J Clin Oncol.* 2004; 22(11):2133-2140.

42. Aaltomaa S, Karja V, Lipponen P, et al. Expression of Ki-67, cyclin D1 and apoptosis markers correlated with survival in prostate cancer patients treated by radiCal prostatectomy. Anticancer Res. 2006; 26(6C):4873-4878.

43. Morris D S, Tomlins S A, Montie J E, Chinnaiyan A M. The discovery and application of gene fusions in prostate cancer. *BJU Int.* 2008.

44. Kim J, Jia L, Stallcup M R, Coetzee G A. The role of protein kinase A pathway and cAMP responsive element-binding protein in androgen receptor-mediated transcription at the prostate-specific antigen locus. *J Mol Endocrinol.* 2005; 34(1):107-118.

45. Shimizu Y, Segawa T, Inoue T, et al. Increased Akt and phosphorylated Akt expression are associated with malignant biological features of prostate cancer in Japanese men. *BJU Int.* 2007; 100(3):685-690.

46. Wang Y, Kreisberg J I, Ghosh P M. Cross-talk between the androgen receptor and the phosphatidylinositol 3-kinase/Akt pathway in prostate cancer. *Curr Cancer Drug Targets.* 2007; 7(6):591-604.

47. McCall P, Gemmell L K, Mukherjee R, Bartlett J M, Edwards J. Phosphorylation of the androgen receptor is associated with reduced survival in hormone-refractory prostate cancer patients. *Br J Cancer.* 2008; 98(6):1094-1101.

48. de la Taille A, Katz A E, Bagiella E, et al. Microvessel density as a predictor of PSA recurrence after radical prostatectomy. A comparison of CD34 and CD31. *Am J Clin Pathol.* 2000; 113(4):555-562.

49. Halvorsen O J, Haukaas S, Hoisaeter P A, Akslen L A. Independent prognostic importance of microvessel density in clinically localized prostate cancer. Anticancer Res. 2000; 20(5C):3791-3799.

50. Khatami A, Pihl C G, Norrby K, Hugosson J, Damber J E. Is tumor vascularity in prostate core biopsies a predictor of PSA recurrence after radical prostatectomy? *Acta Oncol.* 2005; 44(4):362-368.

51. Cristianini N, Shawe-Taylor J. An introduction to support vector machines and other kernel-based learning methods. Cambridge, UK: Cambridge University Press; 2000.

52. Lee Y-J, Mangasarian O L, Wolberg W H. Breast cancer survival and chemotherapy: a support vector machine analysis. *DIMACS Series in Discrete Mathematics and Theoretical Computer Science.* 2000; 55:1-10.

53. van Diest P J, Fleege J C, Baak J P. Syntactic structure analysis in invasive breast cancer: analysis of reproducibility, biologic background, and prognostic value. Hum Pathol. 1992; 23(8):876-883.

54. Coleman K, van Diest P J, Baak J P, Mullaney J. Syntactic structure analysis in uveal melanomas. *Br J Opthalmol.* 1994; 78(11):871-874.

55. Jain, A. K., 1989. *Fundamentals of Digital Image Processing.* Englewood Cliffs, N.J.: Prentice Hall.

TABLE 1

Morphometric Features (e.g., measurable in images of H&E-stained tissue) In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| HE02_Art_Are_Mean | Color and morphometric features of identified artifacts |
| HE02_Art_Are_Std | |
| HE02_Art_Are_Tot | |
| HE02_Art_ElpFit_Mean | |
| HE02_Art_ElpFit_Std | |
| HE02_Art_LOW_Mean | |
| HE02_Art_LOW_Std | |
| HE02_Art_Num | |
| HE02_Art_OrgBri_Mean | |
| HE02_Art_OrgBri_Std | |
| HE02_Art_Ptr_Mean | |
| HE02_Art_Ptr_Std | |
| HE02_CluNuc_Are_Mean | Color and morphometric features of clustered nuclei |
| HE02_CluNuc_Are_Std | |
| HE02_CluNuc_Are_Tot | |
| HE02_CluNuc_Num | |
| HE02_Cra_Are_Mean | Color and morphometric features of luminal content |
| HE02_Cra_Are_Std | |
| HE02_Cra_Are_Tot | |
| HE02_Cra_Num | |
| HE02_Cra_OrgBlu_MeanMean | |
| HE02_Cra_OrgBlu_MeanStd | |
| HE02_Cra_OrgBri_Mean | |
| HE02_Cra_OrgBri_Std | |
| HE02_Cra_OrgGre_MeanMean | |
| HE02_Cra_OrgGre_MeanStd | |
| HE02_Cra_OrgH_Mean | |
| HE02_Cra_OrgH_Std | |
| HE02_Cra_OrgI_Mean | |
| HE02_Cra_OrgI_Std | |
| HE02_Cra_OrgQ_Mean | |
| HE02_Cra_OrgQ_Std | |
| HE02_Cra_OrgRed_MeanMean | |
| HE02_Cra_OrgRed_MeanStd | |
| HE02_Cra_OrgS_Mean | |
| HE02_Cra_OrgS_Std | |
| HE02_Cra_OrgV_Mean | |
| HE02_Cra_OrgV_Std | |
| HE02_Cra_OrgY_Mean | |
| HE02_Cra_OrgY_Std | |
| HE02_CytOGU_Are_Tot | Morphometric and color features of cytoplasm within and outside of gland units. |
| HE02_CytOutGU_Are_Tot | |
| HE02_CytOutGU_OrgBlu_MeanMean | |
| HE02_CytOutGU_OrgBlu_MeanStd | |
| HE02_CytOutGU_OrgGre_MeanMean | |
| HE02_CytOutGU_OrgGre_MeanStd | |
| HE02_CytOutGU_OrgRed_MeanMean | |
| HE02_CytOutGU_OrgRed_MeanStd | |
| HE02_CytWIGU_Are_Tot | |
| HE02_CytWinGU_Are_Tot | |
| HE02_CytWinGU_OrgBlu_MeanMean | |
| HE02_CytWinGU_OrgBlu_MeanStd | |
| HE02_CytWinGU_OrgGre_MeanMean | |
| HE02_CytWinGU_OrgGre_MeanStd | |
| HE02_CytWinGU_OrgRed_MeanMean | |
| HE02_CytWinGU_OrgRed_MeanStd | |
| HE02_Cyt_Are_Mean | Morphometric and color properties of cytoplasm |
| HE02_Cyt_Are_Std | |
| HE02_Cyt_Are_Tot | |
| HE02_Cyt_Num | |
| HE02_Cyt_OrgBlu_MeanMean | |
| HE02_Cyt_OrgBlu_MeanStd | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE02_Cyt_OrgBri_Mean | |
| HE02_Cyt_OrgBri_Std | |
| HE02_Cyt_OrgGre_MeanMean | |
| HE02_Cyt_OrgGre_MeanStd | |
| HE02_Cyt_OrgH_Mean | |
| HE02_Cyt_OrgH_Std | |
| HE02_Cyt_OrgI_Mean | |
| HE02_Cyt_OrgI_Std | |
| HE02_Cyt_OrgQ_Mean | |
| HE02_Cyt_OrgQ_Std | |
| HE02_Cyt_OrgRed_MeanMean | |
| HE02_Cyt_OrgRed_MeanStd | |
| HE02_Cyt_OrgS_Mean | |
| HE02_Cyt_OrgS_Std | |
| HE02_Cyt_OrgV_Mean | |
| HE02_Cyt_OrgV_Std | |
| HE02_Cyt_OrgY_Mean | |
| HE02_Cyt_OrgY_Std | |
| HE02_DStr_Are_Mean | Morphometric and color properties of dark stroma |
| HE02_DStr_Are_Std | |
| HE02_DStr_Are_Tot | |
| HE02_DStr_Num | |
| HE02_DStr_OrgBlu_MeanMean | |
| HE02_DStr_OrgBlu_MeanStd | |
| HE02_DStr_OrgBri_Mean | |
| HE02_DStr_OrgBri_Std | |
| HE02_DStr_OrgGre_MeanMean | |
| HE02_DStr_OrgGre_MeanStd | |
| HE02_DStr_OrgH_Mean | |
| HE02_DStr_OrgH_Std | |
| HE02_DStr_OrgI_Mean | |
| HE02_DStr_OrgI_Std | |
| HE02_DStr_OrgQ_Mean | |
| HE02_DStr_OrgQ_Std | |
| HE02_DStr_OrgRed_MeanMean | |
| HE02_DStr_OrgRed_MeanStd | |
| HE02_DStr_OrgS_Mean | |
| HE02_DStr_OrgS_Std | |
| HE02_DStr_OrgV_Mean | |
| HE02_DStr_OrgV_Std | |
| HE02_DStr_OrgY_Mean | |
| HE02_DStr_OrgY_Std | |
| HE02_DarNucBin0_1_Are_Mean | Morphometric properties of dark nuclei divided into bins, and also of different combinations of those bins. |
| HE02_DarNucBin0_1_Are_Tot | |
| HE02_DarNucBin0_1_Num | |
| HE02_DarNucBin0_2_Are_Mean | |
| HE02_DarNucBin0_2_Are_Tot | |
| HE02_DarNucBin0_2_Num | |
| HE02_DarNucBin0_3_Are_Mean | |
| HE02_DarNucBin0_3_Are_Tot | |
| HE02_DarNucBin0_3_Num | |
| HE02_DarNucBin0_4_Are_Mean | |
| HE02_DarNucBin0_4_Are_Tot | |
| HE02_DarNucBin0_4_Num | |
| HE02_DarNucBin0_5_Are_Mean | |
| HE02_DarNucBin0_5_Are_Tot | |
| HE02_DarNucBin0_5_Num | |
| HE02_DarNucBin0_6_Are_Mean | |
| HE02_DarNucBin0_6_Are_Tot | |
| HE02_DarNucBin0_6_Num | |
| HE02_DarNucBin0_7_Are_Mean | |
| HE02_DarNucBin0_7_Are_Tot | |
| HE02_DarNucBin0_7_Num | |
| HE02_DarNucBin0_8_Are_Mean | |
| HE02_DarNucBin0_8_Are_Tot | |
| HE02_DarNucBin0_8_Num | |
| HE02_DarNucBin0_Are_Mean | |
| HE02_DarNucBin0_Are_Tot | |
| HE02_DarNucBin0_Num | |
| HE02_DarNucBin1_2_Are_Mean | |
| HE02_DarNucBin1_2_Are_Tot | |
| HE02_DarNucBin1_2_Num | |
| HE02_DarNucBin1_3_Are_Mean | |
| HE02_DarNucBin1_3_Are_Tot | |
| HE02_DarNucBin1_3_Num | |
| HE02_DarNucBin1_4_Are_Mean | |
| HE02_DarNucBin1_4_Are_Tot | |
| HE02_DarNucBin1_4_Num | |
| HE02_DarNucBin1_5_Are_Mean | |
| HE02_DarNucBin1_5_Are_Tot | |
| HE02_DarNucBin1_5_Num | |
| HE02_DarNucBin1_6_Are_Mean | |
| HE02_DarNucBin1_6_Are_Tot | |
| HE02_DarNucBin1_6_Num | |
| HE02_DarNucBin1_7_Are_Mean | |
| HE02_DarNucBin1_7_Are_Tot | |
| HE02_DarNucBin1_7_Num | |
| HE02_DarNucBin1_8_Are_Mean | |
| HE02_DarNucBin1_8_Are_Tot | |
| HE02_DarNucBin1_8_Num | |
| HE02_DarNucBin1_Are_Mean | |
| HE02_DarNucBin1_Are_Tot | |
| HE02_DarNucBin1_Num | |
| HE02_DarNucBin2_3_Are_Mean | |
| HE02_DarNucBin2_3_Are_Tot | |
| HE02_DarNucBin2_3_Num | |
| HE02_DarNucBin2_4_Are_Mean | |
| HE02_DarNucBin2_4_Are_Tot | |
| HE02_DarNucBin2_4_Num | |
| HE02_DarNucBin2_5_Are_Mean | |
| HE02_DarNucBin2_5_Are_Tot | |
| HE02_DarNucBin2_5_Num | |
| HE02_DarNucBin2_6_Are_Mean | |
| HE02_DarNucBin2_6_Are_Tot | |
| HE02_DarNucBin2_6_Num | |
| HE02_DarNucBin2_7_Are_Mean | |
| HE02_DarNucBin2_7_Are_Tot | |
| HE02_DarNucBin2_7_Num | |
| HE02_DarNucBin2_8_Are_Mean | |
| HE02_DarNucBin2_8_Are_Tot | |
| HE02_DarNucBin2_8_Num | |
| HE02_DarNucBin2_Are_Mean | |
| HE02_DarNucBin2_Are_Tot | |
| HE02_DarNucBin2_Num | |
| HE02_DarNucBin3_4_Are_Mean | |
| HE02_DarNucBin3_4_Are_Tot | |
| HE02_DarNucBin3_4_Num | |
| HE02_DarNucBin3_5_Are_Mean | |
| HE02_DarNucBin3_5_Are_Tot | |
| HE02_DarNucBin3_5_Num | |
| HE02_DarNucBin3_6_Are_Mean | |
| HE02_DarNucBin3_6_Are_Tot | |
| HE02_DarNucBin3_6_Num | |
| HE02_DarNucBin3_7_Are_Mean | |
| HE02_DarNucBin3_7_Are_Tot | |
| HE02_DarNucBin3_7_Num | |
| HE02_DarNucBin3_8_Are_Mean | |
| HE02_DarNucBin3_8_Are_Tot | |
| HE02_DarNucBin3_8_Num | |
| HE02_DarNucBin3_Are_Mean | |
| HE02_DarNucBin3_Are_Tot | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| HE02_DarNucBin3_Num | |
| HE02_DarNucBin4_5_Are_Mean | |
| HE02_DarNucBin4_5_Are_Tot | |
| HE02_DarNucBin4_5_Num | |
| HE02_DarNucBin4_6_Are_Mean | |
| HE02_DarNucBin4_6_Are_Tot | |
| HE02_DarNucBin4_6_Num | |
| HE02_DarNucBin4_7_Are_Mean | |
| HE02_DarNucBin4_7_Are_Tot | |
| HE02_DarNucBin4_7_Num | |
| HE02_DarNucBin4_8_Are_Mean | |
| HE02_DarNucBin4_8_Are_Tot | |
| HE02_DarNucBin4_8_Num | |
| HE02_DarNucBin4_Are_Mean | |
| HE02_DarNucBin4_Are_Tot | |
| HE02_DarNucBin4_Num | |
| HE02_DarNucBin5_6_Are_Mean | |
| HE02_DarNucBin5_6_Are_Tot | |
| HE02_DarNucBin5_6_Num | |
| HE02_DarNucBin5_7_Are_Mean | |
| HE02_DarNucBin5_7_Are_Tot | |
| HE02_DarNucBin5_7_Num | |
| HE02_DarNucBin5_8_Are_Mean | |
| HE02_DarNucBin5_8_Are_Tot | |
| HE02_DarNucBin5_8_Num | |
| HE02_DarNucBin5_Are_Mean | |
| HE02_DarNucBin5_Are_Tot | |
| HE02_DarNucBin5_Num | |
| HE02_DarNucBin6_7_Are_Mean | |
| HE02_DarNucBin6_7_Are_Tot | |
| HE02_DarNucBin6_7_Num | |
| HE02_DarNucBin6_8_Are_Mean | |
| HE02_DarNucBin6_8_Are_Tot | |
| HE02_DarNucBin6_8_Num | |
| HE02_DarNucBin6_Are_Mean | |
| HE02_DarNucBin6_Are_Tot | |
| HE02_DarNucBin6_Num | |
| HE02_DarNucBin7_8_Are_Mean | |
| HE02_DarNucBin7_8_Are_Tot | |
| HE02_DarNucBin7_8_Num | |
| HE02_DarNucBin7_Are_Mean | |
| HE02_DarNucBin7_Are_Tot | |
| HE02_DarNucBin7_Num | |
| HE02_DarNucBin8_Are_Mean | |
| HE02_DarNucBin8_Are_Tot | |
| HE02_DarNucBin8_Num | |
| HE02_ENOutGU_Are_Mean | Morphometric and color properties of epithelial nuclei within and outside of gland units. |
| HE02_ENOutGU_Are_StdMean | |
| HE02_ENOutGU_Are_Tot | |
| HE02_ENOutGU_OrgBlu_MeanMean | |
| HE02_ENOutGU_OrgBlu_MeanStd | |
| HE02_ENOutGU_OrgGre_MeanMean | |
| HE02_ENOutGU_OrgGre_MeanStd | |
| HE02_ENOutGU_OrgRed_MeanMean | |
| HE02_ENOutGU_OrgRed_MeanStd | |
| HE02_ENWinGU_Are_Mean | |
| HE02_ENWinGU_Are_StdMean | |
| HE02_ENWinGU_Are_Tot | |
| HE02_ENWinGU_OrgBlu_MeanMean | |
| HE02_ENWinGU_OrgBlu_MeanStd | |
| HE02_ENWinGU_OrgGre_MeanMean | |
| HE02_ENWinGU_OrgGre_MeanStd | |
| HE02_ENWinGU_OrgRed_MeanMean | |
| HE02_ENWinGU_OrgRed_MeanStd | |
| HE02_EpiCluNuc_Are_Mean | Morphometric features of clustered epithelial nuclei |
| HE02_EpiCluNuc_Are_Std | |
| HE02_EpiCluNuc_Are_Tot | |
| HE02_EpiCluNuc_Num | |
| HE02_EpiIsoNuc_Are_Mean | Morphometric features of isolated epithelial nuclei |
| HE02_EpiIsoNuc_Are_Median | |
| HE02_EpiIsoNuc_Are_Std | |
| HE02_EpiIsoNuc_Are_Tot | |
| HE02_EpiIsoNuc_Num | |
| HE02_EpiNucAt0Dia_Are_Tot | Area of epithelial nuclei certain predefined pixels away from lumens |
| HE02_EpiNucAt1Dia_Are_Tot | |
| HE02_EpiNucAt2Dia_Are_Tot | |
| HE02_EpiNucAt3Dia_Are_Tot | |
| HE02_EpiNucAt4Dia_Are_Tot | |
| HE02_EpiNucAt5Dia_Are_Tot | |
| HE02_EpiNucDen01_Are_Mean | Color and morphometric features of epithelial nuclei divided into bins based on nuclear density/proximity to neighbors. |
| HE02_EpiNucDen01_Are_Std | |
| HE02_EpiNucDen01_Are_Tot | |
| HE02_EpiNucDen01_Num | |
| HE02_EpiNucDen01_OrgBri_Mean | |
| HE02_EpiNucDen01_OrgBri_Std | |
| HE02_EpiNucDen02_Are_Mean | |
| HE02_EpiNucDen02_Are_Std | |
| HE02_EpiNucDen02_Are_Tot | |
| HE02_EpiNucDen02_Num | |
| HE02_EpiNucDen02_OrgBri_Mean | |
| HE02_EpiNucDen02_OrgBri_Std | |
| HE02_EpiNucDen03_Are_Mean | |
| HE02_EpiNucDen03_Are_Std | |
| HE02_EpiNucDen03_Are_Tot | |
| HE02_EpiNucDen03_Num | |
| HE02_EpiNucDen03_OrgBri_Mean | |
| HE02_EpiNucDen03_OrgBri_Std | |
| HE02_EpiNucDen04_Are_Mean | |
| HE02_EpiNucDen04_Are_Std | |
| HE02_EpiNucDen04_Are_Tot | |
| HE02_EpiNucDen04_Num | |
| HE02_EpiNucDen04_OrgBri_Mean | |
| HE02_EpiNucDen04_OrgBri_Std | |
| HE02_EpiNucDen05_Are_Mean | |
| HE02_EpiNucDen05_Are_Std | |
| HE02_EpiNucDen05_Are_Tot | |
| HE02_EpiNucDen05_Num | |
| HE02_EpiNucDen05_OrgBri_Mean | |
| HE02_EpiNucDen05_OrgBri_Std | |
| HE02_EpiNucDen06_Are_Mean | |
| HE02_EpiNucDen06_Are_Std | |
| HE02_EpiNucDen06_Are_Tot | |
| HE02_EpiNucDen06_Num | |
| HE02_EpiNucDen06_OrgBri_Mean | |
| HE02_EpiNucDen06_OrgBri_Std | |
| HE02_EpiNucDen07_Are_Mean | |
| HE02_EpiNucDen07_Are_Std | |
| HE02_EpiNucDen07_Are_Tot | |
| HE02_EpiNucDen07_Num | |
| HE02_EpiNucDen07_OrgBri_Mean | |
| HE02_EpiNucDen07_OrgBri_Std | |
| HE02_EpiNucDen08_Are_Mean | |
| HE02_EpiNucDen08_Are_Std | |
| HE02_EpiNucDen08_Are_Tot | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| HE02_EpiNucDen08_Num | |
| HE02_EpiNucDen08_OrgBri_Mean | |
| HE02_EpiNucDen08_OrgBri_Std | |
| HE02_EpiNucDen09_Are_Mean | |
| HE02_EpiNucDen09_Are_Std | |
| HE02_EpiNucDen09_Are_Tot | |
| HE02_EpiNucDen09_Num | |
| HE02_EpiNucDen09_OrgBri_Mean | |
| HE02_EpiNucDen09_OrgBri_Std | |
| HE02_EpiNucDen10_Are_Mean | |
| HE02_EpiNucDen10_Are_Std | |
| HE02_EpiNucDen10_Are_Tot | |
| HE02_EpiNucDen10_Num | |
| HE02_EpiNucDen10_OrgBri_Mean | |
| HE02_EpiNucDen10_OrgBri_Std | |
| HE02_EpiNucOGU_Are_Mean | Average area of epithelial nuclei outside of gland units |
| HE02_EpiNucOGU_Are_Tot | Total area of epithelial nuclei outside of gland units |
| HE02_EpiNucSizBin0_1_Are_Mean | Morphometric and color features of different combinations of bins where epithelial nuclei have been binned depending on size. |
| HE02_EpiNucSizBin0_1_Are_Tot | |
| HE02_EpiNucSizBin0_1_Blu_Mean | |
| HE02_EpiNucSizBin0_1_Blu_MeanStd | |
| HE02_EpiNucSizBin0_1_Bri_Mean | |
| HE02_EpiNucSizBin0_1_Gre_Mean | |
| HE02_EpiNucSizBin0_1_Gre_MeanStd | |
| HE02_EpiNucSizBin0_1_Num | |
| HE02_EpiNucSizBin0_1_Red_Mean | |
| HE02_EpiNucSizBin0_1_Red_MeanStd | |
| HE02_EpiNucSizBin0_2_Are_Mean | |
| HE02_EpiNucSizBin0_2_Are_Tot | |
| HE02_EpiNucSizBin0_2_Blu_Mean | |
| HE02_EpiNucSizBin0_2_Blu_MeanStd | |
| HE02_EpiNucSizBin0_2_Bri_Mean | |
| HE02_EpiNucSizBin0_2_Gre_Mean | |
| HE02_EpiNucSizBin0_2_Gre_MeanStd | |
| HE02_EpiNucSizBin0_2_Num | |
| HE02_EpiNucSizBin0_2_Red_Mean | |
| HE02_EpiNucSizBin0_2_Red_MeanStd | |
| HE02_EpiNucSizBin0_3_Are_Mean | |
| HE02_EpiNucSizBin0_3_Are_Tot | |
| HE02_EpiNucSizBin0_3_Blu_Mean | |
| HE02_EpiNucSizBin0_3_Blu_MeanStd | |
| HE02_EpiNucSizBin0_3_Bri_Mean | |
| HE02_EpiNucSizBin0_3_Gre_Mean | |
| HE02_EpiNucSizBin0_3_Gre_MeanStd | |
| HE02_EpiNucSizBin0_3_Num | |
| HE02_EpiNucSizBin0_3_Red_Mean | |
| HE02_EpiNucSizBin0_3_Red_MeanStd | |
| HE02_EpiNucSizBin0_4_Are_Mean | |
| HE02_EpiNucSizBin0_4_Are_Tot | |
| HE02_EpiNucSizBin0_4_Blu_Mean | |
| HE02_EpiNucSizBin0_4_Blu_MeanStd | |
| HE02_EpiNucSizBin0_4_Bri_Mean | |
| HE02_EpiNucSizBin0_4_Gre_Mean | |
| HE02_EpiNucSizBin0_4_Gre_MeanStd | |
| HE02_EpiNucSizBin0_4_Num | |
| HE02_EpiNucSizBin0_4_Red_Mean | |
| HE02_EpiNucSizBin0_4_Red_MeanStd | |
| HE02_EpiNucSizBin0_5_Are_Mean | |
| HE02_EpiNucSizBin0_5_Are_Tot | |
| HE02_EpiNucSizBin0_5_Blu_Mean | |
| HE02_EpiNucSizBin0_5_Blu_MeanStd | |
| HE02_EpiNucSizBin0_5_Bri_Mean | |
| HE02_EpiNucSizBin0_5_Gre_Mean | |
| HE02_EpiNucSizBin0_5_Gre_MeanStd | |
| HE02_EpiNucSizBin0_5_Num | |
| HE02_EpiNucSizBin0_5_Red_Mean | |
| HE02_EpiNucSizBin0_5_Red_MeanStd | |
| HE02_EpiNucSizBin0_6_Are_Mean | |
| HE02_EpiNucSizBin0_6_Are_Tot | |
| HE02_EpiNucSizBin0_6_Blu_Mean | |
| HE02_EpiNucSizBin0_6_Blu_MeanStd | |
| HE02_EpiNucSizBin0_6_Bri_Mean | |
| HE02_EpiNucSizBin0_6_Gre_Mean | |
| HE02_EpiNucSizBin0_6_Gre_MeanStd | |
| HE02_EpiNucSizBin0_6_Num | |
| HE02_EpiNucSizBin0_6_Red_Mean | |
| HE02_EpiNucSizBin0_6_Red_MeanStd | |
| HE02_EpiNucSizBin0_7_Are_Mean | |
| HE02_EpiNucSizBin0_7_Are_Tot | |
| HE02_EpiNucSizBin0_7_Blu_Mean | |
| HE02_EpiNucSizBin0_7_Blu_MeanStd | |
| HE02_EpiNucSizBin0_7_Bri_Mean | |
| HE02_EpiNucSizBin0_7_Gre_Mean | |
| HE02_EpiNucSizBin0_7_Gre_MeanStd | |
| HE02_EpiNucSizBin0_7_Num | |
| HE02_EpiNucSizBin0_7_Red_Mean | |
| HE02_EpiNucSizBin0_7_Red_MeanStd | |
| HE02_EpiNucSizBin0_8_Are_Mean | |
| HE02_EpiNucSizBin0_8_Are_Tot | |
| HE02_EpiNucSizBin0_8_Blu_Mean | |
| HE02_EpiNucSizBin0_8_Blu_MeanStd | |
| HE02_EpiNucSizBin0_8_Bri_Mean | |
| HE02_EpiNucSizBin0_8_Gre_Mean | |
| HE02_EpiNucSizBin0_8_Gre_MeanStd | |
| HE02_EpiNucSizBin0_8_Num | |
| HE02_EpiNucSizBin0_8_Red_Mean | |
| HE02_EpiNucSizBin0_8_Red_MeanStd | |
| HE02_EpiNucSizBin0_Are_Mean | |
| HE02_EpiNucSizBin0_Are_Tot | |
| HE02_EpiNucSizBin0_Blu_Mean | |
| HE02_EpiNucSizBin0_Blu_MeanStd | |
| HE02_EpiNucSizBin0_Bri_Mean | |
| HE02_EpiNucSizBin0_Gre_Mean | |
| HE02_EpiNucSizBin0_Gre_MeanStd | |
| HE02_EpiNucSizBin0_Num | |
| HE02_EpiNucSizBin0_Red_Mean | |
| HE02_EpiNucSizBin0_Red_MeanStd | |
| HE02_EpiNucSizBin1_2_Are_Mean | |
| HE02_EpiNucSizBin1_2_Are_Tot | |
| HE02_EpiNucSizBin1_2_Blu_Mean | |
| HE02_EpiNucSizBin1_2_Blu_MeanStd | |
| HE02_EpiNucSizBin1_2_Bri_Mean | |
| HE02_EpiNucSizBin1_2_Gre_Mean | |
| HE02_EpiNucSizBin1_2_Gre_MeanStd | |
| HE02_EpiNucSizBin1_2_Num | |
| HE02_EpiNucSizBin1_2_Red_Mean | |
| HE02_EpiNucSizBin1_2_Red_MeanStd | |
| HE02_EpiNucSizBin1_3_Are_Mean | |
| HE02_EpiNucSizBin1_3_Are_Tot | |
| HE02_EpiNucSizBin1_3_Blu_Mean | |
| HE02_EpiNucSizBin1_3_Blu_MeanStd | |
| HE02_EpiNucSizBin1_3_Bri_Mean | |
| HE02_EpiNucSizBin1_3_Gre_Mean | |
| HE02_EpiNucSizBin1_3_Gre_MeanStd | |
| HE02_EpiNucSizBin1_3_Num | |
| HE02_EpiNucSizBin1_3_Red_Mean | |
| HE02_EpiNucSizBin1_3_Red_MeanStd | |
| HE02_EpiNucSizBin1_4_Are_Mean | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| HE02_EpiNucSizBin1_4_Are_Tot | |
| HE02_EpiNucSizBin1_4_Blu_Mean | |
| HE02_EpiNucSizBin1_4_Blu_MeanStd | |
| HE02_EpiNucSizBin1_4_Bri_Mean | |
| HE02_EpiNucSizBin1_4_Gre_Mean | |
| HE02_EpiNucSizBin1_4_Gre_MeanStd | |
| HE02_EpiNucSizBin1_4_Num | |
| HE02_EpiNucSizBin1_4_Red_Mean | |
| HE02_EpiNucSizBin1_4_Red_MeanStd | |
| HE02_EpiNucSizBin1_5_Are_Mean | |
| HE02_EpiNucSizBin1_5_Are_Tot | |
| HE02_EpiNucSizBin1_5_Blu_Mean | |
| HE02_EpiNucSizBin1_5_Blu_MeanStd | |
| HE02_EpiNucSizBin1_5_Bri_Mean | |
| HE02_EpiNucSizBin1_5_Gre_Mean | |
| HE02_EpiNucSizBin1_5_Gre_MeanStd | |
| HE02_EpiNucSizBin1_5_Num | |
| HE02_EpiNucSizBin1_5_Red_Mean | |
| HE02_EpiNucSizBin1_5_Red_MeanStd | |
| HE02_EpiNucSizBin1_6_Are_Mean | |
| HE02_EpiNucSizBin1_6_Are_Tot | |
| HE02_EpiNucSizBin1_6_Blu_Mean | |
| HE02_EpiNucSizBin1_6_Blu_MeanStd | |
| HE02_EpiNucSizBin1_6_Bri_Mean | |
| HE02_EpiNucSizBin1_6_Gre_Mean | |
| HE02_EpiNucSizBin1_6_Gre_MeanStd | |
| HE02_EpiNucSizBin1_6_Num | |
| HE02_EpiNucSizBin1_6_Red_Mean | |
| HE02_EpiNucSizBin1_6_Red_MeanStd | |
| HE02_EpiNucSizBin1_7_Are_Mean | |
| HE02_EpiNucSizBin1_7_Are_Tot | |
| HE02_EpiNucSizBin1_7_Blu_Mean | |
| HE02_EpiNucSizBin1_7_Blu_MeanStd | |
| HE02_EpiNucSizBin1_7_Bri_Mean | |
| HE02_EpiNucSizBin1_7_Gre_Mean | |
| HE02_EpiNucSizBin1_7_Gre_MeanStd | |
| HE02_EpiNucSizBin1_7_Num | |
| HE02_EpiNucSizBin1_7_Red_Mean | |
| HE02_EpiNucSizBin1_7_Red_MeanStd | |
| HE02_EpiNucSizBin1_8_Are_Mean | |
| HE02_EpiNucSizBin1_8_Are_Tot | |
| HE02_EpiNucSizBin1_8_Blu_Mean | |
| HE02_EpiNucSizBin1_8_Blu_MeanStd | |
| HE02_EpiNucSizBin1_8_Bri_Mean | |
| HE02_EpiNucSizBin1_8_Gre_Mean | |
| HE02_EpiNucSizBin1_8_Gre_MeanStd | |
| HE02_EpiNucSizBin1_8_Num | |
| HE02_EpiNucSizBin1_8_Red_Mean | |
| HE02_EpiNucSizBin1_8_Red_MeanStd | |
| HE02_EpiNucSizBin1_Are_Mean | |
| HE02_EpiNucSizBin1_Are_Tot | |
| HE02_EpiNucSizBin1_Blu_Mean | |
| HE02_EpiNucSizBin1_Blu_MeanStd | |
| HE02_EpiNucSizBin1_Bri_Mean | |
| HE02_EpiNucSizBin1_Gre_Mean | |
| HE02_EpiNucSizBin1_Gre_MeanStd | |
| HE02_EpiNucSizBin1_Num | |
| HE02_EpiNucSizBin1_Red_Mean | |
| HE02_EpiNucSizBin1_Red_MeanStd | |
| HE02_EpiNucSizBin2_3_Are_Mean | |
| HE02_EpiNucSizBin2_3_Are_Tot | |
| HE02_EpiNucSizBin2_3_Blu_Mean | |
| HE02_EpiNucSizBin2_3_Blu_MeanStd | |
| HE02_EpiNucSizBin2_3_Bri_Mean | |
| HE02_EpiNucSizBin2_3_Gre_Mean | |
| HE02_EpiNucSizBin2_3_Gre_MeanStd | |
| HE02_EpiNucSizBin2_3_Num | |
| HE02_EpiNucSizBin2_3_Red_Mean | |
| HE02_EpiNucSizBin2_3_Red_MeanStd | |
| HE02_EpiNucSizBin2_4_Are_Mean | |
| HE02_EpiNucSizBin2_4_Are_Tot | |
| HE02_EpiNucSizBin2_4_Blu_Mean | |
| HE02_EpiNucSizBin2_4_Blu_MeanStd | |
| HE02_EpiNucSizBin2_4_Bri_Mean | |
| HE02_EpiNucSizBin2_4_Gre_Mean | |
| HE02_EpiNucSizBin2_4_Gre_MeanStd | |
| HE02_EpiNucSizBin2_4_Num | |
| HE02_EpiNucSizBin2_4_Red_Mean | |
| HE02_EpiNucSizBin2_4_Red_MeanStd | |
| HE02_EpiNucSizBin2_5_Are_Mean | |
| HE02_EpiNucSizBin2_5_Are_Tot | |
| HE02_EpiNucSizBin2_5_Blu_Mean | |
| HE02_EpiNucSizBin2_5_Blu_MeanStd | |
| HE02_EpiNucSizBin2_5_Bri_Mean | |
| HE02_EpiNucSizBin2_5_Gre_Mean | |
| HE02_EpiNucSizBin2_5_Gre_MeanStd | |
| HE02_EpiNucSizBin2_5_Num | |
| HE02_EpiNucSizBin2_5_Red_Mean | |
| HE02_EpiNucSizBin2_5_Red_MeanStd | |
| HE02_EpiNucSizBin2_6_Are_Mean | |
| HE02_EpiNucSizBin2_6_Are_Tot | |
| HE02_EpiNucSizBin2_6_Blu_Mean | |
| HE02_EpiNucSizBin2_6_Blu_MeanStd | |
| HE02_EpiNucSizBin2_6_Bri_Mean | |
| HE02_EpiNucSizBin2_6_Gre_Mean | |
| HE02_EpiNucSizBin2_6_Gre_MeanStd | |
| HE02_EpiNucSizBin2_6_Num | |
| HE02_EpiNucSizBin2_6_Red_Mean | |
| HE02_EpiNucSizBin2_6_Red_MeanStd | |
| HE02_EpiNucSizBin2_7_Are_Mean | |
| HE02_EpiNucSizBin2_7_Are_Tot | |
| HE02_EpiNucSizBin2_7_Blu_Mean | |
| HE02_EpiNucSizBin2_7_Blu_MeanStd | |
| HE02_EpiNucSizBin2_7_Bri_Mean | |
| HE02_EpiNucSizBin2_7_Gre_Mean | |
| HE02_EpiNucSizBin2_7_Gre_MeanStd | |
| HE02_EpiNucSizBin2_7_Num | |
| HE02_EpiNucSizBin2_7_Red_Mean | |
| HE02_EpiNucSizBin2_7_Red_MeanStd | |
| HE02_EpiNucSizBin2_8_Are_Mean | |
| HE02_EpiNucSizBin2_8_Are_Tot | |
| HE02_EpiNucSizBin2_8_Blu_Mean | |
| HE02_EpiNucSizBin2_8_Blu_MeanStd | |
| HE02_EpiNucSizBin2_8_Bri_Mean | |
| HE02_EpiNucSizBin2_8_Gre_Mean | |
| HE02_EpiNucSizBin2_8_Gre_MeanStd | |
| HE02_EpiNucSizBin2_8_Num | |
| HE02_EpiNucSizBin2_8_Red_Mean | |
| HE02_EpiNucSizBin2_8_Red_MeanStd | |
| HE02_EpiNucSizBin2_Are_Mean | |
| HE02_EpiNucSizBin2_Are_Tot | |
| HE02_EpiNucSizBin2_Blu_Mean | |
| HE02_EpiNucSizBin2_Blu_MeanStd | |
| HE02_EpiNucSizBin2_Bri_Mean | |
| HE02_EpiNucSizBin2_Gre_Mean | |
| HE02_EpiNucSizBin2_Gre_MeanStd | |
| HE02_EpiNucSizBin2_Num | |
| HE02_EpiNucSizBin2_Red_Mean | |
| HE02_EpiNucSizBin2_Red_MeanStd | |
| HE02_EpiNucSizBin3_4_Are_Mean | |
| HE02_EpiNucSizBin3_4_Are_Tot | |
| HE02_EpiNucSizBin3_4_Blu_Mean | |
| HE02_EpiNucSizBin3_4_Blu_MeanStd | |
| HE02_EpiNucSizBin3_4_Bri_Mean | |
| HE02_EpiNucSizBin3_4_Gre_Mean | |
| HE02_EpiNucSizBin3_4_Gre_MeanStd | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
| --- | --- |
| HE02_EpiNucSizBin3_4_Num | |
| HE02_EpiNucSizBin3_4_Red_Mean | |
| HE02_EpiNucSizBin3_4_Red_MeanStd | |
| HE02_EpiNucSizBin3_5_Are_Mean | |
| HE02_EpiNucSizBin3_5_Are_Tot | |
| HE02_EpiNucSizBin3_5_Blu_Mean | |
| HE02_EpiNucSizBin3_5_Blu_MeanStd | |
| HE02_EpiNucSizBin3_5_Bri_Mean | |
| HE02_EpiNucSizBin3_5_Gre_Mean | |
| HE02_EpiNucSizBin3_5_Gre_MeanStd | |
| HE02_EpiNucSizBin3_5_Num | |
| HE02_EpiNucSizBin3_5_Red_Mean | |
| HE02_EpiNucSizBin3_5_Red_MeanStd | |
| HE02_EpiNucSizBin3_6_Are_Mean | |
| HE02_EpiNucSizBin3_6_Are_Tot | |
| HE02_EpiNucSizBin3_6_Blu_Mean | |
| HE02_EpiNucSizBin3_6_Blu_MeanStd | |
| HE02_EpiNucSizBin3_6_Bri_Mean | |
| HE02_EpiNucSizBin3_6_Gre_Mean | |
| HE02_EpiNucSizBin3_6_Gre_MeanStd | |
| HE02_EpiNucSizBin3_6_Num | |
| HE02_EpiNucSizBin3_6_Red_Mean | |
| HE02_EpiNucSizBin3_6_Red_MeanStd | |
| HE02_EpiNucSizBin3_7_Are_Mean | |
| HE02_EpiNucSizBin3_7_Are_Tot | |
| HE02_EpiNucSizBin3_7_Blu_Mean | |
| HE02_EpiNucSizBin3_7_Blu_MeanStd | |
| HE02_EpiNucSizBin3_7_Bri_Mean | |
| HE02_EpiNucSizBin3_7_Gre_Mean | |
| HE02_EpiNucSizBin3_7_Gre_MeanStd | |
| HE02_EpiNucSizBin3_7_Num | |
| HE02_EpiNucSizBin3_7_Red_Mean | |
| HE02_EpiNucSizBin3_7_Red_MeanStd | |
| HE02_EpiNucSizBin3_8_Are_Mean | |
| HE02_EpiNucSizBin3_8_Are_Tot | |
| HE02_EpiNucSizBin3_8_Blu_Mean | |
| HE02_EpiNucSizBin3_8_Blu_MeanStd | |
| HE02_EpiNucSizBin3_8_Bri_Mean | |
| HE02_EpiNucSizBin3_8_Gre_Mean | |
| HE02_EpiNucSizBin3_8_Gre_MeanStd | |
| HE02_EpiNucSizBin3_8_Num | |
| HE02_EpiNucSizBin3_8_Red_Mean | |
| HE02_EpiNucSizBin3_8_Red_MeanStd | |
| HE02_EpiNucSizBin3_Are_Mean | |
| HE02_EpiNucSizBin3_Are_Tot | |
| HE02_EpiNucSizBin3_Blu_Mean | |
| HE02_EpiNucSizBin3_Blu_MeanStd | |
| HE02_EpiNucSizBin3_Bri_Mean | |
| HE02_EpiNucSizBin3_Gre_Mean | |
| HE02_EpiNucSizBin3_Gre_MeanStd | |
| HE02_EpiNucSizBin3_Num | |
| HE02_EpiNucSizBin3_Red_Mean | |
| HE02_EpiNucSizBin3_Red_MeanStd | |
| HE02_EpiNucSizBin4_5_Are_Mean | |
| HE02_EpiNucSizBin4_5_Are_Tot | |
| HE02_EpiNucSizBin4_5_Blu_Mean | |
| HE02_EpiNucSizBin4_5_Blu_MeanStd | |
| HE02_EpiNucSizBin4_5_Bri_Mean | |
| HE02_EpiNucSizBin4_5_Gre_Mean | |
| HE02_EpiNucSizBin4_5_Gre_MeanStd | |
| HE02_EpiNucSizBin4_5_Num | |
| HE02_EpiNucSizBin4_5_Red_Mean | |
| HE02_EpiNucSizBin4_5_Red_MeanStd | |
| HE02_EpiNucSizBin4_6_Are_Mean | |
| HE02_EpiNucSizBin4_6_Are_Tot | |
| HE02_EpiNucSizBin4_6_Blu_Mean | |
| HE02_EpiNucSizBin4_6_Blu_MeanStd | |
| HE02_EpiNucSizBin4_6_Bri_Mean | |
| HE02_EpiNucSizBin4_6_Gre_Mean | |
| HE02_EpiNucSizBin4_6_Gre_MeanStd | |
| HE02_EpiNucSizBin4_6_Num | |
| HE02_EpiNucSizBin4_6_Red_Mean | |
| HE02_EpiNucSizBin4_6_Red_MeanStd | |
| HE02_EpiNucSizBin4_7_Are_Mean | |
| HE02_EpiNucSizBin4_7_Are_Tot | |
| HE02_EpiNucSizBin4_7_Blu_Mean | |
| HE02_EpiNucSizBin4_7_Blu_MeanStd | |
| HE02_EpiNucSizBin4_7_Bri_Mean | |
| HE02_EpiNucSizBin4_7_Gre_Mean | |
| HE02_EpiNucSizBin4_7_Gre_MeanStd | |
| HE02_EpiNucSizBin4_7_Num | |
| HE02_EpiNucSizBin4_7_Red_Mean | |
| HE02_EpiNucSizBin4_7_Red_MeanStd | |
| HE02_EpiNucSizBin4_8_Are_Mean | |
| HE02_EpiNucSizBin4_8_Are_Tot | |
| HE02_EpiNucSizBin4_8_Blu_Mean | |
| HE02_EpiNucSizBin4_8_Blu_MeanStd | |
| HE02_EpiNucSizBin4_8_Bri_Mean | |
| HE02_EpiNucSizBin4_8_Gre_Mean | |
| HE02_EpiNucSizBin4_8_Gre_MeanStd | |
| HE02_EpiNucSizBin4_8_Num | |
| HE02_EpiNucSizBin4_8_Red_Mean | |
| HE02_EpiNucSizBin4_8_Red_MeanStd | |
| HE02_EpiNucSizBin4_Are_Mean | |
| HE02_EpiNucSizBin4_Are_Tot | |
| HE02_EpiNucSizBin4_Blu_Mean | |
| HE02_EpiNucSizBin4_Blu_MeanStd | |
| HE02_EpiNucSizBin4_Bri_Mean | |
| HE02_EpiNucSizBin4_Gre_Mean | |
| HE02_EpiNucSizBin4_Gre_MeanStd | |
| HE02_EpiNucSizBin4_Num | |
| HE02_EpiNucSizBin4_Red_Mean | |
| HE02_EpiNucSizBin4_Red_MeanStd | |
| HE02_EpiNucSizBin5_6_Are_Mean | |
| HE02_EpiNucSizBin5_6_Are_Tot | |
| HE02_EpiNucSizBin5_6_Blu_Mean | |
| HE02_EpiNucSizBin5_6_Blu_MeanStd | |
| HE02_EpiNucSizBin5_6_Bri_Mean | |
| HE02_EpiNucSizBin5_6_Gre_Mean | |
| HE02_EpiNucSizBin5_6_Gre_MeanStd | |
| HE02_EpiNucSizBin5_6_Num | |
| HE02_EpiNucSizBin5_6_Red_Mean | |
| HE02_EpiNucSizBin5_6_Red_MeanStd | |
| HE02_EpiNucSizBin5_7_Are_Mean | |
| HE02_EpiNucSizBin5_7_Are_Tot | |
| HE02_EpiNucSizBin5_7_Blu_Mean | |
| HE02_EpiNucSizBin5_7_Blu_MeanStd | |
| HE02_EpiNucSizBin5_7_Bri_Mean | |
| HE02_EpiNucSizBin5_7_Gre_Mean | |
| HE02_EpiNucSizBin5_7_Gre_MeanStd | |
| HE02_EpiNucSizBin5_7_Num | |
| HE02_EpiNucSizBin5_7_Red_Mean | |
| HE02_EpiNucSizBin5_7_Red_MeanStd | |
| HE02_EpiNucSizBin5_8_Are_Mean | |
| HE02_EpiNucSizBin5_8_Are_Tot | |
| HE02_EpiNucSizBin5_8_Blu_Mean | |
| HE02_EpiNucSizBin5_8_Blu_MeanStd | |
| HE02_EpiNucSizBin5_8_Bri_Mean | |
| HE02_EpiNucSizBin5_8_Gre_Mean | |
| HE02_EpiNucSizBin5_8_Gre_MeanStd | |
| HE02_EpiNucSizBin5_8_Num | |
| HE02_EpiNucSizBin5_8_Red_Mean | |
| HE02_EpiNucSizBin5_8_Red_MeanStd | |
| HE02_EpiNucSizBin5_Are_Mean | |
| HE02_EpiNucSizBin5_Are_Tot | |
| HE02_EpiNucSizBin5_Blu_Mean | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE02_EpiNucSizBin5_Blu_MeanStd | |
| HE02_EpiNucSizBin5_Bri_Mean | |
| HE02_EpiNucSizBin5_Gre_Mean | |
| HE02_EpiNucSizBin5_Gre_MeanStd | |
| HE02_EpiNucSizBin5_Num | |
| HE02_EpiNucSizBin5_Red_Mean | |
| HE02_EpiNucSizBin5_Red_MeanStd | |
| HE02_EpiNucSizBin6_7_Are_Mean | |
| HE02_EpiNucSizBin6_7_Are_Tot | |
| HE02_EpiNucSizBin6_7_Blu_Mean | |
| HE02_EpiNucSizBin6_7_Blu_MeanStd | |
| HE02_EpiNucSizBin6_7_Bri_Mean | |
| HE02_EpiNucSizBin6_7_Gre_Mean | |
| HE02_EpiNucSizBin6_7_Gre_MeanStd | |
| HE02_EpiNucSizBin6_7_Num | |
| HE02_EpiNucSizBin6_7_Red_Mean | |
| HE02_EpiNucSizBin6_7_Red_MeanStd | |
| HE02_EpiNucSizBin6_8_Are_Mean | |
| HE02_EpiNucSizBin6_8_Are_Tot | |
| HE02_EpiNucSizBin6_8_Blu_Mean | |
| HE02_EpiNucSizBin6_8_Blu_MeanStd | |
| HE02_EpiNucSizBin6_8_Bri_Mean | |
| HE02_EpiNucSizBin6_8_Gre_Mean | |
| HE02_EpiNucSizBin6_8_Gre_MeanStd | |
| HE02_EpiNucSizBin6_8_Num | |
| HE02_EpiNucSizBin6_8_Red_Mean | |
| HE02_EpiNucSizBin6_8_Red_MeanStd | |
| HE02_EpiNucSizBin6_Are_Mean | |
| HE02_EpiNucSizBin6_Are_Tot | |
| HE02_EpiNucSizBin6_Blu_Mean | |
| HE02_EpiNucSizBin6_Blu_MeanStd | |
| HE02_EpiNucSizBin6_Bri_Mean | |
| HE02_EpiNucSizBin6_Gre_Mean | |
| HE02_EpiNucSizBin6_Gre_MeanStd | |
| HE02_EpiNucSizBin6_Num | |
| HE02_EpiNucSizBin6_Red_Mean | |
| HE02_EpiNucSizBin6_Red_MeanStd | |
| HE02_EpiNucSizBin7_8_Are_Mean | |
| HE02_EpiNucSizBin7_8_Are_Tot | |
| HE02_EpiNucSizBin7_8_Blu_Mean | |
| HE02_EpiNucSizBin7_8_Blu_MeanStd | |
| HE02_EpiNucSizBin7_8_Bri_Mean | |
| HE02_EpiNucSizBin7_8_Gre_Mean | |
| HE02_EpiNucSizBin7_8_Gre_MeanStd | |
| HE02_EpiNucSizBin7_8_Num | |
| HE02_EpiNucSizBin7_8_Red_Mean | |
| HE02_EpiNucSizBin7_8_Red_MeanStd | |
| HE02_EpiNucSizBin7_Are_Mean | |
| HE02_EpiNucSizBin7_Are_Tot | |
| HE02_EpiNucSizBin7_Blu_Mean | |
| HE02_EpiNucSizBin7_Blu_MeanStd | |
| HE02_EpiNucSizBin7_Bri_Mean | |
| HE02_EpiNucSizBin7_Gre_Mean | |
| HE02_EpiNucSizBin7_Gre_MeanStd | |
| HE02_EpiNucSizBin7_Num | |
| HE02_EpiNucSizBin7_Red_Mean | |
| HE02_EpiNucSizBin7_Red_MeanStd | |
| HE02_EpiNucSizBin8_Are_Mean | |
| HE02_EpiNucSizBin8_Are_Tot | |
| HE02_EpiNucSizBin8_Blu_Mean | |
| HE02_EpiNucSizBin8_Blu_MeanStd | |
| HE02_EpiNucSizBin8_Bri_Mean | |
| HE02_EpiNucSizBin8_Gre_Mean | |
| HE02_EpiNucSizBin8_Gre_MeanStd | |
| HE02_EpiNucSizBin8_Num | |
| HE02_EpiNucSizBin8_Red_Mean | |
| HE02_EpiNucSizBin8_Red_MeanStd | |
| HE02_EpiNucWIGU_Are_Mean | Average area of epithelial nuclei within gland units |
| HE02_EpiNucWIGU_Are_Tot | Total area of epithelial nuclei within gland units |
| HE02_EpiNuc_Are_Mean | Color and morphometric features of epithelial nuclei |
| HE02_EpiNuc_Are_Median | |
| HE02_EpiNuc_Are_Std | |
| HE02_EpiNuc_Are_Tot | |
| HE02_EpiNuc_ElpFit_Mean | |
| HE02_EpiNuc_ElpFit_Median | |
| HE02_EpiNuc_ElpFit_Std | |
| HE02_EpiNuc_LOW_Mean | |
| HE02_EpiNuc_LOW_Median | |
| HE02_EpiNuc_LOW_Std | |
| HE02_EpiNuc_Num | |
| HE02_EpiNuc_OrgBlu_MeanMean | |
| HE02_EpiNuc_OrgBlu_MeanStd | |
| HE02_EpiNuc_OrgBri_Mean | |
| HE02_EpiNuc_OrgBri_Std | |
| HE02_EpiNuc_OrgGre_MeanMean | |
| HE02_EpiNuc_OrgGre_MeanStd | |
| HE02_EpiNuc_OrgH_Mean | |
| HE02_EpiNuc_OrgH_Std | |
| HE02_EpiNuc_OrgI_Mean | |
| HE02_EpiNuc_OrgI_Std | |
| HE02_EpiNuc_OrgQ_Mean | |
| HE02_EpiNuc_OrgQ_Std | |
| HE02_EpiNuc_OrgRed_CF100_MeanStd | |
| HE02_EpiNuc_OrgRed_CF200_MeanStd | |
| HE02_EpiNuc_OrgRed_CF300_MeanStd | |
| HE02_EpiNuc_OrgRed_CF400_MeanStd | |
| HE02_EpiNuc_OrgRed_CF500_MeanStd | |
| HE02_EpiNuc_OrgRed_MeanMean | |
| HE02_EpiNuc_OrgRed_MeanStd | |
| HE02_EpiNuc_OrgS_Mean | |
| HE02_EpiNuc_OrgS_Std | |
| HE02_EpiNuc_OrgV_Mean | |
| HE02_EpiNuc_OrgV_Std | |
| HE02_EpiNuc_OrgY_Mean | |
| HE02_EpiNuc_OrgY_Std | |
| HE02_IsoEpiNuc_ElpFit_Mean | Color and morphometric features of isolated epithelial nuclei |
| HE02_IsoEpiNuc_ElpFit_Median | |
| HE02_IsoEpiNuc_ElpFit_Std | |
| HE02_IsoEpiNuc_LOW_Mean | |
| HE02_IsoEpiNuc_LOW_Median | |
| HE02_IsoEpiNuc_LOW_Std | |
| HE02_IsoEpiNuc_OrgBlu_MeanMean | |
| HE02_IsoEpiNuc_OrgBlu_MeanStd | |
| HE02_IsoEpiNuc_OrgBlu_StdMean | |
| HE02_IsoEpiNuc_OrgBri_Mean | |
| HE02_IsoEpiNuc_OrgBri_Std | |
| HE02_IsoEpiNuc_OrgGre_MeanMean | |
| HE02_IsoEpiNuc_OrgGre_MeanStd | |
| HE02_IsoEpiNuc_OrgGre_StdMean | |
| HE02_IsoEpiNuc_OrgRed_MeanMean | |
| HE02_IsoEpiNuc_OrgRed_MeanStd | |
| HE02_IsoEpiNuc_OrgRed_StdMean | |
| HE02_IsoEpiNuc_ShaInd_Mean | |
| HE02_IsoEpiNuc_ShaInd_Std | |
| HE02_IsoNuc_Are_Mean | |
| HE02_IsoNuc_Are_Std | |
| HE02_IsoNuc_Are_Tot | |
| HE02_IsoNuc_Num | |
| HE02_IsoStrNuc_Are_Mean | |
| HE02_IsoStrNuc_Are_Std | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
| --- | --- |
| HE02_IsoStrNuc_Are_Tot | |
| HE02_IsoStrNuc_Num | |
| HE02_LStr_Are_Mean | Color and morphometric features of light stroma |
| HE02_LStr_Are_Std | |
| HE02_LStr_Are_Tot | |
| HE02_LStr_Num | |
| HE02_LStr_OrgBlu_MeanMean | |
| HE02_LStr_OrgBlu_MeanStd | |
| HE02_LStr_OrgBri_Mean | |
| HE02_LStr_OrgBri_Std | |
| HE02_LStr_OrgGre_MeanMean | |
| HE02_LStr_OrgGre_MeanStd | |
| HE02_LStr_OrgH_Mean | |
| HE02_LStr_OrgH_Std | |
| HE02_LStr_OrgI_Mean | |
| HE02_LStr_OrgI_Std | |
| HE02_LStr_OrgQ_Mean | |
| HE02_LStr_OrgQ_Std | |
| HE02_LStr_OrgRed_MeanMean | |
| HE02_LStr_OrgRed_MeanStd | |
| HE02_LStr_OrgS_Mean | |
| HE02_LStr_OrgS_Std | |
| HE02_LStr_OrgV_Mean | |
| HE02_LStr_OrgV_Std | |
| HE02_LStr_OrgY_Mean | |
| HE02_LStr_OrgY_Std | |
| HE02_LigNucBin0_1_Are_Mean | Morphometric features of light nuclei that have been binned |
| HE02_LigNucBin0_1_Are_Tot | |
| HE02_LigNucBin0_1_Num | |
| HE02_LigNucBin0_2_Are_Mean | |
| HE02_LigNucBin0_2_Are_Tot | |
| HE02_LigNucBin0_2_Num | |
| HE02_LigNucBin0_3_Are_Mean | |
| HE02_LigNucBin0_3_Are_Tot | |
| HE02_LigNucBin0_3_Num | |
| HE02_LigNucBin0_4_Are_Mean | |
| HE02_LigNucBin0_4_Are_Tot | |
| HE02_LigNucBin0_4_Num | |
| HE02_LigNucBin0_5_Are_Mean | |
| HE02_LigNucBin0_5_Are_Tot | |
| HE02_LigNucBin0_5_Num | |
| HE02_LigNucBin0_6_Are_Mean | |
| HE02_LigNucBin0_6_Are_Tot | |
| HE02_LigNucBin0_6_Num | |
| HE02_LigNucBin0_7_Are_Mean | |
| HE02_LigNucBin0_7_Are_Tot | |
| HE02_LigNucBin0_7_Num | |
| HE02_LigNucBin0_8_Are_Mean | |
| HE02_LigNucBin0_8_Are_Tot | |
| HE02_LigNucBin0_8_Num | |
| HE02_LigNucBin0_Are_Mean | |
| HE02_LigNucBin0_Are_Tot | |
| HE02_LigNucBin0_Num | |
| HE02_LigNucBin1_2_Are_Mean | |
| HE02_LigNucBin1_2_Are_Tot | |
| HE02_LigNucBin1_2_Num | |
| HE02_LigNucBin1_3_Are_Mean | |
| HE02_LigNucBin1_3_Are_Tot | |
| HE02_LigNucBin1_3_Num | |
| HE02_LigNucBin1_4_Are_Mean | |
| HE02_LigNucBin1_4_Are_Tot | |
| HE02_LigNucBin1_4_Num | |
| HE02_LigNucBin1_5_Are_Mean | |
| HE02_LigNucBin1_5_Are_Tot | |
| HE02_LigNucBin1_5_Num | |
| HE02_LigNucBin1_6_Are_Mean | |
| HE02_LigNucBin1_6_Are_Tot | |
| HE02_LigNucBin1_6_Num | |
| HE02_LigNucBin1_7_Are_Mean | |
| HE02_LigNucBin1_7_Are_Tot | |
| HE02_LigNucBin1_7_Num | |
| HE02_LigNucBin1_8_Are_Mean | |
| HE02_LigNucBin1_8_Are_Tot | |
| HE02_LigNucBin1_8_Num | |
| HE02_LigNucBin1_Are_Mean | |
| HE02_LigNucBin1_Are_Tot | |
| HE02_LigNucBin1_Num | |
| HE02_LigNucBin2_3_Are_Mean | |
| HE02_LigNucBin2_3_Are_Tot | |
| HE02_LigNucBin2_3_Num | |
| HE02_LigNucBin2_4_Are_Mean | |
| HE02_LigNucBin2_4_Are_Tot | |
| HE02_LigNucBin2_4_Num | |
| HE02_LigNucBin2_5_Are_Mean | |
| HE02_LigNucBin2_5_Are_Tot | |
| HE02_LigNucBin2_5_Num | |
| HE02_LigNucBin2_6_Are_Mean | |
| HE02_LigNucBin2_6_Are_Tot | |
| HE02_LigNucBin2_6_Num | |
| HE02_LigNucBin2_7_Are_Mean | |
| HE02_LigNucBin2_7_Are_Tot | |
| HE02_LigNucBin2_7_Num | |
| HE02_LigNucBin2_8_Are_Mean | |
| HE02_LigNucBin2_8_Are_Tot | |
| HE02_LigNucBin2_8_Num | |
| HE02_LigNucBin2_Are_Mean | |
| HE02_LigNucBin2_Are_Tot | |
| HE02_LigNucBin2_Num | |
| HE02_LigNucBin3_4_Are_Mean | |
| HE02_LigNucBin3_4_Are_Tot | |
| HE02_LigNucBin3_4_Num | |
| HE02_LigNucBin3_5_Are_Mean | |
| HE02_LigNucBin3_5_Are_Tot | |
| HE02_LigNucBin3_5_Num | |
| HE02_LigNucBin3_6_Are_Mean | |
| HE02_LigNucBin3_6_Are_Tot | |
| HE02_LigNucBin3_6_Num | |
| HE02_LigNucBin3_7_Are_Mean | |
| HE02_LigNucBin3_7_Are_Tot | |
| HE02_LigNucBin3_7_Num | |
| HE02_LigNucBin3_8_Are_Mean | |
| HE02_LigNucBin3_8_Are_Tot | |
| HE02_LigNucBin3_8_Num | |
| HE02_LigNucBin3_Are_Mean | |
| HE02_LigNucBin3_Are_Tot | |
| HE02_LigNucBin3_Num | |
| HE02_LigNucBin4_5_Are_Mean | |
| HE02_LigNucBin4_5_Are_Tot | |
| HE02_LigNucBin4_5_Num | |
| HE02_LigNucBin4_6_Are_Mean | |
| HE02_LigNucBin4_6_Are_Tot | |
| HE02_LigNucBin4_6_Num | |
| HE02_LigNucBin4_7_Are_Mean | |
| HE02_LigNucBin4_7_Are_Tot | |
| HE02_LigNucBin4_7_Num | |
| HE02_LigNucBin4_8_Are_Mean | |
| HE02_LigNucBin4_8_Are_Tot | |
| HE02_LigNucBin4_8_Num | |
| HE02_LigNucBin4_Are_Mean | |
| HE02_LigNucBin4_Are_Tot | |
| HE02_LigNucBin4_Num | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE02_LigNucBin5_6_Are_Mean | |
| HE02_LigNucBin5_6_Are_Tot | |
| HE02_LigNucBin5_6_Num | |
| HE02_LigNucBin5_7_Are_Mean | |
| HE02_LigNucBin5_7_Are_Tot | |
| HE02_LigNucBin5_7_Num | |
| HE02_LigNucBin5_8_Are_Mean | |
| HE02_LigNucBin5_8_Are_Tot | |
| HE02_LigNucBin5_8_Num | |
| HE02_LigNucBin5_Are_Mean | |
| HE02_LigNucBin5_Are_Tot | |
| HE02_LigNucBin5_Num | |
| HE02_LigNucBin6_7_Are_Mean | |
| HE02_LigNucBin6_7_Are_Tot | |
| HE02_LigNucBin6_7_Num | |
| HE02_LigNucBin6_8_Are_Mean | |
| HE02_LigNucBin6_8_Are_Tot | |
| HE02_LigNucBin6_8_Num | |
| HE02_LigNucBin6_Are_Mean | |
| HE02_LigNucBin6_Are_Tot | |
| HE02_LigNucBin6_Num | |
| HE02_LigNucBin7_8_Are_Mean | |
| HE02_LigNucBin7_8_Are_Tot | |
| HE02_LigNucBin7_8_Num | |
| HE02_LigNucBin7_Are_Mean | |
| HE02_LigNucBin7_Are_Tot | |
| HE02_LigNucBin7_Num | |
| HE02_LigNucBin8_Are_Mean | |
| HE02_LigNucBin8_Are_Tot | |
| HE02_LigNucBin8_Num | |
| HE02_Lum_Are_Mean | Luminal morphometric features |
| HE02_Lum_Are_Median | |
| HE02_Lum_Are_Std | |
| HE02_Lum_Are_Tot | |
| HE02_Lum_ElpFit_Mean | |
| HE02_Lum_ElpFit_Std | |
| HE02_Lum_LOW_Ave | |
| HE02_Lum_LOW_Mean | |
| HE02_Lum_LOW_Std | |
| HE02_Lum_Num | |
| HE02_Lum_Ptr_Mean | |
| HE02_Lum_Ptr_Std | |
| HE02_MDTumor_Are_Tot | Morphometric and color features of the manually defined tumor area. |
| HE02_MDTumor_Num | |
| HE02_MDTumor_OrgBlu_MeanMean | |
| HE02_MDTumor_OrgBlu_MeanStd | |
| HE02_MDTumor_OrgBri_Mean | |
| HE02_MDTumor_OrgBri_Std | |
| HE02_MDTumor_OrgGre_MeanMean | |
| HE02_MDTumor_OrgGre_MeanStd | |
| HE02_MDTumor_OrgH_Mean | |
| HE02_MDTumor_OrgH_Std | |
| HE02_MDTumor_OrgI_Mean | |
| HE02_MDTumor_OrgI_Std | |
| HE02_MDTumor_OrgQ_Mean | |
| HE02_MDTumor_OrgQ_Std | |
| HE02_MDTumor_OrgRed_MeanMean | |
| HE02_MDTumor_OrgRed_MeanStd | |
| HE02_MDTumor_OrgS_Mean | |
| HE02_MDTumor_OrgS_Std | |
| HE02_MDTumor_OrgV_Mean | |
| HE02_MDTumor_OrgV_Std | |
| HE02_MDTumor_OrgY_Mean | |
| HE02_MDTumor_OrgY_Std | |
| HE02_Nuc_Are_Mean | Nuclear features |
| HE02_Nuc_Are_Std | |
| HE02_Nuc_Are_Tot | |
| HE02_Nuc_Num | |
| HE02_PDNuc_Are_Mean | Morphometric and color features of poorly defined nuclei |
| HE02_PDNuc_Are_Std | |
| HE02_PDNuc_Are_Tot | |
| HE02_PDNuc_ElpFit_Mean | |
| HE02_PDNuc_ElpFit_Std | |
| HE02_PDNuc_LOW_Mean | |
| HE02_PDNuc_LOW_Std | |
| HE02_PDNuc_Num | |
| HE02_PDNuc_OrgBlu_MeanMean | |
| HE02_PDNuc_OrgBlu_MeanStd | |
| HE02_PDNuc_OrgBlu_StdMean | |
| HE02_PDNuc_OrgBri_Mean | |
| HE02_PDNuc_OrgBri_Std | |
| HE02_PDNuc_OrgGre_MeanMean | |
| HE02_PDNuc_OrgGre_MeanStd | |
| HE02_PDNuc_OrgGre_StdMean | |
| HE02_PDNuc_OrgRed_MeanMean | |
| HE02_PDNuc_OrgRed_MeanStd | |
| HE02_PDNuc_OrgRed_StdMean | |
| HE02_PDNuc_ShaInd_Mean | |
| HE02_PDNuc_ShaInd_Std | |
| HE02_StrNuc_Are_Mean | Morphometric and color features of stroma nuclei |
| HE02_StrNuc_Are_Median | |
| HE02_StrNuc_Are_Std | |
| HE02_StrNuc_Are_Tot | |
| HE02_StrNuc_ElpFit_Mean | |
| HE02_StrNuc_ElpFit_Median | |
| HE02_StrNuc_ElpFit_Std | |
| HE02_StrNuc_LOW_Mean | |
| HE02_StrNuc_LOW_Median | |
| HE02_StrNuc_LOW_Std | |
| HE02_StrNuc_Num | |
| HE02_StrNuc_OrgBlu_MeanMean | |
| HE02_StrNuc_OrgBlu_MeanStd | |
| HE02_StrNuc_OrgBri_Mean | |
| HE02_StrNuc_OrgBri_Std | |
| HE02_StrNuc_OrgGre_MeanMean | |
| HE02_StrNuc_OrgGre_MeanStd | |
| HE02_StrNuc_OrgH_Mean | |
| HE02_StrNuc_OrgH_Std | |
| HE02_StrNuc_OrgI_Mean | |
| HE02_StrNuc_OrgI_Std | |
| HE02_StrNuc_OrgQ_Mean | |
| HE02_StrNuc_OrgQ_Std | |
| HE02_StrNuc_OrgRed_MeanMean | |
| HE02_StrNuc_OrgRed_MeanStd | |
| HE02_StrNuc_OrgS_Mean | |
| HE02_StrNuc_OrgS_Std | |
| HE02_StrNuc_OrgV_Mean | |
| HE02_StrNuc_OrgV_Std | |
| HE02_StrNuc_OrgY_Mean | |
| HE02_StrNuc_OrgY_Std | |
| HE02_StrPla_Are_Mean | Morphometric features of a combined stroma and cytoplasm object |
| HE02_StrPla_Are_Tot | |
| HE02_StrPla_Num | |
| HE02_StrPla_OrgBlu_MeanMean | |
| HE02_StrPla_OrgBlu_MeanStd | |
| HE02_StrPla_OrgBlu_StdMean | |
| HE02_StrPla_OrgGre_MeanMean | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| HE02_StrPla_OrgGre_MeanStd | |
| HE02_StrPla_OrgGre_StdMean | |
| HE02_StrPla_OrgH_Mean | |
| HE02_StrPla_OrgH_Std | |
| HE02_StrPla_OrgI_Mean | |
| HE02_StrPla_OrgI_Std | |
| HE02_StrPla_OrgQ_Mean | |
| HE02_StrPla_OrgQ_Std | |
| HE02_StrPla_OrgRed_MeanMean | |
| HE02_StrPla_OrgRed_MeanStd | |
| HE02_StrPla_OrgRed_StdMean | |
| HE02_StrPla_OrgS_Mean | |
| HE02_StrPla_OrgS_Std | |
| HE02_StrPla_OrgV_Mean | |
| HE02_StrPla_OrgV_Std | |
| HE02_StrPla_OrgY_Mean | |
| HE02_StrPla_OrgY_Std | |
| HE02_Str_Are_Mean | Morphometric and color features of stroma |
| HE02_Str_Are_Std | |
| HE02_Str_Are_Tot | |
| HE02_Str_Num | |
| HE02_Str_OrgBlu_MeanMean | |
| HE02_Str_OrgBlu_MeanStd | |
| HE02_Str_OrgBri_Mean | |
| HE02_Str_OrgBri_Std | |
| HE02_Str_OrgGre_MeanMean | |
| HE02_Str_OrgGre_MeanStd | |
| HE02_Str_OrgH_Mean | |
| HE02_Str_OrgH_Std | |
| HE02_Str_OrgI_Mean | |
| HE02_Str_OrgI_Std | |
| HE02_Str_OrgQ_Mean | |
| HE02_Str_OrgQ_Std | |
| HE02_Str_OrgRed_MeanMean | |
| HE02_Str_OrgRed_MeanStd | |
| HE02_Str_OrgS_Mean | |
| HE02_Str_OrgS_Std | |
| HE02_Str_OrgV_Mean | |
| HE02_Str_OrgV_Std | |
| HE02_Str_OrgY_Mean | |
| HE02_Str_OrgY_Std | |
| HE02_TumorWoWS_Are_Tot | Morphometric and color features of the tumor area without white space |
| HE02_TumorWoWS_Num | |
| HE02_TumorWoWS_OrgBlu_MeanMean | |
| HE02_TumorWoWS_OrgBlu_MeanStd | |
| HE02_TumorWoWS_OrgBri_Mean | |
| HE02_TumorWoWS_OrgBri_Std | |
| HE02_TumorWoWS_OrgGre_MeanMean | |
| HE02_TumorWoWS_OrgGre_MeanStd | |
| HE02_TumorWoWS_OrgH_Mean | |
| HE02_TumorWoWS_OrgH_Std | |
| HE02_TumorWoWS_OrgI_Mean | |
| HE02_TumorWoWS_OrgI_Std | |
| HE02_TumorWoWS_OrgQ_Mean | |
| HE02_TumorWoWS_OrgQ_Std | |
| HE02_TumorWoWS_OrgRed_MeanMean | |
| HE02_TumorWoWS_OrgRed_MeanStd | |
| HE02_TumorWoWS_OrgS_Mean | |
| HE02_TumorWoWS_OrgS_Std | |
| HE02_TumorWoWS_OrgV_Mean | |
| HE02_TumorWoWS_OrgV_Std | |
| HE02_TumorWoWS_OrgYIQBri_Mean | |
| HE02_TumorWoWS_OrgYIQBri_Std | |
| HE02_TumorWoWS_OrgY_Mean | |
| HE02_TumorWoWS_OrgY_Std | |
| HE02_WDEpiNuc_Are_Mean | Morphometric and color features of well defined epithelial nuclei |
| HE02_WDEpiNuc_Are_Median | |
| HE02_WDEpiNuc_Are_Std | |
| HE02_WDEpiNuc_Are_Tot | |
| HE02_WDEpiNuc_ElpFit_Mean | |
| HE02_WDEpiNuc_ElpFit_Median | |
| HE02_WDEpiNuc_ElpFit_Std | |
| HE02_WDEpiNuc_LOW_Mean | |
| HE02_WDEpiNuc_LOW_Median | |
| HE02_WDEpiNuc_LOW_Std | |
| HE02_WDEpiNuc_Num | |
| HE02_WDEpiNuc_OrgBlu_MeanMean | |
| HE02_WDEpiNuc_OrgBlu_MeanStd | |
| HE02_WDEpiNuc_OrgBlu_StdMean | |
| HE02_WDEpiNuc_OrgBri_Mean | |
| HE02_WDEpiNuc_OrgBri_Std | |
| HE02_WDEpiNuc_OrgGre_MeanMean | |
| HE02_WDEpiNuc_OrgGre_MeanStd | |
| HE02_WDEpiNuc_OrgGre_StdMean | |
| HE02_WDEpiNuc_OrgRed_MeanMean | |
| HE02_WDEpiNuc_OrgRed_MeanStd | |
| HE02_WDEpiNuc_OrgRed_StdMean | |
| HE02_WDEpiNuc_ShaInd_Mean | |
| HE02_WDEpiNuc_ShaInd_Std | |
| HE02_WSAlgInTumAre_Are_Tot | |
| 'mst_mean_length_lum' | Average MST edge length of lumens |
| 'mst_std_length_lum' | Standard deviation of the MST edge length between lumens |
| 'proportion_edge_1_lum' | Proportion of lumens with one MST connecting edge |
| 'proportion_edge_2_lum' | Proportion of lumens with two MST connecting edges. |
| 'proportion_edge_3_lum' | Proportion of lumens with three MST connecting edges |
| 'proportion_edge_4_lum' | Proportion of lumens with four MST connecting edges |
| 'proportion_edge_5_lum' | Proportion of lumens with five MST connecting edges |
| 'HE02_CytOGU_Are_Tot' | Cytoplasm and epithelial features within and outside of gland units |
| 'HE02_CytOutGU_Are_Tot' | |
| 'HE02_CytWIGU_Are_Tot' | |
| 'HE02_CytWinGU_Are_Tot' | |
| 'HE02_EpiNucOGU_Are_Mean' | |
| 'HE02_EpiNucOGU_Are_Tot' | |
| 'HE02_EpiNucWIGU_Are_Mean' | |
| 'HE02_EpiNucWIGU_Are_Tot' | |
| 'HEx2_RelNumIsoEpiNuc2AreaEpiNuc' | Normalized morphometric features of various tissue components |
| 'HEx2_RelNumIsoEpiNuc2MDTumor' | |
| 'HEx2_RelNumWellDefEpiNuc2MDTumor' | |
| 'HEx2_RelNumIsoEpiNuc2NumEpiNuc' | |
| 'HEx2_RelAre_EpiIsoNuc2EpiNucArea' | |
| 'HEx2RelNum_EpiIsoNuc2EpiNucArea' | |
| 'HEx2_nta_Cyt_Are_Tot' | |
| 'HEx2_nta_EpiNuc_Are_Tot' | |
| 'HEx2_nta_Lum_Are_Tot' | |
| 'HEx2_nta_StrNuc_Are_Tot' | |
| 'HEx2_nta_Str_Are_Tot' | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
| --- | --- |
| 'HEx2_nta_LStr_Are_Tot' | |
| 'HEx2_nta_DStr_Are_Tot' | |
| 'HEx2_nta_Cra_Are_Tot' | |
| 'HEx2_nta_IsoNuc_Are_Tot' | |
| 'HEx2_nta_Nuc_Are_Tot' | |
| 'HEx2_nta_EpiIsoNuc_Are_Tot' | |
| 'HEx2_nta_IsoStrNuc_Are_Tot' | |
| 'HEx2_nta_WDEpiNuc_Are_Tot' | |
| 'HEx2_RelAre_IsoNuc2EpiNucArea' | |
| 'HEx2RelAre_EpiIsoNuc2EpiNucArea' | |
| 'HEx2_RelAre_WDEpiNuc2EpiNucArea' | |
| 'HEx2_EpiNucAre2LumMeanAre' | |
| 'HEx2_nrm_ENWinGU_Are_Tot' | |
| 'HEx2_nrm_ENOutGU_Are_Tot' | |
| 'HEx2_nrm_CytWinGU_Are_Tot' | |
| 'HEx2_nrm_CytOutGU_Are_Tot' | |
| 'HEx2_RelArea_EpiNuc_Out2WinGU' | |
| 'HEx2_RelArea_Cyt_Out2WinGU' | |
| 'HEx2_RelArea_ENCyt_Out2WinGU' | |
| 'HEx2_ntaENCytWinGU2Tumor' | |
| 'HEx2_ntaENCYtOutGU2Tumor' | |
| 'HEx2_ntaWhiteSpace' | |
| 'HEx2_nrmMDT_ENWinGU_Are_Tot' | Normalized to the tumor area |
| 'HEx2_nrmMDT_ENOutGU_Are_Tot' | |
| 'HEx2_nrmMDT_CytWinGU_Are_Tot' | |
| 'HEx2_nrmMDT_CytOutGU_Are_Tot' | |
| 'HEx2_nrmLUM_ENWinGU_Are_Tot' | Normalized to luminal area |
| 'HEx2_nrmLUM_ENOutGU_Are_Tot' | |
| 'HEx2_nrmLUM_CytWinGU_Are_Tot' | |
| 'HEx2_nrmLUM_CytOutGU_Are_Tot' | |
| 'HEx2_nrmLUM_EpiNucCytWinGU' | |
| 'HEx2_nrmLUM_EpiNucCytOutGU' | |
| 'HEx2_nrm_ENCytWinGULum_Are_Tot' | |
| 'HEx2_RelArea_ENCytLum_Out2WinGU' | |
| 'HEx2_LumenDensity' | |
| 'HEx2_RelArea_EpiNucCyt_Lum' | |
| 'HEx2_RelArea_IsoEpiNuc_Lumen' | |
| 'HEx2_RelArea_Artifact_Lumen' | |
| 'HEx2_RelArea_EpiNuc_Lumen' | |
| 'HEx2_RelArea_Nuc_Lumen' | |
| 'HEx2_RelArea_EpiNuc_Cyt' | |
| 'HEx2_RelArea_LumContent_Lumen' | |
| 'HEx2_ntaLumContentArea' | |
| 'HEx2_nrm_Cyt_OrgRed_MeanStd' | |
| 'HEx2_nrm_Cyt_OrgGre_MeanStd' | |
| 'HEx2_nrm_Cyt_OrgBlu_MeanStd' | |
| 'HEx2_CytOrgSumRGBMeanStd' | |
| 'HEx2_CytNrmSumRGBMeanStd' | |
| 'HEx2_nrm1_CytOutGU_OrgRedMeanStd' | Normalized color features |
| 'HEx2_nrm1_CytOutGU_OrgGreMeanStd' | |
| 'HEx2_nrm1_CytOutGU_OrgBluMeanStd' | |
| 'HEx2_nrm2_CytOutGU_OrgRedMeanStd' | |
| 'HEx2_nrm2_CytOutGU_OrgGreMeanStd' | |
| 'HEx2_nrm2_CytOutGU_OrgBluMeanStd' | |
| 'HEx2_CytOutGUOrgSumRGBMeanStd' | |
| 'HEx2_CytOutGUNrm1SumRGBMeanStd' | |
| 'HEx2_CytOutGUNrm2SumRGBMeanStd' | |
| 'HEx2_nrm1_CytWinGU_OrgRedMeanStd' | |
| 'HEx2_nrm1_CytWinGU_OrgGreMeanStd' | |
| 'HEx2_nrm1_CytWinGU_OrgBluMeanStd' | |
| 'HEx2_nrm2_CytWinGU_OrgRedMeanStd' | |
| 'HEx2_nrm2_CytWinGU_OrgGreMeanStd' | |
| 'HEx2_nrm2_CytWinGU_OrgBluMeanStd' | |
| 'HEx2_CytWinGUOrgSumRGBMeanStd' | |
| 'HEx2_CytWinGUNrm1SumRGBMeanStd' | |
| 'HEx2_CytWinGUNrm2SumRGBMeanStd' | |
| 'HEx2_nrm_EpiNucOrgRed_MeanStd' | |
| 'HEx2_nrm_EpiNucOrgGre_MeanStd' | |
| 'HEx2_nrm_EpiNucOrgBlu_MeanStd' | |
| 'HEx2_nrmSN_EpiNucOrgRed_MeanStd' | |
| 'HEx2_nrmSN_EpiNucOrgGre_MeanStd' | |
| 'HEx2_nrmSN_EpiNucOrgBlu_MeanStd' | |
| 'HEx2_EpiNucOrgSumRGBMeanStd' | |
| 'HEx2_EpiNucNrmSumRGBMeanStd' | |
| 'HEx2_EpiNucNrmSNSumRGBMeanStd' | |
| 'HEx2_nrm1_ENOutGU_OrgRedMeanStd' | |
| 'HEx2_nrm1_ENOutGU_OrgGreMeanStd' | |
| 'HEx2_nrm1_ENOutGU_OrgBluMeanStd' | |
| 'HEx2_nrm2_ENOutGU_OrgRedMeanStd' | |
| 'HEx2_nrm2_ENOutGU_OrgGreMeanStd' | |
| 'HEx2_nrm2_ENOutGU_OrgBluMeanStd' | |
| 'HEx2_ENOutGUOrgSumRGBMeanStd' | |
| 'HEx2_ENOutGUnrm1SumRGBMeanStd' | |
| 'HEx2_ENOutGUnrm2SumRGBMeanStd' | |
| 'HEx2_nrm1_ENWinGU_OrgRedMeanStd' | |
| 'HEx2_nrm1_ENWinGU_OrgGreMeanStd' | |
| 'HEx2_nrm1_ENWinGU_OrgBluMeanStd' | |
| 'HEx2_nrm2_ENWinGU_OrgRedMeanStd' | |
| 'HEx2_nrm2_ENWinGU_OrgGreMeanStd' | |
| 'HEx2_nrm2_ENWinGU_OrgBluMeanStd' | |
| 'HEx2_ENWinGUOrgSumRGBMeanStd' | |
| 'HEx2_ENWinGUnrm1SumRGBMeanStd' | |
| 'HEx2_ENWinGUnrm2SumRGBMeanStd' | |
| 'HEx2_nrm_EpiNucDen01_Are_Tot' | Density bins normalized by total of all bins |
| 'HEx2_nrm_EpiNucDen02_Are_Tot' | |
| 'HEx2_nrm_EpiNucDen03_Are_Tot' | |
| 'HEx2_nrm_EpiNucDen04_Are_Tot' | |
| 'HEx2_nrm_EpiNucDen05_Are_Tot' | |
| 'HEx2_nrm_EpiNucDen06_Are_Tot' | |
| 'HEx2_nrm_EpiNucDen07_Are_Tot' | |
| 'HEx2_nrm_EpiNucDen08_Are_Tot' | |
| 'HEx2_nrm_EpiNucDen09_Are_Tot' | |
| 'HEx2_nrm_EpiNucDen10_Are_Tot' | |
| 'HEx2_sub_EpiNucDen1_3_Lum' | |
| 'HEx2_RelAreHi2Lo_EpiNucDen_10to2' | |
| 'HEx2_RelAreHi2Lo_EpiNucDen_10to3' | |
| 'HEx2_RelAreHi2Lo_EpiNucDen_10to4' | |
| 'HEx2_RelAreHi2Lo_EpiNucDen_10to5' | |
| 'HEx2_RelAreHi2Lo_EpiNucDen_10to6' | |
| 'HEx2_RelAreHi2Lo_EpiNucDen_10to7' | |
| 'HEx2_RelAreHi2Lo_EpiNucDen_10to8' | |
| 'HEx2_sub_EpiNucDen8_10_Lum' | |
| 'HEx2_nrm_EpiNucAt1Dia_Are_Tot' | |
| 'HEx2_nrm_EpiNucAt2Dia_Are_Tot' | |
| 'HEx2_nrm_EpiNucAt3Dia_Are_Tot' | |
| 'HEx2_nrm_EpiNucAt4Dia_Are_Tot' | |
| 'HEx2_nrm_EpiNucAt5Dia_Are_Tot' | |
| 'HEx2_nrm_EpiNucAt1Dia2MDT' | |
| 'HEx2_nrm_EpiNucAt2Dia2MDT' | |
| 'HEx2_nrm_EpiNucAt3Dia2MDT' | |
| 'HEx2_nrm_EpiNucAt4Dia2MDT' | |
| 'HEx2_nrm_EpiNucAt5Dia2MDT' | |
| 'HEx2_EpiNucBand5minus4' | |
| 'HEx2_EpiNucBand4minus3' | |
| 'HEx2_EpiNucBand3minus2' | |
| 'HEx2_EpiNucBand2minus1' | |
| 'HEx2_nrmEpiNucBand5minus4' | |
| 'HEx2_nrmEpiNucBand5minus3' | |
| 'HEx2_nrmEpiNucBand5minus2' | |
| 'HEx2_nrmEpiNucBand4minus3' | |
| 'HEx2_nrmEpiNucBand4minus2' | |
| 'HEx2_nrmEpiNucBand3minus2' | |
| 'HEx2_nrmEpiNucBand2minus1' | |
| 'HEx2_nrmMDT_EpiNucBand5minus4' | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| 'HEx2_nrmMDT_EpiNucBand5minus3' | |
| 'HEx2_nrmMDT_EpiNucBand5minus2' | |
| 'HEx2_nrmMDT_EpiNucBand4minus3' | |
| 'HEx2_nrmMDT_EpiNucBand4minus2' | |
| 'HEx2_nrmMDT_EpiNucBand3minus2' | |
| 'HEx2_nrmMDT_EpiNucBand2minus1' | |
| 'HEx2_EpiNuc_Num1_8' | |
| 'HEx2_EpiNuc_Are1_8' | |
| 'HEx2_nrmEpiNucSizBin1_Num' | |
| 'HEx2_nrmEpiNucSizBin2_Num' | |
| 'HEx2_nrmEpiNucSizBin3_Num' | |
| 'HEx2_nrmEpiNucSizBin4_Num' | |
| 'HEx2_nrmEpiNucSizBin5_Num' | |
| 'HEx2_nrmEpiNucSizBin6_Num' | |
| 'HEx2_nrmEpiNucSizBin7_Num' | |
| 'HEx2_nrmEpiNucSizBin8_Num' | |
| 'HEx2_nrmEpiNucSizBin1_Are' | |
| 'HEx2_nrmEpiNucSizBin2_Are' | |
| 'HEx2_nrmEpiNucSizBin3_Are' | |
| 'HEx2_nrmEpiNucSizBin4_Are' | |
| 'HEx2_nrmEpiNucSizBin5_Are' | |
| 'HEx2_nrmEpiNucSizBin6_Are' | |
| 'HEx2_nrmEpiNucSizBin7_Are' | |
| 'HEx2_nrmEpiNucSizBin8_Are' | |
| 'min_orig_L_detail1' | Minimum of the variances in the horizontal and vertical detail sub-bands after applying 1 stage of un-decimated wavelet transform to a mask of lumens. |
| 'min_orig_L_detail2' | Minimum of the variances in the horizontal and vertical detail sub-bands after applying 2 stages of un-decimated wavelet transform to a mask of lumens. |
| 'min_orig_L_detail3' | Minimum of the variances in the horizontal and vertical detail sub-bands after applying 3 stages of un-decimated wavelet transform to a mask of lumens. |
| 'min_orig_L_detail4' | Minimum of the variances in the horizontal and vertical detail sub-bands after applying 4 stages of un-decimated wavelet transform to a mask of lumens. |
| 'min_orig_L_detail5' | Minimum of the variances in the horizontal and vertical detail sub-bands after applying 5 stages of un-decimated wavelet transform to a mask of lumens. |
| 'min_orig_L_detail6' | Minimum of the variances in the horizontal and vertical detail sub-bands after applying 6 stages of un-decimated wavelet transform to a mask of lumens. |
| 'min_orig_L_detail7' | Minimum of the variances in the horizontal and vertical detail sub-bands after applying 7 stages of un-decimated wavelet transform to a mask of lumens. |
| 'max_orig_L_detail1' | Maximum of the variances in the horizontal and vertical detail sub-bands after applying 1 stage of un-decimated wavelet transform to a mask of lumens. |
| 'max_orig_L_detail2' | Maximum of the variances in the horizontal and vertical detail sub-bands after applying 2 stages of un-decimated wavelet transform to a mask of lumens. |
| 'max_orig_L_detail3' | Maximum of the variances in the horizontal and vertical detail sub-bands after applying 3 stages of un-decimated wavelet transform to a mask of lumens. |
| 'max_orig_L_detail4' | Maximum of the variances in the horizontal and vertical detail sub-bands after applying 4 stages of un-decimated wavelet transform to a mask of lumens. |
| 'max_orig_L_detail5' | Maximum of the variances in the horizontal and vertical detail sub-bands after applying 5 stages of un-decimated wavelet transform to a mask of lumens. |
| 'max_orig_L_detail6' | Maximum of the variances in the horizontal and vertical detail sub-bands after applying 6 stages of un-decimated wavelet transform to a mask of lumens. |
| 'max_orig_L_detail7' | Maximum of the variances in the horizontal and vertical detail sub-bands after applying 7 stages of un-decimated wavelet transform to a mask of lumens. |
| 'sum_orig_L_detail1' Sum | Sum of the variances in the horizontal and vertical detail sub-bands after applying 1 stage of un-decimated wavelet transform to a mask of lumens. |
| 'sum_orig_L_detail2' | Sum of the variances in the horizontal and vertical detail sub-bands after applying 2 stages of un-decimated wavelet transform to a mask of lumens. |
| 'sum_orig_L_detail3' | Sum of the variances in the horizontal and vertical detail sub-bands after applying 3 stages of un-decimated wavelet transform to a mask of lumens. |
| 'sum_orig_L_detail4' | Sum of the variances in the horizontal and vertical detail sub-bands after applying 4 stages of un-decimated wavelet transform to a mask of lumens. |

TABLE 1-continued

Morphometric Features (e.g., measurable in images of H&E-stained tissue) In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| 'sum_orig_L_detail5' | Sum of the variances in the horizontal and vertical detail sub-bands after applying 5 stages of un-decimated wavelet transform to a mask of lumens. |
| 'sum_orig_L_detail6' | Sum of the variances in the horizontal and vertical detail sub-bands after applying 6 stages of un-decimated wavelet transform to a mask of lumens. |
| 'sum_orig_L_detail7' | Sum of the variances in the horizontal and vertical detail sub-bands after applying 7 stages of un-decimated wavelet transform to a mask of lumens. |
| 'WaveletRatio_Lumendiag_6_5' | Ratio of the variances in the diagnoal detail sub-bands after applying 6 and 5 stages of undecimated wavelet transform to a mask of lumens. |
| HE03_CluNuc_Are_Mean | Measurements on Clustered Nuclei |
| HE03_CluNuc_Are_Std | |
| HE03_CluNuc_Are_Tot | |
| HE03_CluNuc_Num | |
| HE03_Cyt_Are_Mean | Morphometric and color measurements on cytoplasm |
| HE03_Cyt_Are_Std | |
| HE03_Cyt_Are_Tot | |
| HE03_Cyt_Num | |
| HE03_Cyt_OrgBlu_MeanMean | |
| HE03_Cyt_OrgBlu_MeanStd | |
| HE03_Cyt_OrgBri_Mean | |
| HE03_Cyt_OrgBri_Std | |
| HE03_Cyt_OrgGre_MeanMean | |
| HE03_Cyt_OrgGre_MeanStd | |
| HE03_Cyt_OrgH_Mean | |
| HE03_Cyt_OrgH_Std | |
| HE03_Cyt_OrgI_Mean | |
| HE03_Cyt_OrgI_Std | |
| HE03_Cyt_OrgQ_Mean | |
| HE03_Cyt_OrgQ_Std | |
| HE03_Cyt_OrgRed_MeanMean | |
| HE03_Cyt_OrgRed_MeanStd | |
| HE03_Cyt_OrgS_Mean | |
| HE03_Cyt_OrgS_Std | |
| HE03_Cyt_OrgV_Mean | |
| HE03_Cyt_OrgV_Std | |
| HE03_Cyt_OrgY_Mean | |
| HE03_Cyt_OrgY_Std | |
| HE03_DarNucBin0_3_Are_Mean | Morphometric and color measurements on Dark Nuclei |
| HE03_DarNucBin0_3_Are_Tot | |
| HE03_DarNucBin0_3_Num | |
| HE03_DarNucBin0_5_Are_Mean | |
| HE03_DarNucBin0_5_Are_Tot | |
| HE03_DarNucBin0_5_Num | |
| HE03_DarNucBin0_7_Are_Mean | |
| HE03_DarNucBin0_7_Are_Tot | |
| HE03_DarNucBin0_7_Num | |
| HE03_DarNucBin0_Are_Mean | |
| HE03_DarNucBin0_Are_Tot | |
| HE03_DarNucBin0_Num | |
| HE03_DarNucBin1_3_Are_Mean | |
| HE03_DarNucBin1_3_Are_Tot | |
| HE03_DarNucBin1_3_Num | |
| HE03_DarNucBin1_5_Are_Mean | |
| HE03_DarNucBin1_5_Are_Tot | |
| HE03_DarNucBin1_5_Num | |
| HE03_DarNucBin1_7_Are_Mean | |
| HE03_DarNucBin1_7_Are_Tot | |
| HE03_DarNucBin1_7_Num | |
| HE03_DarNucBin1_Are_Mean | |
| HE03_DarNucBin1_Are_Tot | |
| HE03_DarNucBin1_Num | |
| HE03_DarNucBin2_3_Are_Mean | |
| HE03_DarNucBin2_3_Are_Tot | |
| HE03_DarNucBin2_3_Num | |
| HE03_DarNucBin2_5_Are_Mean | |
| HE03_DarNucBin2_5_Are_Tot | |
| HE03_DarNucBin2_5_Num | |
| HE03_DarNucBin2_7_Are_Mean | |
| HE03_DarNucBin2_7_Are_Tot | |
| HE03_DarNucBin2_7_Num | |
| HE03_DarNucBin2_Are_Mean | |
| HE03_DarNucBin2_Are_Tot | |
| HE03_DarNucBin2_Num | |
| HE03_DarNucBin3_5_Are_Mean | |
| HE03_DarNucBin3_5_Are_Tot | |
| HE03_DarNucBin3_5_Num | |
| HE03_DarNucBin3_7_Are_Mean | |
| HE03_DarNucBin3_7_Are_Tot | |
| HE03_DarNucBin3_7_Num | |
| HE03_DarNucBin3_Are_Mean | |
| HE03_DarNucBin3_Are_Tot | |
| HE03_DarNucBin3_Num | |
| HE03_DarNucBin4_5_Are_Mean | |
| HE03_DarNucBin4_5_Are_Tot | |
| HE03_DarNucBin4_5_Num | |
| HE03_DarNucBin4_7_Are_Mean | |
| HE03_DarNucBin4_7_Are_Tot | |
| HE03_DarNucBin4_7_Num | |
| HE03_DarNucBin4_Are_Mean | |
| HE03_DarNucBin4_Are_Tot | |
| HE03_DarNucBin4_Num | |
| HE03_DarNucBin5_7_Are_Mean | |
| HE03_DarNucBin5_7_Are_Tot | |
| HE03_DarNucBin5_7_Num | |
| HE03_DarNucBin5_Are_Mean | |
| HE03_DarNucBin5_Are_Tot | |
| HE03_DarNucBin5_Num | |
| HE03_DarNucBin6_7_Are_Mean | |
| HE03_DarNucBin6_7_Are_Tot | |
| HE03_DarNucBin6_7_Num | |
| HE03_DarNucBin6_Are_Mean | |
| HE03_DarNucBin6_Are_Tot | |
| HE03_DarNucBin6_Num | |
| HE03_DarNucBin7_Are_Mean | |
| HE03_DarNucBin7_Are_Tot | |
| HE03_DarNucBin7_Num | |
| HE03_DarNucBin8_Are_Mean | |
| HE03_DarNucBin8_Are_Tot | |
| HE03_DarNucBin8_Num | |
| HE03_EpiCluNuc_Are_Mean | Measurements on epithelial clustered nuclei |
| HE03_EpiCluNuc_Are_Std | |
| HE03_EpiCluNuc_Are_Tot | |
| HE03_EpiCluNuc_Num | |
| HE03_EpiIsoNuc_Are_Mean | Measurements on epithelial isolated nuclei |
| HE03_EpiIsoNuc_Are_Median | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| HE03_EpiIsoNuc_Are_Std | |
| HE03_EpiIsoNuc_Are_Tot | |
| HE03_EpiIsoNuc_Num | |
| HE03_EpiNucEro1_Blu_MeanStd | Color measurements of eroded epithelial nuclei |
| HE03_EpiNucEro1_Blu_StdMean | |
| HE03_EpiNucEro1_Bri_MeanStd | |
| HE03_EpiNucEro1_Bri_StdMean | |
| HE03_EpiNucEro1_Gre_MeanStd | |
| HE03_EpiNucEro1_Gre_StdMean | |
| HE03_EpiNucEro1_Red_MeanStd | |
| HE03_EpiNucEro1_Red_StdMean | |
| HE03_EpiNucEro2_Blu_MeanStd | |
| HE03_EpiNucEro2_Blu_StdMean | |
| HE03_EpiNucEro2_Bri_MeanStd | |
| HE03_EpiNucEro2_Bri_StdMean | |
| HE03_EpiNucEro2_Gre_MeanStd | |
| HE03_EpiNucEro2_Gre_StdMean | |
| HE03_EpiNucEro2_Red_MeanStd | |
| HE03_EpiNucEro2_Red_StdMean | |
| HE03_EpiNucSizBin0_1_Are_Mean | Color and area measurements of epithelial nuclei divided into different bins based on size. |
| HE03_EpiNucSizBin0_2_Are_Mean | |
| HE03_EpiNucSizBin0_3_Are_Mean | |
| HE03_EpiNucSizBin0_3_Blu_Mean | |
| HE03_EpiNucSizBin0_3_Blu_MeanStd | |
| HE03_EpiNucSizBin0_3_Blu_RA | |
| HE03_EpiNucSizBin0_3_Blu_RAStd | |
| HE03_EpiNucSizBin0_3_Blu_StdMean | |
| HE03_EpiNucSizBin0_3_Bri_Mean | |
| HE03_EpiNucSizBin0_3_Bri_MeanStd | |
| HE03_EpiNucSizBin0_3_Bri_RA | |
| HE03_EpiNucSizBin0_3_Bri_StdMean | |
| HE03_EpiNucSizBin0_3_Gre_Mean | |
| HE03_EpiNucSizBin0_3_Gre_MeanStd | |
| HE03_EpiNucSizBin0_3_Gre_RA | |
| HE03_EpiNucSizBin0_3_Gre_RAStd | |
| HE03_EpiNucSizBin0_3_Gre_StdMean | |
| HE03_EpiNucSizBin0_3_Red_Mean | |
| HE03_EpiNucSizBin0_3_Red_MeanStd | |
| HE03_EpiNucSizBin0_3_Red_RA | |
| HE03_EpiNucSizBin0_3_Red_RAStd | |
| HE03_EpiNucSizBin0_3_Red_StdMean | |
| HE03_EpiNucSizBin0_4_Are_Mean | |
| HE03_EpiNucSizBin0_5_Are_Mean | |
| HE03_EpiNucSizBin0_5_Blu_Mean | |
| HE03_EpiNucSizBin0_5_Blu_MeanStd | |
| HE03_EpiNucSizBin0_5_Blu_RA | |
| HE03_EpiNucSizBin0_5_Blu_RAStd | |
| HE03_EpiNucSizBin0_5_Blu_StdMean | |
| HE03_EpiNucSizBin0_5_Bri_Mean | |
| HE03_EpiNucSizBin0_5_Bri_MeanStd | |
| HE03_EpiNucSizBin0_5_Bri_RA | |
| HE03_EpiNucSizBin0_5_Bri_StdMean | |
| HE03_EpiNucSizBin0_5_Gre_Mean | |
| HE03_EpiNucSizBin0_5_Gre_MeanStd | |
| HE03_EpiNucSizBin0_5_Gre_RA | |
| HE03_EpiNucSizBin0_5_Gre_RAStd | |
| HE03_EpiNucSizBin0_5_Gre_StdMean | |
| HE03_EpiNucSizBin0_5_Red_Mean | |
| HE03_EpiNucSizBin0_5_Red_MeanStd | |
| HE03_EpiNucSizBin0_5_Red_RA | |
| HE03_EpiNucSizBin0_5_Red_RAStd | |
| HE03_EpiNucSizBin0_5_Red_StdMean | |
| HE03_EpiNucSizBin0_6_Are_Mean | |
| HE03_EpiNucSizBin0_7_Are_Mean | |
| HE03_EpiNucSizBin0_7_Blu_Mean | |
| HE03_EpiNucSizBin0_7_Blu_MeanStd | |
| HE03_EpiNucSizBin0_7_Blu_RA | |
| HE03_EpiNucSizBin0_7_Blu_RAStd | |
| HE03_EpiNucSizBin0_7_Blu_StdMean | |
| HE03_EpiNucSizBin0_7_Bri_Mean | |
| HE03_EpiNucSizBin0_7_Bri_MeanStd | |
| HE03_EpiNucSizBin0_7_Bri_RA | |
| HE03_EpiNucSizBin0_7_Bri_StdMean | |
| HE03_EpiNucSizBin0_7_Gre_Mean | |
| HE03_EpiNucSizBin0_7_Gre_MeanStd | |
| HE03_EpiNucSizBin0_7_Gre_RA | |
| HE03_EpiNucSizBin0_7_Gre_RAStd | |
| HE03_EpiNucSizBin0_7_Gre_StdMean | |
| HE03_EpiNucSizBin0_7_Red_Mean | |
| HE03_EpiNucSizBin0_7_Red_MeanStd | |
| HE03_EpiNucSizBin0_7_Red_RA | |
| HE03_EpiNucSizBin0_7_Red_RAStd | |
| HE03_EpiNucSizBin0_7_Red_StdMean | |
| HE03_EpiNucSizBin0_8_Are_Mean | |
| HE03_EpiNucSizBin0_Are_Mean | |
| HE03_EpiNucSizBin0_Are_Tot | |
| HE03_EpiNucSizBin0_Blu_Mean | |
| HE03_EpiNucSizBin0_Blu_MeanStd | |
| HE03_EpiNucSizBin0_Bri_Mean | |
| HE03_EpiNucSizBin0_Gre_Mean | |
| HE03_EpiNucSizBin0_Gre_MeanStd | |
| HE03_EpiNucSizBin0_Num | |
| HE03_EpiNucSizBin0_Red_Mean | |
| HE03_EpiNucSizBin0_Red_MeanStd | |
| HE03_EpiNucSizBin1_2_Are_Mean | After dividing epithelial nuclei into different bins based on size, color and area measurements of various combinations of the bins. |
| HE03_EpiNucSizBin1_3_Are_Mean | |
| HE03_EpiNucSizBin1_3_Blu_Mean | |
| HE03_EpiNucSizBin1_3_Blu_MeanStd | |
| HE03_EpiNucSizBin1_3_Blu_RA | |
| HE03_EpiNucSizBin1_3_Blu_RAStd | |
| HE03_EpiNucSizBin1_3_Blu_StdMean | |
| HE03_EpiNucSizBin1_3_Bri_Mean | |
| HE03_EpiNucSizBin1_3_Bri_MeanStd | |
| HE03_EpiNucSizBin1_3_Bri_RA | |
| HE03_EpiNucSizBin1_3_Bri_StdMean | |
| HE03_EpiNucSizBin1_3_Gre_Mean | |
| HE03_EpiNucSizBin1_3_Gre_MeanStd | |
| HE03_EpiNucSizBin1_3_Gre_RA | |
| HE03_EpiNucSizBin1_3_Gre_RAStd | |
| HE03_EpiNucSizBin1_3_Gre_StdMean | |
| HE03_EpiNucSizBin1_3_Red_Mean | |
| HE03_EpiNucSizBin1_3_Red_MeanStd | |
| HE03_EpiNucSizBin1_3_Red_RA | |
| HE03_EpiNucSizBin1_3_Red_RAStd | |
| HE03_EpiNucSizBin1_3_Red_StdMean | |
| HE03_EpiNucSizBin1_4_Are_Mean | |
| HE03_EpiNucSizBin1_5_Are_Mean | |
| HE03_EpiNucSizBin1_5_Blu_Mean | |
| HE03_EpiNucSizBin1_5_Blu_MeanStd | |
| HE03_EpiNucSizBin1_5_Blu_RA | |
| HE03_EpiNucSizBin1_5_Blu_RAStd | |
| HE03_EpiNucSizBin1_5_Blu_StdMean | |
| HE03_EpiNucSizBin1_5_Bri_Mean | |
| HE03_EpiNucSizBin1_5_Bri_MeanStd | |
| HE03_EpiNucSizBin1_5_Bri_RA | |
| HE03_EpiNucSizBin1_5_Bri_StdMean | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| HE03_EpiNucSizBin1_5_Gre_Mean | |
| HE03_EpiNucSizBin1_5_Gre_MeanStd | |
| HE03_EpiNucSizBin1_5_Gre_RA | |
| HE03_EpiNucSizBin1_5_Gre_RAStd | |
| HE03_EpiNucSizBin1_5_Gre_StdMean | |
| HE03_EpiNucSizBin1_5_Red_Mean | |
| HE03_EpiNucSizBin1_5_Red_MeanStd | |
| HE03_EpiNucSizBin1_5_Red_RA | |
| HE03_EpiNucSizBin1_5_Red_RAStd | |
| HE03_EpiNucSizBin1_5_Red_StdMean | |
| HE03_EpiNucSizBin1_6_Are_Mean | |
| HE03_EpiNucSizBin1_7_Are_Mean | |
| HE03_EpiNucSizBin1_7_Blu_Mean | |
| HE03_EpiNucSizBin1_7_Blu_MeanStd | |
| HE03_EpiNucSizBin1_7_Blu_RA | |
| HE03_EpiNucSizBin1_7_Blu_RAStd | |
| HE03_EpiNucSizBin1_7_Blu_StdMean | |
| HE03_EpiNucSizBin1_7_Bri_Mean | |
| HE03_EpiNucSizBin1_7_Bri_MeanStd | |
| HE03_EpiNucSizBin1_7_Bri_RA | |
| HE03_EpiNucSizBin1_7_Bri_StdMean | |
| HE03_EpiNucSizBin1_7_Gre_Mean | |
| HE03_EpiNucSizBin1_7_Gre_MeanStd | |
| HE03_EpiNucSizBin1_7_Gre_RA | |
| HE03_EpiNucSizBin1_7_Gre_RAStd | |
| HE03_EpiNucSizBin1_7_Gre_StdMean | |
| HE03_EpiNucSizBin1_7_Red_Mean | |
| HE03_EpiNucSizBin1_7_Red_MeanStd | |
| HE03_EpiNucSizBin1_7_Red_RA | |
| HE03_EpiNucSizBin1_7_Red_RAStd | |
| HE03_EpiNucSizBin1_7_Red_StdMean | |
| HE03_EpiNucSizBin1_8_Are_Mean | |
| HE03_EpiNucSizBin1_Are_Mean | |
| HE03_EpiNucSizBin1_Are_Tot | |
| HE03_EpiNucSizBin1_Blu_Mean | |
| HE03_EpiNucSizBin1_Blu_MeanStd | |
| HE03_EpiNucSizBin1_Bri_Mean | |
| HE03_EpiNucSizBin1_Gre_Mean | |
| HE03_EpiNucSizBin1_Gre_MeanStd | |
| HE03_EpiNucSizBin1_Num | |
| HE03_EpiNucSizBin1_Red_Mean | |
| HE03_EpiNucSizBin1_Red_MeanStd | |
| HE03_EpiNucSizBin2_3_Are_Mean | |
| HE03_EpiNucSizBin2_3_Blu_Mean | |
| HE03_EpiNucSizBin2_3_Blu_MeanStd | |
| HE03_EpiNucSizBin2_3_Blu_RA | |
| HE03_EpiNucSizBin2_3_Blu_RAStd | |
| HE03_EpiNucSizBin2_3_Blu_StdMean | |
| HE03_EpiNucSizBin2_3_Bri_Mean | |
| HE03_EpiNucSizBin2_3_Bri_MeanStd | |
| HE03_EpiNucSizBin2_3_Bri_RA | |
| HE03_EpiNucSizBin2_3_Bri_StdMean | |
| HE03_EpiNucSizBin2_3_Gre_Mean | |
| HE03_EpiNucSizBin2_3_Gre_MeanStd | |
| HE03_EpiNucSizBin2_3_Gre_RA | |
| HE03_EpiNucSizBin2_3_Gre_RAStd | |
| HE03_EpiNucSizBin2_3_Gre_StdMean | |
| HE03_EpiNucSizBin2_3_Red_Mean | |
| HE03_EpiNucSizBin2_3_Red_MeanStd | |
| HE03_EpiNucSizBin2_3_Red_RA | |
| HE03_EpiNucSizBin2_3_Red_RAStd | |
| HE03_EpiNucSizBin2_3_Red_StdMean | |
| HE03_EpiNucSizBin2_4_Are_Mean | |
| HE03_EpiNucSizBin2_5_Are_Mean | |
| HE03_EpiNucSizBin2_5_Blu_Mean | |
| HE03_EpiNucSizBin2_5_Blu_MeanStd | |
| HE03_EpiNucSizBin2_5_Blu_RA | |
| HE03_EpiNucSizBin2_5_Blu_RAStd | |
| HE03_EpiNucSizBin2_5_Blu_StdMean | |
| HE03_EpiNucSizBin2_5_Bri_Mean | |
| HE03_EpiNucSizBin2_5_Bri_MeanStd | |
| HE03_EpiNucSizBin2_5_Bri_RA | |
| HE03_EpiNucSizBin2_5_Bri_StdMean | |
| HE03_EpiNucSizBin2_5_Gre_Mean | |
| HE03_EpiNucSizBin2_5_Gre_MeanStd | |
| HE03_EpiNucSizBin2_5_Gre_RA | |
| HE03_EpiNucSizBin2_5_Gre_RAStd | |
| HE03_EpiNucSizBin2_5_Gre_StdMean | |
| HE03_EpiNucSizBin2_5_Red_Mean | |
| HE03_EpiNucSizBin2_5_Red_MeanStd | |
| HE03_EpiNucSizBin2_5_Red_RA | |
| HE03_EpiNucSizBin2_5_Red_RAStd | |
| HE03_EpiNucSizBin2_5_Red_StdMean | |
| HE03_EpiNucSizBin2_6_Are_Mean | |
| HE03_EpiNucSizBin2_7_Are_Mean | |
| HE03_EpiNucSizBin2_7_Blu_Mean | |
| HE03_EpiNucSizBin2_7_Blu_MeanStd | |
| HE03_EpiNucSizBin2_7_Blu_RA | |
| HE03_EpiNucSizBin2_7_Blu_RAStd | |
| HE03_EpiNucSizBin2_7_Blu_StdMean | |
| HE03_EpiNucSizBin2_7_Bri_Mean | |
| HE03_EpiNucSizBin2_7_Bri_MeanStd | |
| HE03_EpiNucSizBin2_7_Bri_RA | |
| HE03_EpiNucSizBin2_7_Bri_StdMean | |
| HE03_EpiNucSizBin2_7_Gre_Mean | |
| HE03_EpiNucSizBin2_7_Gre_MeanStd | |
| HE03_EpiNucSizBin2_7_Gre_RA | |
| HE03_EpiNucSizBin2_7_Gre_RAStd | |
| HE03_EpiNucSizBin2_7_Gre_StdMean | |
| HE03_EpiNucSizBin2_7_Red_Mean | |
| HE03_EpiNucSizBin2_7_Red_MeanStd | |
| HE03_EpiNucSizBin2_7_Red_RA | |
| HE03_EpiNucSizBin2_7_Red_RAStd | |
| HE03_EpiNucSizBin2_7_Red_StdMean | |
| HE03_EpiNucSizBin2_8_Are_Mean | |
| HE03_EpiNucSizBin2_Are_Mean | |
| HE03_EpiNucSizBin2_Are_Tot | |
| HE03_EpiNucSizBin2_Blu_Mean | |
| HE03_EpiNucSizBin2_Blu_MeanStd | |
| HE03_EpiNucSizBin2_Bri_Mean | |
| HE03_EpiNucSizBin2_Gre_Mean | |
| HE03_EpiNucSizBin2_Gre_MeanStd | |
| HE03_EpiNucSizBin2_Num | |
| HE03_EpiNucSizBin2_Red_Mean | |
| HE03_EpiNucSizBin2_Red_MeanStd | |
| HE03_EpiNucSizBin3_4_Are_Mean | |
| HE03_EpiNucSizBin3_5_Are_Mean | |
| HE03_EpiNucSizBin3_5_Blu_Mean | |
| HE03_EpiNucSizBin3_5_Blu_MeanStd | |
| HE03_EpiNucSizBin3_5_Blu_RA | |
| HE03_EpiNucSizBin3_5_Blu_RAStd | |
| HE03_EpiNucSizBin3_5_Blu_StdMean | |
| HE03_EpiNucSizBin3_5_Bri_Mean | |
| HE03_EpiNucSizBin3_5_Bri_MeanStd | |
| HE03_EpiNucSizBin3_5_Bri_RA | |
| HE03_EpiNucSizBin3_5_Bri_StdMean | |
| HE03_EpiNucSizBin3_5_Gre_Mean | |
| HE03_EpiNucSizBin3_5_Gre_MeanStd | |
| HE03_EpiNucSizBin3_5_Gre_RA | |
| HE03_EpiNucSizBin3_5_Gre_RAStd | |
| HE03_EpiNucSizBin3_5_Gre_StdMean | |
| HE03_EpiNucSizBin3_5_Red_Mean | |
| HE03_EpiNucSizBin3_5_Red_MeanStd | |
| HE03_EpiNucSizBin3_5_Red_RA | |
| HE03_EpiNucSizBin3_5_Red_RAStd | |
| HE03_EpiNucSizBin3_5_Red_StdMean | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE03_EpiNucSizBin3_6_Are_Mean | |
| HE03_EpiNucSizBin3_7_Are_Mean | |
| HE03_EpiNucSizBin3_7_Blu_Mean | |
| HE03_EpiNucSizBin3_7_Blu_MeanStd | |
| HE03_EpiNucSizBin3_7_Blu_RA | |
| HE03_EpiNucSizBin3_7_Blu_RAStd | |
| HE03_EpiNucSizBin3_7_Blu_StdMean | |
| HE03_EpiNucSizBin3_7_Bri_Mean | |
| HE03_EpiNucSizBin3_7_Bri_MeanStd | |
| HE03_EpiNucSizBin3_7_Bri_RA | |
| HE03_EpiNucSizBin3_7_Bri_StdMean | |
| HE03_EpiNucSizBin3_7_Gre_Mean | |
| HE03_EpiNucSizBin3_7_Gre_MeanStd | |
| HE03_EpiNucSizBin3_7_Gre_RA | |
| HE03_EpiNucSizBin3_7_Gre_RAStd | |
| HE03_EpiNucSizBin3_7_Gre_StdMean | |
| HE03_EpiNucSizBin3_7_Red_Mean | |
| HE03_EpiNucSizBin3_7_Red_MeanStd | |
| HE03_EpiNucSizBin3_7_Red_RA | |
| HE03_EpiNucSizBin3_7_Red_RAStd | |
| HE03_EpiNucSizBin3_7_Red_StdMean | |
| HE03_EpiNucSizBin3_8_Are_Mean | |
| HE03_EpiNucSizBin3_Are_Mean | |
| HE03_EpiNucSizBin3_Are_Tot | |
| HE03_EpiNucSizBin3_Blu_Mean | |
| HE03_EpiNucSizBin3_Blu_MeanStd | |
| HE03_EpiNucSizBin3_Bri_Mean | |
| HE03_EpiNucSizBin3_Gre_Mean | |
| HE03_EpiNucSizBin3_Gre_MeanStd | |
| HE03_EpiNucSizBin3_Num | |
| HE03_EpiNucSizBin3_Red_Mean | |
| HE03_EpiNucSizBin3_Red_MeanStd | |
| HE03_EpiNucSizBin4_5_Are_Mean | |
| HE03_EpiNucSizBin4_5_Blu_Mean | |
| HE03_EpiNucSizBin4_5_Blu_MeanStd | |
| HE03_EpiNucSizBin4_5_Blu_RA | |
| HE03_EpiNucSizBin4_5_Blu_RAStd | |
| HE03_EpiNucSizBin4_5_Blu_StdMean | |
| HE03_EpiNucSizBin4_5_Bri_Mean | |
| HE03_EpiNucSizBin4_5_Bri_MeanStd | |
| HE03_EpiNucSizBin4_5_Bri_RA | |
| HE03_EpiNucSizBin4_5_Bri_StdMean | |
| HE03_EpiNucSizBin4_5_Gre_Mean | |
| HE03_EpiNucSizBin4_5_Gre_MeanStd | |
| HE03_EpiNucSizBin4_5_Gre_RA | |
| HE03_EpiNucSizBin4_5_Gre_RAStd | |
| HE03_EpiNucSizBin4_5_Gre_StdMean | |
| HE03_EpiNucSizBin4_5_Red_Mean | |
| HE03_EpiNucSizBin4_5_Red_MeanStd | |
| HE03_EpiNucSizBin4_5_Red_RA | |
| HE03_EpiNucSizBin4_5_Red_RAStd | |
| HE03_EpiNucSizBin4_5_Red_StdMean | |
| HE03_EpiNucSizBin4_6_Are_Mean | |
| HE03_EpiNucSizBin4_7_Are_Mean | |
| HE03_EpiNucSizBin4_7_Blu_Mean | |
| HE03_EpiNucSizBin4_7_Blu_MeanStd | |
| HE03_EpiNucSizBin4_7_Blu_RA | |
| HE03_EpiNucSizBin4_7_Blu_RAStd | |
| HE03_EpiNucSizBin4_7_Blu_StdMean | |
| HE03_EpiNucSizBin4_7_Bri_Mean | |
| HE03_EpiNucSizBin4_7_Bri_MeanStd | |
| HE03_EpiNucSizBin4_7_Bri_RA | |
| HE03_EpiNucSizBin4_7_Bri_StdMean | |
| HE03_EpiNucSizBin4_7_Gre_Mean | |
| HE03_EpiNucSizBin4_7_Gre_MeanStd | |
| HE03_EpiNucSizBin4_7_Gre_RA | |
| HE03_EpiNucSizBin4_7_Gre_RAStd | |
| HE03_EpiNucSizBin4_7_Gre_StdMean | |
| HE03_EpiNucSizBin4_7_Red_Mean | |
| HE03_EpiNucSizBin4_7_Red_MeanStd | |
| HE03_EpiNucSizBin4_7_Red_RA | |
| HE03_EpiNucSizBin4_7_Red_RAStd | |
| HE03_EpiNucSizBin4_7_Red_StdMean | |
| HE03_EpiNucSizBin4_8_Are_Mean | |
| HE03_EpiNucSizBin4_Are_Mean | |
| HE03_EpiNucSizBin4_Are_Tot | |
| HE03_EpiNucSizBin4_Blu_Mean | |
| HE03_EpiNucSizBin4_Blu_MeanStd | |
| HE03_EpiNucSizBin4_Bri_Mean | |
| HE03_EpiNucSizBin4_Gre_Mean | |
| HE03_EpiNucSizBin4_Gre_MeanStd | |
| HE03_EpiNucSizBin4_Num | |
| HE03_EpiNucSizBin4_Red_Mean | |
| HE03_EpiNucSizBin4_Red_MeanStd | |
| HE03_EpiNucSizBin5_6_Are_Mean | |
| HE03_EpiNucSizBin5_7_Are_Mean | |
| HE03_EpiNucSizBin5_7_Blu_Mean | |
| HE03_EpiNucSizBin5_7_Blu_MeanStd | |
| HE03_EpiNucSizBin5_7_Blu_RA | |
| HE03_EpiNucSizBin5_7_Blu_RAStd | |
| HE03_EpiNucSizBin5_7_Blu_StdMean | |
| HE03_EpiNucSizBin5_7_Bri_Mean | |
| HE03_EpiNucSizBin5_7_Bri_MeanStd | |
| HE03_EpiNucSizBin5_7_Bri_RA | |
| HE03_EpiNucSizBin5_7_Bri_StdMean | |
| HE03_EpiNucSizBin5_7_Gre_Mean | |
| HE03_EpiNucSizBin5_7_Gre_MeanStd | |
| HE03_EpiNucSizBin5_7_Gre_RA | |
| HE03_EpiNucSizBin5_7_Gre_RAStd | |
| HE03_EpiNucSizBin5_7_Gre_StdMean | |
| HE03_EpiNucSizBin5_7_Red_Mean | |
| HE03_EpiNucSizBin5_7_Red_MeanStd | |
| HE03_EpiNucSizBin5_7_Red_RA | |
| HE03_EpiNucSizBin5_7_Red_RAStd | |
| HE03_EpiNucSizBin5_7_Red_StdMean | |
| HE03_EpiNucSizBin5_8_Are_Mean | |
| HE03_EpiNucSizBin5_Are_Mean | |
| HE03_EpiNucSizBin5_Are_Tot | |
| HE03_EpiNucSizBin5_Blu_Mean | |
| HE03_EpiNucSizBin5_Blu_MeanStd | |
| HE03_EpiNucSizBin5_Bri_Mean | |
| HE03_EpiNucSizBin5_Gre_Mean | |
| HE03_EpiNucSizBin5_Gre_MeanStd | |
| HE03_EpiNucSizBin5_Num | |
| HE03_EpiNucSizBin5_Red_Mean | |
| HE03_EpiNucSizBin5_Red_MeanStd | |
| HE03_EpiNucSizBin6_7_Are_Mean | |
| HE03_EpiNucSizBin6_7_Blu_Mean | |
| HE03_EpiNucSizBin6_7_Blu_MeanStd | |
| HE03_EpiNucSizBin6_7_Blu_RA | |
| HE03_EpiNucSizBin6_7_Blu_RAStd | |
| HE03_EpiNucSizBin6_7_Blu_StdMean | |
| HE03_EpiNucSizBin6_7_Bri_Mean | |
| HE03_EpiNucSizBin6_7_Bri_MeanStd | |
| HE03_EpiNucSizBin6_7_Bri_RA | |
| HE03_EpiNucSizBin6_7_Bri_StdMean | |
| HE03_EpiNucSizBin6_7_Gre_Mean | |
| HE03_EpiNucSizBin6_7_Gre_MeanStd | |
| HE03_EpiNucSizBin6_7_Gre_RA | |
| HE03_EpiNucSizBin6_7_Gre_RAStd | |
| HE03_EpiNucSizBin6_7_Gre_StdMean | |
| HE03_EpiNucSizBin6_7_Red_Mean | |
| HE03_EpiNucSizBin6_7_Red_MeanStd | |
| HE03_EpiNucSizBin6_7_Red_RA | |

TABLE 1-continued

Morphometric Features (e.g., measurable in images of H&E-stained tissue) In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
|---|---|
| HE03_EpiNucSizBin6_7_Red_RAStd | |
| HE03_EpiNucSizBin6_7_Red_StdMean | |
| HE03_EpiNucSizBin6_8_Are_Mean | |
| HE03_EpiNucSizBin6_Are_Mean | |
| HE03_EpiNucSizBin6_Are_Tot | |
| HE03_EpiNucSizBin6_Blu_Mean | |
| HE03_EpiNucSizBin6_Blu_MeanStd | |
| HE03_EpiNucSizBin6_Bri_Mean | |
| HE03_EpiNucSizBin6_Gre_Mean | |
| HE03_EpiNucSizBin6_Gre_MeanStd | |
| HE03_EpiNucSizBin6_Num | |
| HE03_EpiNucSizBin6_Red_Mean | |
| HE03_EpiNucSizBin6_Red_MeanStd | |
| HE03_EpiNucSizBin7_8_Are_Mean | |
| HE03_EpiNucSizBin7_Are_Mean | |
| HE03_EpiNucSizBin7_Are_Tot | |
| HE03_EpiNucSizBin7_Blu_Mean | |
| HE03_EpiNucSizBin7_Blu_MeanStd | |
| HE03_EpiNucSizBin7_Bri_Mean | |
| HE03_EpiNucSizBin7_Gre_Mean | |
| HE03_EpiNucSizBin7_Gre_MeanStd | |
| HE03_EpiNucSizBin7_Num | |
| HE03_EpiNucSizBin7_Red_Mean | |
| HE03_EpiNucSizBin7_Red_MeanStd | |
| HE03_EpiNucSizBin8_Are_Mean | |
| HE03_EpiNucSizBin8_Are_Tot | |
| HE03_EpiNucSizBin8_Blu_Mean | |
| HE03_EpiNucSizBin8_Blu_MeanStd | |
| HE03_EpiNucSizBin8_Bri_Mean | |
| HE03_EpiNucSizBin8_Gre_Mean | |
| HE03_EpiNucSizBin8_Gre_MeanStd | |
| HE03_EpiNucSizBin8_Num | |
| HE03_EpiNucSizBin8_Red_Mean | |
| HE03_EpiNucSizBin8_Red_MeanStd | |
| HE03_EpiNuc_Are_Mean | Morphometric, color and area measurements of epithelial nuclei |
| HE03_EpiNuc_Are_Median | |
| HE03_EpiNuc_Are_Std | |
| HE03_EpiNuc_Are_Tot | |
| HE03_EpiNuc_ElpFit_Mean | |
| HE03_EpiNuc_ElpFit_Median | |
| HE03_EpiNuc_ElpFit_Std | |
| HE03_EpiNuc_LOW_Mean | |
| HE03_EpiNuc_LOW_Median | |
| HE03_EpiNuc_LOW_Std | |
| HE03_EpiNuc_Num | |
| HE03_EpiNuc_OrgBlu_MeanMean | |
| HE03_EpiNuc_OrgBlu_MeanStd | |
| HE03_EpiNuc_OrgBri_Mean | |
| HE03_EpiNuc_OrgBri_Std | |
| HE03_EpiNuc_OrgGre_MeanMean | |
| HE03_EpiNuc_OrgGre_MeanStd | |
| HE03_EpiNuc_OrgH_Mean | |
| HE03_EpiNuc_OrgH_Std | |
| HE03_EpiNuc_OrgI_Mean | |
| HE03_EpiNuc_OrgI_Std | |
| HE03_EpiNuc_OrgQ_Mean | |
| HE03_EpiNuc_OrgQ_Std | |
| HE03_EpiNuc_OrgRed_MeanMean | |
| HE03_EpiNuc_OrgRed_MeanStd | |
| HE03_EpiNuc_OrgS_Mean | |
| HE03_EpiNuc_OrgS_Std | |
| HE03_EpiNuc_OrgV_Mean | |
| HE03_EpiNuc_OrgV_Std | |
| HE03_EpiNuc_OrgY_Mean | |
| HE03_EpiNuc_OrgY_Std | |
| HE03_IsoEpiNuc_ElpFit_Mean | Morphometric, color and area measurements of isolated epithelial and stroma nuclei |
| HE03_IsoEpiNuc_ElpFit_Median | |
| HE03_IsoEpiNuc_ElpFit_Std | |
| HE03_IsoEpiNuc_LOW_Mean | |
| HE03_IsoEpiNuc_LOW_Median | |
| HE03_IsoEpiNuc_LOW_Std | |
| HE03_IsoEpiNuc_OrgBlu_MeanMean | |
| HE03_IsoEpiNuc_OrgBlu_MeanStd | |
| HE03_IsoEpiNuc_OrgBlu_StdMean | |
| HE03_IsoEpiNuc_OrgBri_Mean | |
| HE03_IsoEpiNuc_OrgBri_Std | |
| HE03_IsoEpiNuc_OrgGre_MeanMean | |
| HE03_IsoEpiNuc_OrgGre_MeanStd | |
| HE03_IsoEpiNuc_OrgGre_StdMean | |
| HE03_IsoEpiNuc_OrgRed_MeanMean | |
| HE03_IsoEpiNuc_OrgRed_MeanStd | |
| HE03_IsoEpiNuc_OrgRed_StdMean | |
| HE03_IsoEpiNuc_ShaInd_Mean | |
| HE03_IsoEpiNuc_ShaInd_Std | |
| HE03_IsoNuc_Are_Mean | |
| HE03_IsoNuc_Are_Std | |
| HE03_IsoNuc_Are_Tot | |
| HE03_IsoNuc_Num | |
| HE03_IsoStrNuc_Are_Mean | |
| HE03_IsoStrNuc_Are_Std | |
| HE03_IsoStrNuc_Are_Tot | |
| HE03_IsoStrNuc_Num | |
| HE03_LENSizBin0_Are_Mean | Color and morphometric measurements of likely epithelial nuclei |
| HE03_LENSizBin0_Are_Tot | |
| HE03_LENSizBin0_Num | |
| HE03_LENSizBin1_Are_Mean | |
| HE03_LENSizBin1_Are_Tot | |
| HE03_LENSizBin1_Num | |
| HE03_LENSizBin2_Are_Mean | |
| HE03_LENSizBin2_Are_Tot | |
| HE03_LENSizBin2_Num | |
| HE03_LENSizBin3_Are_Mean | |
| HE03_LENSizBin3_Are_Tot | |
| HE03_LENSizBin3_Num | |
| HE03_LENSizBin4_Are_Mean | |
| HE03_LENSizBin4_Are_Tot | |
| HE03_LENSizBin4_Num | |
| HE03_LENSizBin5_Are_Mean | |
| HE03_LENSizBin5_Are_Tot | |
| HE03_LENSizBin5_Num | |
| HE03_LENSizBin6_Are_Mean | |
| HE03_LENSizBin6_Are_Tot | |
| HE03_LENSizBin6_Num | |
| HE03_LENSizBin7_Are_Mean | |
| HE03_LENSizBin7_Are_Tot | |
| HE03_LENSizBin7_Num | |
| HE03_LENSizBin8_Are_Mean | |
| HE03_LENSizBin8_Are_Tot | |
| HE03_LENSizBin8_Num | |
| HE03_LEN_Are_Mean | |
| HE03_LEN_Are_Q50 | |
| HE03_LEN_Are_Q75 | |
| HE03_LEN_Are_Q90 | |
| HE03_LEN_Are_Q95 | |
| HE03_LEN_Are_Tot | |
| HE03_LEN_Com_Mean | |
| HE03_LEN_ElpFit_Mean | |
| HE03_LEN_Num | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE03_LEN_OrgBlu_MeanMean | |
| HE03_LEN_OrgBlu_MeanStd | |
| HE03_LEN_OrgBlu_StdMean | |
| HE03_LEN_OrgBri_MeanMean | |
| HE03_LEN_OrgBri_StdMean | |
| HE03_LEN_OrgGre_MeanMean | |
| HE03_LEN_OrgGre_MeanStd | |
| HE03_LEN_OrgGre_StdMean | |
| HE03_LEN_OrgH_MeanMean | |
| HE03_LEN_OrgH_StdMean | |
| HE03_LEN_OrgI_MeanMean | |
| HE03_LEN_OrgQ_MeanMean | |
| HE03_LEN_OrgRed_MeanMean | |
| HE03_LEN_OrgRed_MeanStd | |
| HE03_LEN_OrgRed_StdMean | |
| HE03_LEN_OrgS_MeanMean | |
| HE03_LEN_OrgS_StdMean | |
| HE03_LEN_OrgV_MeanMean | |
| HE03_LEN_OrgV_StdMean | |
| HE03_LEN_OrgY_MeanMean | |
| HE03_LEN_Rou_Mean | |
| HE03_LEN_ShaInd_Mean | |
| HE03_LENw0N_Are_Mean | |
| HE03_LENw0N_Are_Tot | |
| HE03_LENw0N_Com_Mean | |
| HE03_LENw0N_ElpFit_Mean | |
| HE03_LENw0N_Num | |
| HE03_LENw0N_OrgBlu_MeanMean | |
| HE03_LENw0N_OrgBlu_MeanStd | |
| HE03_LENw0N_OrgBlu_StdMean | |
| HE03_LENw0N_OrgBri_MeanMean | |
| HE03_LENw0N_OrgBri_StdMean | |
| HE03_LENw0N_OrgGre_MeanMean | |
| HE03_LENw0N_OrgGre_MeanStd | |
| HE03_LENw0N_OrgGre_StdMean | |
| HE03_LENw0N_OrgH_MeanMean | |
| HE03_LENw0N_OrgH_StdMean | |
| HE03_LENw0N_OrgI_MeanMean | |
| HE03_LENw0N_OrgQ_MeanMean | |
| HE03_LENw0N_OrgRed_MeanMean | |
| HE03_LENw0N_OrgRed_MeanStd | |
| HE03_LENw0N_OrgRed_StdMean | |
| HE03_LENw0N_OrgS_MeanMean | |
| HE03_LENw0N_OrgS_StdMean | |
| HE03_LENw0N_OrgV_MeanMean | |
| HE03_LENw0N_OrgV_StdMean | |
| HE03_LENw0N_OrgY_MeanMean | |
| HE03_LENw0N_Rou_Mean | |
| HE03_LENw0N_ShaInd_Mean | |
| HE03_LENw1N_Are_Mean | |
| HE03_LENw1N_Are_Tot | |
| HE03_LENw1N_Com_Mean | |
| HE03_LENw1N_ElpFit_Mean | |
| HE03_LENw1N_Num | |
| HE03_LENw1N_OrgBlu_MeanMean | |
| HE03_LENw1N_OrgBlu_MeanStd | |
| HE03_LENw1N_OrgBlu_StdMean | |
| HE03_LENw1N_OrgBri_MeanMean | |
| HE03_LENw1N_OrgBri_StdMean | |
| HE03_LENw1N_OrgGre_MeanMean | |
| HE03_LENw1N_OrgGre_MeanStd | |
| HE03_LENw1N_OrgGre_StdMean | |
| HE03_LENw1N_OrgH_MeanMean | |
| HE03_LENw1N_OrgH_StdMean | |
| HE03_LENw1N_OrgI_MeanMean | |
| HE03_LENw1N_OrgQ_MeanMean | |
| HE03_LENw1N_OrgRed_MeanMean | |
| HE03_LENw1N_OrgRed_MeanStd | |
| HE03_LENw1N_OrgRed_StdMean | |
| HE03_LENw1N_OrgS_MeanMean | |
| HE03_LENw1N_OrgS_StdMean | |
| HE03_LENw1N_OrgV_MeanMean | |
| HE03_LENw1N_OrgV_StdMean | |
| HE03_LENw1N_OrgY_MeanMean | |
| HE03_LENw1N_Rou_Mean | |
| HE03_LENw1N_ShaInd_Mean | |
| HE03_LENw2N_Are_Mean | |
| HE03_LENw2N_Are_Tot | |
| HE03_LENw2N_Com_Mean | |
| HE03_LENw2N_ElpFit_Mean | |
| HE03_LENw2N_Num | |
| HE03_LENw2N_OrgBlu_MeanMean | |
| HE03_LENw2N_OrgBlu_MeanStd | |
| HE03_LENw2N_OrgBlu_StdMean | |
| HE03_LENw2N_OrgBri_MeanMean | |
| HE03_LENw2N_OrgBri_StdMean | |
| HE03_LENw2N_OrgGre_MeanMean | |
| HE03_LENw2N_OrgGre_MeanStd | |
| HE03_LENw2N_OrgGre_StdMean | |
| HE03_LENw2N_OrgH_MeanMean | |
| HE03_LENw2N_OrgH_StdMean | |
| HE03_LENw2N_OrgI_MeanMean | |
| HE03_LENw2N_OrgQ_MeanMean | |
| HE03_LENw2N_OrgRed_MeanMean | |
| HE03_LENw2N_OrgRed_MeanStd | |
| HE03_LENw2N_OrgRed_StdMean | |
| HE03_LENw2N_OrgS_MeanMean | |
| HE03_LENw2N_OrgS_StdMean | |
| HE03_LENw2N_OrgV_MeanMean | |
| HE03_LENw2N_OrgV_StdMean | |
| HE03_LENw2N_OrgY_MeanMean | |
| HE03_LENw2N_Rou_Mean | |
| HE03_LENw2N_ShaInd_Mean | |
| HE03_LigNucBin0_3_Are_Mean | Color and morphometric measurements of light nuclei |
| HE03_LigNucBin0_3_Are_Tot | |
| HE03_LigNucBin0_3_Num | |
| HE03_LigNueBin0_5_Are_Mean | |
| HE03_LigNucBin0_5_Are_Tot | |
| HE03_LigNucBin0_5_Num | |
| HE03_LigNucBin0_7_Are_Mean | |
| HE03_LigNucBin0_7_Are_Tot | |
| HE03_LigNucBin0_7_Num | |
| HE03_LigNucBin0_Are_Mean | |
| HE03_LigNucBin0_Are_Tot | |
| HE03_LigNucBin0_Num | |
| HE03_LigNucBin1_3_Are_Mean | |
| HE03_LigNucBin1_3_Are_Tot | |
| HE03_LigNucBin1_3_Num | |
| HE03_LigNueBin1_5_Are_Mean | |
| HE03_LigNucBin1_5_Are_Tot | |
| HE03_LigNucBin1_5_Num | |
| HE03_LigNucBin1_7_Are_Mean | |
| HE03_LigNueBin1_7_Are_Tot | |
| HE03_LigNucBin1_7_Num | |
| HE03_LigNucBin1_Are_Mean | |
| HE03_LigNucBin1_Are_Tot | |
| HE03_LigNueBin1_Num | |
| HE03_LigNucBin2_3_Are_Mean | |
| HE03_LigNucBin2_3_Are_Tot | |
| HE03_LigNucBin2_3_Num | |
| HE03_LigNucBin2_5_Are_Mean | |
| HE03_LigNucBin2_5_Are_Tot | |
| HE03_LigNucBin2_5_Num | |
| HE03_LigNucBin2_7_Are_Mean | |
| HE03_LigNucBin2_7_Are_Tot | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| HE03_LigNucBin2_7_Num | |
| HE03_LigNucBin2_Are_Mean | |
| HE03_LigNucBin2_Are_Tot | |
| HE03_LigNucBin2_Num | |
| HE03_LigNucBin3_5_Are_Mean | |
| HE03_LigNucBin3_5_Are_Tot | |
| HE03_LigNucBin3_5_Num | |
| HE03_LigNucBin3_7_Are_Mean | |
| HE03_LigNucBin3_7_Are_Tot | |
| HE03_LigNucBin3_7_Num | |
| HE03_LigNucBin3_Are_Mean | |
| HE03_LigNucBin3_Are_Tot | |
| HE03_LigNucBin3_Num | |
| HE03_LigNucBin4_5_Are_Mean | |
| HE03_LigNucBin4_5_Are_Tot | |
| HE03_LigNucBin4_5_Num | |
| HE03_LigNucBin4_7_Are_Mean | |
| HE03_LigNucBin4_7_Are_Tot | |
| HE03_LigNucBin4_7_Num | |
| HE03_LigNucBin4_Are_Mean | |
| HE03_LigNucBin4_Are_Tot | |
| HE03_LigNucBin4_Num | |
| HE03_LigNucBin5_7_Are_Mean | |
| HE03_LigNucBin5_7_Are_Tot | |
| HE03_LigNucBin5_7_Num | |
| HE03_LigNucBin5_Are_Mean | |
| HE03_LigNucBin5_Are_Tot | |
| HE03_LigNucBin5_Num | |
| HE03_LigNucBin6_7_Are_Mean | |
| HE03_LigNucBin6_7_Are_Tot | |
| HE03_LigNucBin6_7_Num | |
| HE03_LigNucBin6_Are_Mean | |
| HE03_LigNucBin6_Are_Tot | |
| HE03_LigNucBin6_Num | |
| HE03_LigNucBin7_Are_Mean | |
| HE03_LigNucBin7_Are_Tot | |
| HE03_LigNucBin7_Num | |
| HE03_LigNucBin8_Are_Mean | |
| HE03_LigNucBin8_Are_Tot | |
| HE03_LigNucBin8_Num | |
| HE03_NoWhi_Are_Tot | |
| HE03_NucLikTis_Are_Tot | |
| HE03_Nuc_Are_Mean | Area features of all nuclei |
| HE03_Nuc_Are_Std | |
| HE03_Nuc_Are_Tot | |
| HE03_Nuc_Num | |
| HE03_Nuclli_Are_Mean | Area features of nucleoli |
| HE03_Nuclli_Are_Q50 | |
| HE03_Nuclli_Are_Q75 | |
| HE03_Nuclli_Are_Q90 | |
| HE03_Nuclli_Are_Q95 | |
| HE03_PDNuc_Are_Mean | Color and morphometric features of poorly defined nuclei |
| HE03_PDNuc_Are_Std | |
| HE03_PDNuc_Are_Tot | |
| HE03_PDNuc_ElpFit_Mean | |
| HE03_PDNuc_ElpFit_Std | |
| HE03_PDNuc_LOW_Mean | |
| HE03_PDNuc_LOW_Std | |
| HE03_PDNuc_Num | |
| HE03_PDNuc_OrgBlu_MeanMean | |
| HE03_PDNuc_OrgBlu_MeanStd | |
| HE03_PDNuc_OrgBlu_StdMean | |
| HE03_PDNuc_OrgBri_Mean | |
| HE03_PDNuc_OrgBri_Std | |
| HE03_PDNuc_OrgGre_MeanMean | |
| HE03_PDNuc_OrgGre_MeanStd | |
| HE03_PDNuc_OrgGre_StdMean | |
| HE03_PDNuc_OrgRed_MeanMean | |
| HE03_PDNuc_OrgRed_MeanStd | |
| HE03_PDNuc_OrgRed_StdMean | |
| HE03_PDNuc_ShaInd_Mean | |
| HE03_PDNuc_ShaInd_Std | |
| HE03_StrNuc_Are_Mean | Color and morphometric features of stroma nuclei |
| HE03_StrNuc_Are_Median | |
| HE03_StrNuc_Are_Std | |
| HE03_StrNuc_Are_Tot | |
| HE03_StrNuc_ElpFit_Mean | |
| HE03_StrNuc_ElpFit_Median | |
| HE03_StrNuc_ElpFit_Std | |
| HE03_StrNuc_LOW_Mean | |
| HE03_StrNuc_LOW_Median | |
| HE03_StrNuc_LOW_Std | |
| HE03_StrNuc_Num | |
| HE03_StrNuc_OrgBlu_MeanMean | |
| HE03_StrNuc_OrgBlu_MeanStd | |
| HE03_StrNuc_OrgBri_Mean | |
| HE03_StrNuc_OrgBri_Std | |
| HE03_StrNuc_OrgGre_MeanMean | |
| HE03_StrNuc_OrgGre_MeanStd | |
| HE03_StrNuc_OrgH_Mean | |
| HE03_StrNuc_OrgH_Std | |
| HE03_StrNuc_OrgI_Mean | |
| HE03_StrNuc_OrgI_Std | |
| HE03_StrNuc_OrgQ_Mean | |
| HE03_StrNuc_OrgQ_Std | |
| HE03_StrNuc_OrgRed_MeanMean | |
| HE03_StrNuc_OrgRed_MeanStd | |
| HE03_StrNuc_OrgS_Mean | |
| HE03_StrNuc_OrgS_Std | |
| HE03_StrNuc_OrgV_Mean | |
| HE03_StrNuc_OrgV_Std | |
| HE03_StrNuc_OrgY_Mean | |
| HE03_StrNuc_OrgY_Std | |
| HE03_Str_Are_Mean | Color and morphometric measurements of stroma |
| HE03_Str_Are_Std | |
| HE03_Str_Are_Tot | |
| HE03_Str_Num | |
| HE03_Str_OrgBlu_MeanMean | |
| HE03_Str_OrgBlu_MeanStd | |
| HE03_Str_OrgBri_Mean | |
| HE03_Str_OrgBri_Std | |
| HE03_Str_OrgGre_MeanMean | |
| HE03_Str_OrgGre_MeanStd | |
| HE03_Str_OrgH_Mean | |
| HE03_Str_OrgH_Std | |
| HE03_Str_OrgI_Mean | |
| HE03_Str_OrgI_Std | |
| HE03_Str_OrgQ_Mean | |
| HE03_Str_OrgQ_Std | |
| HE03_Str_OrgRed_MeanMean | |
| HE03_Str_OrgRed_MeanStd | |
| HE03_Str_OrgS_Mean | |
| HE03_Str_OrgS_Std | |
| HE03_Str_OrgV_Mean | |
| HE03_Str_OrgV_Std | |
| HE03_Str_OrgY_Mean | |
| HE03_Str_OrgY_Std | |
| HE03_WDEpiNuc_Are_Mean | Color and morphometric measurements of well defined epithelial nuclei |
| HE03_WDEpiNuc_Are_Median | |
| HE03_WDEpiNuc_Are_Std | |

TABLE 1-continued

Morphometric Features (e.g., measurable in images of H&E-stained tissue)
In some embodiments, features in Table 1 having a prefix of "HE03" or
"HEx3" are measured in tissue images at 40x magnification. HE03 features
may be measured directly from the images, whereas HEx3 features are
derived/calculated from the HE03 features. In some embodiments, features
in Table 1 having a prefix of "HE02" or "HEx2" are measured in tissue
images at 20x magnification. HE02 features may be measured directly
from the images, whereas HEx2 features are derived/calculated from
the HE02 features.

| Feature | Description |
|---|---|
| HE03_WDEpiNuc_Are_Tot | |
| HE03_WDEpiNuc_ElpFit_Mean | |
| HE03_WDEpiNuc_ElpFit_Median | |
| HE03_WDEpiNuc_ElpFit_Std | |
| HE03_WDEpiNuc_LOW_Mean | |
| HE03_WDEpiNuc_LOW_Median | |
| HE03_WDEpiNuc_LOW_Std | |
| HE03_WDEpiNuc_Num | |
| HE03_WDEpiNuc_OrgBlu_MeanMean | |
| HE03_WDEpiNuc_OrgBlu_MeanStd | |
| HE03_WDEpiNuc_OrgBlu_StdMean | |
| HE03_WDEpiNuc_OrgBri_Mean | |
| HE03_WDEpiNuc_OrgBri_Std | |
| HE03_WDEpiNuc_OrgGre_MeanMean | |
| HE03_WDEpiNuc_OrgGre_MeanStd | |
| HE03_WDEpiNuc_OrgGre_StdMean | |
| HE03_WDEpiNuc_OrgRed_MeanMean | |
| HE03_WDEpiNuc_OrgRed_MeanStd | |
| HE03_WDEpiNuc_OrgRed_StdMean | |
| HE03_WDEpiNuc_ShaInd_Mean | |
| HE03_WDEpiNuc_ShaInd_Std | |
| HE03_Whi_Are_Tot | |
| 'HEx2_LENwNcli_NumTotal' | Normalized measurements of likely epithelial nuclei |
| 'HEx2_LENwNcli_AreTotal' | |
| 'HEx3_RelNumw0Nucleoli' | Proportions of numbers of nucleoli |
| 'HEx3_RelNumw1Nucleoli' | |
| 'HEx3_RelNumw2Nucleoli' | |
| 'HEx3_RelNumwNucleoli' | |
| 'HEx3_RelAreaw0Nucleoli' | |
| 'HEx3_RelAreaw1Nucleoli' | |
| 'HEx3_RelAreaw2Nucleoli' | |
| 'HEx3_RelAreawNucleoli' | |
| 'HEx3_nrmSN_EpiNuc_OrgRed_MnMn' | Normalized color features of epithelial nuclei. SN indicates normalization by Stroma Nuclei |
| 'HEx3_nrmS_EpiNuc_OrgRed_MnMn' | |
| 'HEx3_nrmSN_EpiNuc_OrgGre_MnMn' | |
| 'HEx3_nrmS_EpiNuc_OrgGre_MnMn' | |
| 'HEx3_nrmSN_EpiNuc_OrgBlu_MnMn' | |
| 'HEx3_nrmS_EpiNuc_OrgBlu_MnMn' | |
| 'HEx3_nrmSN_EpiNuc_OrgQ_Mn' | |
| 'HEx3_nrmS_EpiNuc_OrgQ_Mn' | |
| 'HEx3_nrmSN_EpiNuc_OrgI_Mn' | |
| 'HEx3_nrmS_EpiNuc_OrgI_Mn' | |
| 'HEx3_nrm_EpiNucOrgRed_MeanStd' | |
| 'HEx3_nrm_EpiNucOrgGre_MeanStd' | |
| 'HEx3_nrm_EpiNucOrgBlu_MeanStd' | |
| 'HEx3_nrmSN_EpiNucOrgRed_MeanStd' | |
| 'HEx3_nrmSN_EpiNucOrgGre_MeanStd' | |
| 'HEx3_nrmSN_EpiNucOrgBlu_MeanStd' | |
| 'HEx3_nrmSN2_EpiNucOrgRed_MeanStd' | |
| 'HEx3_nrmSN2_EpiNucOrgGre_MeanStd' | |
| 'HEx3_nrmSN2_EpiNucOrgBlu_MeanStd' | |
| 'HEx3_nrmS_EpiNucOrgRed_MeanStd' | |
| 'HEx3_nrmS_EpiNucOrgGre_MeanStd' | |
| 'HEx3_nrmS_EpiNucOrgBlu_MeanStd' | |
| 'HEx3_EpiNucOrgSumRGBMeanStd' | |
| 'HEx3_EpiNucNrmSumRGBMeanStd' | |
| 'HEx3_EpiNucNrmSNSumRGBMeanStd' | |
| 'HEx3_nrm_EpNucBin0_7_Red_StdMean' | |
| 'HEx3_nrm_EpNucBin0_7_Gre_StdMean' | |
| 'HEx3_nrm_EpNucBin0_7_Blu_StdMean' | |
| 'HEx3_nrmSN_EpNucBn0_7_RedStdMean' | |
| 'HEx3_nrmSN_EpNucBn0_7_GreStdMean' | |
| 'HEx3_nrmSN_EpNucBn0_7_BluStdMean' | |
| 'HEx3_nrmS_EpNucBn0_7_RedStdMean' | |
| 'HEx3_nrmS_EpNucBn0_7_GreStdMean' | |
| 'HEx3_nrmS_EpNucBn0_7_BluStdMean' | |
| 'HEx3_nrm_EpNucBn4_5_Br_MeanStd' | |
| 'HEx3_nrmSN_EpNucB4_5_Br_MeanStd' | |
| 'HEx3_nrmSN2_EpNucB4_5_Br_MeanStd' | |
| 'HEx3_nrmS_EpNucB4_5_Br_MeanStd' | |
| 'HEx3_nrm_EpNucBn4_5_Br_StdMean' | |
| 'HEx3_nrmSN_EpNucB4_5_Br_StdMean' | |
| 'HEx3_nrmSN2_EpNucB4_5_Br_StdMean' | |
| 'HEx3_nrmS_EpNucB4_5_Br_StdMean' | |
| 'HEx3_nrm_EpNucBn4_5_Red_StdMean' | |
| 'HEx3_nrmSN_EpNucB4_5_Red_StdMean' | |
| 'HEx3_nrmS_EpNucB4_5_Red_StdMean' | |
| 'HEx3_nrm_EpNucBn4_7_Br_MeanStd' | |
| 'HEx3_nrmSN_EpNucB4_7_Br_MeanStd' | |
| 'HEx3_nrmSN2_EpNucB4_7_Br_MeanStd' | |
| 'HEx3_nrm_EpNucBn3_7_Red_StdMean' | |
| 'HEx3_nrmSN_EpNucB3_7_Red_StdMean' | |
| 'HEx3_nrmS_EpNucB3_7_Red_StdMean' | |
| 'HEx3_nrm_EpiNucEr1_Red_MeanStd' | |
| 'HEx3_nrm_EpiNucEr1_Gre_MeanStd' | |
| 'HEx3_nrm_EpiNucEr1_Blu_MeanStd' | |
| 'HEx3_nrm_EpiNucEr1_Bri_MeanStd' | |
| 'HEx3_nrmSN_EpiNucEr1_Red_MeanStd' | |
| 'HEx3_nrmSN_EpiNucEr1_Gre_MeanStd' | |
| 'HEx3_nrmSN_EpiNucEr1_Blu_MeanStd' | |
| 'HEx3_nrmSN_EpiNucEr1_Bri_MeanStd' | |
| 'HEx3_nrmSN2_EpNucEr1_Red_MeanStd' | |
| 'HEx3_nrmSN2_EpNucEr1_Gre_MeanStd' | |
| 'HEx3_nrmSN2_EpNucEr1_Blu_MeanStd' | |
| 'HEx3_nrmSN2_EpNucEr1_Bri_MeanStd' | |
| 'HEx3_ENEr1orgSumRGBMeanStd' | |
| 'HEx3_ENEr1nrmSumRGBMeanStd' | |
| 'HEx3_nrm_EpiNucEr2_Red_MeanStd' | |
| 'HEx3_nrm_EpiNucEr2_Gre_MeanStd' | |
| 'HEx3_nrm_EpiNucEr2_Blu_MeanStd' | |
| 'HEx3_ENEr2orgSumRGBMeanStd' | |
| 'HEx3_ENEr2nrmSumRGBMeanStd' | |
| 'HEx3_nrm_TiEpiNuc_Are_Tot' | Normalized area features of epithelial nuclei in total, clustered, isolated, and likely groups. |
| 'HEx3_nrm_TiEpiCluNuc_Are_Tot' | |
| 'HEx3_nrm_TiEpiCluNuc_Num' | |
| 'HEx3_nrm_TiEpiIsoNuc_Are_Tot' | |
| 'HEx3_nrm_TiEpiIsoNuc_Num' | |
| 'HEx3_nrm_TiEpiNuc_Num' | |
| 'HEx3_nrm_TiEpiNuc_NucLikTis' | |
| 'HEx3_nrm_EpiNuc_Are_Tot2Cyt' | |
| 'HEx3_nrm_EpiCluNuc_Are_Tot2Cyt' | |
| 'HEx3_nrm_EpiCluNuc_Num2Cyt' | |
| 'HEx3_nrm_EpiIsoNuc_Are_Tot2Cyt' | |
| 'HEx3_nrm_EpiIsoNuc_Num2Cyt' | |
| 'HEx3_nrm_EpiNuc_Num2Cyt' | |
| 'HEx3_nrm_NucLikTis2Cyt' | |
| 'HEx3_TotArea_EpNucBin' | |
| 'HEx3_TotArea_LENucBin' | |
| 'HEx3_nrm_EpiNucSizBin0_Are_Tot' | Normalized bins of epithelial nuclei divided by size |
| 'HEx3_nrm_EpiNucSizBin1_Are_Tot' | |
| 'HEx3_nrm_EpiNucSizBin2_Are_Tot' | |
| 'HEx3_nrm_EpiNucSizBin3_Are_Tot' | |
| 'HEx3_nrm_EpiNucSizBin4_Are_Tot' | |
| 'HEx3_nrm_EpiNucSizBin5_Are_Tot' | |
| 'HEx3_nrm_EpiNucSizBin6_Are_Tot' | |
| 'HEx3_nrm_EpiNucSizBin7_Are_Tot' | |
| 'HEx3_nrm_EpiNucSizBin8_Are_Tot' | |

TABLE 1-continued

Morphometric Features (e.g., measurable in images of H&E-stained tissue)
In some embodiments, features in Table 1 having a prefix of "HE03" or "HEx3" are measured in tissue images at 40x magnification. HE03 features may be measured directly from the images, whereas HEx3 features are derived/calculated from the HE03 features. In some embodiments, features in Table 1 having a prefix of "HE02" or "HEx2" are measured in tissue images at 20x magnification. HE02 features may be measured directly from the images, whereas HEx2 features are derived/calculated from the HE02 features.

| Feature | Description |
| --- | --- |
| 'HEx3_nrm_LENSizBin0_Are_Tot' | Normalized bins of likely epithelial nuclei divided by size |
| 'HEx3_nrm_LENSizBin1_Are_Tot' | |
| 'HEx3_nrm_LENSizBin2_Are_Tot' | |
| 'HEx3_nrm_LENSizBin3_Are_Tot' | |
| 'HEx3_nrm_LENSizBin4_Are_Tot' | |
| 'HEx3_nrm_LENSizBin5_Are_Tot' | |
| 'HEx3_nrm_LENSizBin6_Are_Tot' | |
| 'HEx3_nrm_LENSizBin7_Are_Tot' | |
| 'HEx3_nrm_LENSizBin8_Are_Tot' | |
| 'HEx3_A0' | |
| 'HEx3_A1' | |
| 'HEx3_nrm0_DarNucBin0_Are_Tot' | Normalized bins of dark nuclei |
| 'HEx3_nrm0_DarNucBin0_3_Are_Tot' | |
| 'HEx3_nrm0_DarNucBin0_5_Are_Tot' | |
| 'HEx3_nrm0_DarNucBin0_7_Are_Tot' | |
| 'HEx3_nrm0_DarNucBin1_Are_Tot' | |
| 'HEx3_nrm0_DarNucBin1_3_Are_Tot' | |
| 'HEx3_nrm0_DarNucBin1_5_Are_Tot' | |
| 'HEx3_nrm0_DarNucBin1_7_Are_Tot' | |
| 'HEx3_nrm0_DarNucBin2_Are_Tot' | |
| 'HEx3_nrm0_DarNucBin2_3_Are_Tot' | |
| 'HEx3_nrm0_DarNucBin2_5_Are_Tot' | |
| 'HEx3_nrm0_DarNucBin2_7_Are_Tot' | |
| 'HEx3_nrm0_DarNucBin3_Are_Tot' | |
| 'HEx3_nrm0_DarNucBin3_5_Are_Tot' | |
| 'HEx3_nrm0_DarNucBin3_7_Are_Tot' | |
| 'HEx3_nrm0_DarNucBin4_Are_Tot' | |
| 'HEx3_nrm0_DarNucBin4_5_Are_Tot' | |
| 'HEx3_nrm0_DarNucBin4_7_Are_Tot' | |
| 'HEx3_nrm0_DarNucBin5_Are_Tot' | |
| 'HEx3_nrm0_DarNucBin5_7_Are_Tot' | |
| 'HEx3_nrm0_DarNucBin6_Are_Tot' | |
| 'HEx3_nrm0_DarNucBin6_7_Are_Tot' | |
| 'HEx3_nrm0_DarNucBin7_Are_Tot' | |
| 'HEx3_nrm0_DarNucBin8_Are_Tot' | |
| 'HEx3_nrm1_DarNucBin0_Are_Tot' | |
| 'HEx3_nrm1_DarNucBin0_3_Are_Tot' | |
| 'HEx3_nrm1_DarNucBin0_5_Are_Tot' | |
| 'HEx3_nrm1_DarNucBin0_7_Are_Tot' | |
| 'HEx3_nrm1_DarNucBin1_Are_Tot' | |
| 'HEx3_nrm1_DarNucBin1_3_Are_Tot' | |
| 'HEx3_nrm1_DarNucBin1_5_Are_Tot' | |
| 'HEx3_nrm1_DarNucBin1_7_Are_Tot' | |
| 'HEx3_nrm1_DarNucBin2_Are_Tot' | |
| 'HEx3_nrm1_DarNucBin2_3_Are_Tot' | |
| 'HEx3_nrm1_DarNucBin2_5_Are_Tot' | |
| 'HEx3_nrm1_DarNucBin2_7_Are_Tot' | |
| 'HEx3_nrm1_DarNucBin3_Are_Tot' | |
| 'HEx3_nrm1_DarNucBin3_5_Are_Tot' | |
| 'HEx3_nrm1_DarNucBin3_7_Are_Tot' | |
| 'HEx3_nrm1_DarNucBin4_Are_Tot' | |
| 'HEx3_nrm1_DarNucBin4_5_Are_Tot' | |
| 'HEx3_nrm1_DarNucBin4_7_Are_Tot' | |
| 'HEx3_nrm1_DarNucBin5_Are_Tot' | |
| 'HEx3_nrm1_DarNucBin5_7_Are_Tot' | |
| 'HEx3_nrm1_DarNucBin6_Are_Tot' | |
| 'HEx3_nrm1_DarNucBin6_7_Are_Tot' | |
| 'HEx3_nrm1_DarNucBin7_Are_Tot' | |
| 'HEx3_nrm1_DarNucBin8_Are_Tot' | |

TABLE 2

Morphometric Features (e.g., measurable in images of tissue subject to multiplex immunofluorescence (IF))

| Feature | Description |
| --- | --- |
| 'fd_3_8' | Fractal dimension of gland objects as identified by CK18. |
| 'fd_3_8_fillholes' | Fractal dimension of gland objects as identified by CK18, with luminal holes filled in during pre-processing. |
| 'mst_mean_length_epinuc' | Average MST length between epithelial nuclei |
| 'mst_std_length_epinuc' | Standard Deviation of MST length between epithelial nuclei |
| 'proportion_edge_1_epinuc' | Proportion of epithelial nuclei with one MST connecting edge. |
| 'proportion_edge_2_epinuc' | Proportion of epithelial nuclei with two MST connecting edges. |
| 'proportion_edge_3_epinuc' | Proportion of epithelial nuclei with three MST connecting edges. |
| 'proportion_edge_4_epinuc' | Proportion of epithelial nuclei with four MST connecting edges. |
| 'proportion_edge_5_epinuc' | Proportion of epithelial nuclei with five MST connecting edges. |
| 'mst_mean_length_intra_epinuc' | Average MST length between epithelial nuclei that are restricted to CK18 positive space, i.e. constrained by glands. |
| 'mst_std_length_intra_epinuc' | Standard Deviation of MST length between epithelial nuclei that are restricted to CK18 positive space, i.e. constrained by glands. |
| 'mst_mean_length_strnuc' | Average MST length between stroma nuclei |
| 'mst_std_length_strnuc' | Standard Deviation of MST length between stroma nuclei |
| 'proportion_edge_1_strnuc' | Proportion of stroma nuclei with one MST connecting edge. |
| 'proportion_edge_2_strnuc' | Proportion of stroma nuclei with two MST connecting edges. |
| 'proportion_edge_3_strnuc' | Proportion of stroma nuclei with three MST connecting edges. |
| 'proportion_edge_4_strnuc' | Proportion of stroma nuclei with four MST connecting edges. |
| 'proportion_edge_5_strnuc' | Proportion of stroma nuclei with five MST connecting edges. |
| 'mst_mean_length_endnuc' | Average MST length between endothelial nuclei |
| 'mst_std_length_endnuc' | Standard Deviation of MST length between endothelial nuclei |
| 'proportion_edge_1_endnuc' | Proportion of endothelial nuclei with one MST connecting edge. |
| 'proportion_edge_2_endnuc' | Proportion of endothelial nuclei with two MST connecting edges. |
| 'proportion_edge_3_endnuc' | Proportion of endothelial nuclei with three MST connecting edges. |
| 'proportion_edge_4_endnuc' | Proportion of endothelial nuclei with four MST connecting edges. |
| 'proportion_edge_5_endnuc' | Proportion of endothelial nuclei with five MST connecting edges. |
| 'iforig_approximation_1' | Variance of pixel values in the approximation sub-band after applying 1 stage of undecimated wavelet transform to a mask of epithelial cytoplasm as identified by CK18. |
| 'iforig_approximation_2' | Variance of pixel values in the approximation sub-band after applying 2 stages of undecimated wavelet transform to a mask of epithelial cytoplasm as identified by CK18. |
| 'iforig_approximation_3' | Variance of pixel values in the approximation sub-band after applying 3 stages of undecimated wavelet transform to a mask of epithelial cytoplasm as identified by CK18. |
| 'iforig_approximation_4' | Variance of pixel values in the approximation sub-band after applying 4 stages of undecimated wavelet transform to a mask of epithelial cytoplasm as identified by CK18. |

TABLE 2-continued

Morphometric Features (e.g., measurable in images of tissue subject to multiplex immunofluorescence (IF))

| Feature | Description |
| --- | --- |
| 'iforig_approximation_5' | Variance of pixel values in the approximation sub-band after applying 5 stages of undecimated wavelet transform to a mask of epithelial cytoplasm as identified by CK18. |
| 'iforig_approximation_6' | Variance of pixel values in the approximation sub-band after applying 6 stages of undecimated wavelet transform to a mask of epithelial cytoplasm as identified by CK18. |
| 'iforig_approximation_7' | Variance of pixel values in the approximation sub-band after applying 7 stages of undecimated wavelet transform to a mask of epithelial cytoplasm as identified by CK18. |
| 'iforig_horiz_detail_1' | Variance of pixel values in the horizontal detail sub-band after applying 1 stage of undecimated wavelet transform to a mask of epithelial cytoplasm as identified by CK18. |
| 'iforig_horiz_detail_2' | Variance of pixel values in the horizontal detail sub-band after applying 2 stages of undecimated wavelet transform to a mask of epithelial cytoplasm as identified by CK18. |
| 'iforig_horiz_detail_3' | Variance of pixel values in the horizontal detail sub-band after applying 3 stages of undecimated wavelet transform to a mask of epithelial cytoplasm as identified by CK18. |
| 'iforig_horiz_detail_4' | Variance of pixel values in the horizontal detail sub-band after applying 4 stages of undecimated wavelet transform to a mask of epithelial cytoplasm as identified by CK18. |
| 'iforig_horiz_detail_5' | Variance of pixel values in the horizontal detail sub-band after applying 5 stages of undecimated wavelet transform to a mask of epithelial cytoplasm as identified by CK18. |
| 'iforig_horiz_detail_6' | Variance of pixel values in the horizontal detail sub-band after applying 6 stages of undecimated wavelet transform to a mask of epithelial cytoplasm as identified by CK18. |
| 'iforig_horiz_detail_7' | Variance of pixel values in the horizontal detail sub-band after applying 7 stages of undecimated wavelet transform to a mask of epithelial cytoplasm as identified by CK18. |
| 'iforig_vert_detail_1' | Variance of pixel values in the vertical detail sub-band after applying 1 stage of undecimated wavelet transform to a mask of epithelial cytoplasm as identified by CK18. |
| 'iforig_vert_detail_2' | Variance of pixel values in the vertical detail sub-band after applying 2 stages of undecimated wavelet transform to a mask of epithelial cytoplasm as identified by CK18. |
| 'iforig_vert_detail_3' | Variance of pixel values in the vertical detail sub-band after applying 3 stages of undecimated wavelet transform to a mask of epithelial cytoplasm as identified by CK18. |
| 'iforig_vert_detail_4' | Variance of pixel values in the vertical detail sub-band after applying 4 stages of undecimated wavelet transform to a mask of epithelial cytoplasm as identified by CK18. |
| 'iforig_vert_detail_5' | Variance of pixel values in the vertical detail sub-band after applying 5 stages of undecimated wavelet transform to a mask of epithelial cytoplasm as identified by CK18. |
| 'iforig_vert_detail_6' | Variance of pixel values in the vertical detail sub-band after applying 6 stages of undecimated wavelet transform to a mask of epithelial cytoplasm as identified by CK18. |
| 'iforig_vert_detail_7' | Variance of pixel values in the vertical detail sub-band after applying 7 stages of undecimated wavelet transform to a mask of epithelial cytoplasm as identified by CK18. |
| 'iforig_diag_detail_1' | Variance of pixel values in the diagonal detail sub-band after applying 1 stage of undecimated wavelet transform to a mask of epithelial cytoplasm as identified by CK18. |
| 'iforig_diag_detail_2' | Variance of pixel values in the diagonal detail sub-band after applying 2 stages of undecimated wavelet transform to a mask of epithelial cytoplasm as identified by CK18. |
| 'iforig_diag_detail_3' | Variance of pixel values in the diagonal detail sub-band after applying 3 stages of undecimated wavelet transform to a mask of epithelial cytoplasm as identified by CK18. |
| 'iforig_diag_detail_4' | Variance of pixel values in the diagonal detail sub-band after applying 4 stages of undecimated wavelet transform to a mask of epithelial cytoplasm as identified by CK18. |
| 'iforig_diag_detail_5' | Variance of pixel values in the diagonal detail sub-band after applying 5 stages of undecimated wavelet transform to a mask of epithelial cytoplasm as identified by CK18. |
| 'iforig_diag_detail_6' | Variance of pixel values in the diagonal detail sub-band after applying 6 stages of undecimated wavelet transform to a mask of epithelial cytoplasm as identified by CK18. |
| 'iforig_diag_detail_7' | Variance of pixel values in the diagonal detail sub-band after applying 7 stages of undecimated wavelet transform to a mask of epithelial cytoplasm as identified by CK18. |
| 'min_IForig_detail1' | Minimum of above defined features "iforig_horiz_detail_1" and "iforig_vert_detail_1". |
| 'min_IForig_detail2' | Minimum of above defined features "iforig_horiz_detail_2" and "iforig_vert_detail_2". |
| 'min_IForig_detail3' | Minimum of above defined features "iforig_horiz_detail_3" and "iforig_vert_detail_3". |
| 'min_IForig_detail4' | Minimum of above defined features "iforig_horiz_detail_4" and "iforig_vert_detail_4". |
| 'min_IForig_detail5' | Minimum of above defined features "iforig_horiz_detail_5" and "iforig_vert_detail_5". |
| 'min_IForig_detail6' | Minimum of above defined features "iforig_horiz_detail_6" and "iforig_vert_detail_6". |
| 'min_IForig_detail7' | Minimum of above defined features "iforig_horiz_detail_7" and "iforig_vert_detail_7". |
| 'max_IForig_detail1' | Maximum of above defined features "iforig_horiz_detail_1" and "iforig_vert_detail_1". |
| 'max_IForig_detail2' | Maximum of above defined features "iforig_horiz_detail_2" and "iforig_vert_detail_2". |
| 'max_IForig_detail3' | Maximum of above defined features "iforig_horiz_detail_3" and "iforig_vert_detail_3". |

TABLE 2-continued

Morphometric Features (e.g., measurable in images of tissue subject to multiplex immunofluorescence (IF))

| Feature | Description |
|---|---|
| 'max_IForig_detail4' | Maximum of above defined features "iforig_horiz_detail_4" and "iforig_vert_detail_4". |
| 'max_IForig_detail5' | Maximum of above defined features "iforig_horiz_detail_5" and "iforig_vert_detail_5". |
| 'max_IForig_detail6' | Maximum of above defined features "iforig_horiz_detail_6" and "iforig_vert_detail_6". |
| 'max_IForig_detail7' | Maximum of above defined features "iforig_horiz_detail_7" and "iforig_vert_detail_7". |
| 'sum_IForig_detail1' | Sum of above defined features "iforig_horiz_detail_1" and "iforig_vert_detail_1". |
| 'sum_IForig_detail2' | Sum of above defined features "iforig_horiz_detail_2" and "iforig_vert_detail_2". |
| 'sum_IForig_detail3' | Sum of above defined features "iforig_horiz_detail_3" and "iforig_vert_detail_3". |
| 'sum_IForig_detail4' | Sum of above defined features "iforig_horiz_detail_4" and "iforig_vert_detail_4". |
| 'sum_IForig_detail5' | Sum of above defined features "iforig_horiz_detail_5" and "iforig_vert_detail_5". |
| 'sum_IForig_detail6' | Sum of above defined features "iforig_horiz_detail_6" and "iforig_vert_detail_6". |
| 'sum_IForig_detail7' | Sum of above defined features "iforig_horiz_detail_7" and "iforig_vert_detail_7". |
| 'IFwaveletratio_diag6_7' | Ratio of the above defined features "iforig_diag_detail_6" and "iforig_diag_detail_7" |

TABLE 3

Molecular Immunofluorescence (IF) Features
In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IF01_AMACR_Threshold' | AMACR Threshold |
| 'IF01_AR_Percentile' | AR specific features |
| 'IF01_AR_Threshold' | |
| 'IF01_AR_Trigger' | |
| 'IF01_BasNuc_Area' | Basil Nuclei features |
| 'IF01_BasNuc_DAPI_Mean' | |
| 'IF01_BasNuc_p63_Mean' | |
| 'IF01_CK18_AMACRpObj_AMACR_Mean' | CK18 alone and with AMACR intensity and morphometric features |
| 'IF01_CK18_AMACRpObj_AreaTotal' | |
| 'IF01_CK18_AreaTotal' | |
| 'IF01_CK18_CK18_Mean' | |
| 'IF01_CK18_Threshold' | |
| 'IF01_CytAMACRn_AMACR_MeanMean' | |
| 'IF01_CytAMACRn_AMACR_StdMean' | |
| 'IF01_CytAMACRn_AMACR_StdStd' | |
| 'IF01_CytAMACRn_AreaTotal' | |
| 'IF01_CytAMACRp_AMACR_MeanMean' | |
| 'IF01_CytAMACRp_AMACR_StdMean' | |
| 'IF01_CytAMACRp_AMACR_StdStd' | |
| 'IF01_CytAMACRp_AreaTotal' | |
| 'IF01_Cyt_AR_Mean' | Intensity features and percentiles of AR in cytoplasm (CK18) |
| 'IF01_Cyt_AR_Perc_02' | |
| 'IF01_Cyt_AR_Perc_05' | |
| 'IF01_Cyt_AR_Perc_10' | |
| 'IF01_Cyt_AR_Perc_15' | |
| 'IF01_Cyt_AR_Perc_20' | |
| 'IF01_Cyt_AR_Perc_25' | |
| 'IF01_Cyt_AR_Perc_30' | |
| 'IF01_Cyt_AR_Perc_35' | |
| 'IF01_Cyt_AR_Perc_40' | |
| 'IF01_Cyt_AR_Perc_45' | |
| 'IF01_Cyt_AR_Perc_50' | |
| 'IF01_Cyt_AR_Perc_55' | |
| 'IF01_Cyt_AR_Perc_60' | |
| 'IF01_Cyt_AR_Perc_65' | |
| 'IF01_Cyt_AR_Perc_70' | |
| 'IF01_Cyt_AR_Perc_75' | |
| 'IF01_Cyt_AR_Perc_80' | |
| 'IF01_Cyt_AR_Perc_85' | |
| 'IF01_Cyt_AR_Perc_90' | |
| 'IF01_Cyt_AR_Perc_95' | |
| 'IF01_Cyt_AR_Perc_99' | |
| 'IF01_CytoAMACRn_AMACR_MeanStd' | |
| 'IF01_CytoAMACRp_AMACR_MeanStd' | |
| 'IF01_DAPI_Threshold' | |
| 'IF01_EpiNucARnAMACRn_AR_Mean2' | Intensity features of AR and AMACR in epithelial nuclei |
| 'IF01_EpiNucARnAMACRn_AR_MeanMean' | |
| 'IF01_EpiNucARnAMACRn_AR_MeanStd' | |
| 'IF01_EpiNucARnAMACRn_AR_StdMean' | |
| 'IF01_EpiNucARnAMACRn_AR_StdStd' | |
| 'IF01_EpiNucARnAMACRn_AreaTotal' | |
| 'IF01_EpiNucARnAMACRp_AR_Mean2' | |
| 'IF01_EpiNucARnAMACRp_AR_MeanMean' | |
| 'IF01_EpiNucARnAMACRp_AR_MeanStd' | |
| 'IF01_EpiNucARnAMACRp_AR_StdMean' | |
| 'IF01_EpiNucARnAMACRp_AR_StdStd' | |
| 'IF01_EpiNucARnAMACRp_AreaTotal' | |
| 'IF01_EpiNucARn_ARFlux_Mean' | |
| 'IF01_EpiNucARn_AR_Mean' | |
| 'IF01_EpiNucARn_Num' | |
| 'IF01_EpiNucARpAMACRn_AR_Mean2' | |
| 'IF01_EpiNucARpAMACRn_AR_MeanMean' | |
| 'IF01_EpiNucARpAMACRn_AR_MeanStd' | |
| 'IF01_EpiNucARpAMACRn_AR_StdMean' | |
| 'IF01_EpiNucARpAMACRn_AR_StdStd' | |
| 'IF01_EpiNucARpAMACRn_AreaTotal' | |
| 'IF01_EpiNucARpAMACRp_AR_Mean2' | |
| 'IF01_EpiNucARpAMACRp_AR_MeanMean' | |
| 'IF01_EpiNucARpAMACRp_AR_MeanStd' | |
| 'IF01_EpiNucARpAMACRp_AR_StdMean' | |
| 'IF01_EpiNucARpAMACRp_AR_StdStd' | |
| 'IF01_EpiNucARpAMACRp_AreaTotal' | |
| 'IF01_EpiNucARp_ARFlux_Mean' | |
| 'IF01_EpiNucARp_AR_Mean' | |
| 'IF01_EpiNucARp_DensityBin01_Area' | |
| 'IF01_EpiNucARp_DensityBin02_Area' | |
| 'IF01_EpiNucARp_DensityBin03_Area' | |
| 'IF01_EpiNucARp_DensityBin04_Area' | |
| 'IF01_EpiNucARp_DensityBin05_Area' | |
| 'IF01_EpiNucARp_DensityBin06_Area' | |
| 'IF01_EpiNucARp_DensityBin07_Area' | |
| 'IF01_EpiNucARp_DensityBin08_Area' | |
| 'IF01_EpiNucARp_DensityBin09_Area' | |
| 'IF01_EpiNucARp_DensityBin10_Area' | |
| 'IF01_EpiNucARp_Num' | Percentiles of AR positive intensity |

TABLE 3-continued

Molecular Immunofluorescence (IF) Features

In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IF01_EpiNucARp_Perc_02' | |
| 'IF01_EpiNucARp_Perc_05' | |
| 'IF01_EpiNucARp_Perc_10' | |
| 'IF01_EpiNucARp_Perc_15' | |
| 'IF01_EpiNucARp_Perc_20' | |
| 'IF01_EpiNucARp_Perc_25' | |
| 'IF01_EpiNucARp_Perc_30' | |
| 'IF01_EpiNucARp_Perc_35' | |
| 'IF01_EpiNucARp_Perc_40' | |
| 'IF01_EpiNucARp_Perc_45' | |
| 'IF01_EpiNucARp_Perc_50' | |
| 'IF01_EpiNucARp_Perc_55' | |
| 'IF01_EpiNucARp_Perc_60' | |
| 'IF01_EpiNucARp_Perc_65' | |
| 'IF01_EpiNucARp_Perc_70' | |
| 'IF01_EpiNucARp_Perc_75' | |
| 'IF01_EpiNucARp_Perc_80' | |
| 'IF01_EpiNucARp_Perc_85' | |
| 'IF01_EpiNucARp_Perc_90' | |
| 'IF01_EpiNucARp_Perc_95' | |
| 'IF01_EpiNucARp_Perc_99' | |
| 'IF01_EpiNuc_ARFlux_Mean' | |
| 'IF01_EpiNuc_AR_Mean' | |
| 'IF01_EpiNuc_AR_Perc_02' | |
| 'IF01_EpiNuc_AR_Perc_05' | |
| 'IF01_EpiNuc_AR_Perc_10' | |
| 'IF01_EpiNuc_AR_Perc_15' | |
| 'IF01_EpiNuc_AR_Perc_20' | |
| 'IF01_EpiNuc_AR_Perc_25' | |
| 'IF01_EpiNuc_AR_Perc_30' | |
| 'IF01_EpiNuc_AR_Perc_35' | |
| 'IF01_EpiNuc_AR_Perc_40' | |
| 'IF01_EpiNuc_AR_Perc_45' | |
| 'IF01_EpiNuc_AR_Perc_50' | |
| 'IF01_EpiNuc_AR_Perc_55' | |
| 'IF01_EpiNuc_AR_Perc_60' | |
| 'IF01_EpiNuc_AR_Perc_65' | |
| 'IF01_EpiNuc_AR_Perc_70' | |
| 'IF01_EpiNuc_AR_Perc_75' | |
| 'IF01_EpiNuc_AR_Perc_80' | |
| 'IF01_EpiNuc_AR_Perc_85' | |
| 'IF01_EpiNuc_AR_Perc_90' | |
| 'IF01_EpiNuc_AR_Perc_95' | |
| 'IF01_EpiNuc_AR_Perc_99' | |
| 'IF01_EpiNuc_AreaTotal' | |
| 'IF01_EpiNuc_DAPI_Mean' | |
| 'IF01_EpiNuc_DensityBin01_Area' | |
| 'IF01_EpiNuc_DensityBin02_Area' | |
| 'IF01_EpiNuc_DensityBin03_Area' | |
| 'IF01_EpiNuc_DensityBin04_Area' | |
| 'IF01_EpiNuc_DensityBin05_Area' | |
| 'IF01_EpiNuc_DensityBin06_Area' | |
| 'IF01_EpiNuc_DensityBin07_Area' | |
| 'IF01_EpiNuc_DensityBin08_Area' | |
| 'IF01_EpiNuc_DensityBin09_Area' | |
| 'IF01_EpiNuc_DensityBin10_Area' | |
| 'IF01_EpiNuc_Hot2AMACRn_AR_Mean' | Features relative to extremely high levels of AR (HOT) that are calculated using the percentiles of AR in epithelial nuclei |
| 'IF01_EpiNuc_Hot2AMACRn_Area' | |
| 'IF01_EpiNuc_Hot2AMACRp_AR_Mean' | |
| 'IF01_EpiNuc_Hot2AMACRp_Area' | |
| 'IF01_EpiNuc_Hot2_AR_Mean' | |
| 'IF01_EpiNuc_Hot2_Area' | |
| 'IF01_EpiNuc_HotAMACRn_AR_Mean' | |
| 'IF01_EpiNuc_HotAMACRn_Area' | |
| 'IF01_EpiNuc_HotAMACRp_AR_Mean' | |
| 'IF01_EpiNuc_HotAMACRp_Area' | |
| 'IF01_EpiNuc_Hot_AR_Mean' | |
| 'IF01_EpiNuc_Hot_Area' | |
| 'IF01_EpiNuc_NormARIntBin00_Area' | |
| 'IF01_EpiNuc_NormARIntBin01_Area' | |
| 'IF01_EpiNuc_NormARIntBin02_Area' | |
| 'IF01_EpiNuc_NormARIntBin03_Area' | |
| 'IF01_EpiNuc_NormARIntBin04_Area' | |
| 'IF01_EpiNuc_NormARIntBin05_Area' | |
| 'IF01_EpiNuc_NormARIntBin06_Area' | |
| 'IF01_EpiNuc_NormARIntBin07_Area' | |
| 'IF01_EpiNuc_NormARIntBin08_Area' | |
| 'IF01_EpiNuc_NormARIntBin09_Area' | |
| 'IF01_EpiNuc_NormARIntBin10_Area' | |
| 'IF01_EpiNuc_Num' | |
| 'IF01_GU_Area' | |
| 'IF01_HMWCKSignal_Area' | |
| 'IF01_HMWCKSignal_HMWCK_Mean' | |
| 'IF01_HMWCK_Threshold' | |
| 'IF01_NGA_Area' | Non Gland associated features |
| 'IF01_NGA_Number' | |
| 'IF01_Nuc_DAPI_Mean' | |
| 'IF01_P63_Threshold' | |
| 'IF01_Scene_AMACR_Mean' | |
| 'IF01_Scene_AR_Mean' | |
| 'IF01_Scene_CK18_Mean' | |
| 'IF01_Scene_DAPI_Mean' | |
| 'IF01_Scene_HMWCK_Mean' | |
| 'IF01_Scene_p63_Mean' | |
| 'IF01_StrNuc_AR_Mean' | AR in Stroma Nuclei features |
| 'IF01_StrNuc_AR_Mean2' | |
| 'IF01_StrNuc_AR_Perc_02' | |
| 'IF01_StrNuc_AR_Perc_05' | |
| 'IF01_StrNuc_AR_Perc_10' | |
| 'IF01_StrNuc_AR_Perc_15' | |
| 'IF01_StrNuc_AR_Perc_20' | |
| 'IF01_StrNuc_AR_Perc_25' | |
| 'IF01_StrNuc_AR_Perc_30' | |
| 'IF01_StrNuc_AR_Perc_35' | |
| 'IF01_StrNuc_AR_Perc_40' | |
| 'IF01_StrNuc_AR_Perc_45' | |
| 'IF01_StrNuc_AR_Perc_50' | |
| 'IF01_StrNuc_AR_Perc_55' | |
| 'IF01_StrNuc_AR_Perc_60' | |
| 'IF01_StrNuc_AR_Perc_65' | |
| 'IF01_StrNuc_AR_Perc_70' | |
| 'IF01_StrNuc_AR_Perc_75' | |
| 'IF01_StrNuc_AR_Perc_80' | |
| 'IF01_StrNuc_AR_Perc_85' | |
| 'IF01_StrNuc_AR_Perc_90' | |
| 'IF01_StrNuc_AR_Perc_95' | |
| 'IF01_StrNuc_AR_Perc_99' | |
| 'IF01_StrNuc_AreaTotal' | |
| 'IF01_StrNuc_DAPI_Mean' | |
| 'IF01_StrNuc_Num' | |
| 'IF01_Stroma_AR_Mean' | |
| 'IF01_Stroma_AR_Perc_02' | |
| 'IF01_Stroma_AR_Perc_05' | |
| 'IF01_Stroma_AR_Perc_10' | |
| 'IF01_Stroma_AR_Perc_15' | |
| 'IF01_Stroma_AR_Perc_20' | |
| 'IF01_Stroma_AR_Perc_25' | |
| 'IF01_Stroma_AR_Perc_30' | |
| 'IF01_Stroma_AR_Perc_35' | |
| 'IF01_Stroma_AR_Perc_40' | |
| 'IF01_Stroma_AR_Perc_45' | |
| 'IF01_Stroma_AR_Perc_50' | |
| 'IF01_Stroma_AR_Perc_55' | |

TABLE 3-continued

Molecular Immunofluorescence (IF) Features

In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IF01_Stroma_AR_Perc_60' | |
| 'IF01_Stroma_AR_Perc_65' | |
| 'IF01_Stroma_AR_Perc_70' | |
| 'IF01_Stroma_AR_Perc_75' | |
| 'IF01_Stroma_AR_Perc_80' | |
| 'IF01_Stroma_AR_Perc_85' | |
| 'IF01_Stroma_AR_Perc_90' | |
| 'IF01_Stroma_AR_Perc_95' | |
| 'IF01_Stroma_AR_Perc_99' | |
| 'IFx1_EpiNucARp_AreaTotal' | Normalized Area and intensity features |
| 'IFx1_EpiNucARn_AreaTotal' | |
| 'IFx1_RelAreCyt_AMACRp2Cyt' | |
| 'IFx1_RelAreNGA2Cyt' | |
| 'IFx1_RelAreEpi_ARp2EN' | |
| 'IFx1_RelAreEpi_ARpAMACRp2EN' | |
| 'IFx1_RelAreEpi_ARpAMACRn2EN' | |
| 'IFx1_RelAreEpi_ARnAMACRp2EN' | |
| 'IFx1_RelAreEpi_ARnAMACRn2EN' | |
| 'IFx1_RelAreEpi_Hot22EN' | |
| 'IFx1_RelAreEpi_Hot2EN' | |
| 'IFx1_RelAreEpi_HotAMACRp2EN' | |
| 'IFx1_RelAreEpi_Hot2AMACRp2EN' | |
| 'IFx1_RelAreEpi_HotAMACRn2EN' | |
| 'IFx1_RelAreEpi_Hot2AMACRn2EN' | |
| 'IFx1HotInt_nrmStrNuc85' | |
| 'IFx1_EN_NormARTotIntBin00' | |
| 'IFx1_EN_NormARTotIntBin01' | |
| 'IFx1_EN_NormARTotIntBin02' | |
| 'IFx1_EN_NormARTotIntBin03' | |
| 'IFx1_EN_NormARTotIntBin04' | |
| 'IFx1_EN_NormARTotIntBin05' | |
| 'IFx1_EN_NormARTotIntBin06' | |
| 'IFx1_EN_NormARTotIntBin07' | |
| 'IFx1_EN_NormARTotIntBin08' | |
| 'IFx1_EN_NormARTotIntBin09' | |
| 'IFx1_EN_NormARTotIntBin10' | |
| 'IFx1_Sum_BinEN_ARTotInt01_03' | |
| 'IFx1_Sum_BinEN_ARTotInt04_06' | |
| 'IFx1_Sum_BinEN_ARTotInt07_09' | |
| 'IFx1_EN_ARTotInt_Avg' | |
| 'IFx1_RelAre_EpiNucARp_Density01' | |
| 'IFx1_RelAre_EpiNucARp_Density02' | |
| 'IFx1_RelAre_EpiNucARp_Density03' | |
| 'IFx1_RelAre_EpiNucARp_Density04' | |
| 'IFx1_RelAre_EpiNucARp_Density05' | |
| 'IFx1_RelAre_EpiNucARp_Density06' | |
| 'IFx1_RelAre_EpiNucARp_Density07' | |
| 'IFx1_RelAre_EpiNucARp_Density08' | |
| 'IFx1_RelAre_EpiNucARp_Density09' | |
| 'IFx1_RelAre_EpiNucARp_Density10' | |
| 'IFx1_Sum_EpiNucARp_Density01_03' | |
| 'IFx1_Sum_EpiNucARp_Density04_06' | |
| 'IFx1_Sum_EpiNucARp_Density07_09' | |
| 'IFx1_RelAre_EpiNuc_Density01' | |
| 'IFx1_RelAre_EpiNuc_Density02' | |
| 'IFx1_RelAre_EpiNuc_Density03' | |
| 'IFx1_RelAre_EpiNuc_Density04' | |
| 'IFx1_RelAre_EpiNuc_Density05' | |
| 'IFx1_RelAre_EpiNuc_Density06' | |
| 'IFx1_RelAre_EpiNuc_Density07' | |
| 'IFx1_RelAre_EpiNuc_Density08' | |
| 'IFx1_RelAre_EpiNuc_Density09' | |
| 'IFx1_RelAre_EpiNuc_Density10' | |
| 'IFx1_Sum_EpiNuc_Density01_03' | |
| 'IFx1_Sum_EpiNuc_Density04_06' | |
| 'IFx1_Sum_EpiNuc_Density07_09' | |
| 'IFx1_ExInd_EN_ARp' | |
| 'IFx1_RatiInt_CytAMACRp2n' | |
| 'IFx1_RatiInt_AR_EpN2Cyt' | |
| 'IFx1_RatiInt_ARp_EpN2Cyt' | |
| 'IFx1_RatiInt_ARp_EpN2CtAMACRp' | |
| 'IFx1_RatiInt_ARp_EpN2CtAMACRn' | |
| 'IFx1_RatInt_ENARpAMACRp2AnAMp' | |
| 'IFx1_RatInt_ENARpAMACRn2AnAMn' | |
| 'IFx1_Rati_EpNARpAMACRp2ART' | |
| 'IFx1_Rati_EpNARpAMACRn2ART' | |
| 'IFx1_Rati_EpNARp2ART' | |
| 'IFx1_Rati_EpNAR2ART' | |
| 'IF01_Rati_EN_Flux_ARp2AR' | |
| 'IF01_Rati_EN_Flux_ARp2ARn' | |
| 'IFx1_ExInd_EN_AMACRp' | |
| 'IFx1_ExInd_EN_AMACRn' | |
| 'IFx1_nExInd_EN_AMACRp' | |
| 'IF01_nExInd_EN_AMACRn' | |
| 'IF01_nExInd_EN_ARp' | |
| 'IFx1_RelRise_EpiNuc_AR_StrNuc' | Dynamic range of AR, difference in epithelial nuclei percentiles relative to Stroma nuclei percentiles |
| 'IFx1_RelRise_EpiNuc_AR_THR' | Dynamic range of AR, difference in epithelial nuclei percentiles relative to the AR threshold |
| 'IF02_AMACR_Threshold' | AMACR Threshold |
| 'IF02_CD34_Area' | |
| 'IF02_CD34ProximalCut05_Area' | Features to detect CD34 proximal to blood vessels |
| 'IF02_CD34Proximal_AMACRn_Area' | |
| 'IF02_CD34Proximal_AMACRp_Area' | |
| 'IF02_CD34Proximal_Area' | |
| 'IF02_CK18_AreaTotal' | |
| 'IF02_CK18_Threshold' | |
| 'IF02_Cyt_Ki67_Mean' | Ki67 intensities and percentiles in cytoplasm (CK18) |
| 'IF02_Cyt_Ki67_Perc_02' | |
| 'IF02_Cyt_Ki67_Perc_05' | |
| 'IF02_Cyt_Ki67_Perc_10' | |
| 'IF02_Cyt_Ki67_Perc_15' | |
| 'IF02_Cyt_Ki67_Perc_20' | |
| 'IF02_Cyt_Ki67_Perc_25' | |
| 'IF02_Cyt_Ki67_Perc_30' | |
| 'IF02_Cyt_Ki67_Perc_35' | |
| 'IF02_Cyt_Ki67_Perc_40' | |
| 'IF02_Cyt_Ki67_Perc_45' | |
| 'IF02_Cyt_Ki67_Perc_50' | |
| 'IF02_Cyt_Ki67_Perc_55' | |
| 'IF02_Cyt_Ki67_Perc_60' | |
| 'IF02_Cyt_Ki67_Perc_65' | |
| 'IF02_Cyt_Ki67_Perc_70' | |
| 'IF02_Cyt_Ki67_Perc_75' | |
| 'IF02_Cyt_Ki67_Perc_80' | |
| 'IF02_Cyt_Ki67_Perc_85' | |
| 'IF02_Cyt_Ki67_Perc_90' | |
| 'IF02_Cyt_Ki67_Perc_95' | |
| 'IF02_Cyt_Ki67_Perc_99' | |
| 'IF02_Cyt_pAKT_Mean' | pAKT intensities and percentiles in cytoplasm (CK18) |
| 'IF02_Cyt_pAKT_Perc_02' | |
| 'IF02_Cyt_pAKT_Perc_05' | |
| 'IF02_Cyt_pAKT_Perc_10' | |
| 'IF02_Cyt_pAKT_Perc_15' | |
| 'IF02_Cyt_pAKT_Perc_20' | |
| 'IF02_Cyt_pAKT_Perc_25' | |
| 'IF02_Cyt_pAKT_Perc_30' | |
| 'IF02_Cyt_pAKT_Perc_35' | |
| 'IF02_Cyt_pAKT_Perc_40' | |

TABLE 3-continued

Molecular Immunofluorescence (IF) Features
In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IF02_Cyt_pAKT_Perc_45' | |
| 'IF02_Cyt_pAKT_Perc_50' | |
| 'IF02_Cyt_pAKT_Perc_55' | |
| 'IF02_Cyt_pAKT_Perc_60' | |
| 'IF02_Cyt_pAKT_Perc_65' | |
| 'IF02_Cyt_pAKT_Perc_70' | |
| 'IF02_Cyt_pAKT_Perc_75' | |
| 'IF02_Cyt_pAKT_Perc_80' | |
| 'IF02_Cyt_pAKT_Perc_85' | |
| 'IF02_Cyt_pAKT_Perc_90' | |
| 'IF02_Cyt_pAKT_Perc_95' | |
| 'IF02_Cyt_pAKT_Perc_99' | |
| 'IF02_DAPI_Threshold' | |
| 'IF02_EpiNuc_Area' | |
| 'IF02_EpiNuc_Ki67Neg_Area' | Ki67 morphometric and area features in epithelial nuclei |
| 'IF02_EpiNuc_Ki67Neg_Ki67_Mean' | |
| 'IF02_EpiNuc_Ki67Neg_Ki67_Std' | |
| 'IF02_EpiNuc_Ki67Pos_Area' | |
| 'IF02_EpiNuc_Ki67Pos_Ki67_Mean' | |
| 'IF02_EpiNuc_Ki67Pos_Ki67_Std' | |
| 'IF02_EpiNuc_Ki67_Mean' | |
| 'IF02_EpiNuc_Ki67_Perc_02' | |
| 'IF02_EpiNuc_Ki67_Perc_05' | |
| 'IF02_EpiNuc_Ki67_Perc_10' | |
| 'IF02_EpiNuc_Ki67_Perc_15' | |
| 'IF02_EpiNuc_Ki67_Perc_20' | |
| 'IF02_EpiNuc_Ki67_Perc_25' | |
| 'IF02_EpiNuc_Ki67_Perc_30' | |
| 'IF02_EpiNuc_Ki67_Perc_35' | |
| 'IF02_EpiNuc_Ki67_Perc_40' | |
| 'IF02_EpiNuc_Ki67_Perc_45' | |
| 'IF02_EpiNuc_Ki67_Perc_50' | |
| 'IF02_EpiNuc_Ki67_Perc_55' | |
| 'IF02_EpiNuc_Ki67_Perc_60' | |
| 'IF02_EpiNuc_Ki67_Perc_65' | |
| 'IF02_EpiNuc_Ki67_Perc_70' | |
| 'IF02_EpiNuc_Ki67_Perc_75' | |
| 'IF02_EpiNuc_Ki67_Perc_80' | |
| 'IF02_EpiNuc_Ki67_Perc_85' | |
| 'IF02_EpiNuc_Ki67_Perc_90' | |
| 'IF02_EpiNuc_Ki67_Perc_95' | |
| 'IF02_EpiNuc_Ki67_Perc_99' | |
| 'IF02_EpiNuc_Ki67_Std' | |
| 'IF02_EpiNuc_Ki67nAMACRn_Area' | Joint Ki67 and AMACR features in epithelial nuclei |
| 'IF02_EpiNuc_Ki67nAMACRn_Ki67_Mn' | |
| 'IF02_EpiNuc_Ki67nAMACRn_Ki67_Std' | |
| 'IF02_EpiNuc_Ki67nAMACRn_Num' | |
| 'IF02_EpiNuc_Ki67nAMACRp_Area' | |
| 'IF02_EpiNuc_Ki67nAMACRp_Ki67_Mn' | |
| 'IF02_EpiNuc_Ki67nAMACRp_Ki67_Std' | |
| 'IF02_EpiNuc_Ki67nAMACRp_Num' | |
| 'IF02_EpiNuc_Ki67nPAKTn_Area' | Joint Ki67 and pAKT features in epithelial nuclei |
| 'IF02_EpiNuc_Ki67nPAKTp_Area' | |
| 'IF02_EpiNuc_Ki67pAMACRn_Area' | |
| 'IF02_EpiNuc_Ki67pAMACRn_Ki67_Mn' | |
| 'IF02_EpiNuc_Ki67pAMACRn_Ki67_Std' | |
| 'IF02_EpiNuc_Ki67pAMACRn_Num' | |
| 'IF02_EpiNuc_Ki67pAMACRp_Area' | |
| 'IF02_EpiNuc_Ki67pAMACRp_Ki67_Mn' | |
| 'IF02_EpiNuc_Ki67pAMACRp_Ki67_Std' | |
| 'IF02_EpiNuc_Ki67pAMACRp_Num' | |
| 'IF02_EpiNuc_Ki67pPAKTn_Area' | |
| 'IF02_EpiNuc_Ki67pPAKTp_Area' | |
| 'IF02_EpiNuc_Num' | |
| 'IF02_EpiNuc_pAKTNeg_Area' | pAKT intensity and morphometric features |
| 'IF02_EpiNuc_pAKTNeg_pAKT_Mean' | |
| 'IF02_EpiNuc_pAKTNeg_pAKT_Std' | |
| 'IF02_EpiNuc_pAKTPos_Area' | |
| 'IF02_EpiNuc_pAKTPos_pAKT_Mean' | |
| 'IF02_EpiNuc_pAKTPos_pAKT_Std' | |
| 'IF02_EpiNuc_pAKT_Mean' | |
| 'IF02_EpiNuc_pAKT_Perc_02' | |
| 'IF02_EpiNuc_pAKT_Perc_05' | |
| 'IF02_EpiNuc_pAKT_Perc_10' | |
| 'IF02_EpiNuc_pAKT_Perc_15' | |
| 'IF02_EpiNuc_pAKT_Perc_20' | |
| 'IF02_EpiNuc_pAKT_Perc_25' | |
| 'IF02_EpiNuc_pAKT_Perc_30' | |
| 'IF02_EpiNuc_pAKT_Perc_35' | |
| 'IF02_EpiNuc_pAKT_Perc_40' | |
| 'IF02_EpiNuc_pAKT_Perc_45' | |
| 'IF02_EpiNuc_pAKT_Perc_50' | |
| 'IF02_EpiNuc_pAKT_Perc_55' | |
| 'IF02_EpiNuc_pAKT_Perc_60' | |
| 'IF02_EpiNuc_pAKT_Perc_65' | |
| 'IF02_EpiNuc_pAKT_Perc_70' | |
| 'IF02_EpiNuc_pAKT_Perc_75' | |
| 'IF02_EpiNuc_pAKT_Perc_80' | |
| 'IF02_EpiNuc_pAKT_Perc_85' | |
| 'IF02_EpiNuc_pAKT_Perc_90' | |
| 'IF02_EpiNuc_pAKT_Perc_95' | |
| 'IF02_EpiNuc_pAKT_Perc_99' | |
| 'IF02_EpiNuc_pAKT_Std' | |
| 'IF02_EpiNuc_pAKTnAMACRn_Area' | Joint pAKT and AMACR features. |
| 'IF02_EpiNuc_pAKTnAMACRn_Num' | |
| 'IF02_EpiNuc_pAKTnAMACRn_pAKT_Mn' | |
| 'IF02_EpiNuc_pAKTnAMACRn_pAKT_Std' | |
| 'IF02_EpiNuc_pAKTnAMACRp_Area' | |
| 'IF02_EpiNuc_pAKTnAMACRp_Num' | |
| 'IF02_EpiNuc_pAKTnAMACRp_pAKT_Mn' | |
| 'IF02_EpiNuc_pAKTnAMACRp_pAKT_Std' | |
| 'IF02_EpiNuc_pAKTpAMACRn_Area' | |
| 'IF02_EpiNuc_pAKTpAMACRn_Num' | |
| 'IF02_EpiNuc_pAKTpAMACRn_pAKT_Mn' | |
| 'IF02_EpiNuc_pAKTpAMACRn_pAKT_Std' | |
| 'IF02_EpiNuc_pAKTpAMACRp_Area' | |
| 'IF02_EpiNuc_pAKTpAMACRp_Num' | |
| 'IF02_EpiNuc_pAKTpAMACRp_pAKT_Mn' | |
| 'IF02_EpiNuc_pAKTpAMACRp_pAKT_Std' | |
| 'IF02_GU_Area' | |
| 'IF02_Ki67_Percentile' | |
| 'IF02_Ki67_Threshold' | |
| 'IF02_Ki67_Trigger' | |
| 'IF02_NGA_Area' | Non Gland Associated area |
| 'IF02_StrNuc_Area' | |
| 'IF02_StrNuc_Ki67_Mean' | Ki67 features in Stroma Nuclei |
| 'IF02_StrNuc_Ki67_Perc_02' | |
| 'IF02_StrNuc_Ki67_Perc_05' | |
| 'IF02_StrNuc_Ki67_Perc_10' | |
| 'IF02_StrNuc_Ki67_Perc_15' | |
| 'IF02_StrNuc_Ki67_Perc_20' | |
| 'IF02_StrNuc_Ki67_Perc_25' | |
| 'IF02_StrNuc_Ki67_Perc_30' | |
| 'IF02_StrNuc_Ki67_Perc_35' | |
| 'IF02_StrNuc_Ki67_Perc_40' | |
| 'IF02_StrNuc_Ki67_Perc_45' | |
| 'IF02_StrNuc_Ki67_Perc_50' | |
| 'IF02_StrNuc_Ki67_Perc_55' | |
| 'IF02_StrNuc_Ki67_Perc_60' | |
| 'IF02_StrNuc_Ki67_Perc_65' | |

TABLE 3-continued

Molecular Immunofluorescence (IF) Features

In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IF02_StrNuc_Ki67_Perc_70' | |
| 'IF02_StrNuc_Ki67_Perc_75' | |
| 'IF02_StrNuc_Ki67_Perc_80' | |
| 'IF02_StrNuc_Ki67_Perc_85' | |
| 'IF02_StrNuc_Ki67_Perc_90' | |
| 'IF02_StrNuc_Ki67_Perc_95' | |
| 'IF02_StrNuc_Ki67_Perc_99' | |
| 'IF02_StrNuc_Num' | |
| 'IF02_StrNuc_pAKT_Mean' | pAKT features in stroma nuclei |
| 'IF02_StrNuc_pAKT_Perc_02' | |
| 'IF02_StrNuc_pAKT_Perc_05' | |
| 'IF02_StrNuc_pAKT_Perc_10' | |
| 'IF02_StrNuc_pAKT_Perc_15' | |
| 'IF02_StrNuc_pAKT_Perc_20' | |
| 'IF02_StrNuc_pAKT_Perc_25' | |
| 'IF02_StrNuc_pAKT_Perc_30' | |
| 'IF02_StrNuc_pAKT_Perc_35' | |
| 'IF02_StrNuc_pAKT_Perc_40' | |
| 'IF02_StrNuc_pAKT_Perc_45' | |
| 'IF02_StrNuc_pAKT_Perc_50' | |
| 'IF02_StrNuc_pAKT_Perc_55' | |
| 'IF02_StrNuc_pAKT_Perc_60' | |
| 'IF02_StrNuc_pAKT_Perc_65' | |
| 'IF02_StrNuc_pAKT_Perc_70' | |
| 'IF02_StrNuc_pAKT_Perc_75' | |
| 'IF02_StrNuc_pAKT_Perc_80' | |
| 'IF02_StrNuc_pAKT_Perc_85' | |
| 'IF02_StrNuc_pAKT_Perc_90' | |
| 'IF02_StrNuc_pAKT_Perc_95' | |
| 'IF02_StrNuc_pAKT_Perc_99' | |
| 'IF02_Stroma_Ki67_Mean' | Ki67 features in Stroma |
| 'IF02_Stroma_Ki67_Perc_02' | |
| 'IF02_Stroma_Ki67_Perc_05' | |
| 'IF02_Stroma_Ki67_Perc_10' | |
| 'IF02_Stroma_Ki67_Perc_15' | |
| 'IF02_Stroma_Ki67_Perc_20' | |
| 'IF02_Stroma_Ki67_Perc_25' | |
| 'IF02_Stroma_Ki67_Perc_30' | |
| 'IF02_Stroma_Ki67_Perc_35' | |
| 'IF02_Stroma_Ki67_Perc_40' | |
| 'IF02_Stroma_Ki67_Perc_45' | |
| 'IF02_Stroma_Ki67_Perc_50' | |
| 'IF02_Stroma_Ki67_Perc_55' | |
| 'IF02_Stroma_Ki67_Perc_60' | |
| 'IF02_Stroma_Ki67_Perc_65' | |
| 'IF02_Stroma_Ki67_Perc_70' | |
| 'IF02_Stroma_Ki67_Perc_75' | |
| 'IF02_Stroma_Ki67_Perc_80' | |
| 'IF02_Stroma_Ki67_Perc_85' | |
| 'IF02_Stroma_Ki67_Perc_90' | |
| 'IF02_Stroma_Ki67_Perc_95' | |
| 'IF02_Stroma_Ki67_Perc_99' | |
| 'IF02_Stroma_pAKT_Mean' | pAKT features in Stroma |
| 'IF02_Stroma_pAKT_Perc_02' | |
| 'IF02_Stroma_pAKT_Perc_05' | |
| 'IF02_Stroma_pAKT_Perc_10' | |
| 'IF02_Stroma_pAKT_Perc_15' | |
| 'IF02_Stroma_pAKT_Perc_20' | |
| 'IF02_Stroma_pAKT_Perc_25' | |
| 'IF02_Stroma_pAKT_Perc_30' | |
| 'IF02_Stroma_pAKT_Perc_35' | |
| 'IF02_Stroma_pAKT_Perc_40' | |
| 'IF02_Stroma_pAKT_Perc_45' | |
| 'IF02_Stroma_pAKT_Perc_50' | |
| 'IF02_Stroma_pAKT_Perc_55' | |
| 'IF02_Stroma_pAKT_Perc_60' | |
| 'IF02_Stroma_pAKT_Perc_65' | |
| 'IF02_Stroma_pAKT_Perc_70' | |
| 'IF02_Stroma_pAKT_Perc_75' | |
| 'IF02_Stroma_pAKT_Perc_80' | |
| 'IF02_Stroma_pAKT_Perc_85' | |
| 'IF02_Stroma_pAKT_Perc_90' | |
| 'IF02_Stroma_pAKT_Perc_95' | |
| 'IF02_Stroma_pAKT_Perc_99' | |
| 'IF02_Tumor_Area' | |
| 'IF02_pAKT_Threshold' | |
| 'IFx2_RelAreEN_Ki67p_Area2EN' | Normalized area features |
| 'IFx2_RelAreEN_Ki67p_Area2MDT' | |
| 'IFx2_RelAreEN_Ki67p_Area2GU' | |
| 'IFx2_RelAreEN_Ki67pAMACRp2EN' | |
| 'IFx2_RelAreEN_Ki67pAMACRn2EN' | |
| 'IFx2_RelAreEN_Ki67nAMACRp2EN' | |
| 'IFx2_RelAreEN_Ki67nAMACRn2EN' | |
| 'IFx2_RelAreEN_pAKTp2_Area2EN' | |
| 'IFx2_RelAreEN_pAKTp_Area2MDT' | |
| 'IFx2_RelAreEN_pAKTp_Area2GU' | |
| 'IFx2_RelAreEN_pAKTpAMACRp2EN' | |
| 'IFx2_RelAreEN_pAKTpAMACRn2EN' | |
| 'IFx2_RelAreEN_pAKTnAMACRp2EN' | |
| 'IFx2_RelAreEN_pAKTnAMACRn2EN' | |
| 'IFx2_sumRelAreEN_Ki67_pAKT' | |
| 'IFx2_RelAre_GU2MDT' | |
| 'IFx2_RelAre_CK182MDT' | |
| 'IFx2_RelAre_EN_Ki67nPAKTn2EN' | |
| 'IFx2_RelAre_EN_Ki67nPAKTp2EN' | |
| 'IFx2_RelAre_EN_Ki67pPAKTn2EN' | |
| 'IFx2_RelAre_EN_Ki67pPAKTp2EN' | |
| 'IFx2_RelAre_EN_Ki67nPAKTn2GU' | |
| 'IFx2_RelAre_EN_Ki67nPAKTp2GU' | |
| 'IFx2_RelAre_EN_Ki67pPAKTn2GU' | |
| 'IFx2_RelAre_EN_Ki67pPAKTp2GU' | |
| 'IFx2_RelAre_EN_Ki67nPAKTn2MDT' | |
| 'IFx2_RelAre_EN_Ki67nPAKTp2MDT' | |
| 'IFx2_RelAre_EN_Ki67pPAKTn2MDT' | |
| 'IFx2_RelAre_EN_Ki67pPAKTp2MDT' | |
| 'IFx2_sumRelAreKi67npPAKTpn' | Normalized intensity features |
| 'IFx2_nrmKi67pMean2EpiNucMean' | |
| 'IFx2_nrmKi67pMean2Thrh' | |
| 'IFx2_nrmKi67pMean2StrNucMean' | |
| 'IFx2_nrmKi67pMean2StrNucP50' | |
| 'IFx2_nrmKi67pMean2StrNucP95' | |
| 'IFx2_nrmKi67pAMACRpMean2SNmn' | |
| 'IFx2_nrmKi67pAMACRnMean2SNmn' | |
| 'IFx2_nrmKi67nAMACRpMean2SNmn' | |
| 'IFx2_nrmKi67nAMACRnMean2SNmn' | |
| 'IFx2_nrmKi67pAMACRpMean2Thrh' | |
| 'IFx2_nrmKi67pAMACRnMean2Thrh' | |
| 'IFx2_nrmKi67nAMACRpMean2Thrh' | |
| 'IFx2_nrmKi67nAMACRnMean2Thrh' | |
| 'IFx2_nrmKi67pAMACRpMean2SNp50' | |
| 'IFx2_nrmKi67pAMACRnMean2SNp50' | |
| 'IFx2_nrmKi67nAMACRpMean2SNp50' | |
| 'IFx2_nrmKi67nAMACRnMean2SNp50' | |
| 'IFx2_nrmKi67pAMACRpMean2SNp95' | |
| 'IFx2_nrmKi67pAMACRnMean2SNp95' | |
| 'IFx2_nrmKi67nAMACRpMean2SNp95' | |
| 'IFx2_nrmKi67nAMACRnMean2SNp95' | |
| 'IFx2_nrmKi67nMean2Thrh' | |
| 'IFx2_nrmKi67EpiNucMean2Thrsh' | |
| 'IFx2_nrmEpiNucKi67IntTotal2MDT' | |
| 'IFx2_nrmEpiNucKi67pIntTotal2MDT' | |
| 'IFx2_nrmEpiNucKi67nIntTotal2MDT' | |
| 'IFx2_nrmEpiNucKi67IntTotal2GU' | |
| 'IFx2_nrmEpiNucKi67pIntTotal2GU' | |
| 'IFx2_nrmEpiNucKi67nIntTotal2GU' | |
| 'IFx2_nrmEpiNucKi67IntTotal2EN' | |
| 'IFx2_nrmEpiNucKi67pIntTotal2EN' | |
| 'IFx2_nrmEpiNucKi67nIntTotal2EN' | |

TABLE 3-continued

Molecular Immunofluorescence (IF) Features

In some embodiments, features in Table 3 having the prefix "IF01" are measured through the use of MPLEX 1 as described above, whereas "IFx1" refers to features derived/calculated from the MPLEX 1 features. Similarly, in some embodiments, "IF02" refers to features measured through the use of MPLEX 2 described above, whereas "IFx2" refers to features derived/calculated from the MPLEX 2 features.

| Feature | Description |
|---|---|
| 'IFx2_RatiEpiNucKi67pInt2MDT' | |
| 'IFx2_nrmEpiNuc_Ki67_p02Thrh' | |
| 'IFx2_nrmEpiNuc_Ki67_p05Thrh' | |
| 'IFx2_nrmEpiNuc_Ki67_p10Thrh' | |
| 'IFx2_nrmEpiNuc_Ki67_p15Thrh' | |
| 'IFx2_nrmEpiNuc_Ki67_p20Thrh' | |
| 'IFx2_nrmEpiNuc_Ki67_p25Thrh' | |
| 'IFx2_nrmEpiNuc_Ki67_p30Thrh' | |
| 'IFx2_nrmEpiNuc_Ki67_p35Thrh' | |
| 'IFx2_nrmEpiNuc_Ki67_p40Thrh' | |
| 'IFx2_nrmEpiNuc_Ki67_p45Thrh' | |
| 'IFx2_nrmEpiNuc_Ki67_p50Thrh' | |
| 'IFx2_nrmEpiNuc_Ki67_p55Thrh' | |
| 'IFx2_nrmEpiNuc_Ki67_p60Thrh' | |
| 'IFx2_nrmEpiNuc_Ki67_p65Thrh' | |
| 'IFx2_nrmEpiNuc_Ki67_p70Thrh' | |
| 'IFx2_nrmEpiNuc_Ki67_p75Thrh' | |
| 'IFx2_nrmEpiNuc_Ki67_p80Thrh' | |
| 'IFx2_nrmEpiNuc_Ki67_p85Thrh' | |
| 'IFx2_nrmEpiNuc_Ki67_p90Thrh' | |
| 'IFx2_nrmEpiNuc_Ki67_p95Thrh' | |
| 'IFx2_nrmEpiNuc_Ki67_p99Thrh' | |
| 'IFx2_RelRiseKi67StrNuc' | |
| 'IFx2_RelRiseKi67Thrh' | |
| 'IFx2_nrmpAKTpMean2EpiNucMean' | |
| 'IFx2_nrmpAKTpMean2Thrh' | |
| 'IFx2_nrmpAKTpMean2StrNucMean' | |
| 'IFx2_nrmpAKTpMean2StrNucP50' | |
| 'IFx2_nrmpAKTpMean2StrNucP95' | |
| 'IFx2_nrmpAKTpAMACRpMean2SNmn' | |
| 'IFx2_nrmpAKTpAMACRpMean2Thrh' | |
| 'IFx2_nrmpAKTpAMACRpMean2SNp50' | |
| 'IFx2_nrmpAKTpAMACRpMean2SNp95' | |
| 'IFx2_nrmpAKTEpiNucMean2Thrsh' | |
| 'IFx2_nrmEpiNucpAKTIntTotal2MDT' | |
| 'IFx2_nrmEpiNucpAKTIntTotal2GU' | |
| 'IFx2_nrmEpiNucpAKTIntTotal2EN' | |
| 'IFx2_nrmEpiNuc_pAKT_p02Thrh' | |
| 'IFx2_nrmEpiNuc_pAKT_p05Thrh' | |
| 'IFx2_nrmEpiNuc_pAKT_p10Thrh' | |
| 'IFx2_nrmEpiNuc_pAKT_p15Thrh' | |
| 'IFx2_nrmEpiNuc_pAKT_p20Thrh' | |
| 'IFx2_nrmEpiNuc_pAKT_p25Thrh' | |
| 'IFx2_nrmEpiNuc_pAKT_p30Thrh' | |
| 'IFx2_nrmEpiNuc_pAKT_p35Thrh' | |
| 'IFx2_nrmEpiNuc_pAKT_p40Thrh' | |
| 'IFx2_nrmEpiNuc_pAKT_p45Thrh' | |
| 'IFx2_nrmEpiNuc_pAKT_p50Thrh' | |
| 'IFx2_nrmEpiNuc_pAKT_p55Thrh' | |
| 'IFx2_nrmEpiNuc_pAKT_p60Thrh' | |
| 'IFx2_nrmEpiNuc_pAKT_p65Thrh' | |
| 'IFx2_nrmEpiNuc_pAKT_p70Thrh' | |
| 'IFx2_nrmEpiNuc_pAKT_p75Thrh' | |
| 'IFx2_nrmEpiNuc_pAKT_p80Thrh' | |
| 'IFx2_nrmEpiNuc_pAKT_p85Thrh' | |
| 'IFx2_nrmEpiNuc_pAKT_p90Thrh' | |
| 'IFx2_nrmEpiNuc_pAKT_p95Thrh' | |
| 'IFx2_nrmEpiNuc_pAKT_p99Thrh' | |
| 'IFx2_RelRisepAKTStrNuc' | |
| 'IFx2_RelRisepAKTThrh' | |
| 'IFx2_RelArea_EpiNuc2Cyt' | |
| 'IFx2_RelAreCD34_ProxArea2EN' | Normalizations of CD34 proximal area to blood vessels |
| 'IFx2_RelAreCD34_ProxAMACRn2EN' | |
| 'IFx2_RelAreCD34_ProxAMACRp2EN' | |
| 'IFx2_RelAreCD34_ProxArea2CK18' | |
| 'IFx2_RelAreCD34_ProxAMACRn2CK18' | |
| 'IFx2_RelAreCD34_ProxAMACRp2CK18' | |
| 'IFx2_RelAre_CD34Prox2CD34' | |
| 'IFx2_RelAre_CD34ProxAMACRn2CD34' | |
| 'IFx2_RelAre_CD34ProxAMACRp2CD34' | |
| 'IFx2_RelAre_Ki67PosArea2CD34' | |
| 'IFx2_RelAre_pAKTPosArea2CD34' | |
| 'IFx2_RelAr_CD34Proxcut052EN' | |
| 'IFx2_RelAr_CD34Proxcut052MDT' | |
| 'IFx2_RelAreCD34_ProxArea2EN' | |
| 'IFx2_RelAreCD34_ProxAMACRn2EN' | |
| 'IFx2_RelAreCD34_ProxAMACRp2EN' | |
| 'IFx2_RelAreCD34_ProxArea2CK18' | |

TABLE 4

Clinical Features

| Feature |
|---|
| Number of total biopsy cores |
| Percent of positive biopsy cores |
| Age |
| Length of tumor in biopsy cores |
| Percent of tumor in biopsy cores |

What is claimed is:

1. A system for determining the risk of occurrence of prostate cancer in a patient, the system comprising:

(1) a fluorescence imaging device configured to record at least one sample image of a tissue sample of a patient, the tissue sample treated with a plurality of fluorochrome labeled antibodies, wherein the antibodies are selected to bind with at least AR and Ki67;

(2) a database configured to store patient data including clinical feature data values for the patient comprising a value indicative of the biopsy Gleason score (bGS) and biopsy Gleason grade (bGG) of the patient and a value indicative of the level of Prostate Specific Antigen (PSA) in the blood of the patient;

(3) a processor configured by code executing therein to perform the following:
  a. evaluate the at least one sample image recorded by the imaging device and generate:
    (i) one or more molecular feature values indicative of a combined AR dynamic range where the measured bGG values is $\leq 3$, and a total Ki67 where the measured bGG value is $4 \geq$ by applying at least a segmentation analysis to the sample image using a quad-tree function to differentiate the sample image into background and non-background objects where the background objects have an average pixel intensity below a predetermined threshold; and
    (ii) a plurality of morphometric measurements, including: (a) a mean distance between epithelial tumor cells (MST) where the bGG value is 3 or the actual Gleason grade when bGG is 4 or higher, and (b) an area of isolated (non-lumen associated) tumor epithelial cells relative to tumor area value;
  b. combine the molecular feature values, morphometric measurements and clinical feature data values into a patient database;

c. evaluate the patient data with a Support Vector Regression for Censored Data (SVRc) algorithm executed as code by the processor, the SVRc algorithm configured to output a value corresponding to a risk score for cancer occurrence based on the patient data, wherein the SVRc algorithm is generated by performing regression, using code executed in the processor, on patient entries in a censored and uncensored patient database, where each patient entry in the censored and uncensored patient database includes data corresponding to the clinical feature data values, molecular feature values and morphometric measurements of the patient data, and where the population includes members where a cancer occurrence status is known (uncensored members) and members where a cancer occurrence status is unknown (censored members), and the regression includes implementing, as code executed in the processor, a first loss function on the censored member data such that:

$$\text{Loss}(f(x), y, s=1) = \begin{cases} C_s^*(e - \varepsilon_s^*) & e > \varepsilon_s^* \\ 0 & -\varepsilon_s \leq e \leq \varepsilon_s^* \\ C_s(\varepsilon_s - e) & e < -\varepsilon_s \end{cases}$$

where $e = f(x) - y$; and $\in$ and C values differentiate the penalties incurred for $f(x) > 0$ versus $f(x) < 0$; and a second loss function on the uncensored member data such that:

$$\text{Loss}(f(x), y, s=0) = \begin{cases} C_n^*(e - \varepsilon_n^*) & e > \varepsilon \\ 0 & -\varepsilon_n \leq e \leq \varepsilon_n^*, \\ C_n(\varepsilon_n - e) & e < -\varepsilon_n, \end{cases}$$

where $e = f(x) - y$ and $\in_n^* \leq \in_n$ and $C_n^* \geq C_n$ and where $f(x)$ is the predicted time to event for sample x, s is the censorship value, and y is a target value corresponding to either the actual time to cancer reoccurrence for an entry in the censored and uncensored patient database where a cancer occurrence status is uncensored, or the last known observation time for the entry in the censored and uncensored patient database where the cancer occurrence status is censored;

d. assigns the patient to a low risk of cancer occurrence category where the output value is below 30 and assigns the patient to a high risk category where the output value is above 30; and e. generates a report based on the updated patient database.

2. A method for determining the risk of occurrence of prostate cancer in a patient, the method comprising:

(1) capturing, with a fluorescence imaging device, at least one sample image of a tissue sample treated with a plurality of fluorochrome labeled antibodies, wherein the antibodies are selected to bind with at least AR and Ki67;

(2) accessing from a database, using a processor configured by code executing therein, a patient dataset containing clinical feature data values for the patient corresponding to at least a value indicative of the biopsy Gleason score (bGS) and biopsy Gleason grade (bGG) of the patient obtained from a tissue sample of the patient and a value indicative of the level of Prostate Specific Antigen (PSA) in the blood of the patient;

(3) evaluating, using the processor, the at least one sample image recorded by the imaging device and deriving:

a. one or more molecular feature values indicative of a combined AR dynamic range where the measured bGG values is <=3, and a total Ki67 where the measured bGG value is 4>=by applying at least a segmentation analysis to the sample image using a quad-tree function to differentiate the sample image into background and non-background objects where the background objects have an average intensity below a predetermined threshold; and b. a plurality of morphometric measurements, including: (a) a mean distance between epithelial tumor cells where the bGG value is <=3, and (b) an area of isolated (non-lumen associated) tumor epithelial cells relative to tumor area value;

(4) updating the patient dataset using the processor, by associating with each patient dataset the derived molecular feature values and morphometric measurements;

(5) evaluating, using the processor, the updated patient dataset of step (4) with a Support Vector Regression for Censored Data (SVRc) algorithm configured as code executing in the processor, where the SVRc algorithm configures the processor to output a value corresponding to a risk score for cancer occurrence according to a support vector regression model generated from a censored and uncensored patient database, where each entry of the censored and uncensored patient database has data corresponding to the clinical, molecular and morphometric features of the patient dataset, and where the censored and uncensored patient database includes patient entries where a final health outcome for a patient is known (uncensored) and patient entries where the final health outcome for a patient is unknown (censored), and the SVRc algorithm evaluates the patient dataset according to the following:

$\in(x) = W^\tau \Phi(x) + b;$ where $\in(x)$ is a linear regression function on a feature space F, $\in(x)$ being the predicted time to event of sample x, W is a vector in F, $\Phi(x)$ is a mapping function to map x to a vector in F, b is the y-intercept, where W and b are obtained from an epsilon-insensitive loss function:

$\min(W,b) P = \frac{1}{2} W^\tau W + C \Sigma_{i=1}^n (\xi_i + \xi_i^*)$ such that:

$y_i - (W^\tau \Phi(x_i) + b) \leq \in + \xi_i$ $(W^\tau \Phi(x_i) + b) - y_i \leq \in + \xi_i^*$ $\xi^i, \xi_i^* > 0, i = 1 \ldots n;$ where $\in$, C and $\xi$ are constants;

(6) assigning the patient to a risk of cancer occurrence based on the output value of step (5), using the processor, wherein if the output value is below 30.19, then the patient is assigned a low risk of cancer occurrence and if the output model value is above 30.19, then the patient is assigned a high risk of cancer occurrence; and (7) generating, using the processor, a report based on the risk of cancer occurrence assigned to the patient in step (6).

3. The system of claim 1, wherein the computer-generated morphometric measurements include one or more measurements of a minimum spanning tree (MST) identified in the one or more images of tissue subject to multiplex immunofluorescence (IF).

4. The system of claim 3, wherein the one or more measurements of the minimum spanning tree (MST) comprises one or more measurements of a MST of epithelial nuclei identified in the one or more images of tissue subject to multiplex immunofluorescence (IF).

5. The system of claim 4, wherein the one or more measurements of the minimum spanning tree (MST) comprises average edge length in the MST of epithelial nuclei as identified in the one or more images of tissue subject to multiplex immunofluorescence (IF).

6. The system of claim 1, wherein the plurality of morphometric measurements include one or more measurements of the fractal dimension (FD) measured in the one or more images of tissue subject to multiplex immunofluorescence (IF).

7. The system of claim 6, wherein the one or more measurements of the fractal dimension (FD) comprises one or more measurements of the fractal dimension of one or more glands identified in the one or more images of tissue subject to multiplex IF.

8. The system of claim 7, wherein the one or more measurements of the fractal dimension of one or more glands comprises one or more measurements of the fractal dimension of gland boundaries between glands and stroma.

9. The system of claim 7, wherein the one or more measurements of the fractal dimension of one or more glands comprises one or more measurements of the fractal dimension of gland boundaries between glands and stroma and between glands and lumen.

\* \* \* \* \*